US008178672B2

(12) United States Patent
Ashwell et al.

(10) Patent No.: US 8,178,672 B2
(45) Date of Patent: May 15, 2012

(54) SYNTHESIS OF IMIDAZOOXAZOLE AND IMIDAZOTHIAZOLE INHIBITORS OF P38 MAP KINASE

(75) Inventors: Mark A. Ashwell, Carlisle, MA (US); Manish Tandon, Framingham, MA (US); Jean-Marc Lapierre, Pelham, NH (US)

(73) Assignee: ArQule, Inc., Woburn, MA (US)

( * ) Notice: Subject to any disclaimer, the term of this patent is extended or adjusted under 35 U.S.C. 154(b) by 820 days.

(21) Appl. No.: 11/665,193

(22) PCT Filed: Oct. 19, 2005

(86) PCT No.: PCT/US2005/037390
§ 371 (c)(1),
(2), (4) Date: Dec. 15, 2008

(87) PCT Pub. No.: WO2006/044869
PCT Pub. Date: Apr. 27, 2006

(65) Prior Publication Data
US 2009/0111985 A1   Apr. 30, 2009

Related U.S. Application Data

(60) Provisional application No. 60/619,876, filed on Oct. 19, 2004.

(51) Int. Cl.
C07D 403/12 (2006.01)
C07D 403/14 (2006.01)
C07D 401/14 (2006.01)
C07D 497/04 (2006.01)
C07D 498/04 (2006.01)
C07D 235/02 (2006.01)
A61K 31/506 (2006.01)

(52) U.S. Cl. ........ 544/330; 544/331; 548/154; 548/218; 514/275

(58) Field of Classification Search .................. 544/330, 544/331; 514/275; 548/154, 218
See application file for complete search history.

(56) References Cited

U.S. PATENT DOCUMENTS

| 3,455,924 A | 7/1969 | Lednicer | 260/256.4 |
| 4,794,114 A | 12/1988 | Bender et al. | 514/333 |
| 4,892,578 A | 1/1990 | Chang et al. | 71/94 |
| 5,317,019 A | 5/1994 | Bender et al. | 514/224.2 |
| 5,747,498 A | 5/1998 | Schnur et al. | 514/259 |
| 5,777,097 A | 7/1998 | Lee et al. | 536/24.31 |
| 5,783,664 A | 7/1998 | Lee et al. | 530/350 |
| 5,869,043 A | 2/1999 | McDonnell et al. | 424/94.1 |
| 5,871,974 A | 2/1999 | Lee et al. | 435/7.1 |
| 5,955,366 A | 9/1999 | Lee et al. | 435/471 |
| 5,994,412 A | 11/1999 | Lee et al. | 514/721 |
| 6,033,873 A | 3/2000 | McDonnell et al. | 435/69.1 |
| 6,090,626 A | 7/2000 | Monia et al. | 435/375 |
| 6,162,613 A | 12/2000 | Su et al. | 435/15 |
| 6,187,799 B1 | 2/2001 | Wood et al. | 514/363 |
| 6,302,838 B1 | 10/2001 | O'Reilly et al. | 574/365 |
| 6,344,476 B1 | 2/2002 | Ranges et al. | 514/447 |
| 6,376,214 B1 | 4/2002 | Kumar | 435/69.1 |
| 6,387,641 B1 | 5/2002 | Bellon et al. | 435/15 |
| 6,410,518 B1 | 6/2002 | Monia | 514/44 |
| 6,437,147 B1 | 8/2002 | Andersen et al. | 548/304.1 |
| 6,683,100 B2 | 1/2004 | Van Hoogevest | 514/365 |
| 6,689,883 B1 | 2/2004 | Dumas et al. | 544/235 |
| 6,806,258 B2 | 10/2004 | Monia | 514/44 |
| 6,900,221 B1 | 5/2005 | Norris et al. | 514/266.4 |
| 7,449,458 B2 | 11/2008 | Bhamidipati et al. | 514/230.5 |
| 7,501,430 B2* | 3/2009 | Lapierre et al. | 514/275 |
| 7,528,121 B2 | 5/2009 | Heron et al. | 514/81 |
| 7,902,192 B2* | 3/2011 | Ashwell et al. | 514/235.8 |
| 2001/0009675 A1 | 7/2001 | Blanchard et al. | 424/445 |
| 2002/0042517 A1 | 4/2002 | Uday et al. | 546/285 |
| 2002/0058659 A1 | 5/2002 | Andersen et al. | 514/234.5 |
| 2002/0137774 A1 | 9/2002 | Riedl et al. | 514/353 |
| 2002/0165394 A1 | 11/2002 | Dumas et al. | 546/143 |
| 2003/0078432 A1 | 4/2003 | Letavic et al. | 548/181 |
| 2003/0125359 A1 | 7/2003 | Lyons et al. | 514/350 |
| 2003/0144278 A1 | 7/2003 | Riedl et al. | 514/227.8 |
| 2003/0181442 A1 | 9/2003 | Riedl et al. | 514/227.5 |
| 2003/0207872 A1 | 11/2003 | Riedl et al. | 514/227.8 |
| 2003/0207914 A1 | 11/2003 | Dumas et al. | 514/307 |
| 2003/0216396 A1 | 11/2003 | Dumas et al. | 514/247 |
| 2003/0216646 A1 | 11/2003 | Dumas et al. | 514/350 |
| 2004/0023961 A1 | 2/2004 | Dumas et al. | 514/238.8 |
| 2004/0087626 A1 | 5/2004 | Renhowe et al. | 514/338 |
| 2004/0122237 A1 | 6/2004 | Amiri et al. | 548/161 |
| 2006/0116357 A1 | 6/2006 | Heron et al. | 514/80 |
| 2007/0270384 A1 | 11/2007 | Pittam et al. | 514/80 |
| 2007/0270418 A1 | 11/2007 | Ashwell et al. | 514/233.2 |
| 2007/0280418 A1* | 12/2007 | Weil | 378/65 |
| 2007/0281955 A1* | 12/2007 | Lapierre et al. | 514/275 |
| 2008/0032967 A1 | 2/2008 | Ashwell et al. | 514/217.05 |
| 2008/0045481 A1 | 2/2008 | Sependa et al. | 514/80 |
| 2009/0111985 A1 | 4/2009 | Ashwell et al. | 544/331 |
| 2009/0136499 A1 | 5/2009 | Lapierre et al. | 424/133.1 |
| 2010/0183600 A1 | 7/2010 | Lapierre et al. | 424/133.1 |

FOREIGN PATENT DOCUMENTS

EP    0951467    4/2003
(Continued)

OTHER PUBLICATIONS

Wolff, Manfred E. "Burger's Medicinal Chemistry, 5ed, Part 1", John Wiley & Sons, 1995, pp. 975-977.*

(Continued)

Primary Examiner — Venkataraman Balasubramanian
(74) Attorney, Agent, or Firm — Sunstein Kann Murphy & Timbers LLP

(57) ABSTRACT

An efficient route for the synthesis is of formula (I) of imidazooxazole and imidazothiazole inhibitors of the p38 MAP kinase pathway, useful as therapeutics for disease conditions including inflammation and auto-immune responses is described.

22 Claims, 14 Drawing Sheets

FOREIGN PATENT DOCUMENTS

| | | |
|---|---|---|
| EP | 1114051 | 4/2003 |
| EP | 1449834 | 8/2004 |
| WO | WO 91/00092 | 1/1991 |
| WO | WO 95/03297 | 2/1995 |
| WO | WO 97/32604 | 9/1997 |
| WO | WO 97/36587 | 10/1997 |
| WO | WO 98/52559 | 11/1998 |
| WO | WO 99/20624 | 4/1999 |
| WO | WO 99/32106 | 7/1999 |
| WO | WO 99/32436 | 7/1999 |
| WO | WO 99/32455 | 7/1999 |
| WO | WO 00/12074 | 3/2000 |
| WO | WO 00/42012 | 7/2000 |
| WO | WO 00/71535 | 11/2000 |
| WO | WO 01/14375 | 3/2001 |
| WO | WO 02/04447 | 1/2002 |
| WO | WO 02/062763 | 8/2002 |
| WO | WO 02/083628 | 10/2002 |
| WO | WO 02/083667 | 10/2002 |
| WO | WO 02/085857 | 10/2002 |
| WO | WO 03/000682 A1 | 1/2003 |
| WO | WO 03/033502 | 4/2003 |
| WO | WO 03/047523 | 6/2003 |
| WO | WO 03/047579 | 6/2003 |
| WO | WO 03/068223 | 8/2003 |
| WO | WO 03/068229 | 8/2003 |
| WO | WO 03/068746 | 8/2003 |
| WO | WO 03/087087 | 10/2003 |
| WO | WO 03/102139 | 12/2003 |
| WO | WO 2004/005283 | 1/2004 |
| WO | WO 2004/014870 | 2/2004 |
| WO | WO 2004/019941 | 3/2004 |
| WO | WO 2004/037789 | 5/2004 |
| WO | WO 2004/072025 | 8/2004 |
| WO | WO 2004/080464 | 9/2004 |
| WO | WO 2004/085399 | 10/2004 |
| WO | WO 2004/087905 | 10/2004 |
| WO | WO 2004/089929 | 10/2004 |
| WO | WO 2004/110990 A2 | 12/2004 |
| WO | WO 2005/023761 | 3/2005 |
| WO | WO 2006/044869 | 4/2006 |
| WO | WO 2007/123892 | 11/2007 |

OTHER PUBLICATIONS

Banker, G.S. et al, "Modern Pharmaceutics, 3ed.", Marcel Dekker, New York. 1996, pp. 451 and 596.*
Fresneda et al., "Synthetic Studies Towards the 2-Aminopyrimidine Alkaloids Variolins and Meridianins from Marine Origin," Tetrahedron Letters, 41(24):4777-4780 (2000).
Adams et al. Pyrimidinylimidazole Inhibitors of p38: Cyclic N-1 Imidazole Substituents Enhance p38 Kinase Inhibition and Oral Activity, Bioorg. Med. Chem. Lett., 11:2867-2870 (2001).
Adams, et al. Pyrimidinylimidazole Inhibors of CSBP/p38 Kinase Demonstraing Decreased Inhibition of Hepatic Sytochrome P450 Enzymes, Bioorg. Med. Chem. Lett., 8:3111-3116 (1998).
Allen, et al. "CI-1040 (PD184352), A Targeted Signal Transduction Inhibitor of MEK (MAPKK)," Semin. Oncol. 30 (5 Suppl 16), pp. 105-116, (2003).
Badger et al., Pharmacological Profile of SB 203580, a Selective Inhibitor of Cytokine Suppressive Binding Protein/p38 Kinase, in Animal Models of Arthritis, Bon Resorption, Endotixin Shock and Immune Function, J. Pharmacol. Exp. Ther., 279:1453-1461 (1996).
Bingham, The Pathogenesis of Rheumatiod Arthritis: Pivotal Cytokines Involved in Degradation and inflammation, J. Rheumatol. Suppl., 65:3-9 (2002).
Boehm et al., New Inhibitors of p38 Kinase, Expert Opinion on therapeutic Patents, 10(1):25-37 (2002).
Bondeson et al., Tumour Necrosis Factor as a therapeutic Target in Rheumatiod Arthritis and other Chronic inflammatory Diseases: The Clinical Experience with Infliximab (REMICADE), Int. J. Clin. Pract., 55:211-216 (2001).
Bradley and Robinson, Kationoid Reactivity of Aromatic Compounds. Part I, (Database Beilstein, Beilstein Institute zur Foerderung der Wissenschaften), Accession No. 316203, J. Chem. Soc. 1254-1263 (1932).
Brinkman et al., Engagement of Tumor Necrosis Factor (TNF) Receptor 1 Leades to ATF-2-andp38 Mitogen—Activated Protein Kinase-Dependent TNF-alpha Gene Expression, J. Biol. Chem., 274:30882-30886 (1999).
Bundgaard, Design of Prodrugs, p. 1 (1985).
Damasio, Alzheimer's Disease and Related Dementias, Cecil Textbook of Medicine, 20$^{th}$ Edition, vol. 2, pp. 1992-1996 (1996).
Davies, et al., "Mutations of the BRAF Gene in Human Cancer," Nature, 417, pp. 949-954 (2002).
Dong et al., MAP Kinases in the Immune Response, Annu. Rev. Immunol., 20:55-72 (2002).
Douglas, Jr., Introduction of Viral Diseases, Cecil Textbook of Medicine, 20$^{th}$ Edition, vol. 2, pp. 1739-1747 (1996).
English et al., Pharmacological Inhibitors of MAPK Pathways, Trends in Pharmacological Sciences, 23:40-45 (2002).
Enslen et al., Selective Activation of p38 Mitogen-Activated Protein (MAP) Kinase Isoforms by the MAP Kinase Kinases MKK3 and MKK6, J. boil. Chem., 273:1741-1748 (1998).
Feldmann et al., Role of cytokines in Rheumatoid Arthritis, Annu. Rev. immunol., 14:397-440 (1996).
Fuchs et al. Stability of the ATF2 transcription factor is Regulated by Phosphorylation and Dephosphorylation, J. Biol Chem., 275:12560-12564 (2000).
Griswold et al., Differentiation in vivo of Classical non-Steroidal Antiinflammatory Drugs from Cytokine Suppresive Antiinflartimatory drugs and Other Pharmacological Casses using Mouse Tumour Necrosis factor Alpha Production, Drugs exp. Clin. Res., 19:243-248 (1993).
Hoeflich, et al., Oncogenic BRAF Is Required for Tumor Growth and Maintenance in Melanoma Models, Cancer Res., 66(2), pp. 999-1006 (2006).
Joe, et al., Animal Models of Rheumatoid Arthritis and Related Inflammation, Curr. Rheumatol. Rep., 1:139-148 (1999).
Keesler, et al., Purification and Activation of Recombinant p38 Isoforms Alpha, Beta, Gamma, and Delta, Protein Expr. Purif, 14:221-228 (1998).
Keffer, et al., Transgenic Mice Expressing Human Tumour Necrosis Factor: A Predictive Genetic Model of Arthritis, EMBO J., 10:4025-4031 (1991).
Laufer, et al., An in vitro Screening Assay for the Detection of Inhibitors of Proinflammatory Cytokine Synthesis: a Useful Tool for the Development of New Antiarthritic and Disease Modifying Drugs, Osteoarthritis Cartilage, 10:961-967 (2002).
Laufer, et al., From Imidazoles to Pyrimidines: New Inhibitors of Cytokine Release, J. Med. Chem., 45:2733-2740 (2002).
Layzer, Degenerative Diseases of the Nervous System, Cecil Textbook of Medicine, 20$^{th}$ Edition, vol. 2, pp. 2050-2057 (1996).
Lee, et al., A Protein Kinase Involved in the Regulation of Inflammatory Cytokine Biosynthesis, Nature, 372:739-746 (1994).
Lee, et al., Bicyclic Imidazoles as a Novel Class of Cytokine Biosynthesis Inhibitors, Ann. N.Y. Acad. Sci., 696:149-170 (1993).
Lee, et al., Inhibition of p38 MAP Kinase as a Therapeutic Strategy, Immunopharmacology, 47:185-201 (2000).
Li, et al., Selective Killing of Cancer Cells by Beta-Lapachone: Direct Checkpoint Activation as a Strategy Against Cancer, Proc. Natl. Acad. Sci. USA., 100(5), pp. 2674-2678 (2003).
Liverton, et al., Design and Synthesis of Potent, Selective, and Orally Bioavailable Tetrasubstituted Imidazole Inhibitors of p38 Mitogen-Activated Proteins Kinase, J. Med. Chem., 42:2180-2190 (1999).
Marais, et al., Control of the ERK MAP Kinase Cascade by Ras and Raf, Cancer Surv., 27. pp. 101-125 (1996).
McLay, et al., The Discovery of RPR 200765A, a p38 MAP Kinase Inhibitor Displaying a Good Oral Anti-Arthritic Efficacy, Bioorg. Med. Chem., 9:537-554 (2001).
Mekonnen, et al., A New and Facile Synthesis of Imidazo[2,1-b]Oxazoles, J. Heterocyclic Chem., 34:589-599 (1997).
Ono, et al., The p38 Signal Transduction Pathway: Activation and Function, Cell. Signal., 12:1-13 (2000).
OSI Pharmaceuticals, Inc. and Genetech, Inc., Full prescription information for Tarceva® erlotinib tablets, 4 pages (2007).
Pargellis, et al., Inhibition of p38 MAP Kinase by Utilizing a Novel Allosteric Binding Site, Nat. Struct. Biol., 9:268-272 (2002).

Pugsley, Etanercept, Immunex, Curr. Opin. Investig. Drugs, 2:1725-1731 (2001).

Raingeaud, et al., MKK3- and MKK6-Regulated Gene Expression is Mediated by the p38 Mitogen-Activated Protein Kinase Signal Transduction Pathway, Mol. Cell. Biol., 16:1247-1255 (1996).

Raingeaud, et al., Pro-Inflammatory Cytokines and Environmental Stress Cause p38 Mitogen-Activated Protein Kinase Activation by Dual Phosphorylation on Tyrosine and Threonine, J. Biol. Chem., 270:7420-7426 (1995).

Rautio, et al., Prodrugs: design and clinical applications, Nature Reviews/Drug Discovery, vol. 7, pp. 255-270, Mar. 2008.

Regan, et al., Pyrazole Urea-Based Inhibitors of p38 MAP Kinase: From Lead Compound to Clinical Candidate, J. Med. Chem., 45:2994-3008 (2002).

Revesz, et al., SAR of 4-Hydroxypiperidine and Hydroxyalkyl Substituted Heterocycles as Novel p38 Map Kinase Inhibitors, Bioorg. Med. Chem. Lett., 10:1261-1264 (2000).

Robinson, et al., Mitogen-Activated Protein Kinase Pathways, Curr, Opin. Cell Biol., 9, pp. 180-186, 1997.

Sharma, et al., Mutant v599EB-Raf Regulates Growth and Vascular Development of Malignant Melanoma Tumors, Cancer Res., 65(6), pp. 2412-2421, 2005.

Simone, Oncology: Introduction, Cecil Textbook of Medicine, $20^{th}$ Edition, vol. 1, pp. 1004-1010 (1996).

Smith et al., Recent Advances in the Research and Development of RAF Kanase Inhibitors, Current Topics in Medicinal Chemistry, 2006, 6, 1071-1089.

Turconi, et al., Synthesis of a New Class of 2,3-Dihydro-2-0xo-1H-Benzimidazole-1-Carboxylic Acid Derivatives as Highly Potent 5-$HT_3$ Receptor Antagonists, J. Med. Chem., 33:2101-2108 (1990).

Tuveson, et al., BRAF as a Potential Therapeutic Target in Melanoma and Other Maliganancies, Cancer Cell, 4, pp. 95-98 (2003).

Ulrich, Chapter 4: Crystal Characteristics, Kirk Othmer Encyclopedia of Chemical Technology, 7 pages, Aug. 2002.

Vippagunta et al., Crystalline Solids, Advanced Drug Delivery Reviews, 48, pp. 3-26 (2001).

Wellbrock, et al. BRAF Is an Oncogene in Melanocytes, Cancer Res., 64, pp. 2338-2342, 2004.

West, Solid Solutions, Solid State Chemistry and its applications, pp. 358 & 365 (1988).

Wilhelm et. al., Bay 43-9006 Exhibits Broad Spectrum Oral Antitumor Activity and Targets the RAF/MEK/ERK Pathway and Receptor Tyrosine Kinases Involved in Tumor Progression and Angiogenesis, Cancer Research 64, 7099-7109, Oct. 1, 2004.

Xing, BRAF Mutation in Thyroid Cancer, Endocrine-Related Cancer, 12, pp. 245-262, 2005.

International Searching Authority, International Preliminary Report on Patentability and the Written Opinion of the International Searching Authority, International Application No. PCT/US2004/15368, dated Feb. 21, 2006, 12 pages.

International Searching Authority, International Preliminary Report on Patentability and the Written Opinion of the International Searching Authority, International Application No. PCT/US2007/009348, dated Oct. 22, 2008, 9 pages.

International Searching Authority, International Preliminary Report on Patentability and the Written Opinion of the International Searching Authority, International Application No. PCT/US2005/037390, dated Apr. 24, 2007, 7 pages.

International Searching Authority, International Search Report—International Application No. PCT/US2009/066826, dated May 19, 2010, together with the Written Opinion of the International Searching Authority, 16 pages.

European Patent Office, Extended European Search Report—European Application No. 10175256.6-1211, dated Sep. 30, 2010, 7 pages.

European Patent Office, Extended European Search Report—European Application No. 10179473.3-1211, dated Nov. 3, 2010, 6 pages.

* cited by examiner

SYNTHESIS OF IMIDAZOOXAZOLE AND IMIDAZOTHIAZOLE INHIBITORS OF P38 MAP KINASE

CROSS-REFERENCE TO RELATED APPLICATIONS

This application is a national phase application under 35 U.S.C. §371 of International Application Number PCT/US2005/037390, filed Oct. 19, 2005, the disclosure of which is incorporated by reference in its entirety, and which claims priority to and the benefit under 35 U.S.C. §119 of U.S. Provisional Application No. 60/619,876, filed Oct. 19, 2004, which application is incorporated by reference in its entirety.

BACKGROUND OF THE INVENTION

Many chronic and acute conditions are associated with perturbation of the inflammatory response. A large number of cytokines participate in this response, including, but not limited to, IL-1, IL-6, TL-8 and TNFα. Although these cytokines are normally expressed in response to many physiological stimuli, excess, unregulated, or excess and unregulated production of these cytokines often leads to inflammation and tissue damage. This is one mechanism by which diseases such as rheumatoid arthritis mediate morbidity (Keffer, J., et al, EMBO J., 13: 4025-4031, 1991, Feldmann, M., et al, Annu. Rev. Immunol., 14: 397-440, 1996 and Bingham, C. O., J. Rheumatol. Suppl., 65: 3-9, 2002). Currently there are several therapeutic agents that aim to reduce systemic levels of proinflammatory cytokines such as TNFα (Pugsley, M. K. Curr. Opin. Invest. Drugs, 2: 1725-1731, 2001 and Bondeson, J. and Maini, R. N., J. Clin. Pract., 55: 211-216, 2001), thus ameliorating the disease. These therapeutics act directly to reduce circulating levels or neutralize activity of the cytokine. However, these therapeutics do not directly block intracellular proteins that regulate the expression and secretion of proinflammatory cytokines or regulate the expression of other mediators of inflammation and tissue destruction.

The p38 MAP Kinase (p38, also known as CSBP or SAPK) signaling pathway has been reported to be responsible for the expression of pro-inflammatory cytokines that are elevated in many inflammatory and auto-immune diseases (see, e.g., Dong, C., et al., Annu. Rev. Immunol., 20: 55-72, 2002 and references cited therein). Thus, inhibitors of any part of the p38 MAP Kinase pathway or inhibitors of pathways that regulate the p38 MAP Kinase pathway may be useful as therapeutics for diseases or conditions in which inflammation or auto-immune responses are involved. (Lee, J. C., et al, Immunopharm, 47: 185-201, 2000). This pathway has been shown to be activated by cellular stressors, such as osmotic shock, UV light, free radicals, bacterial toxins, viruses, cytokines, and chemokines, to name a few, and in response, mediates the expression of several cytokines including, but not limited to, IL-1, IL-6, IL-8 and TNFα (Ono, K. and Han, J., Cellular Signalling, 12: 1-13, 2000 and references cited therein).

Typically the p38 MAP kinase pathway is directly or indirectly activated by cell surface receptors, such as receptor tyrosine kinases, chemokine or G protein-coupled receptors, which have been activated by a specific ligand, e.g., cytokines, chemokines or lipopolysaccharide (LPS) binding to a cognate receptor. Subsequently, p38 MAP kinase is activated by phosphorylation on residues threonine 180 and tyrosine 182. After activation, p38 MAP kinase can phosphorylate other intracellular proteins, including protein kinases, and can be translocated to the cell nucleus, where it phosphorylates and activates transcription factors leading to the expression of pro-inflammatory cytokines and other proteins that contribute to the inflammatory response, cell adhesion, and proteolytic degradation. For example, in cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of physiological responses to cellular stress, acute or chronic cellular stress leads to the excess, unregulated, or excess and unregulated expression of pro-inflammatory cytokines. This, in turn, leads to tissue damage, often resulting in pain and debilitation. The fact that there are four known isoforms of p38 MAP kinase (p38α, p38β, p38δ and p38γ), each showing different expression levels, tissue distributions and regulation, support the concept that they are involved in the etiology or sequalae of many diseases and physiological disturbances.

Indeed, many autoimmune diseases and diseases associated with chronic inflammation, as well as acute responses, have been linked to activation of p38 MAP kinase and over-expression or dysregulation of inflammatory cytokines. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; cancer; restenosis; silicosis; pulmonary sarcosis; bone resorption diseases, such as osteoporosis; graft-versus-host reaction; and auto-immune diseases, such as Multiple Sclerosis, lupus and fibromyalgia; AIDS and other viral diseases such as Herpes Zoster, Herpes Simplex I or II, influenza virus and cytomegalovirus; and diabetes mellitus.

Many studies have shown that reducing the activity of p38 MAP kinase, its upstream activators or its downstream effectors, either through genetic or chemical means, blunts the inflammatory response and prevents or minimizes tissue damage (see, e.g., English, J. M. and Cobb, M. H., Trends in Pharmacol. Sci., 23: 40-45, 2002; and Dong, C., et al, Annu. Rev. Immunol., 20: 55-72, 2002). Thus, inhibitors of p38 activity, which also inhibit excess or unregulated cytokine production and may inhibit more than a single pro-inflammatory cytokine, may be useful as anti-inflammatory agents and therapeutics. Furthermore, the large number of diseases associated with p38 MAP kinase-associated inflammatory responses indicates that there is a need for effective methods for treating these conditions. As of the filing date of the present application, however, there are no approved drugs available that are known to directly inhibit the p38 MAP kinase family of enzymes, and those approved drugs that act by reducing or neutralizing cytokine levels through binding to the cytokine are generally not orally bioavailable and must therefore be administered by techniques such as injection.

Compounds of the present invention are useful in treating cancers or in methods for treating p38 MAP kinase- and cytokine-associated conditions. Compounds and methods for treating p38 MAP kinase- and cytokine-associated conditions have been described in co-pending PCT application PCT/US04/15368, filed May 14, 2004, which is incorporated by reference herein in its entirety. Methods for the efficient synthesis of imidazooxazole and imidazothiazole p38 MAP kinase inhibitors are described herein.

SUMMARY OF THE INVENTION

The present invention relates to a synthetic route for the preparation of imidazooxazole and imidazothiazole compounds formula (I)

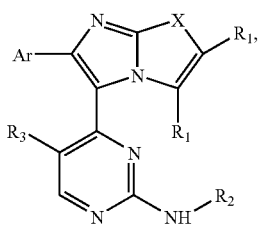
(I)

or a salt or prodrug thereof, comprising:
(a) reacting a compound of formula III

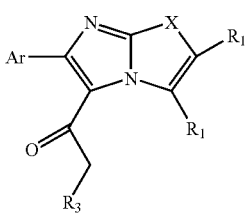
(III)

with N,N-dimethylformamide dimethyl acetal to form a compound of formula IV

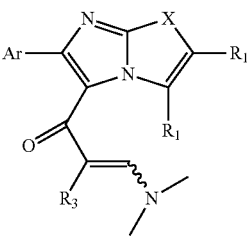
(IV)

and (b) reacting said compound of formula IV with a guanidino compound of formula V:

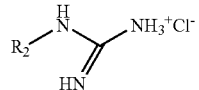
(V)

to form said compound of formula I, wherein:
X is O or $S(O)_m$ and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —NO$_2$; —OH; —O—($C_1$-$C_6$ alkyl); a heterocycle optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; aryl optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; —COOH; —(CH$_2$)$_{0-3}$—C(=O)O—($C_1$-$C_6$ alkyl); —OC(=O)—($C_1$-$C_6$ alkyl); $C_1$-$C_8$ alkyl; $C_1$-$C_8$ fluoro-substituted alkyl; $C_3$-$C_8$ cycloalkyl; $C_3$-$C_8$ fluoro-substituted cycloalkyl; —O-(aryl); —OC(=O)-(aryl optionally and independently substituted with halogen, —CN, —NO$_2$, —OH, —O—($C_1$-$C_6$ alkyl), phenyl, —COOH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—$C_1$-$C_4$ fluoro-substituted alkyl), or —N($C_1$-$C_4$ fluoro-substituted alkyl)$_2$); —NR$_8$R$_9$; —(NH)—($C_1$-$C_4$ fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; an ester-linked amino acid; and an amide-linked amino acid;
R$_1$ groups are independently selected from the group consisting of hydrogen, —CN, —COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —CH$_2$-(aryl), —CH$_2$-(halogen-substituted aryl), and —C(=O)—NR$_4$R$_5$;
R$_2$ is independently selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more R$_2$-substituents independently selected from the group consisting of: hydroxyl group, —COOH, oxo, fluorine, thiol, cyano, nitro, —NR$_6$R$_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—NR$_8$R$_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl, wherein when, $R_2$ is aryl, said one or more $R_2$-substitutents further include chlorine, bromine and iodine and further wherein, when $R_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

$R_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$, and the amide nitrogen of —C(=O)—$NR_4R_5$ form a cyclic structure and $R_1$ is of the form:

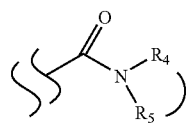

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl; and $R_8$ are $R_9$ are each independently selected from the group consisting of hydrogen, $C_1$-$C_6$ alkyl, $C_3$-$C_8$ cycloalkyl, aryl, and heterocyclyl.

The present invention also relates to a method for preparing a compound of formula IA

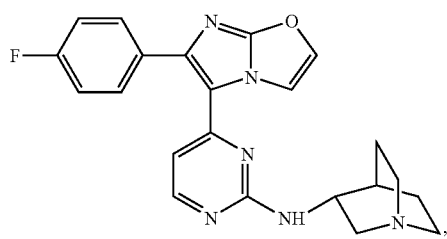

(IA)

or a salt or prodrug thereof, comprising:

(a) reacting a compound of formula IIIA

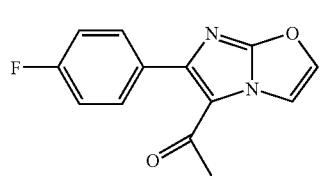

(IIIA)

with N,N-dimethylformamide dimethyl acetal to form a compound of formula IVA,

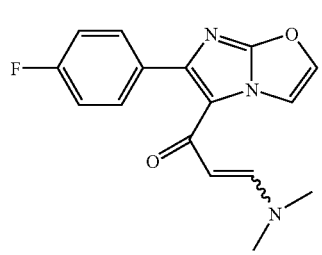

(IVA)

and (b) reacting a compound of formula IVA with a 3-guanidinoquinuclidine of formula VA

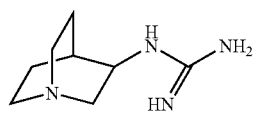

(VA)

to form said compound of formula IA;
wherein said compound of formula IIIA is prepared by:
i) reacting said 2-amino-1,3-oxazole:

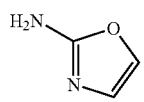

with 4-fluorophenacyl bromide to form the a keto-oxazole-imine having the formula:

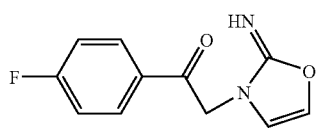

ii) forming the corresponding imidazo[2,1-b]oxazole of formula IIA:

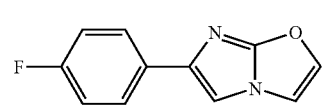

(IIA)

in the presence of one or more dehydrating reagents, and iii) reacting a compound of formula IIA with acetic anhydride to form said compound of formula IIIA.

The present invention also relates to a method for preparing a compound of formula I

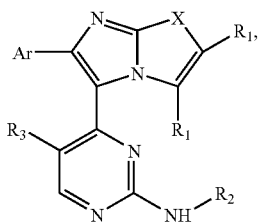

(I)

or a salt or prodrug thereof, comprising:
(a) reacting a compound of formula IV

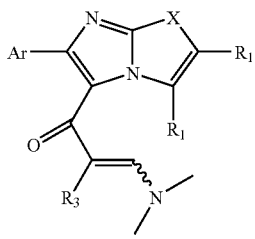

(IV)

with a guanidino compound of formula V

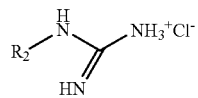

(V)

to form said compound of formula I, wherein:
X is O or S(O), and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$ fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

R$_1$ groups are independently selected from the group consisting of hydrogen, —CN, —COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_2$ is independently selected from the group consisting of C$_1$-C$_{10}$ alkyl, C$_3$-C$_{10}$ cycloalkyl, heterocyclyl, and aryl; wherein said C$_1$-C$_{10}$ alkyl, C$_3$-C$_{10}$ cycloalkyl, heterocyclyl, and aryl groups may be substituted with one or more R$_2$-substituents independently selected from the group consisting of: hydroxyl group, —COOH, oxo, fluorine, thiol, cyano, nitro, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)—NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl;

wherein when, R$_2$ is aryl, said one or more R$_2$-substitutents further include chlorine, bromine and iodine; and wherein, when R$_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, C$_1$-C$_6$ alkyl, C$_3$-C$_8$ cycloalkyl, C$_2$-C$_6$ alkenyl, C$_2$-C$_6$ alkynyl, aryl, —C(=O)—NR$_8$R$_9$, C$_1$-C$_6$ alkylcarbonyl, —C(=O)aryl, —C(=O)O-aryl, C$_1$-C$_6$ alkoxycarbonyl, C$_1$-C$_6$ alkylsulfonyl, arylsulfonyl, and heterocyclyl;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$, and the amide nitrogen of —C(=O)—NR$_4$R$_5$ form a cyclic structure and R$_1$ is of the form:

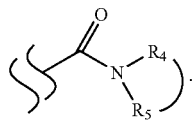

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl; and $R_8$ are $R_9$ are each independently selected from the group consisting of hydrogen, $C_1$-$C_6$ alkyl, $C_3$-$C_8$ cycloalkyl, aryl, and heterocyclyl.

The present invention further relates to a method for preparing a compound of formula Z

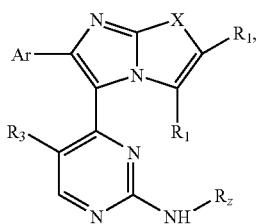

or a salt or prodrug thereof, comprising:

(a) reacting a compound of formula III

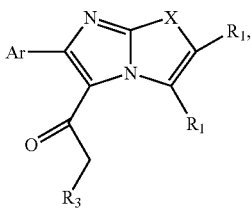

with N,N-dimethylformamide dimethyl acetal to form a compound of formula IV

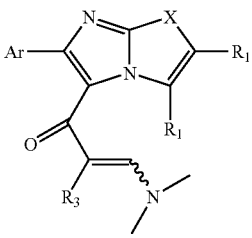

(b) reacting said compound of formula IV with a guanidino compound of formula V:

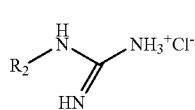

where the $R_2$ substituent of said compound of formula V is a heterocycle having an endocyclic nitrogen atom bearing a hydrogen atom, or a heterocycle having endocyclic nitrogen atoms with at least one nitrogen bearing a hydrogen atom, to form an intermediate of the form

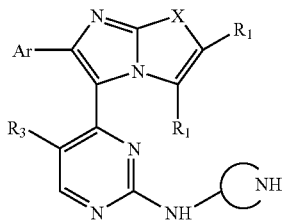

where

represents a heterocycle having an endocyclic nitrogen atom bearing a hydrogen atom, or a heterocycle having endocyclic nitrogen atoms with at least one nitrogen bearing a hydrogen atom; and (c) reacting said intermediate with a compound selected from the group consisting of a sulfonyl chloride of the form Cl—S(=O)$_2$alkyl, a sulfonyl chloride of the form Cl—S(=O)$_2$—$R_{12}$—$(R_{13})_{0-4}$, an isocyanate of the form O=C=N—$R_{17}$—$R_{18}$, a chloroformate of the form Cl—(C=O)—O—$R_{17}$—$R_{18}$, a chlorothiolformate of the form Cl—(C=O)—S—$R_{17}$—$R_{18}$, an acid chloride of the form Cl—C(=O)—$R_{14}$—$R_{15}$, and a carboxylic acid of the form HO—C(=O)—$R_{14}$—$R_{15}$;

to form a compound of formula Z wherein:
  X is O or S(O)$_m$ and m is 0, 1, or 2;
  Ar is
    2,3-dihydro-benzo[1,4]dioxin-6-yl;
    benzo[1,3]dioxol-5-yl;
    an aryl group; or
    an aryl group substituted with one or more substituents independently selected from the group consisting of halogen; —CN; —NO$_2$; —OH; —O—($C_1$-$C_6$ alkyl); a heterocycle optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; aryl optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$ fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

R$_1$ groups are independently selected from the group consisting of hydrogen, —CN, —COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_z$ is an independently selected nitrogen-containing heterocycle having an endocyclic nitrogen atom or endocyclic nitrogen atoms, wherein said independently selected nitrogen-containing heterocycle may be substituted with one or more R$_z$-substituents independently selected from the group consisting of hydroxyl group, —COOH, oxo, fluorine, thiol, —CN, —NO$_2$, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl, wherein said endocyclic nitrogen atom or endocyclic nitrogen atoms is substituted with one or more substituents independently selected from the group consisting C$_1$-C$_6$ alkylsulfonyl, R$_{10}$ and R$_{11}$;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$, and the amide nitrogen of —C(=O)—NR$_4$R$_5$ form a cyclic structure and R$_1$ is of the form:

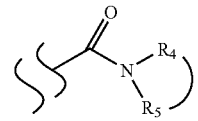

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl;

R$_8$ are R$_9$ are each independently selected from the group consisting of hydrogen, C$_1$-C$_6$ alkyl, C$_3$-C$_8$ cycloalkyl, aryl, and heterocyclyl;

R$_{10}$ is —S(=O)$_2$—R$_{12}$—(R$_{13}$)$_{0-4}$;

R$_{11}$ is independently selected from the group consisting of —C(=O)—R$_{14}$—R$_{15}$ and —C(=O)—R$_{16}$—R$_{17}$—R$_{18}$;

R$_{12}$ is phenyl or a 5-6 membered nitrogen-containing heteroaryl group;

R$_{13}$ is independently selected from the group consisting of halogen, cyano, —NC(=O)CH$_3$, —(C$_1$-C$_6$)alkyl, —(CH$_2$)$_{0-4}$—COOH, (C$_1$-C$_6$)alkoxy, (C$_1$-C$_6$)halogen-substituted alkyl, (C$_1$-C$_6$)halogen-substituted alkoxy, and phenoxy;

R$_{14}$ is independently selected from the group consisting of (C$_1$-C$_6$)alkyl and a bond;

R$_{15}$ is independently selected from the group consisting of —CH(NH$_2$)(C$_1$-C$_4$ alkyl-COOH); (C$_1$-C$_6$)alkyl optionally substituted with one or more substituents independently selected from the group consisting of C$_1$-C$_6$ alkoxy, —OH, —(NH)C(=O)—CH$_3$, —NH$_2$, and —N(CH$_3$)$_2$; (C$_3$-C$_{10}$)cycloalkyl; (C$_1$-C$_6$)alkoxy; heterocyclyl; aryl optionally substituted with one or more substituents independently selected from the group consisting of halogen, C$_1$-C$_6$ alkoxy, —NH$_2$, —(NH)(C$_1$-C$_4$)alkyl, and —N(C$_1$-C$_4$ alkyl)$_2$; —S-aryl optionally substituted with one or more independently selected (C$_1$-C$_6$)alkyl groups; and aryloxy optionally substituted with one or more substituents independently selected from the group consisting of halogen, —NH$_2$, —(NH)—C$_1$-C$_4$ alkyl, and —N(C$_1$-C$_4$ alkyl)$_2$;

R$_{16}$ is independently selected from the group consisting of O, —(NH)—, and S;

R$_{17}$ is independently selected from the group consisting of (C$_1$-C$_6$)alkyl and a bond; and R$_{18}$ is independently selected from the group consisting of (C$_1$-C$_6$)alkyl; (C$_3$-C$_{10}$)cycloalkyl; heterocyclyl; and aryl, optionally substituted with one or more substituents independently selected from the group consisting of halogen, (C$_1$-C$_6$) alkyl, (C$_1$-C$_3$) halogen-substituted alkyl, (C$_1$-C$_6$)alkoxy, —NO$_2$, —NH$_2$, —(NH)—(C$_1$-C$_4$)alkyl, and —N(C$_1$-C$_4$ alkyl)$_2$.

The present invention additionally relates to compounds of formula Z:

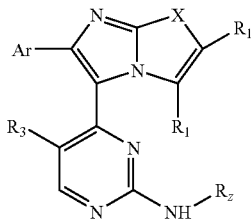

wherein:

X is O or S(O)$_m$ and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$ fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

R$_1$ groups are independently selected from the group consisting of hydrogen, —CN, COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_z$ is an independently selected nitrogen-containing heterocycle having an endocyclic nitrogen atom or endocyclic nitrogen atoms, wherein said independently selected nitrogen-containing heterocycle may be substituted with one or more R$_z$-substituents independently selected from the group consisting of hydroxyl group, —COOH, oxo, fluorine, thiol, —CN, —NO$_2$, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl, wherein said endocyclic nitrogen atom or endocyclic nitrogen atoms is substituted with one or more substituents independently selected from the group consisting C$_1$-C$_6$ alkylsulfonyl, R$_{10}$ and R$_{11}$;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$, and the amide nitrogen of —C(=O)—NR$_4$R$_5$ form a cyclic structure and R$_1$ is of the form:

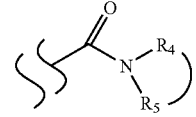

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl;

R$_8$ are R$_9$ are each independently selected from the group consisting of hydrogen, C$_1$-C$_6$ alkyl, C$_3$-C$_8$ cycloalkyl, aryl, and heterocyclyl;

R$_{10}$ is —S(=O)$_2$—R$_{12}$—(R$_{13}$)$_{0-4}$;

R$_{11}$ is independently selected from the group consisting of —C(=O)—R$_{14}$—R$_{15}$ and —C(=O)—R$_{16}$—R$_{17}$—R$_{18}$;

R$_{12}$ is phenyl or a 5-6 membered nitrogen-containing heteroaryl group;

R$_{13}$ is independently selected from the group consisting of halogen, cyano, —NC(=O)CH$_3$, —(C$_1$-C$_6$)alkyl, —(CH$_2$)$_{0-4}$—COOH, (C$_1$-C$_6$)alkoxy, (C$_1$-C$_6$)halogen-substituted alkyl, (C$_1$-C$_6$)halogen-substituted alkoxy, and phenoxy;

R$_{14}$ is independently selected from the group consisting of (C$_1$-C$_6$)alkyl and a bond;

R$_{15}$ is independently selected from the group consisting of —CH(NH$_2$)(C$_1$-C$_4$ alkyl-COOH); (C$_1$-C$_6$)alkyl optionally substituted with one or more substituents independently selected from the group consisting of C$_1$-C$_6$ alkoxy, —OH, —(NH)C(=O)—CH$_3$, —NH$_2$, and —N(CH$_3$)$_2$; (C$_3$-C$_{10}$)cycloalkyl; ($C_1$-$C_6$)alkoxy; heterocyclyl; aryl optionally substituted with one or more substituents independently selected from the group consisting of halogen, $C_1$-$C_6$ alkoxy, —$NH_2$, —(NH)—($C_1$-$C_4$)alkyl, and —N($C_1$-$C_4$ alkyl)$_2$; —S-aryl optionally substituted with one or more independently selected ($C_1$-$C_6$)alkyl groups; and aryloxy optionally substituted with one or more substituents independently selected from the group consisting of halogen, —$NH_2$, —(NH)—$C_1$-$C_4$ alkyl, and —N($C_1$-$C_4$ alkyl)$_2$;

$R_{16}$ is independently selected from the group consisting of O, —(NH)—, and S;

$R_{17}$ is independently selected from the group consisting of ($C_1$-$C_6$)alkyl and a bond; and $R_{18}$ is independently selected from the group consisting of ($C_1$-$C_6$)alkyl; ($C_3$-$C_{10}$)cycloalkyl; heterocyclyl; and aryl, optionally substituted with one or more substituents independently selected from the group consisting of halogen, ($C_1$-$C_6$) alkyl, ($C_1$-$C_3$)halogen-substituted alkyl, ($C_1$-$C_6$)alkoxy, —$NO_2$, —$NH_2$, —(NH)—($C_1$-$C_4$)alkyl, and —N($C_1$-$C_4$ alkyl)$_2$;

or a pharmaceutically acceptable salt, prodrug, metabolite, analog or derivative thereof.

DESCRIPTION OF THE DRAWINGS

FIG. 1 additionally indicates the route of preparation of compounds of formula IV from compounds of formula II, and the preparation of compounds of formula V starting with primary amines. In addition, the figure indicates the preparation of compounds of formula Z from selected compounds of formula I.

FIG. 2A sets forth the appearance of a blank run. FIGS. 2B-2H are chromatograms of the indicated compounds. FIG. 2I is a representative chromatogram of (R)—N-{4-[6-(4-fluorophenyl)imidazo[2,1-b][1,3]oxazol-5-yl]pyrimidin-2-yl}quinuclidine-3-amine prepared in accordance with the method of example 34. Details of the chromatographic procedure are described in Example 37.

FIGS. 3A-3D set forth chiral chromatographic analysis of (R)—N-{4-[6-(4-fluorophenyl)imidazo[2,1-b][1,3]oxazol-5-yl]pyrimidin-2-yl}quinuclidine-3-amine and (S)—N-{4-[6-(4-fluorophenyl)imidazo[2,1-b][1,3]oxazol-5-yl]pyrimidin-2-yl}quinuclidine-3-amine. FIGS. 3A-3D illustrate the chromatographic profile of a sample blank, 5 µg of the R enantiomer, 5 µg of the S enantiomer, and a mixture of 4.902 µg of the R and 0.098 µg of the S enantiomers, respectively. Details of the chromatographic procedure are described in Example 38.

DETAILED DESCRIPTION OF THE INVENTION

Figure 1:
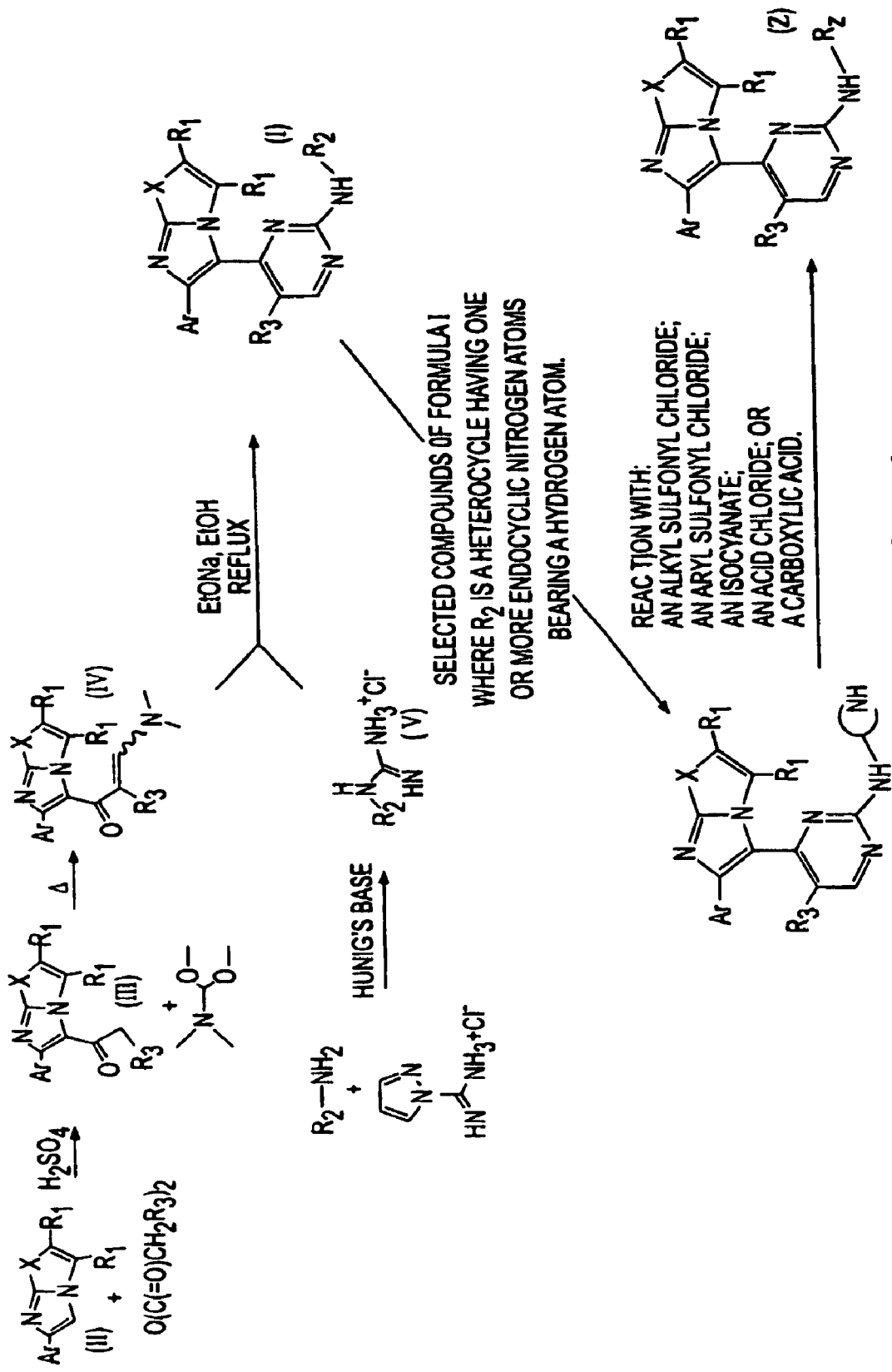
FIG. 1 illustrates a convergent synthesis of compounds of formula I and formula Z from compounds of formulas III, IV, and V.

In an embodiment, the present invention provides a high yield method of preparing imidazooxazole and imidazothiazole compounds, such as for example compounds of formula I and formula Z, that may be used for example as anti-cancer agents and p38 MAP kinase inhibitors. In another embodiment, any of the methods of the present invention for preparing a compound, including for example methods for preparing a compound of formula I or formula Z, may be used to prepare pharmaceutically acceptable salts, prodrugs, metabolites, analogs or derivatives of the compound.

In an embodiment, the present invention provides a method of preparing a compound of formula I

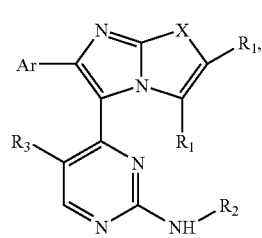

or a salt or a prodrug thereof, comprising:
(a) reacting a compound of formula III

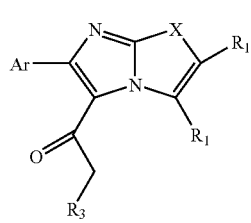

with N,N-dimethylformamide dimethyl acetal to form a compound of formula IV

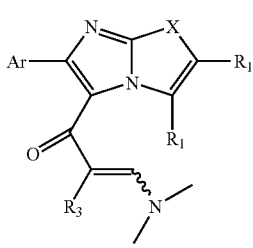

and (b) reacting said compound of formula IV with a guanidino compound of formula V

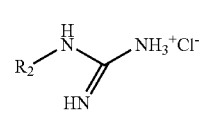

to form said compound of formula I, wherein:
X is O or S(O)$_m$ and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —$NO_2$; —OH; —O—($C_1$-$C_6$ alkyl); a heterocycle optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-

$C_4$ fluoro-substituted alkyl), and —N($C_1$-$C_4$ fluoro-substituted alkyl)$_2$; aryl optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; —COOH; —(CH$_2$)$_{0-3}$—C(=O)O—($C_1$-$C_6$ alkyl); —OC(=O)—($C_1$-$C_6$ alkyl); $C_1$-$C_8$ alkyl; $C_1$-$C_8$ fluoro-substituted alkyl; $C_3$-$C_8$ cycloalkyl; $C_3$-$C_8$ fluoro-substituted cycloalkyl; —O-(aryl); —OC(=O)-(aryl optionally and independently substituted with halogen, —CN, —NO$_2$, —OH, —O—($C_1$-$C_6$ alkyl), phenyl, —COOH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), or —N($C_1$-$C_4$ fluoro-substituted alkyl)$_2$); —NR$_8$R$_9$; —(NH)—($C_1$-$C_4$ fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—$C_1$-$C_4$ fluoro-substituted alkyl), and —N($C_1$-$C_4$ fluoro-substituted alkyl)$_2$; an ester-linked amino acid; and an amide-linked amino acid;

R$_1$ groups are independently selected from the group consisting of hydrogen, —CN, —COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_2$ is independently selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more R$_2$-substituents independently selected from the group consisting of: hydroxyl group, —COOH, oxo, fluorine, thiol, cyano, nitro, —NR$_6$R$_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—NR$_8$R$_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl;

wherein when, R$_2$ is aryl, said one or more R$_2$-substitutents ether include chlorine, bromine and iodine; and wherein, when R$_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—NR$_8$R$_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

R$_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

R$_4$ and R$_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, R$_4$ and R$_5$ taken together are $C_2$-$C_7$ alkyl or $C_2$-$C_7$ fluoro-substituted alkyl, such that R$_4$, R$_5$, and the amide nitrogen of —C(=O)—NR$_4$R$_5$ form a cyclic structure and R$_1$ is of the form:

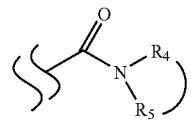

R$_6$ is selected from the group consisting of $C_1$-$C_6$ alkyl and aryl;

R$_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—NR$_8$R$_9$, —SO$_2$—$C_1$-$C_6$ alkyl, —SO$_2$—$C_3$-$C_8$ cycloalkyl —SO$_2$-aryl, and —SO$_2$-heterocyclyl; and R$_8$ are R$_9$ are each independently selected from the group consisting of hydrogen, $C_1$-$C_6$ alkyl, $C_3$-$C_8$ cycloalkyl, aryl, and heterocyclyl.

The present invention also relates to a method for preparing a compound of formula IA, or a salt or prodrug thereof, comprising:

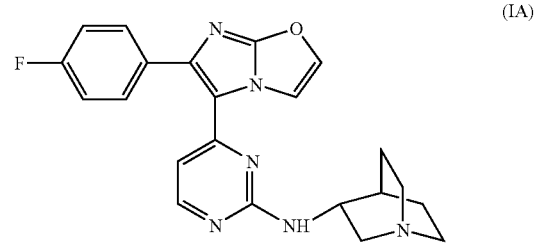

(IA)

(a) reacting a compound of formula IIIA

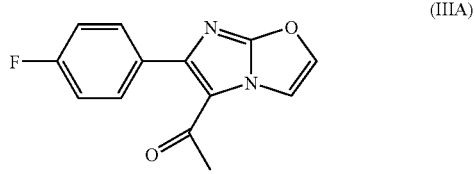

(IIIA)

with N,N-dimethylformamide dimethyl acetal to form a compound of formula IVA,

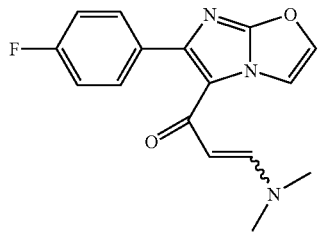

and (b) reacting a compound of formula IVA with a 3-guanidinoquinuclidine of formula VA

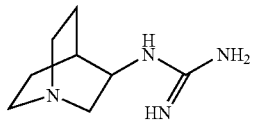

to form said compound of formula IA;
wherein said compound of formula IIIA is prepared by:
    i) reacting said 2-amino-1,3-oxazole:

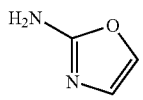

with 4-fluorophenacyl bromide to form the a keto-oxazole-imine having the formula:

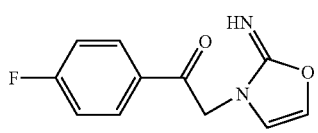

ii) forming the corresponding imidazo[2,1-b]oxazole of formula IIA:

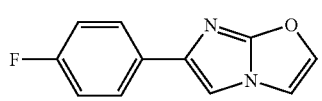

in the presence of one or more dehydrating reagents, and
    iii) reacting a compound of formula IIA with acetic anhydride to form said compound of formula IIIA.

The present invention also relates to a method for preparing a compound of formula I, or a salt or prodrug thereof, comprising:

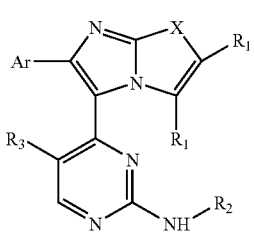

(a) reacting a compound of formula IV

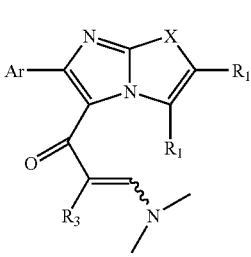

with a guanidino compound of formula V

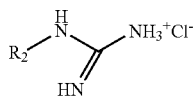

to form said compound of formula I, wherein:
    X is O or $S(O)_m$ and m is 0, 1, or 2;
    Ar is
    2,3-dihydro-benzo[1,4]dioxin-6-yl;
    benzo[1,3]dioxol-5-yl;
    an aryl group; or
    an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, $C_3$-$C_8$ fluoro-substituted cycloalkyl, —$NR_8R_9$, —(NH)—($C_1$-$C_4$ fluoro-substituted alkyl), or —N($C_1$-$C_4$ fluoro-substituted alkyl)$_2$); —$NR_8R_9$; —(NH)—($C_1$-$C_4$ fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; an ester-linked amino acid; and an amide-linked amino acid;

$R_1$ groups are independently selected from the group consisting of hydrogen, —CN, —COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —$CH_2$-(aryl), —$CH_2$-(halogen-substituted aryl), and —C(=O)—$NR_4R_5$;

$R_2$ is independently selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more $R_2$-substituents independently selected from the group consisting of: hydroxyl group, —COOH, oxo, fluorine, thiol, cyano, nitro, —$NR_6R_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—$NR_8R_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl;

wherein when, $R_2$ is aryl, said one or more $R_2$-substitutents further include chlorine, bromine and iodine; and wherein, when $R_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

$R_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$, and the amide nitrogen of —C(=O)—$NR_4R_5$ form a cyclic structure and $R_1$ is of the form:

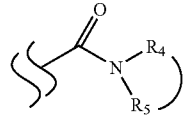

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl; and $R_8$ are $R_9$ are each independently selected from the group consisting of hydrogen, $C_1$-$C_6$ alkyl, $C_3$-$C_8$ cycloalkyl, aryl, and heterocyclyl.

In one embodiment of the synthesis of formula I, the method of synthesis of synthesis relates to the methods preparation of compounds of formula I(i),

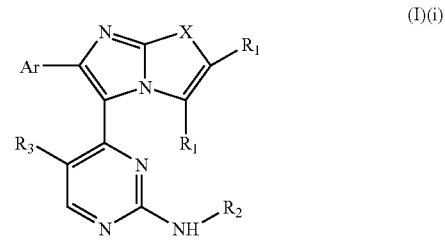

comprising:
(a) reacting a compound of formula III

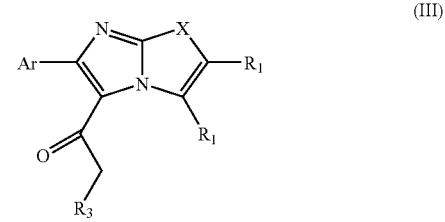

with N,N-dimethylformamide dimethyl acetal to form a compound of formula IV

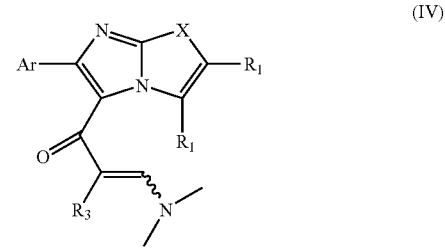

and (b) reacting said compound of formula IV with a guanidino compound of formula V

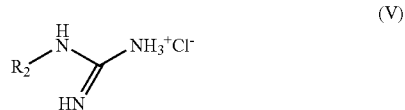

(V)

to form said compound of formula I(i), wherein:

X is O or S(O)$_m$ and m is 0, 1, or 2;

Ar is an aryl group, or an aryl group substituted with one or more substituents independently selected from the group consisting of halogen, —CN, —OCH$_3$, —COOH, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl;

R$_1$ groups are independently selected from the group consisting of hydrogen, —CN, —COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_2$ is independently selected from the group consisting of C$_1$-C$_{10}$ alkyl, C$_3$-C$_{10}$ cycloalkyl, heterocyclyl, and aryl; wherein said C$_1$-C$_{10}$ alkyl, C$_3$-C$_{10}$ cycloalkyl, heterocyclyl, and aryl groups may be substituted with one or more R$_2$-substituents independently selected from the group consisting of: hydroxyl group, —COOH, oxo, fluorine, thiol, cyano, nitro, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_6$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)—NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl;

wherein when, R$_2$ is aryl, said one or more R$_2$-substitutents further include chlorine, bromine and iodine; and wherein, when R$_2$ is a heterocycle having an endocyclic nitrogen atom or endocyclic nitrogen atoms, said endocyclic nitrogen atom or endocyclic nitrogen atoms may be substituted with one or more moieties independently selected from the group consisting of: hydrogen, C$_1$-C$_6$ alkyl, C$_3$-C$_8$ cycloalkyl, C$_2$-C$_6$ alkenyl, C$_2$-C$_6$ alkynyl, aryl, —C(=O)—NR$_8$R$_9$, C$_1$-C$_6$ alkylcarbonyl, —C(=O)-aryl, —C(=O)—O-aryl, C$_1$-C$_6$ alkoxycarbonyl, C$_1$-C$_6$ alkylsulfonyl, arylsulfonyl, and heterocyclyl;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$, and the amide nitrogen of —C(=O)—NR$_4$R$_5$ form a cyclic structure and R$_1$ is of the form:

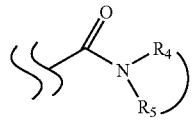

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl; and R$_8$ are R$_9$ are each independently selected from the group consisting of hydrogen, C$_1$-C$_6$ alkyl, C$_3$-C$_8$ cycloalkyl, aryl, and a heterocyclyl moiety.

In another embodiment, the method synthesis of compounds of formula I relates to a method for preparing a compound of formula I(i),

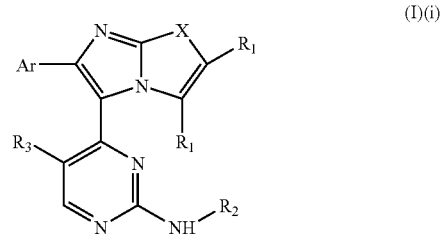

(I)(i)

or a salt thereof, comprising the step of: (a) reacting a compound of formula IV

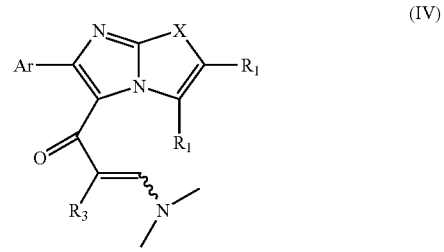

(IV)

with a guanidino compound of formula V

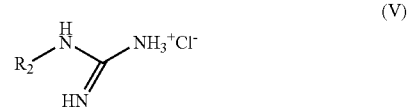

(V)

to form said compound of formula I(i), wherein:

X is O or S(O)$_m$ and m is 0, 1, or 2;

Ar is an aryl group, or an aryl group substituted with one or more substituents independently selected from the group consisting of halogen, —CN, —OCH$_3$, —COOH, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl;

R$_1$ groups are independently selected from the group consisting of hydrogen, —CN, —COOH, halogen, C$_1$-C$_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —$CH_2$-(aryl), —$CH_2$-(halogen-substituted aryl), and —C(=O)—$NR_4R_5$;

$R_2$ is independently selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more $R_2$-substituents independently selected from the group consisting of: hydroxyl group, —COOH, oxo, fluorine, thiol, cyano, nitro, —$NR_6R_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—$NR_8R_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl;

wherein when, $R_2$ is aryl, said one or more $R_2$-substitutents further include chlorine, bromine and iodine; and wherein, when $R_2$ is a heterocycle having an endocyclic nitrogen atom or endocyclic nitrogen atoms, said endocyclic nitrogen atom or endocyclic nitrogen atoms may be substituted with one or more moieties independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

$R_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$, and the amide nitrogen of —C(=O)—$NR_4R_5$ form a cyclic structure and $R_1$ is of the form:

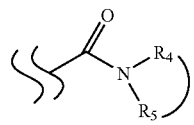

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl; and $R_8$ are $R_9$ are each independently selected from the group consisting of hydrogen, $C_1$-$C_6$ alkyl, $C_3$-$C_8$ cycloalkyl, aryl, and a heterocyclyl moiety.

In an embodiment, one or more of the methods of synthesis described herein may be employed to prepare compounds of formula I or I(i), wherein Ar is an optionally substituted phenyl ring; X is O or S; $R_1$ is independently selected from H, $C_1$-$C_6$ alkyl, or $C_1$-$C_6$ fluoro-substituted alkyl; $R_3$ is selected from H, $C_1$-$C_8$ alkyl, or $C_1$-$C_8$ fluoro-substituted alkyl; and $R_2$ is an optionally substituted heterocycle. In another preferred embodiment, compounds of formula I or I(i) may be prepared, wherein $R_2$ is an optionally substituted monocyclic or bicyclic heterocycle, or in another embodiment, $R_2$ is an optionally substituted azacycle.

In another embodiment, the synthetic methods described herein may be employed to prepare compound of formula I or I(i), wherein Ar is a phenyl ring optionally substituted with one or more substituents independently selected from: halogen, $C_1$-$C_6$ alkyl, or $C_1$-$C_6$ fluoro-substituted alkyl; X is O or S; $R_1$ is independently selected from H, $C_1$-$C_6$ alkyl, or $C_1$-$C_6$ fluoro-substituted alkyl; $R_3$ is selected from H, $C_1$-$C_6$ alkyl, or $C_1$-$C_6$ fluoro-substituted alkyl; and $R_2$ is an azacycle optionally bearing one or more substituents. In another preferred embodiment, compounds of formula I or I(i) are synthesized, wherein the optional substituents of the $R_2$ azacycle are independently selected from: $C_1$-$C_6$ alkyl, $C_1$-$C_6$ fluoro-substituted alkyl, $C_1$-$C_6$ alkoxy, $C_1$-$C_6$ fluoro-substituted alkoxy, —C(=O)—$NR_8R_9$, $C_1$-$C_6$ alkylcarbonyl, $C_1$-$C_6$ alkoxycarbonyl, $C_1$-$C_6$ alkylsulfonyl, or arylsulfonyl, wherein the substituents of endocyclic nitrogen atoms in the azacycle are independently selected from hydrogen, $C_1$-$C_6$ alkyl, $C_3$-$C_6$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, or arylsulfonyl.

In another embodiment, the synthetic methods described herein may be employed to prepare compound of formula I or I(i), wherein Ar is a phenyl ring optionally substituted with one or more substituents independently selected from: halogen, $C_1$-$C_6$ alkyl, or $C_1$-$C_6$ fluoro-substituted alkyl; X is O or S; $R_1$ substituents are independently selected from H, $C_1$-$C_4$ alkyl, or $C_1$-$C_4$ fluoro-substituted alkyl; $R_3$ is selected from H, $C_1$-$C_4$ alkyl, or $C_1$-$C_4$ fluoro-substituted alkyl; and $R_2$ is an azacycle optionally bearing one or more substituents. In another preferred embodiment, the optional substituents of the $R_2$ azacycle are independently selected from: $C_1$-$C_6$ alkyl, $C_1$-$C_6$ fluoro-substituted alkyl, $C_1$-$C_6$ alkylcarbonyl, $C_1$-$C_6$ alkoxycarbonyl, $C_1$-$C_6$ alkylsulfonyl, or arylsulfonyl; wherein the substituents of endocyclic nitrogen atoms in the azacycle are independently selected from hydrogen, $C_1$-$C_6$ alkyl, $C_3$-$C_6$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, or arylsulfonyl.

In another embodiment, the synthetic methods described herein may be employed to prepare a compound of formula I or I(i), wherein Ar is phenyl ring optionally substituted with one or more substituents independently selected from: halogen, $C_1$-$C_6$ alkyl, or $C_1$-$C_6$ fluoro-substituted alkyl; X is O; the $R_1$ substituents are independently selected from H, $C_1$-$C_4$ alkyl, or $C_1$-$C_4$ fluoro-substituted alkyl; $R_3$ is selected from H, $C_1$-$C_4$ alkyl, or $C_1$-$C_4$ fluoro-substituted alkyl; and $R_2$ is an optionally substituted azacycle selected from pyrrolidinyl, piperidinyl, piperazinyl, morpholino, azepinyl, quinuclidinyl (1-azabicyclo[2.2.2]octanyl) or tropanyl (8-methyl-8-azabicyclo[3.2.1]octanyl), where the optional substituents of the $R_2$ azacycle are independently selected from: $C_1$-$C_6$ alkyl, $C_1$-$C_6$ fluoro-substituted alkyl, $C_1$-$C_6$ alkylcarbonyl, $C_1$-$C_6$ alkoxycarbonyl, $C_1$-$C_6$ alkylsulfonyl or arylsulfonyl, and wherein the substituents of endocyclic nitrogen atoms in the azacycle are independently selected from hydrogen, $C_1$-$C_6$ alkyl, $C_3$-$C_6$ cycloalkyl, $C_2$-$C_6$ alkenyl, $C_2$-$C_6$ alkynyl, aryl, —C(=O)—NR$_8$R$_9$, C$_1$-C$_6$ alkylcarbonyl, —C(=O)-aryl, —C(=O)—O-aryl, C$_1$-C$_6$ alkoxycarbonyl, C$_1$-C$_6$ alkylsulfonyl or arylsulfonyl.

In another embodiment, the synthetic methods described herein may be employed to prepare a compound of formula I or I(i), wherein R$_2$ is a nitrogen-containing heterocyclic substituent. In preferred embodiments, R$_2$ is azetidinyl, pyrrolidinyl, or piperidinyl. In other preferred embodiments, R$_2$ is 2-azetidinyl or 3-azetidinyl. In other preferred embodiments, R$_2$ is 2-pyrrolidinyl or 3-pyrrolidinyl. In other preferred embodiments, R$_2$ is 2-piperidinyl, 3-piperidinyl, or 4-piperidinyl.

In a preferred embodiment, the synthetic methods described herein may be employed to prepare a compound of formula I or I(i), wherein R$_2$ is an azacycle. In more preferred embodiments, the synthetic methods may be used to prepare a compound of formula I or I(i), wherein R$_2$ is a substituted azetidinyl, pyrrolidinyl, or piperidinyl group. In other more preferred embodiments, the synthesis methods may be used to prepare a compound of formula I or I(i), wherein R$_2$ is a substituted 2-azetidinyl or substituted 3-azetidinyl. In other more preferred embodiments, a compound of formula I or I(i) is prepared, wherein R$_2$ is a substituted 2-pyrrolidinyl or a substituted 3-pyrrolidinyl. In other more preferred embodiments, R$_2$ is a substituted 2-piperidinyl, a substituted 3-piperidinyl, or a substituted 4-piperidinyl.

In an embodiment, the synthetic methods described herein may be employed to prepare a compound of formula I or I(i), wherein X is O, and R$_2$ is a nitrogen-containing heterocyclic substituent. In preferred embodiments, X is O, and R$_2$ is a substituted azetidinyl, a substituted pyrrolidinyl, or a substituted piperidinyl. In other preferred embodiments, X is O, and R$_2$ is a substituted 2-azetidinyl or a substituted 3-azetidinyl. In other preferred embodiments, X is O, and R$_2$ is a substituted 2-pyrrolidinyl or a substituted 3-pyrrolidinyl. In other preferred embodiments, X is O, and R$_2$ is a substituted 2-piperidinyl, a substituted 3-piperidinyl, or a substituted 4-piperidinyl.

In an embodiment, the synthetic methods described herein may be employed to prepare a compound of formula I or I(i), wherein X is S, and R$_2$ is a nitrogen-containing heterocyclic substituent. In further preferred embodiments, X is S, and R$_2$ is a substituted azetidinyl, a substituted pyrrolidinyl, or a substituted piperidinyl. In other preferred embodiments, X is S, and R$_2$ is a substituted 2-azetidinyl or a substituted 3-azetidinyl. In other preferred embodiments, X is S, and R$_2$ is a substituted 2-pyrrolidinyl or a substituted 3-pyrrolidinyl. In other preferred embodiments, X is S, and R$_2$ is a substituted 2-piperidinyl, a substituted 3-piperidinyl, or a substituted 4-piperidinyl.

The present invention further relates to a method for preparing a compound of formula Z

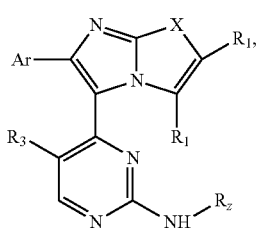

or a salt or prodrug thereof, comprising:

(a) reacting a compound of formula III

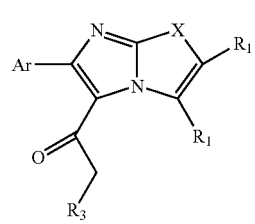

with N,N-dimethylformamide dimethyl acetal to form a compound of formula IV

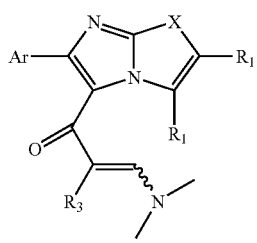

(b) reacting said compound of formula IV with a guanidino compound of formula V:

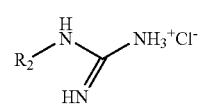

where the R$_2$ substituent of said compound of formula V is a heterocycle having an endocyclic nitrogen atom bearing a hydrogen atom, or a heterocycle having endocyclic nitrogen atoms with at least one nitrogen bearing a hydrogen atom, to form an intermediate of the form

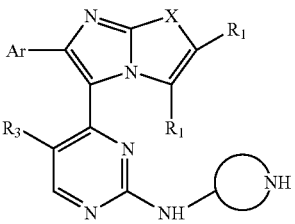

where

represents a heterocycle having an endocyclic nitrogen atom bearing a hydrogen atom, or a heterocycle having endocyclic nitrogen atoms with at least one nitrogen bearing a hydrogen atom; and (c) reacting said intermediate with a compound selected from the group consisting of a sulfonyl chloride of the form Cl—S (=O)$_2$alkyl, a sulfonyl chloride of the form Cl—S(=O)$_2$—R$_{12}$—(R$_{13}$)$_{0-4}$, an isocyanate of the form O=C=N—R$_{17}$—R$_{18}$, a chloroformate of the form Cl—(C=O)O—R$_{17}$—R$_{18}$, a chlorothiolformate of the form Cl—(C=O)S—R$_{17}$—R$_{18}$, an acid chloride of the form Cl—C(=O)—R$_{14}$—R$_{15}$, and a carboxylic acid of the form HO—C(=O)R$_{14}$—R$_{15}$;

to form a compound of formula Z wherein:

X is O or S(O)$_m$ and m is 0, 1, or 2;

Ar is 2,3-dihydro-benzo[1,4]dioxin-6-yl;

benzo[1,3]dioxol-5-yl;

an aryl group; or an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$ fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

R$_1$ groups are independently selected from the group consisting of hydrogen, —CN, COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_z$ is an independently selected nitrogen-containing heterocycle having an endocyclic nitrogen atom or endocyclic nitrogen atoms, wherein said independently selected nitrogen-containing heterocycle may be substituted with one or more R$_z$-substituents independently selected from the group consisting of hydroxyl group, —COOH, oxo, fluorine, thiol, —CN, —NO$_2$, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl, wherein said endocyclic nitrogen atom or endocyclic nitrogen atoms is substituted with one or more substituents independently selected from the group consisting C$_1$-C$_6$ alkylsulfonyl, R$_{10}$ and R$_{11}$;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$ and the amide nitrogen of —C(=O)—NR$_4$R$_5$ form a cyclic structure and R$_1$ is of the form:

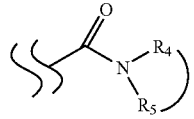

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl;

R$_8$ are R$_9$ are each independently selected from the group consisting of hydrogen, C$_1$-C$_6$ alkyl, C$_3$-C$_8$ cycloalkyl, aryl, and heterocyclyl;

R$_{10}$ is —S(=O)$_2$—R$_{12}$—(R$_{13}$)$_{0-4}$;

R$_{11}$ is independently selected from the group consisting of —C(=O)—R$_{14}$—R$_{15}$ and —C(=O)—R$_{16}$—R$_{17}$—R$_{18}$;

R$_{12}$ is phenyl or a 5-6 membered nitrogen-containing heteroaryl group;

R$_{13}$ is independently selected from the group consisting of halogen, cyano, —NC(=O)CH$_3$, —(C$_1$-C$_6$)alkyl, —(CH$_2$)$_{0-4}$—COOH, (C$_1$-C$_6$)alkoxy, (C$_1$-C$_6$)halogen-substituted alkyl, (C$_1$-C$_6$)halogen-substituted alkoxy, and phenoxy;

R$_{14}$ is independently selected from the group consisting of (C$_1$-C$_6$)alkyl and a bond;

R$_{15}$ is independently selected from the group consisting of —CH(NH$_2$)(C$_1$-C$_4$ alkyl-COOH); (C$_1$-C$_6$)alkyl optionally substituted with one or more substituents independently selected from the group consisting of C$_1$-C$_6$ alkoxy, —OH, (NH)C(=O)—CH$_3$, —NH$_2$, and —N(CH$_3$)$_2$; (C$_3$-C$_{10}$)cycloalkyl; (C$_1$-C$_6$)alkoxy; heterocyclyl; aryl optionally substituted with one or more substituents independently selected from the group consisting of halogen, C$_1$-C$_6$ alkoxy, —NH$_2$, —(NH)—(C$_1$-C$_4$)alkyl, and —N(C$_1$-C$_4$ alkyl)$_2$; —S-aryl optionally substituted with one or more independently selected (C$_1$-C$_6$)alkyl groups; and aryloxy optionally substituted with one or more substituents independently selected from the group consisting of halogen, —NH$_2$, —(NH)—C$_1$-C$_4$ alkyl; and —N(C$_1$-C$_4$ alkyl)$_2$;

$R_{16}$ is independently selected from the group consisting of O, —(NH)—, and S;

$R_{17}$ is independently selected from the group consisting of ($C_1$-$C_6$)alkyl and a bond; and $R_{18}$ is independently selected from the group consisting of ($C_1$-$C_6$)alkyl; ($C_3$-$C_{10}$)cycloalkyl; heterocyclyl; and aryl, optionally substituted with one or more substituents independently selected from the group consisting of halogen, ($C_1$-$C_6$) alkyl, ($C_1$-$C_3$)halogen-substituted alkyl, ($C_1$-$C_6$)alkoxy, —$NO_2$, —$NH_2$, —(NH)—($C_1$-$C_4$)alkyl, and —N($C_1$-$C_4$ alkyl)$_2$.

The present invention further relates to a method for preparing a compound of formula Z

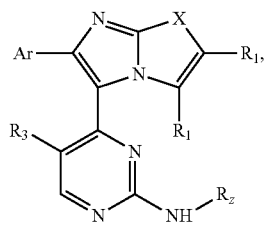

(Z)

or a salt or prodrug thereof, comprising:
(a) reacting a compound of formula IV

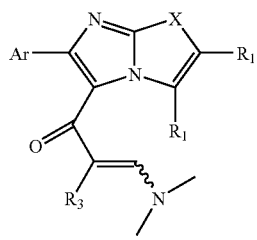

(IV)

with a guanidino compound of formula V:

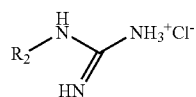

(V)

where the $R_2$ substituent of said compound of formula V is a heterocycle having an endocyclic nitrogen atom bearing a hydrogen atom, or a heterocycle having endocyclic nitrogen atoms with at least one nitrogen bearing a hydrogen atom, to form an intermediate of the form

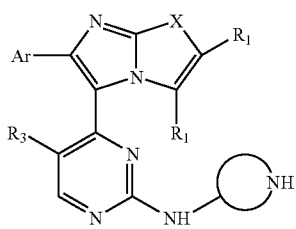

where

represents a heterocycle having an endocyclic nitrogen atom bearing a hydrogen atom, or a heterocycle having endocyclic nitrogen atoms with at least one nitrogen bearing a hydrogen atom; and (c) reacting said intermediate with a compound selected from the group consisting of a sulfonyl chloride of the form Cl—S(=O)$_2$alkyl, a sulfonyl chloride of the form Cl—S(=O)$_2$—$R_{12}$—($R_{13}$)$_{0-4}$, an isocyanate of the form O=C=N—$R_{17}$—$R_{18}$, a chloroformate of the form Cl—(C=O)—O—$R_{17}$—$R_{18}$, a chlorothiolformate of the form Cl—(C=O)—S—$R_{17}$—$R_{18}$, an acid chloride of the form Cl—C(=O)—$R_{14}$—$R_{15}$, and a carboxylic acid of the form HO—C(=O)—$R_{14}$—$R_{15}$;

to form a compound of formula Z wherein:
X is O or S(O)$_m$ and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —$NO_2$; —OH; —O—($C_1$-$C_6$ alkyl); a heterocycle optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; aryl optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; —COOH; —($CH_2$)$_{0-3}$—C(=O)O—($C_1$-$C_6$ alkyl); —OC(=O)—($C_1$-$C_6$ alkyl); $C_1$-$C_8$ alkyl; $C_1$-$C_8$ fluoro-substituted alkyl; $C_3$-$C_8$ cycloalkyl; $C_3$-$C_8$ fluoro-substituted cycloalkyl; —O-(aryl); —OC(=O)-(aryl optionally and independently substituted with halogen, —CN, —$NO_2$, —OH, —O—($C_1$-$C_6$ alkyl), phenyl, —COOH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), or —N($C_1$-$C_4$ fluoro-substituted alkyl)$_2$); —$NR_8R_9$; —(NH)—($C_1$-$C_4$ fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—$C_1$-$C_4$ fluoro-substituted alkyl), and —N($C_1$-$C_4$ fluoro-substituted alkyl)$_2$; an ester-linked amino acid; and an amide-linked amino acid;

$R_1$ groups are independently selected from the group consisting of hydrogen, —CN, COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_z$ is an independently selected nitrogen-containing heterocycle having an endocyclic nitrogen atom or endocyclic nitrogen atoms, wherein said independently selected nitrogen-containing heterocycle may be substituted with one or more R$_z$-substituents independently selected from the group consisting of hydroxyl group, —COOH, oxo, fluorine, thiol, —CN, —NO$_2$, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl, wherein said endocyclic nitrogen atom or endocyclic nitrogen atoms is substituted with one or more substituents independently selected from the group consisting C$_1$-C$_6$ alkylsulfonyl, R$_{10}$ and R$_{11}$;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$, and the amide nitrogen of —C(=O)—NR$_4$R$_5$ form a cyclic structure and R$_1$ is of the form:

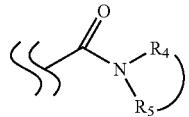

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl;

R$_8$ are R$_9$ are each independently selected from the group consisting of hydrogen, C$_1$-C$_6$ alkyl, C$_3$-C$_8$ cycloalkyl, aryl, and heterocyclyl;

R$_{10}$ is —S(=O)$_2$—R$_{12}$—(R$_{13}$)$_{0-4}$;

R$_{11}$ is independently selected from the group consisting of —C(=O)—R$_{14}$—R$_{15}$ and —C(=O)—R$_{16}$—R$_{17}$—R$_{18}$;

R$_{12}$ is phenyl or a 5-6 membered nitrogen-containing heteroaryl group;

R$_{13}$ is independently selected from the group consisting of halogen, cyano, —NC(=O)CH$_3$, —(C$_1$-C$_6$)alkyl, —(CH$_2$)$_{0-4}$—COOH, (C$_1$-C$_6$)alkoxy, (C$_1$-C$_6$)halogen-substituted alkyl, (C$_1$-C$_6$)halogen-substituted alkoxy, and phenoxy;

R$_{14}$ is independently selected from the group consisting of (C$_1$-C$_6$)alkyl and a bond;

R$_{15}$ is independently selected from the group consisting of —CH(NH$_2$)(C$_1$-C$_4$ alkyl-COOH); (C$_1$-C$_6$)alkyl optionally substituted with one or more substituents independently selected from the group consisting of C$_1$-C$_6$ alkoxy, —OH, —(NH)C(=O)—CH$_3$, —NH$_2$, and —N(CH$_3$)$_2$; (C$_3$-C$_{10}$)cycloalkyl; (C$_1$-C$_6$)alkoxy; heterocyclyl; aryl optionally substituted with one or more substituents independently selected from the group consisting of halogen, C$_1$-C$_6$ alkoxy, —NH$_2$, —(NH)—(C$_1$-C$_4$)alkyl, and —N(C$_1$-C$_4$ alkyl)$_2$; —S-aryl optionally substituted with one or more independently selected (C$_1$-C$_6$)alkyl groups; and aryloxy optionally substituted with one or more substituents independently selected from the group consisting of halogen, —NH$_2$, —(NH)—C$_1$-C$_4$ alkyl, and —N(C$_1$-C$_4$ alkyl)$_2$;

R$_{16}$ is independently selected from the group consisting of O, —(NH)—, and S;

R$_{17}$ is independently selected from the group consisting of (C$_1$-C$_6$)alkyl and a bond; and R$_{18}$ is independently selected from the group consisting of (C$_1$-C$_6$)alkyl; (C$_3$-C$_{10}$)cycloalkyl; heterocyclyl; and aryl, optionally substituted with one or more substituents independently selected from the group consisting of halogen, (C$_1$-C$_6$) alkyl, (C$_1$-C$_3$)halogen-substituted alkyl, (C$_1$-C$_6$)alkoxy, —NO$_2$, —NH$_2$, —(NH)—(C$_1$-C$_4$)alkyl, and —N(C$_1$-C$_4$ alkyl)$_2$.

In an embodiment, compounds of formula Z may be synthesized by the methods herein to produce various embodiments of formula Z, including preferred embodiments, as exemplified hereinbelow in section "III. Compounds of formula Z."

I. Definitions

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Alkyl groups may be denoted by a range, thus, for example, a C$_1$-C$_6$ alkyl group is an alkyl group having from one to six carbon atoms in the straight or branched alkyl backbone. Substituted and unsubstituted alkyl groups may independently be C$_1$-C$_5$alkyl, C$_1$-C$_6$alkyl, C$_1$-C$_{10}$ alkyl, C$_3$-C$_{10}$ alkyl, or C$_5$-C$_{10}$ alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., C$_3$-C$_6$ cycloalkyl) is a ring structure having between 3 and 6 carbon atoms in the ring. When no range is given, then cycloalkyl has between three to eight carbon atoms (C$_3$-C$_8$ cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, or eight, or from four to eight carbon atoms in the ring structure.

The term "alkenyl" refers to a hydrocarbon radical having at least one carbon-carbon double bond. A C$_2$-C$_6$ alkenyl group is an alkenyl group having from two to six carbon atoms in straight or branched alkenyl backbone. Exemplary alkenyl radicals include, without limitation, vinyl, propenyl, 2-butenyl, and the like.

The term "alkynyl," as used herein, refers to a hydrocarbon radical having at least one carbon-carbon triple bond. A C$_2$-C$_6$ alkynyl group is an alkynyl group having from two to six carbon atoms in straight or branched alkynyl backbone. Exemplary alkynyl moieties include propynyl, 3-hexynyl, and the like.

The term "aryl" refers to an aromatic carbocyclic or heteroaromatic moiety, having one, two, or three rings. An aryl group may be carbocyclic or may optionally contain from 1-4 heteroatoms (such as nitrogen, sulfur, or oxygen) in the aromatic ring. Exemplary aryl radicals include, without limitation, phenyl, naphthyl, pyridyl, pyrimidyl, triazyl, quinazolinyl, quinolinyl, isoquinolinyl, thiazolyl, benzothiophenyl, furanyl, imidazolyl, and the like.

The term "heterocyclyl" or "heterocycle" refers to a stable non-aromatic 3-7 membered monocyclic heterocyclic ring or 8-11 membered bicyclic heterocyclic ring which is either saturated or unsaturated, and may be fused, spiro or bridged to form additional rings. Each heterocycle consists of one or more carbon atoms and from one to four heteroatoms selected from the group consisting of nitrogen, oxygen and sulfur. A heterocyclyl radical may be attached at any endocyclic carbon which results in the creation of a stable structure. Preferred heterocycles include 3-7 membered monocyclic heterocycles (more preferably 5-7-membered monocyclic heterocycles) and 8-10 membered bicyclic heterocycles. Examples of such groups include azetidinyl, piperidinyl, pyranyl, piperazinyl, pyrrolidinyl, morpholinyl, thiamorpholinyl, thiamorpholinyl sulfone, oxopiperidinyl, oxopyrrolidinyl, oxoazepinyl, azepinyl, isoxazolyl, tetrahydropyranyl, tetrahydrofuranyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydro-furanyl, dihydropyranyl, tetrahydrofurofuranyl and tetrahydropyranofuranyl. A heterocycle may be optionally substituted at atoms other than endocyclic oxygen and endocyclic nitrogen atoms with one or more independently selected substituents. Although an endocyclic oxygen may not be substituted, endocyclic nitrogen atom may be substituted. An "azacycle," as used herein, refers to an endocyclic-nitrogen-containing heterocycle as described above. Preferred azacycles include (without limitation) substituted or unsubstituted pyrrolidinyl, piperidinyl, piperazinyl, morpholino, azepinyl, quinuclidinyl (1-azabicyclo[2.2.2]octanyl) and tropanyl (8-methyl-8-azabicyclo[3.2.1]octanyl).

The term "halogen" refers to an atom selected from fluorine, chlorine, bromine, and iodine. Preferred halogens are fluorine, chlorine, and bromine.

For the purpose of the present invention, halogen-substituted means substituted with one or more independently selected halogen atoms, and fluoro-substituted means substituted with one or more fluorine atoms.

The terms alkoxy, and fluoro-substituted alkoxy, refer to the functionalities (alkyl) and —O-(fluoro-substituted alkyl) respectively, where alkyl is as defined above. Where more than one alkyloxy or fluoro-substituted alkyloxy groups are present, each may be independently selected. In some embodiments, alkoxy, and fluorine-substituted alkoxy have from 1 to 6 carbon atoms; in other embodiments, they have from 2 to 6 carbon atoms and in other embodiments, they may have from 5 to 8 carbon atoms.

The terms cycloalkyloxy and fluoro-substituted cycloalkyloxy refer to the functionalities —O-(cycloalkyl) and —O-(fluoro-substituted cycloalkyl) respectively, where cycloalkyl is as defined above and may be substituted as described for alkyl and cycloalkyl groups. Where more than one cycloalkyloxy or fluoro-substituted cycloalkyloxy groups are present, each may be independently selected. In some embodiments, cycloalkyloxy and fluoro-substituted cycloalkyloxy groups may have between three and nine carbon atoms in the carbocyclic ring. In some preferred embodiments, cycloalkyloxy and fluoro-substituted cycloalkyloxy groups have from four to nine or from four to six carbon atoms in the ring structure. In other preferred embodiments, they may selected to have four, five, six, seven, eight, or nine carbon atoms in the ring structure.

The terms cycloalkyloxycarbonyl, heterocyclyloxycarbonyl refer to the functionalities —C(=O)—O-(cycloalkyl) and —C(=O)—O-(heterocyclyl) respectively, where cycloalkyl and heterocyclyl are as defined above. In preferred embodiments of cycloalkyloxycarbonyl, the cycloalkyl moiety may have between three and nine carbon atoms in the carbocyclic ring. In other preferred embodiments, cycloalkyl moiety of cycloalkyloxycarbonyl groups has three, four, five, six, seven, eight, or nine carbon atoms in the ring structure.

The terms alkoxycarbonyl, and fluoro-substituted alkoxycarbonyl refer to the functionalities —C(=O)—O-(alkyl) and —C(=O)—O-(fluoro-substituted alkyl) respectively. The groups $C_1$-$C_6$ alkoxycarbonyl, and $C_1$-$C_6$ fluoro-substituted alkoxycarbonyl have between 1 and 6 carbon atoms in the alkyl or fluoro-substituted alkyl moieties. In other embodiments, alkyloxy carbonyl and fluoro-substituted alkoxycarbonyl may have from 3 to 6 carbon atoms in their alkyl or fluoro-substituted alkyl moieties.

For the purpose of substituents on a compound of the present invention, an amino acid means an amino acid selected from alanine, valine, leucine, isoleucine, phenylalanine, tryptophan, methionine, glycine, serine, threonine, cysteine, tyrosine, asparagine, glutamine, aspartic acid, glutamic acid, lysine, arginine, proline, or histidine. Amino acids present as substituents may be linked through a carboxylic acid group of the amino acid, or through an amino group of the amino acid. Where the linkage is through the carboxyl group of the amino acid via an oxygen atom, it may be denoted an ester-linked amino acid. An ester-linked amino acid such as glycine would thus appear as a —O—C(=O)CH$_2$—NH$_2$ group. Where the linkage is through a carboxyl group of the amino acid via a nitrogen atom, it may be referred to as an amide-linked amino acid. An amide-linked amino acid such as glycine would thus appear as a —N—C(=O)CH$_2$—NH$_2$ group.

II. Synthesis of Imidazo Inhibitors

In general, the synthesis methods described herein may employ a variety of commercially available starting materials including precursors of formulas A-C as shown herein, compounds known in the literature, readily-prepared intermediates prepared by employing standard synthetic methods and procedures. Standard synthetic methods and procedures for the preparation of organic molecules and functional group transformations and manipulations can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. The following descriptions of synthetic methods are designed to illustrate, but not limit, general procedures for the preparation of compounds of the invention.

The synthesis of compounds of formula I and formula Z according to the present method proceeds via a convergent synthetic route, illustrated in FIG. 1, in which an independently prepared imidazooxazole or imidazothiazole compound of formula IV (see Scheme I) is prepared and reacted with an independently prepared guanidino compound of formula V (see Scheme II) to yield a product of formula I (see Scheme III). The preparation of compounds of formula IV is exemplified in Scheme I. The preparation of compounds of formula V is illustrated for example in Scheme II. The coupling of compounds IV and V is illustrated for example in FIG. 1 and Scheme III. Routes for the preparation of compounds of formula Z, where $R_z$ is a nitrogen-containing heterocycle bearing one or more alkylsulfonyl, $R_{10}$, or $R_{11}$ substituents on an endocyclic nitrogen atom are exemplified in section II(d)(2).

The preparation of compounds of formula IV is illustrated for example in Scheme I beginning with compounds of formula II, which are generally accessible through a variety of synthetic routes.

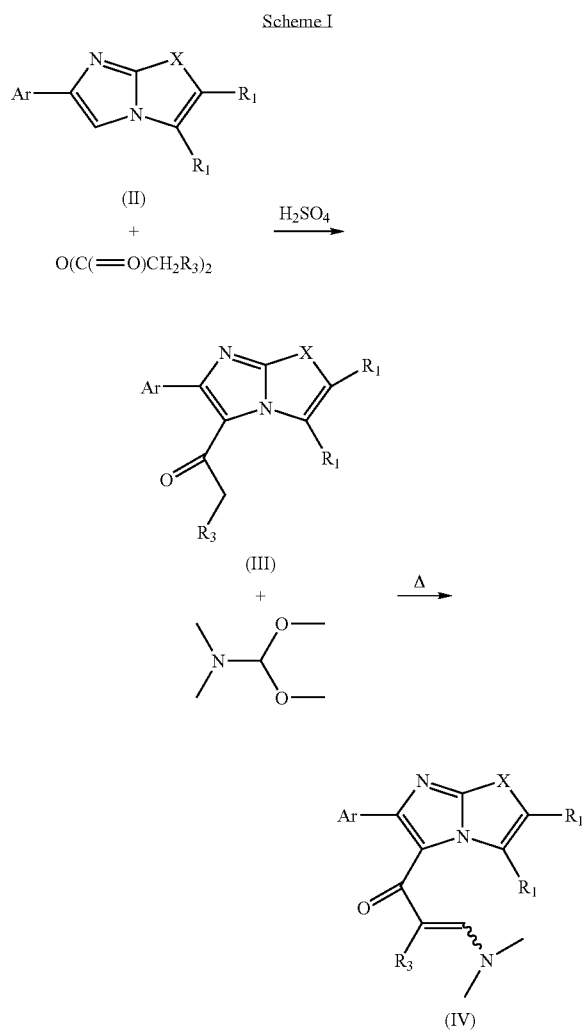

II(a) Preparation of Compounds Having Formula II

A number of routes are available for the preparation of compounds of formula II. One route of preparation for compounds of formula II is through the coupling of an appropriately substituted precursor molecule having the formula A:

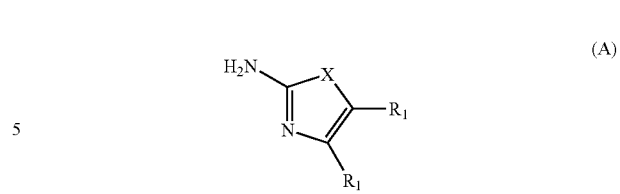

with a precursor aryl acyl-halide of formula B:

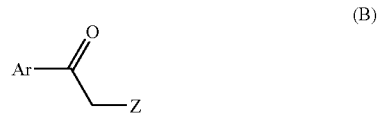

to form an intermediate of the structure:

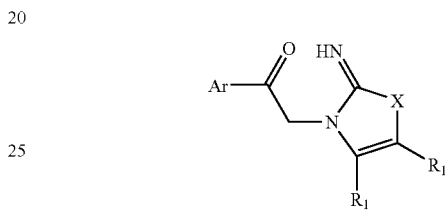

where X is O or $S(O)_m$ and m is 0, 1, or 2, Ar is an aromatic group as described above, and $R_1$ is independently selected as described above and Z is a halogen atom. The coupling of precursors A and B may be conducted under a variety of conditions, in a suitable solvent. Exemplary reaction conditions including reacting the compounds in absolute ethanol or a mixture of tetrahydrofuran and acetonitrile from 7:13 volume:volume (v/v) to 1:4 v/v at room temperature for the coupling of oxazoles and under reflux for the coupling of thiazoles. Other suitable solvents include polar protic solvents such as low boiling alcohols or mixtures thereof, tetrahydrofuran (THF), dimethylformamide (DMF), N,N-dimethyl-acetamide (DMA), dimethylsulfoxide (DMSO), dioxane.

Subsequent dehydration of the intermediate derived by the coupling of precursors A and B to form a compound of formula II may be accomplished with a variety of reagents under suitable conditions. One preferred method is the reaction with $TiCl_4$: toluene 15:85 v/v under reflux. Other suitable Lewis acids include titanium tetraisopropoxide, $ZnCl_2$, $MgBr_2$, and the like.

In a preferred embodiment, the precursor of formula A is a 2-amino-oxazole (X is oxygen). A variety of 2-amino-oxazoles are commercially available for use in the described synthetic process. The preparation of 2-amino-oxazoles may also be achieved by known methods such as Harrison's procedure as described in Cockerill et al., in Synthesis 9: 591-93 (1976) or the procedure described in Lindsey et al. *Construction of Previously Inaccessible 2-amino-4-benzyl substituted oxazoles*, Tetrahedron Letters 45: 867-68 (2004). In addition, 2-amino-oxazole, although commercially available (Sigma-Aldrich), may be prepared by reacting cyanamide in tetrahydrofuran (THF) with an aqueous solution of 2-hydroxyacetaldehyde as described in copending application PCT/US04/15368 and Example 35.

In another preferred embodiment, precursors of formula B are phenyl acylhalides that may bear one or more substitutents on the phenyl ring (Ar is phenyl or substituted phenyl).

A number of phenyl acylhalides are commercially available including 2'-bromoacetophenone, 2-bromo-4'-fluoroacetophenone, and 2-bromo-2',4'-difluoroacetophenone (Sigma-Aldrich). Alternatively, the desired phenacyl halide may be prepared by other suitable means including Friedel-Crafts acylation of appropriately substituted benzene molecules with an acylhalide (e.g., the reaction of fluoro-benzene with bromoacetyl bromide in the presence of AlCl₃ to produce 2-bromo-4'-fluoroacetophenone).

In one preferred embodiment, the precursor of formula A is a 2-amino-oxazole and the precursor of formula B is a phenyl acylhalide bearing one or more substitutents on the phenyl ring (e.g., 2'-bromoacetophenone or 2-bromo-4'-fluoroacetophenone). Coupling of these precursors and dehydration leads to one group of preferred compound of formula II for the preparation of compounds of formula I. In a related preferred embodiment, the precursor of formula A is 2-amino-oxazole and the precursor of formula B is a phenyl acylhalide (Ar is a phenyl) bearing one or more independently selected halogen or alkyl substitutents on phenyl ring. By way of example, the reaction of 2-amino-oxazole with 2-bromo-4'-fluoroacetophenone (also referred to as 4-fluorophenacyl bromide or 2-bromo-1-(4-fluorophenyl)-ethanone) may be conducted in a mixture of tetrahydrofuran and acetonitrile as described above to form the intermediate:

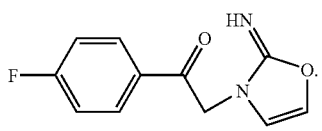

After dehydration of the above intermediate in 15:85 TiCl₄: toluene a compound of formula II where X=oxygen:

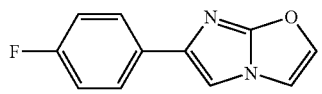

is formed.

In other preferred embodiments, where X is S(O)$_m$ and m is 0, 1, or 2, precursor thiazoles, including 1-3-thiazole-2-amine, 4-methyl-1-3-thiazole-2-amine, 5-methyl-1-3-thiazole-2-amine, and 4,5-dimethyl-1-3-thiazole-2-amine may be purchased commercially. Thiazoles may be converted to compounds of formula II where X is sulfur by reacting them with a precursor of formula B as described above for 2-amino-oxazoles. When such reactions are carried out in an anhydrous alcohol, subsequent reaction with a dehydrating agent may not be required to form a compound of formula II. Thus by way of example the reaction of 2-aminothiazole with 2-bromo-4'-fluoroacetophenone in absolute ethanol:

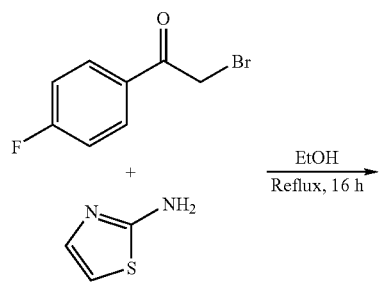

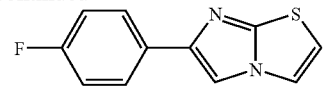

yields a desired product of formula II: 6-(4-fluorophenyl)-imidazo[2,1-b]thiazole, as described in Example 36.

II(b) Conversion of Compounds Having Formula II into Compounds of Formula IV

The preparation of compounds of formula IV from compounds of formula II may be achieved by the reaction of compounds of formula II with an acid anhydride of formula O(C(=O)CH₂R₃)₂ in concentrated H₂SO₄ to form a compound of formula III. The compound of formula III is subsequently reacted with N,N-dimethylformamide dimethyl acetal to yield the desired compound of formula IV.

Typical conditions for the preparation of compounds of formula III are the reaction of compounds of formula II with an anhydride having the formula O(C(=O)CH₂R₃)₂ in the presence of concentrated sulfuric acid (conc. H₂SO₄) at 135° C. for 1.5 hours. Preferred acid anhydrides of the formula O(C(=O)CH₂R₃)₂ include but are not limited to those where R₃ is independently selected from the group consisting of hydrogen, C₁-C₈ alkyl, C₁-C₈ fluoro-substituted alkyl, C₃-C₈ cycloalkyl, C₃-C₈ fluoro-substituted cycloalkyl, aryl, halogen-substituted aryl, heteroaryl, and halogen-substituted heteroaryl. In a preferred embodiment, R₃ is independently selected from the group consisting of hydrogen, C₁-C₈ alkyl, and in another preferred embodiment, R₃ is H and the acid anhydride is acetic anhydride.

Yields of compounds having formula III, under typical reaction conditions based upon the moles compound II employed, range from about 60% up to about 90%, and more frequently range from about 70% to about 80%. The temperature and time of reaction may be altered as necessary to accommodate specific compounds of formula II, The full range of temperatures that are generally useful are from about 25° C. to reflux (approximately 138° C.) or more preferably from about 35° C. to reflux, or more preferably from about 65° C. to reflux or even more preferably from about 100° C. to reflux. At lower temperatures, the reaction time periods may be from about 24 to about 48 hours. With increasing temperatures, the reaction times may be shortened; such shortened reaction times preferably include from about 12 to about 24 hours, or more preferably from about 3 to about 6 hours, or more preferably from about 1 to about 2 hours.

Conversion of compounds of formula III into compounds of formula IV is generally conducted by refluxing the compounds in N,N-dimethylformamide dimethyl acetal. Reaction yields of 85% based upon the quantity of compound III employed are typically achieved following 24 hours of reflux. Where temperature sensitive substituents are present, or where either longer reaction periods or higher reaction temperatures are unnecessary to achieve a suitable yield of product, the reaction time, temperature, or both may be reduced. Thus, while reaction times may readily be varied from about 2 to about 48 hours, reaction for shorter times, including from about 3 to about 6 hours, or about 6 to about 12 hours, or from about 12 to about 24 hours, may be employed. Similarly, while the reaction may be conducted under reflux conditions, lower temperatures may be employed, including for example: reaction at a temperature from about 80° C. to about 100° C., or from about 60° C. to about 80° C. or from about 40° C. to about 60° C. Any combination of the above temperature and time ranges set forth above is within the scope of the disclosure and may be selected by a skilled artisan in accordance with the specific compounds being prepared. Alternatively, one may employ microwave chemistry to reduce the required reaction time.

In one embodiment of the invention, compounds of formula III that are employed in the preparation of compounds of formula I are prepared by reacting a compound of formula II where X is oxygen with an acid anhydride of the form O(C(=O)CH$_2$R$_3$)$_2$, where R$_3$ is as described above.

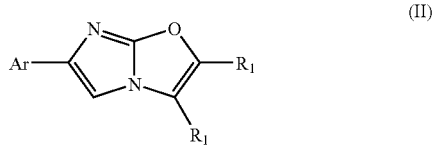

where X = O

In a another embodiment of the invention, compounds of formula III that are employed in the preparation of compounds of formula I are prepared by reacting a compound of formula II where X is oxygen with an acid anhydride of the formula O(C(=O)CH$_2$R$_3$)$_2$ where R$_3$ is H (the acid anhydride is acetic anhydride).

II(c) Preparation of Compounds Having Formula V

The preparation of compounds of formula V, which are reacted with compounds of formula IV to form a product of formula I or formula I(i) (see Scheme III, infra), may be achieved by a variety of suitable routes.

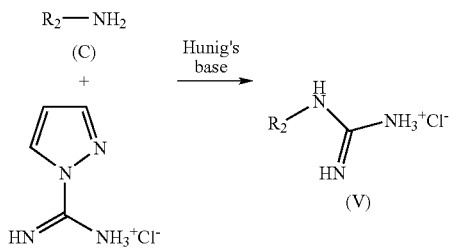

Scheme II illustrates one preferred route for the preparation of compounds of formula V is the reaction of a primary amine precursor of the formula C in Hunig's base (N,N-diisopropylethylamine) with 1H-pyrazole-1-carboximidamide hydrochloride or other commercially available reagents of this type (e.g., 3,5-dimethyl-1H-pyrazole-1-carboximidamide).

Suitable primary amines of the formula R$_2$—NH$_2$ include, but are not limited to primary amines where R$_2$ is independently selected from the group consisting of C$_1$-C$_{10}$ alkyl, C$_3$-C$_{10}$ to cycloalkyl, heterocyclyl, and aryl; wherein said C$_1$-C$_{10}$ to alkyl, C$_3$-C$_{10}$ cycloalkyl, heterocyclyl, and aryl groups may be substituted with one or more R$_2$-substituents independently selected from the group consisting of: hydroxyl group, —COOH, oxo, fluorine, thiol, cyano, nitro, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)—NR$_8$R$_9$, C$_1$-C$_6$ alkylcarbonyl, C$_3$-C$_8$ cycloalkylcarbonyl, heterocyclylcarbonyl, —C(=O)-aryl, —C(=O)-O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl; wherein when, R$_2$ is aryl, said one or more R$_2$-substitutents further include chlorine, bromine and iodine; and wherein, when R$_2$ is a heterocycle having an endocyclic nitrogen atom or endocyclic nitrogen atoms, said endocyclic nitrogen atom or endocyclic nitrogen atoms may be substituted with one or more moieties independently selected from the group consisting of: hydrogen, C$_1$-C$_6$ alkyl, C$_3$-C$_8$ cycloalkyl, C$_2$-C$_6$ alkenyl, C$_2$-C$_6$ alkynyl, aryl, —C(=O)—NR$_8$R$_9$, C$_1$-C$_6$ alkylcarbonyl, —C(=O)-aryl, —C(=O)—O-aryl, C$_1$-C$_6$ alkoxycarbonyl, C$_1$-C$_6$ alkylsulfonyl, arylsulfonyl, and heterocyclyl; and wherein R$_6$, R$_7$, R$_8$, and R$_9$ are as defined above.

The reaction of primary amines with Hunig's base is typically carried out in dimethyl formamide (DMF) at a temperature of about 60° C., about 70° C., about 80° C., or a temperature from about 60° C. to about 80° C., although a skilled artisan will recognize that other suitable solvents and reaction temperature may be employed. In addition to DMF, other suitable polar aprotic solvents including, but not limited to, DMSO, DMF, and THF may be employed. Reaction temperatures may be adjusted from about 25° C. to the reflux temperature of the selected solvent reagent combination. Preferred reaction temperatures are in the range of about 50° C. to about 100° C., or more preferably from about 50° C. to about 90° C. or more preferably from about 60° C. to about 80° C. Yields of guanidino compounds of formula V are typically in the range of 80% to 90% based upon the amount of primary amine employed in the reaction. The required length of reaction time to achieve a desired yield of the guanidino product varies with reaction temperature. Yields of 80% to 90% are generally achieved when the reactions are conducted for about 6 hours between about 60° C. and about 80° C. in DMF. Reaction times may readily be varied from about 1 to about 10 hours, or more preferably from about 4 to about 8 hours. Temperature, reaction times, or a combination thereof may be varied over suitable ranges to maximize product formation.

II(d) The Coupling of Compounds Having Formula IV and Formula V and Modification of Heterocycles Bearing Endocyclic Nitrogens Present in R$_2$ II(d)(1) Coupling of Compounds Having Formula IV and Formula V The coupling of independently prepared compounds of formula IV and formula V to complete the convergent synthesis of compounds of formula I may be conducted in a refluxing mixture of a short chain (C$_1$-C$_6$) aliphatic alcohol and its alkaline metal salt as depicted in Scheme III.

While a variety of alcohols may be employed in the coupling of compounds of formula IV and formula V, the alcohols are more preferably (C$_1$-C$_6$)alkyl alcohols. Exemplary alcohols that may be employed include, but are not limited to, methanol, ethanol, propanol, isopropanol, n-butanol, sec-butanol, tert-butanol, and mixtures thereof. Exemplary alkaline metals that may be employed to form salts of the alcohols include, but are not limited to sodium, lithium, and potassium salts. In one preferred embodiment, the alcohol is methanol or ethanol and the alkaline metal is sodium or potassium. In another preferred embodiment, the alcohol is ethanol, the alkaline metal is sodium, and the reaction is thus carried out in a refluxing mixture of ethanol and sodium ethoxide.

The temperature of the reaction may be varied by heating the reaction to less than the temperature required to achieve reflux, by employing alcohols having different boiling points, or by employing mixtures of the alcohols selected to reflux at a desired temperature. Coupling reactions between compounds of formula IV and formula V typically proceed with a yield of about 40% to about 60% based upon the quantity of compound IV employed in the reaction. These yields are achievable with chemical purity of at least about 40%, or more preferably at least about 60% or more preferably at least about 80%. In a more preferred embodiment, the yields are at least about 90% to at least about 98% of the desired product of formula I.

II(d)(2) Preparation of Compounds of Formula Z

Compounds of formula I wherein $R_2$ is a heterocycle having one or more endocyclic nitrogen atoms may be modified to prepare compounds of formula Z by reacting with an alkylsulfonyl chloride, an arylsulfonyl chloride, an isocyanate, a chloroformate, a chlorothiolformate, an acid chloride, or a carboxylic acid. Some compounds of formula Z may overlap with compounds for formula I. In addition, various compounds of formula Z may be synthesized both by the methods of synthesis for compounds of formula I and also by the methods of synthesis for compounds of formula Z.

In one embodiment, compounds of formula Z may be synthesized by beginning with compounds of formula I or I(i) where $R_2$ is a heterocycle having an endocyclic nitrogen atom or endocyclic nitrogen atoms bearing a hydrogen atom. In another embodiment, compounds of formula Z with an endocyclic nitrogen atom or endocyclic nitrogen atoms bearing hydrogen may be prepared by employing a protective group on the endocyclic nitrogen atom or atoms as desired, and deprotecting to provide a compound with an endocyclic nitrogen or nitrogens bearing hydrogen.

Compounds of formula Z in which $R_z$ is a nitrogen-containing heterocycle bearing one or more $R_{10}$ substituents on endocyclic nitrogen atom may be prepared by reacting a desired sulfonyl chloride of formula Cl—S(=O)$_2$—R$_{12}$—(R$_{13}$)$_{0-4}$ with a compound of formula I having an endocyclic nitrogen atom or endocyclic nitrogen atoms bearing a hydrogen atom. This is exemplified schematically below

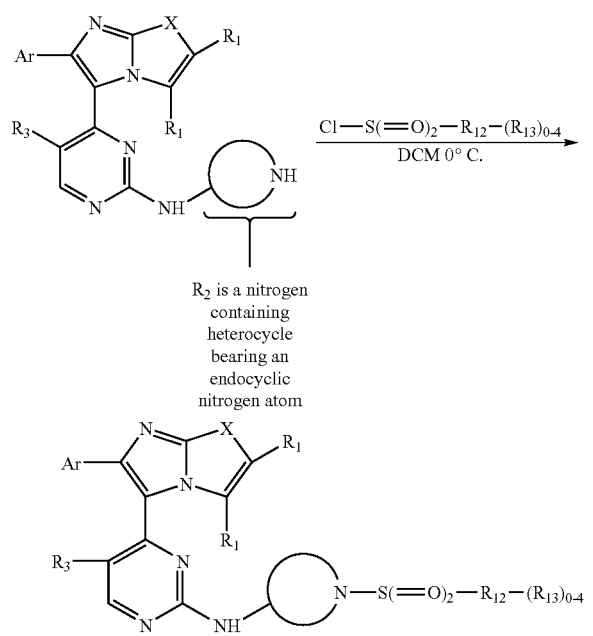

The reaction of sulfonyl chlorides with a compound of formula I having an endocyclic nitrogen atom or endocyclic nitrogen atoms bearing a hydrogen atom is further exemplified by the preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol in example 39. In example 39, the unsubstituted compound of formula I is prepared with a protective group on an endocyclic nitrogen (see 39a-39e). The endocyclic nitrogen is deprotected in 39f and is reacted with the desired sulfonyl chloride in 39g. Subsequent deprotection of the aryl hydroxyl group in 39h yields the product.

In a preferred embodiment, the reaction of a sulfonyl chloride with an endocyclic nitrogen is conducted in a polar aprotic solvent at 0° C. In a more preferred embodiment, the solvent is a chlorinated hydrocarbon, and more preferably dichloromethane (DCM, methylene chloride).

In one embodiment, compounds of formula Z in which $R_z$ is a nitrogen-containing heterocycle bearing one or more $R_{11}$ substituents on endocyclic nitrogen atoms may be prepared by reacting an isocyanate of formula O=C=N—R$_{17}$—R$_{18}$ with a compound of formula I having an endocyclic nitrogen atom or endocyclic nitrogen atoms bearing a hydrogen atom. This is exemplified schematically below

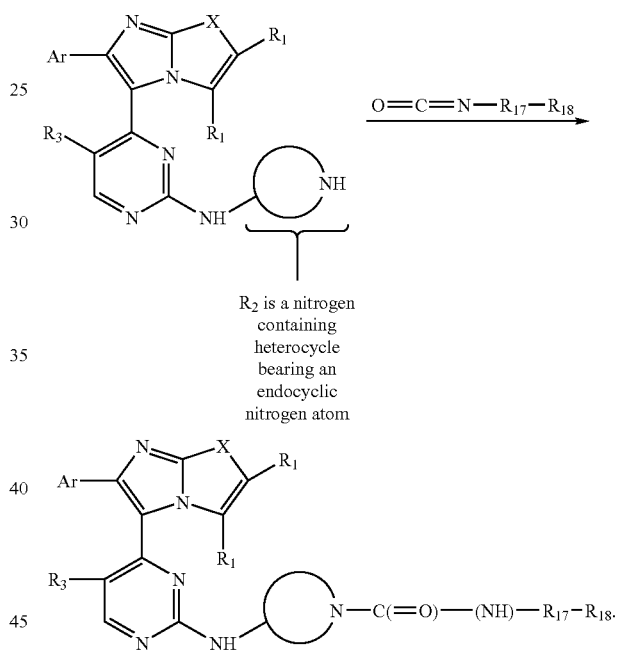

The preparation of N-butyl-4-({4-[6-4-fluorophenyl)imidazo[2,1-b][1,3]oxazol-5-yl]pyrimidin-2-yl}amino)piperidine-1-carboxamide by reacting 4-[6-(4-fluorophenyl)imidazo[2,1-b][1,3]oxazol-5-yl]-N-piperidin-4-ylpyrimidine-2-amine (bis HCl salt) with butyl isocyanate is also illustrated in example 40.

In a preferred embodiment, the reaction of an isocyanate is conducted in a polar aprotic solvent in the presence of a base. In a more preferred embodiment, the reaction is conducted in an alkyl ether, such as tetrahydrofuran, in the presence of a Hunig's base.

In another embodiment, compounds of formula Z in which $R_z$ is a nitrogen-containing heterocycle bearing one or more $R_{11}$ substituents on endocyclic nitrogen atoms may be prepared by reacting a chloroformate of formula Cl—(C=O)O—R$_{17}$—R$_{18}$ with a compound of formula I having an endocyclic nitrogen atom or endocyclic nitrogen atoms bearing a hydrogen atom. This is exemplified schematically below

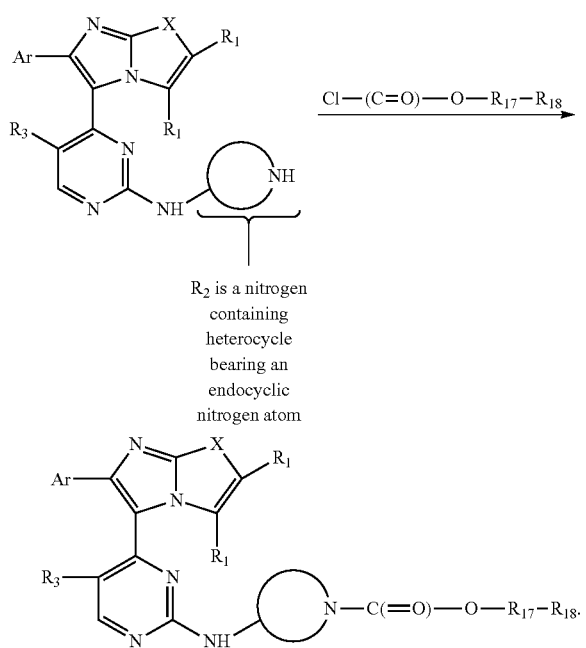

R₂ is a nitrogen containing heterocycle bearing an endocyclic nitrogen atom

The reaction may be conducted in variety of polar aprotic solvents including tetrahydrofuran (THF) or dichloromethane (DCM).

In an additional embodiment, compounds of formula Z in which $R_z$ is a nitrogen-containing heterocycle bearing one or more $R_{11}$ substituents on endocyclic nitrogen atoms may be prepared by reacting a chlorothiolformate of the formula Cl—(C=O)—S—R₁₇—R₁₈ with a compound of formula I having an endocyclic nitrogen atom or endocyclic nitrogen atoms bearing a hydrogen atom. This is exemplified schematically below

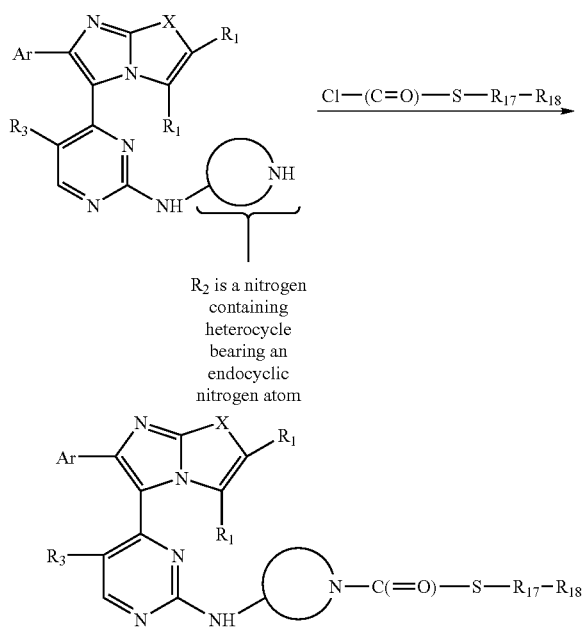

R₂ is a nitrogen containing heterocycle bearing an endocyclic nitrogen atom

The reaction may be conducted in variety of polar aprotic solvents including tetrahydrofuran (THF) or dichloromethane (DCM).

In one embodiment, compounds of formula Z in which $R_z$ is a nitrogen-containing heterocycle bearing one or more $R_{11}$ substituents on endocyclic nitrogen atom may be prepared by reacting a desired acid chloride of the form Cl—C(=O)—R₁₄—R₁₅ or a carboxylic acid of the form HO—C(=O)—R₁₄—R₁₅ with a compound of formula I having an endocyclic nitrogen atom or endocyclic nitrogen atoms bearing a hydrogen atom. This is exemplified schematically below

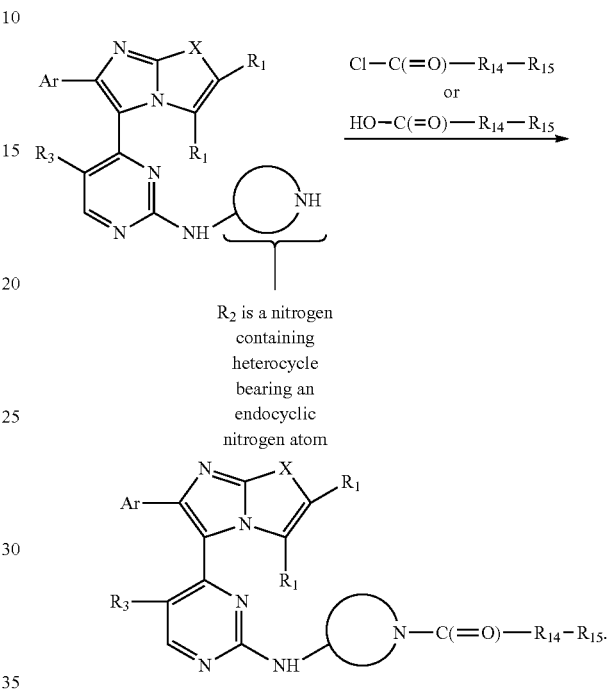

R₂ is a nitrogen containing heterocycle bearing an endocyclic nitrogen atom

The preparation of N-{2-[4-({4-[6-(4-fluorophenyl)imidazo[2,1-b][1,3]oxazol-5-yl]pyrimidin-2-yl}amino)piperidin-1-yl]-2-oxoethyl}acetamide using acetamido glycine is also illustrated in example 41.

In a preferred embodiment, the reaction of acid chlorides of the form Cl—C(=O)—R₁₄—R₁₅ is conducted in a polar aprotic solvent at 0° C. In a more preferred embodiment, the solvent is a chlorinated hydrocarbon, and more preferably dichloromethane (DCM, methylene chloride).

In preferred embodiments, the reaction of a compound of formula I with a carboxylic acid of the form HO—C(=O)—R₁₄—R₁₅, is conducted in a polar aprotic solvent such as DMF or DMSO. In a more preferred embodiment, the reaction is conducted in the presence of a dehydrating agent such as a carbodimide (e.g., dicyclohexyl-carbodiimide) or HBTU. In more preferred embodiments, the reactions are conducted in the presence of both a dehydrating agent and a catalyst or hypernucleophilic catalyst such as dimethylaminopyridine (DMAP).

II(e) The Preparation of Compounds Having a Hydroxyl Group Present on Ar

Compounds of the invention where Ar is an aryl group substituted with a hydroxyl may be prepared by employing protective groups to protect the Ar hydroxyl during synthesis. A variety of protective groups may be employed, including those discussed in and Greene, T. W.; Wuts, P. G. M. Protective Groups in Organic Synthesis. In preferred embodiments of this invention, the methods of synthesis protect the hydroxyl as a methoxy ether. In more preferred methods of synthesizing compounds of formula Z where $R_z$ is a substituted nitrogen-containing heterocycle, Ar hydroxyls may be protected as methoxy ethers. In even more preferred methods of synthesizing compounds of formula Z, where $R_z$ is a nitrogen-containing heterocycle bearing either an $R_{10}$ or an $R_{11}$ substituent on an endocyclic nitrogen atom of the heterocycle, Ar hydroxyls are preferably protected as methoxy ethers. In each of the above-mentioned instances, where Ar hydroxyls are protected as methoxy ethers, the preferred method of deprotection is by $BBr_3$ in $MeCl_2$, preferably at about −78° C.

Although the methods described herein offer ease of preparation and high yields of essentially pure intermediates and final products of formula I and formula Z, where necessary, further recrystallization or chromatography can be employed to remove undesired contaminants or to assess the purity of intermediates and products. Where chromatography is employed, the properties of the intermediates or products, and the nature of contaminants, if any, will affect the choice of chromatographic media. Suitable chromatography media including, but not limited to, silica gel, chiral chromatography media, reverse phase chromatography media, anion exchange media, and cation exchange media may be employed. Chromatography may be carried out in a variety of formats including HPLC, such as that described in FIGS. 2 and 3, and low pressure column chromatography (e.g., flash chromatography) on either the preparative or analytical scale. Chromatography on chiral media, such as that described in FIG. 3, is particularly useful where it is desired to separate the product imidazooxazole and imidazothiazole compounds from stereoisomers such as in the analysis of the stereochemical purity of products.

The convergent synthetic route described offers the advantage of robust chemistry that can accommodate a variety of substituents and produce a high yield of the desired products without contaminants that render the product either difficult to purify or unsuitable for therapeutic uses. The method is adaptable to a variety of synthetic procedures, including the application of microwave chemistry as a means of adjusting reaction time, of one or more of the reaction steps recited above. The instant method offers yields of products of formula I or formula Z of at least about 35%, or more preferably of least about 40%, or more preferably of at least about 50%, or more preferably from at least about 60% based upon the quantity of compound IV committed to the reaction. These yields are achievable with chemical purity of at least about 75%, or more preferably at least about 90%, and more preferably at least about 98%. For example, in the preparation of (R)—N-{4-[6-(4-fluorophenyl)imidazo[2,1-b][1,3]oxazol-5-yl]pyrimidin-2-yl}quinuclidine-3-amine, in example 34, a yield of 46% is achieved based upon the amount of 3-(dimethylamino)-1-[6-(4-fluorophenyl)imidazo[2,1-b][1,3]oxazol-5-yl]prop-2-en-1-one committed to the reaction. As indicated in FIG. 2, the chemical purity of the final product is greater than 98%.

In addition to its ability to produce high yields of product while accommodating a variety of substituents, the methods described herein offer a variety of additional advantages. These advantages include mild coupling conditions, particularly between the compounds of formula IV and V, which permits the introduction of both liable functionalities and chiral centers with retention of stereochemistry. The method is particularly amenable to introduction of stereochemical centers in the pendant group $R_2$, which may be accomplished through the guanidino derivative of the chiral amine precursor. Complete, or virtually complete, retention of stereochemistry at chiral centers introduced in the $R_2$ pendant group may be achieved. When introducing chiral substituents into the compounds of formula I and formula Z, and particularly within substituents $R_2$ and $R_z$, respectively, it is possible to achieve a percent enantiomeric excess (ee) of at least about 75%, or at least about 95% or at least about 98%, or at least about 99%, or at least about 99.5% or about 99.99%; where the percent ee is defined for a pair of enantiomers "M" and "N" as the absolute value of: ((% enantiomer M)−(% enantiomer N)).

The synthetic method is also amenable to the incorporation of detectable labels. Such labels include radioactive and other isotopic labels (e.g., $C^{13}$, $C^{14}$, $O^{16}$, $O^{17}$, $O^{18}$, $N^{15}$, $Br^{77}$, $I^{125}$ etc.). In addition, the compounds themselves may serve as fluorescent labels where the molecule, pendant functionalities, or portions of either have fluorescent properties (e.g., Ar is a fluorescent naphthyl group). The methods of preparation described herein also offer the advantage of producing a single crystal form with no alternative salt forms present that can complicate both isolation and dissolution of the product.

III. Compounds of Formula Z

The present invention also includes and provides compounds of formula Z:

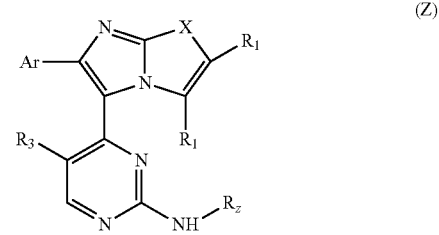

(Z)

wherein:
X is O or $S(O)_m$ and m is 0, 1, or 2;
Ar is
2,3-dihydro-benzo[1,4]dioxin-6-yl;
benzo[1,3]dioxol-5-yl;
an aryl group; or
an aryl group substituted with one or more substituents independently selected from the group consisting of halogen; —CN; —NO$_2$; —OH; —O—($C_1$-$C_6$ alkyl); a heterocycle optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; aryl optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; —COOH; —(CH$_2$)$_{0-3}$—C(=O)O—($C_1$-$C_6$ alkyl); —OC(=O)—$C_1$-$C_6$ alkyl); $C_1$-$C_8$ alkyl; $C_1$-$C_8$ fluoro-substituted alkyl; $C_3$-$C_8$ cycloalkyl; $C_3$-$C_8$ fluoro-substituted cycloalkyl; —O-(aryl); —OC(=O)-(aryl optionally and independently substituted with halogen, —CN, —NO$_2$, —OH, —O—($C_1$-$C_6$ alkyl), phenyl, —COOH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), or —N($C_1$-$C_4$ fluoro-substituted alkyl)$_2$); —NR$_8$R$_9$;

—(NH)—($C_1$-$C_4$ fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —NR$_8$R$_9$, —(NH)—($C_1$-$C_4$ fluoro-substituted alkyl), and —N($C_1$-$C_4$ fluoro-substituted alkyl)$_2$; an ester-linked amino acid; and an amide-linked amino acid;

$R_1$ groups are independently selected from the group consisting of hydrogen, —CN, COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —CH$_2$-(aryl), —CH$_2$-(halogen-substituted aryl), and —C(=O)—NR$_4$R$_5$;

$R_z$ is an independently selected nitrogen-containing heterocycle having an endocyclic nitrogen atom or endocyclic nitrogen atoms, wherein said independently selected nitrogen-containing heterocycle may be substituted with one or more R$_z$-substituents independently selected from the group consisting of hydroxyl group, —COOH, oxo, fluorine, thiol, —CN, —NO$_2$, —NR$_6$R$_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O) NR$_8$R$_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl, wherein said endocyclic nitrogen atom or endocyclic nitrogen atoms is substituted with one or more substituents independently selected from the group consisting $C_1$-$C_6$ alkylsulfonyl, $R_{10}$ and $R_{11}$;

$R_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$ and the amide nitrogen of —C(=O)—NR$_4$R$_5$ form a cyclic structure and $R_1$ is of the form:

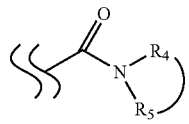

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—NR$_8$R$_9$, —SO$_2$—$C_1$-$C_6$ alkyl, —SO$_2$—$C_3$-$C_8$ cycloalkyl —SO$_2$-aryl, and —SO$_2$-heterocyclyl;

$R_8$ are $R_9$ are each independently selected from the group consisting of hydrogen, $C_1$-$C_6$ alkyl, $C_3$-$C_8$ cycloalkyl, aryl, and heterocyclyl;

$R_{10}$ is —S(=O)$_2$—$R_{12}$—($R_{13}$)$_{0-4}$;

$R_{11}$ is independently selected from the group consisting of —C(=O)—$R_{14}$—$R_{15}$ and —C(=O)—$R_{16}$—$R_{17}$—$R_{18}$;

$R_{12}$ is phenyl or a 5-6 membered nitrogen-containing heteroaryl group;

$R_{13}$ is independently selected from the group consisting of halogen, cyano, —NC(=O)CH$_3$, —($C_1$-$C_6$)alkyl, —(CH$_2$)$_{0-4}$—COOH, ($C_1$-$C_6$)alkoxy, ($C_1$-$C_6$)halogen-substituted alkyl, ($C_1$-$C_6$)halogen-substituted alkoxy, and phenoxy;

$R_{14}$ is independently selected from the group consisting of ($C_1$-$C_6$)alkyl and a bond;

$R_{15}$ is independently selected from the group consisting of —CH(NH$_2$)($C_1$-$C_4$ alkyl-COOH); ($C_1$-$C_6$)alkyl optionally substituted with one or more substituents independently selected from the group consisting of $C_1$-$C_6$ alkoxy, —OH, (NH)C(=O)—CH$_3$, —NH$_2$, and —N(CH$_3$)$_2$; ($C_3$-$C_{10}$)cycloalkyl; ($C_1$-$C_6$)alkoxy; heterocyclyl; aryl optionally substituted with one or more substituents independently selected from the group consisting of halogen, $C_1$-$C_6$ alkoxy, —NH$_2$, —(NH)—($C_1$-$C_4$)alkyl, and —N($C_1$-$C_4$ alkyl)$_2$; —S-aryl optionally substituted with one or more independently selected ($C_1$-$C_6$)alkyl groups; and aryloxy optionally substituted with one or more substituents independently selected from the group consisting of halogen, —NH$_2$, —(NH)—$C_1$-$C_4$ alkyl, and —N($C_1$-$C_4$ alkyl)$_2$;

$R_{16}$ is independently selected from the group consisting of O, —(NH)—, and S;

$R_{17}$ is independently selected from the group consisting of ($C_1$-$C_6$)alkyl and a bond; and $R_{18}$ is independently selected from the group consisting of ($C_1$-$C_6$)alkyl; ($C_3$-$C_{10}$)cycloalkyl; heterocyclyl; and aryl, optionally substituted with one or more substituents independently selected from the group consisting of halogen, ($C_1$-$C_6$) alkyl, ($C_1$-$C_3$)halogen-substituted alkyl, ($C_1$-$C_6$)alkoxy, —NO$_2$, —NH$_2$, —(NH)—($C_1$-$C_4$)alkyl, and —N($C_1$-$C_4$ alkyl)$_2$;

or a pharmaceutically acceptable salt, prodrug, metabolite, analog or derivative thereof.

In some embodiments, compounds of formula Z are provided, wherein Ar is phenyl ring or a phenyl ring substituted with one or two fluorine atoms; X is O or S; $R_1$ is independently selected from H, $C_1$-$C_6$ alkyl, or $C_1$-$C_6$ fluoro-substituted alkyl; and $R_3$ is selected from H, $C_1$-$C_8$ alkyl, or $C_1$-$C_8$ fluoro-substituted alkyl.

In one embodiment, compounds of formula Z are provided, wherein Ar is a phenyl ring optionally substituted with one or more substituents independently selected from: halogen, $C_1$-$C_6$ alkyl, or $C_1$-$C_6$ fluoro-substituted alkyl; X is O or S; $R_1$ is independently selected from H, $C_1$-$C_6$ alkyl, or $C_1$-$C_6$ fluoro-substituted alkyl; $R_3$ is selected from H, $C_1$-$C_6$ alkyl, or $C_1$-$C_6$ fluoro-substituted alkyl; and $R_z$ is a 5 or 6 membered azacycle optionally bearing one or more $R_{10}$ or $R_{11}$ substituents.

In another embodiment, compounds of formula Z are provided, wherein Ar is a phenyl ring optionally substituted with one or more substituents independently selected from: halogen, $C_1$-$C_6$ alkyl, or $C_1$-$C_6$ fluoro-substituted alkyl; X is O or S; $R_1$ is independently selected from H, $C_1$-$C_4$ alkyl, or $C_1$-$C_4$ fluoro-substituted alkyl; $R_3$ is selected from H, $C_1$-$C_4$ alkyl, or $C_1$-$C_4$ fluoro-substituted alkyl; and $R_z$ is a 5 or 6 membered azacycle substituted with one or more $R_{10}$ substituents. In another embodiment, compounds of formula Z are provided, wherein Ar is a phenyl ring optionally substituted with one or more substituents independently selected from: halogen, $C_1$-$C_6$ alkyl, or $C_1$-$C_6$ fluoro-substituted alkyl; X is O or S; $R_1$ is independently selected from H, $C_1$-$C_4$ alkyl, or $C_1$-$C_4$ fluoro-substituted alkyl; $R_3$ is selected from H, $C_1$-$C_4$ alkyl, or $C_1$-$C_4$ fluoro-substituted alkyl; and $R_z$ is a 5 or 6 membered azacycle substituted with one or more $R_{11}$ substituents.

In another embodiment, compounds of formula Z are provided, wherein $R_z$ is a nitrogen-containing heterocyclic substituent selected from the group consisting of azetidinyl, pyrrolidinyl, and piperidinyl. In other preferred embodiments of formula Z, $R_z$ is 2-azetidinyl or 3-azetidinyl. In other preferred embodiments of formula Z, $R_z$ is 2-pyrrolidinyl or 3-pyrrolidinyl. In other preferred embodiments, compounds of formula Z are provided, wherein $R_z$ is 2-piperidinyl, 3-piperidinyl, or 4-piperidinyl.

In a preferred embodiment of formula Z, $R_z$ is a nitrogen-containing heterocyclic substituent as in formula I. In more preferred embodiments, $R_z$ is a substituted azetidinyl, pyrrolidinyl, or piperidinyl. In other more preferred embodiments, $R_z$ is a substituted 2-azetidinyl or substituted 3-azetidinyl. In other more preferred embodiments, $R_z$ is a substituted 2-pyrrolidinyl or a substituted 3-pyrrolidinyl. In other more preferred embodiments, $R_z$ is a substituted 2-piperidinyl, a substituted 3-piperidinyl, or a substituted 4-piperidinyl.

In some preferred embodiments, for compounds of formula Z, $R_z$ is a 2-azetidinyl or a 3-azetidinyl, each bearing an $R_{10}$ group on its endocyclic nitrogen atom. In other preferred embodiments, $R_z$ is a 2-pyrrolidinyl or a 3-pyrrolidinyl, each bearing an $R_{10}$ group on its endocyclic nitrogen atom. In other preferred embodiments, $R_z$ is a substituted 2-piperidinyl, a substituted 3-piperidinyl or a substituted 4-piperidinyl, each of which bears an $R_{10}$ group on its endocyclic nitrogen atom.

In some preferred embodiments, for compounds of formula Z, X is O and $R_z$ is a 2-azetidinyl or a 3-azetidinyl, each bearing an $R_{10}$ group on its endocyclic nitrogen atom. In other preferred embodiments, X is O and $R_z$ is a 2-pyrrolidinyl or a 3-pyrrolidinyl, each bearing an $R_{10}$ group on its endocyclic nitrogen atom. In other preferred embodiments, X is O and $R_z$ is a substituted 2-piperidinyl, a substituted 3-piperidinyl or a substituted 4-piperidinyl, each of which bears an $R_{10}$ group on its endocyclic nitrogen atom.

In some preferred embodiments, for compounds of formula Z, X is S and $R_z$ is a 2-azetidinyl or a 3-azetidinyl, each bearing an $R_{10}$ group on its endocyclic nitrogen atom. In other preferred embodiments, X is S and $R_z$ is a 2-pyrrolidinyl or a 3-pyrrolidinyl, each bearing an $R_{10}$ group on its endocyclic nitrogen atom. In other preferred embodiments, X is S and $R_z$ is a substituted 2-piperidinyl, a substituted 3-piperidinyl or a substituted 4-piperidinyl, each of which bears an $R_{10}$ group on its endocyclic nitrogen atom.

In some preferred embodiments of formula Z, $R_z$ is a 2-azetidinyl or a 3-azetidinyl, each bearing an $R_{11}$ group on its endocyclic nitrogen atom. In other preferred embodiments, $R_z$ is a 2-pyrrolidinyl or a 3-pyrrolidinyl, each bearing an $R_{11}$ group on its endocyclic nitrogen atoms. In other preferred embodiments, $R_z$ is a substituted 2-piperidinyl, a substituted 3-piperidinyl or a substituted 4-piperidinyl, each bearing an $R_{11}$ group on its endocyclic nitrogen atom.

In some preferred embodiments of formula Z, X is O and $R_z$ is a 2-azetidinyl or a 3-azetidinyl, each bearing an $R_{11}$ group on its endocyclic nitrogen atom. In other preferred embodiments, X is O and $R_z$ is a 2-pyrrolidinyl or a 3-pyrrolidinyl, each bearing an $R_{11}$ group on its endocyclic nitrogen atoms. In other preferred embodiments, X is O and $R_z$ is a substituted 2-piperidinyl, a substituted 3-piperidinyl or a substituted 4-piperidinyl, each bearing an $R_{11}$ group on its endocyclic nitrogen atom.

In some preferred embodiments of formula Z, X is S and $R_z$ is a 2-azetidinyl or a 3-azetidinyl, each bearing an $R_{11}$ group on its endocyclic nitrogen atom. In other preferred embodiments, X is S and $R_z$ is a 2-pyrrolidinyl or a 3-pyrrolidinyl, each bearing an $R_{11}$ group on its endocyclic nitrogen atom. In other preferred embodiments, X is S and $R_z$ is a substituted 2-piperidinyl, a substituted 3-piperidinyl or a substituted 4-piperidinyl, each bearing an $R_{11}$ group on its endocyclic nitrogen atom.

In one preferred embodiment, $R_z$ is a nitrogen-containing heterocyclic substituent, wherein an endocyclic nitrogen atom on the nitrogen-containing heterocyclic substituent is substituted by an $R_{10}$ sulfonyl group. In a more preferred embodiment of formula Z, the nitrogen-containing heterocyclic group is selected from a pyrrolidinyl group or a piperidinyl group, and the substituent on the endocyclic nitrogen atom is an $R_{10}$ sulfonyl group In one preferred embodiment, X is O and $R_z$ is a nitrogen-containing heterocyclic substituent, wherein an endocyclic nitrogen atom on the nitrogen-containing heterocyclic substituent is substituted by an $R_{10}$ sulfonyl group. In a more preferred embodiment of formula Z, the nitrogen-containing heterocyclic group is selected from a pyrrolidinyl group or a piperidinyl group, and the substituent on the endocyclic nitrogen atom is an $R_{10}$ sulfonyl group.

In one preferred embodiment, X is S and $R_z$ is a nitrogen-containing heterocyclic substituent, wherein an endocyclic nitrogen atom on the nitrogen-containing heterocyclic substituent is substituted by an $R_{10}$ sulfonyl group. In a more preferred embodiment of formula Z, the nitrogen-containing heterocyclic group is selected from a pyrrolidinyl group or a piperidinyl group, and the substituent on the endocyclic nitrogen atom is an $R_{10}$ sulfonyl group.

In a preferred embodiment of formula Z, $R_z$ is a nitrogen-containing heterocyclic substituent having an endocyclic nitrogen atom on the nitrogen-containing heterocyclic substituent that is substituted by an $R_{11}$ group of the form C(=O)—$R_{14}$—$R_{15}$. In a more preferred embodiment of formula Z, the nitrogen-containing heterocyclic group is selected from a pyrrolidinyl group and a piperidinyl group, and the substituent on the endocyclic nitrogen atom is a C(=O)—$R_{14}$—$R_{15}$ group.

In a preferred embodiment of formula Z, X is O and $R_z$ is a nitrogen-containing heterocyclic substituent having an endocyclic nitrogen atom on the nitrogen-containing heterocycle that is substituted by an $R_{11}$ group of the form C(=O)—$R_{14}$—$R_{15}$. In a more preferred embodiment of formula Z, the nitrogen-containing heterocyclic group is selected from a pyrrolidinyl group and a piperidinyl group, and the substituent on the endocyclic nitrogen atom is a C(=O)—$R_{14}$—$R_{15}$ group.

In a preferred embodiment of formula Z, X is S and $R_z$ is a nitrogen-containing heterocyclic substituent having an endocyclic nitrogen atom on the nitrogen-containing heterocycle that is substituted by an $R_{11}$ group of the form —C(=O)—$R_{14}$—$R_{15}$. In a more preferred embodiment of formula Z, the nitrogen-containing heterocyclic group is selected from a pyrrolidinyl group and a piperidinyl group, and the substituent on the endocyclic nitrogen atom is a —C(=O)—$R_{14}$—$R_{15}$ group.

In another preferred embodiment of formula Z, $R_z$ is a nitrogen-containing heterocyclic substituent having an endocyclic nitrogen atom on the nitrogen-containing heterocycle that is substituted by an $R_{11}$ group of the form C(=O)—

$R_{16}$—$R_{17}$—$R_{18}$. In a more preferred embodiment of formula Z, the nitrogen-containing heterocycle is selected from a pyrrolidinyl group or a piperidinyl group, and the substituent on the endocyclic nitrogen atom is a —C(=O)—$R_{16}$—$R_{17}$—$R_{18}$ group.

In another preferred embodiment of formula Z, X is O and $R_z$ is a nitrogen-containing heterocyclic substituent having an endocyclic nitrogen atom on the nitrogen-containing heterocycle that is substituted by an $R_{11}$ group of the form —C(=O)—$R_{16}$—$R_{17}$—$R_{18}$. In a more preferred embodiment of formula Z, the nitrogen-containing heterocycle is selected from a pyrrolidinyl group or a piperidinyl group, and the substituent on the endocyclic nitrogen atom is a —C(=O)—$R_{16}$—$R_{17}$—$R_{18}$ group.

In another preferred embodiment of formula Z, X is S and $R_z$ is a nitrogen-containing heterocyclic substituent having an endocyclic nitrogen atom on the nitrogen-containing heterocycle that is substituted by an $R_{11}$ group of the form —C(=O)—$R_{16}$—$R_{17}$—$R_{18}$. In a more preferred embodiment of formula Z, the nitrogen-containing heterocycle is selected from a pyrrolidinyl group or a piperidinyl group, and the substituent on the endocyclic nitrogen atom is a —C(=O)—$R_{16}$—$R_{17}$—$R_{18}$ group.

IV. Pharmaceutical Compositions

A compound of the present invention, such as for example a compound of formula I or formula Z, or a pharmaceutically acceptable salt, prodrug, metabolite, analog or derivative thereof, can be incorporated into pharmaceutical compositions suitable for administration. Such compositions typically comprise the compound (i.e., including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration.

Suitable carriers are described in the most recent edition of Remington's Pharmaceutical Sciences, a standard reference text in the field. Preferred examples of such carriers or diluents include, but are not limited to, water, saline, Ringer's solution, dextrose solution, and 5% human serum albumin. Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. A carrier or diluent may include any time-delay material known in the art, such as glyceryl monostearate or glyceryl distearate, alone or with a wax, ethylcellulose, hydroxypropylmethylcellulose, methylmethacrylate or the like.

Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions of the present invention.

Pharmaceutical compositions, such as for example compositions that comprise a compound of formula I or formula Z, may exist in the dosage form as a solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. Water-solubilizing agents such as for example, hydroxypropyl beta cyclodextrin, Poloxamer, Povidone K17, Povidone K12, Tween 80, ethanol, Cremophor/ethanol, polyethylene glycol 400, propylene glycol and Trappsol are contemplated without limitation. Furthermore, oil-based solubilizing agents such as lipiodol and peanut oil, may also be used.

In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like. Liposome formulations, are also contemplated by the present invention, and have been described. See, e.g., U.S. Pat. No. 5,424,073.

For the purposes of the present invention, compounds of the present invention described herein include their pharmacologically acceptable salts, preferably sodium; analogs containing halogen substitutions, preferably chlorine or fluorine; analogs containing ammonium or substituted ammonium salts, preferably secondary or tertiary ammonium salts; analogs containing alkyl, alkenyl, aryl or their alkyl, alkenyl, aryl, halo, alkoxy, alkenyloxy substituted derivatives, preferably methyl, methoxy, ethoxy, or phenylacetate; and natural analogs such as naphthyl acetate. Compounds or derivatives or analogs of the present invention described herein may be conjugated to a water-soluble polymer or may be derivatized with water-soluble chelating agents or radionuclides. Examples of water soluble polymers are, but not limited to: polyglutamic acid polymer, copolymers with polycaprolactone, polyglycolic acid, polylactic acid, polyacrylic acid, poly (2-hydroxyethyl 1-glutamine), carboxymethyl dextran, hyaluronic acid, human serum albumin, polyalginic acid or a combination thereof. Examples of water-soluble chelating agents are, but not limited to: DIPA (diethylenetriaminepentaacetic acid), EDTA, DTTP, DOTA or their water-soluble salts, etc. Examples of radionuclides include, but not limited to: $^{111}$In, $^{90}$Y, $^{166}$Ho, $^{68}$Ga, $^{99m}$Tc, and the like.

In one aspect, a compound of the present invention, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of the present invention, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

A pharmaceutical composition of the invention is formulated to be compatible with its intended route of administration. Exemplary non-limiting routes of administration include parenteral, e.g., intravenous, intradermal, subcutaneous, oral (e.g., inhalation), transdermal (topical), and transmucosal administration. Compounds of the present invention can be administered by any means known in the art. Such means include oral, rectal, nasal, topical (including buccal and sublingual) or parenteral (including subcutaneous, intramuscular, intravenous and intradermal) administration. For ease of administration and comfort to the patient, oral administration is generally preferred. However, oral administration may require the administration of a higher dose than intravenous administration, making intravenous administration preferable. The skilled artisan can determine which form of administration is best in a particular case, balancing dose needed versus the number of times per month administration is necessary.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for treatment. In an exemplary embodiment, a compound of the invention to be used for treatment of cancer may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 70 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

A compound of the present invention may be administered in combination with another pharmaceutical composition, in any manner found appropriate by a clinician in generally accepted efficacious dose ranges, such as those described in the *Physician's Desk Reference*, $59^{th}$ Edition, Thomson PDR (2005) ("PDR"). In an embodiment, administration of a dosage can be repeated, e.g., once weekly, preferably for about 1 to 6 weeks. It is preferred that dosages be administered over a time period of about 30 minutes to about 6 hours, and typically over a period of about 3 hours.

The pharmaceutical compositions described herein may be administered singly and sequentially, or in a cocktail or combination containing both agents or one of the agents with other therapeutic agents, including but not limited to, immunosuppressive agents, potentiators and side-effect relieving agents.

EXAMPLES

Example 1

Preparation of
1-[6-(aryl)imidazo[2,1-b][1,3]oxazol-5-yl]ethanone

1(a) Preparation of 1-[6-(2-chlorophenyl)imidazo[2,1-b][1,3]oxazol-5-yl]ethanone

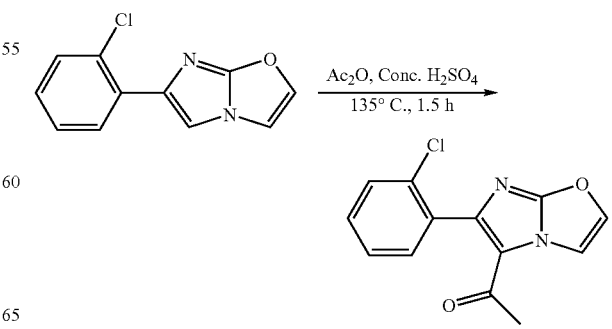

To a mixture of 6-(2-chlorophenyl)-imidazo[2,1-b]oxazole (1.0 g, 4.57 mmol) and acetic anhydride (23 ml) is added 3 drops of concentrated sulfuric acid. The reaction mixture is heated at 135° C. for 1 hour. The reaction mixture is then poured onto 50 ml of ice, and diluted with 100 ml of water and the resulting mixture is extracted three times with 75 ml each of ethyl acetate. The combined extracts are dried with magnesium sulfate, filtered and concentrated in vacuo, to give a brown oil. The product is purified by flash chromatography on silica gel (hexane/ethyl acetate 3:1), yielding 994 mg of an off-white solid (83%). M.p.=121-122° C.; 300 MHz $^1$H NMR (CDCl$_3$) δ: 8.02 (d, J=1.6 Hz, 1H), 7.56-7.38 (m, 5H), 2.05 (s, 3H). LCMS: 261 [M+H]; calc. for $C_{13}H_9ClN_2O_2$: C, 59.84; H, 3.48; N, 10.74; found. C, 60.18; H, 3.16; N, 10.61.

1(b) Preparation of 1-[6-(2,4-difluorophenyl)imidazo[2,1-b][1,3]oxazol-5-yl]ethanone

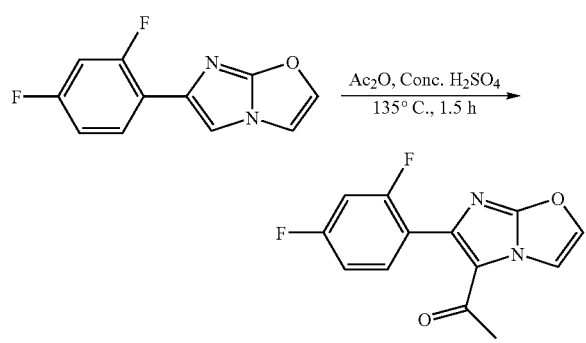

Prepared as described in example 1(a)

M.p.=105-107° C.; 300 MHz $^1$H NMR (CDCl$_3$) δ: 8.03 (s, 1H), 7.6-7.5 (m, 1H), 7.05-6.95 (m, 1H), 2.17 (s, 3H); LCMS: 263 [M+H]; calc. for $C_{13}H_8F_2N_2O_2$: C, 59.55; H, 3.08; N, 10.68; found. C, 59.41; H, 3.04; N, 10.71.

1(c) Preparation of 1-[6-(2-chloro-4-fluorophenyl)imidazo[2,1-b][1,3]oxazol-5-yl]ethanone

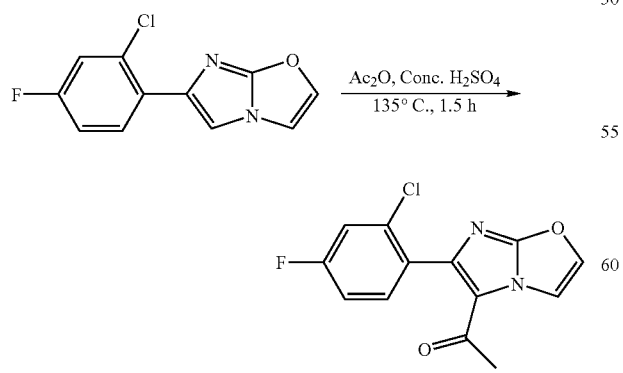

Prepared as described in example 1(a)

M.p.=105-107° C.; 300 MHz $^1$H NMR (CDCl$_3$) δ: 8.03 (s, 1H), 7.6-7.5 (m, 1H), 7.05-6.95 (m, 1H), 2.17 (s, 3H); LCMS: 263 [M+H]; calc. for $C_{13}H_8F_2N_2O_2$: C, 59.55; H, 3.08; N, 10.68; found. C, 59.41; H, 3.04; N, 10.71.

1(d) Preparation of 1-[6-(2-methylphenyl)imidazo[2,1-b][1,3]oxazol-5-yl]ethanone

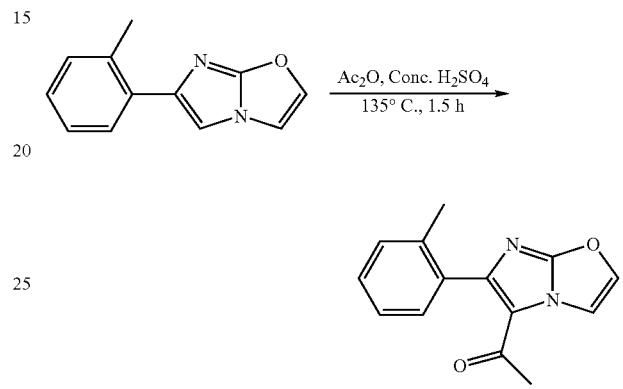

Prepared as described in example 1(a)

M.p.=74° C.; 300 MHz $^1$H NMR (CDCl$_3$) δ: 8.02 (d, J=1.6 Hz, 1H), 7.53 (d, J=1.6 Hz, 1H), 7.4-7.25 (m, 4H), 2.28 (s, 3H), 1.95 (s, 3H). LCMS: 241 [M+H]; calc. for $C_{14}H_{12}N_2O_2$ 0.02 H$_2$O: C, 69.82; H, 5.04; N, 11.64; found. C, 69.87; H, 5.09; N, 11.57.

1(e) Preparation of 1-[6-(3-trifluoromethylphenyl)imidazo[2,1-b][1,3]oxazol-5-yl]ethanone

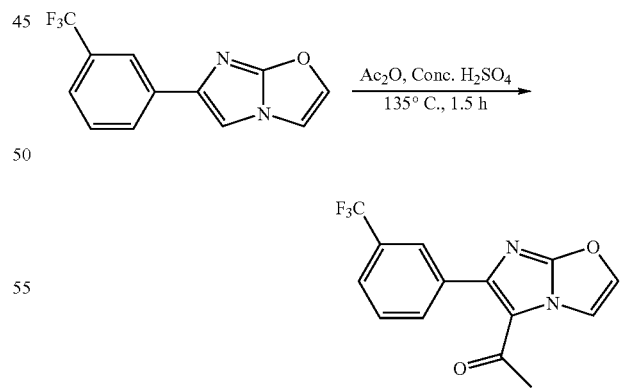

Prepared as described in example 1(a)

M.p.=113° C.; 300 MHz $^1$H NMR (CDCl$_3$) δ: 8.04 (d, J=1.65 Hz, 1H), 7.89 (s, 1H), 7.82-7.79 (m, 1H), 7.76-7.72 (m, 1H), 7.65-7.62 (m, 1H), 7.55-7.54 (m, 1H), 2.19 (s, 3H). LCMS: 295 [M+H]; calc. for $C_{14}H_9F_3N_2O_2$: C, 57.10; H, 3.08; N, 9.52; found. C, 57.34; H, 3.25; N, 9.55.

Example 2

Preparation of 3-(dimethylamino)-1-[6-arylimidazo[2,1-b][1,3]oxazol-5-yl]prop-2-en-1-one

2(a) Preparation of 3-(dimethylamino)-1-[6-(2-chlorophenyl)imidazo[2,1-b][1,3]oxazol-5-yl]prop-2-en-1-one

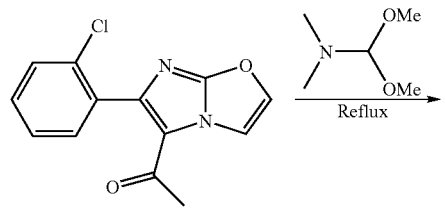

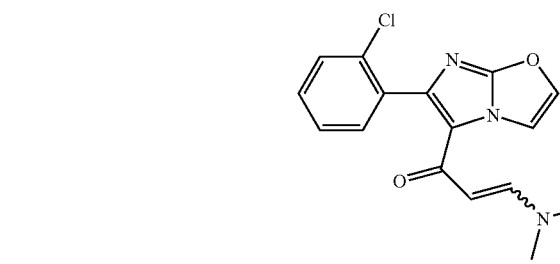

A 50 ml round bottom flask is charged with the 1-[6-(2-chlorophenyl)imidazo[2,1-b][1,3]oxazol-5-yl]ethanone (952 mg, 3.65 mmol) and dimethylformamide dimethylacetal (22 ml). The mixture is refluxed for 5 hours and then cooled to room temperature. The mixture is diluted with ethyl acetate (150 ml) and washed three times with 100 ml each of a saturated sodium chloride solution. The organic phase is dried with magnesium sulfate, filtered and concentrated in vacuo, to give a brown oil. The product is purified by flash chromatography on silica gel (ethyl acetate), yielding 604 mg of a pale brown solid (52%). M.p.=187-189° C.; 300 MHz $^1$H NMR (CDCl$_3$) δ: 8.07 (d, J=1.6 Hz, 1H), 7.62-7.35 (m, 6H), 4.78 (d, J=12.5 Hz), 1H), 3.04-3.01 (m, 3H), 2.4-2.32 (m, 3H). LCMS: 316[M+H]; calc. for C$_{16}$H$_{14}$ClN$_3$O$_2$: C, 60.76; H, 4.49; N, 13.28; found. C, 60.81; H, 4.39; N, 13.35.

2(b) Preparation of 3-(dimethylamino)-1-[6-(2,4-difluorophenyl)imidazo[2,1-b][1,3]oxazol-5-yl]prop-2-en-1-one

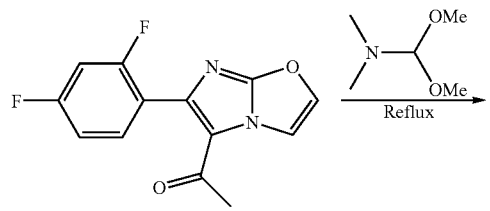

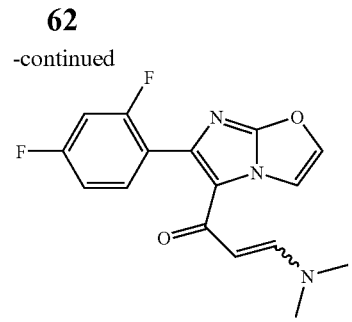

Prepared as described in example 2(a)
M.p.=188-189° C.; 300 MHz $^1$H NMR (CDCl$_3$) δ: 8.06 (s, 1H), 7.7-7.57.45 (m, 3H), 7.1-6.85 (m, 2H), 4.96 (d, J=12.6 Hz, 1H), 3.07 (s, 3H), 2.51 (s, 3H); LCMS: 318 [M+H]; calc. for C$_{16}$H$_{13}$F$_2$N$_3$O$_2$: C, 60.57; H, 4.13; N, 13.24; found. C, 60.29; H, 4.14; N, 13.23.

2(c) Preparation of 3-(dimethylamino)-1-[6-(2-chloro-4-fluorophenyl)-imidazo[2,1-b][1,3]oxazol-5-yl]prop-2-en-1-one Prepared as described in example 2(a)
M.p.=161° C.; 300 MHz $^1$H NMR (CDCl$_3$) δ: 8.05 (m, 1H), 7.65-7.60 (m, 1H), 7.55-7.45 (m, 2H), 7.30-7.24 (m, 1H), 7.15-7.06 (m, 1H), 4.78 (d, J=12.5 Hz, 1H), 3.02 (bs, 3H), 2.44 (bs, 3H). LCMS: 334 [M+H]; calc. for C$_{16}$H$_{13}$ClFN$_3$O$_2$ 0.03 H$_2$O: C, 57.44; H, 3.94; N, 12.57; found. C, 57.48; H, 3.92; N, 12.66.

2(d) Preparation of 3-(dimethylamino)-1-[6-(2-methylphenyl)-imidazo[2,1-b][1,3]oxazol-5-yl]prop-2-en-1-one

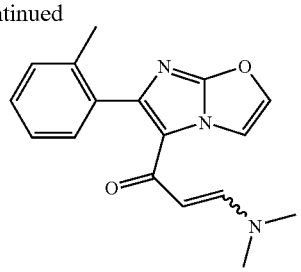

Prepared as described in example 2(a)

M.p.=154-157° C.; 300 MHz $^1$H NMR (CDCl$_3$) δ: 8.07 (d, J=1.7 Hz, 1H), 7.59 (d, J=12.4 Hz, 1H), 7.5-7.2 (m, 5H), 4.80 (d, J=12.4 Hz, 1H), 3.00 (s, 3H), 2.32 (s, 3H), 2.29 (s, 3H); LCMS: 296 [M+H]; calc. for C$_{17}$H$_{17}$N$_3$O$_2$ 0.01 MeOH 0.04 EtOAc: C, 68.87; H, 5.85; N, 14.04; found. C, 68.94; H, 5.77; N, 14.06.

2(e) Preparation of 3-(dimethylamino)-1-[6-(3-trifluoromethylphenyl)-imidazo[2,1-b][1,3]oxazol-5-yl]prop-2-en-1-one

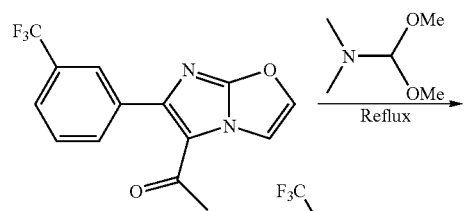

Prepared as described in example 2(a)

M.p.=151-152° C.; 300 MHz $^1$H NMR (CDCl$_3$) δ: 8.05-8.0 (m, 2H), 7.95-7.91 (m, 1H), 7.68-7.45 (m, 4H), 5.15 (d, J=11.2 Hz, 1H), 3.06 (s, 3H), 2.51 (s, 3H). LCMS: 350 [M+H]; calc. for C$_{17}$H$_{14}$F$_3$N$_3$O$_2$: C, 58.40; H, 4.04; N, 12.03; found. C, 58.44; H, 4.10; N, 12.05.

Example 3

Preparation of the Alkylguanidine Hydrochloride

3(a) Preparation of (R)—N-1-azabicyclo[2.2.2]oct-3-ylguanidine Hydrochloride

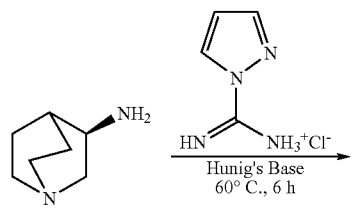

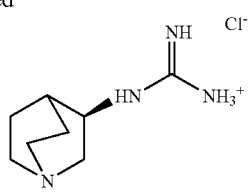

To a mixture of (R)-3-aminoquinuclidine (5.85 g, 46.4 mmol) and pyrazole carbox-amidine hydrochloride (6.80 g, 46.4 mmol) is added Hunig's base (8.07 ml, 46.4 mmol) and DMF (30 ml). The reaction is heated at 70° C. for 40 hours. The reaction is then cooled to room temperature and quenched by adding 400 ml of diethyl ether and stirring at room temperature for 2 hours. Product separates out as a white solid, which is filtered, washed and dried (8.94 g, 94%).

300 MHz $^1$H NMR (DMSO-d$_6$) δ: 8.33 (d, J=7.9 Hz, 1H), 7.21 (br.s, 4H), 3.19 (ddd, J=12.0 11.4 1.8 Hz, 1H), 2.7 (m, 5H), 2.44 (dd, J=13.82.3 Hz, 1H), 1.8 (m, 2H), 1.57 (m, 2H), 1.37 (m, 1H); LCMS: 169 [M+H]. Calc. for C$_8$H$_{16}$N$_4$ 1 HCl 0.5 H$_2$O: C, 44.92; H, 8.49; N, 26.21; found. C, 44.74; H, 8.19; N, 26.62.

3(b) Preparation of (S)—N-1-azabicyclo[2.2.2]oct-3-ylguanidine Hydrochloride

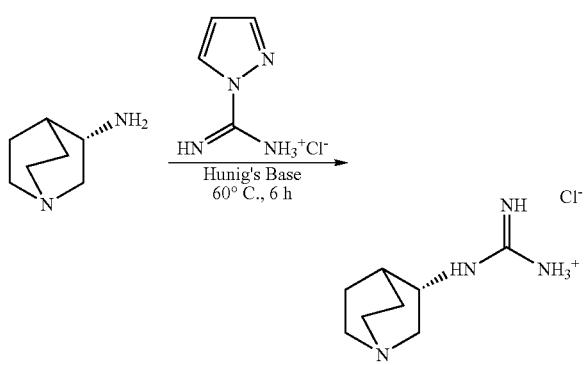

Prepared as described in example 3(a)

300 MHz $^1$H NMR (DMSO-d$_6$) δ: 8.33 (d, J=7.9 Hz, 1H), 7.21 (br.s, 4H), 3.19 (ddd, J=12.0 11.4 1.8 Hz, 1H), 2.7 (m, 5H), 2.44 (dd, J=13.8 2.3 Hz, 1H), 1.8 (m, 2H), 1.57 (m, 2H), 1.37 (m, 1H); LCMS: 169 [M+H]. Calc. for C$_8$H$_{16}$N$_4$ 1 HCl 0.3 H$_2$O: C, 45.69; H, 8.44; N, 26.66; found. C, 45.28; H, 8.26; N, 27.04.

3(c) Preparation of (endo)-N-(8-methyl-8-azabicyclo[3.2.1]oct-3-yl)guanidine Hydrochloride

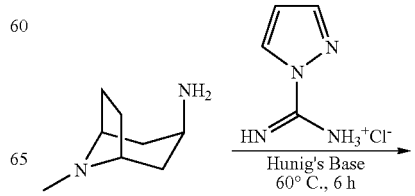

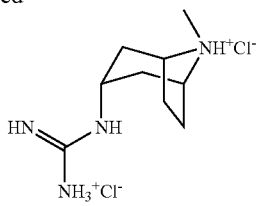

Prepared as described in example 3(a) with the addition of 1 mole equivalent of HCl to the diethyl ether quench prior to stirring.

M.p.=240-244° C.; 300 MHz $^1$H NMR (DMSO-$d_6$) δ: 10.98 (br. s, 1H), 8.31 (d, J=6.3 Hz, 1H), 7.51 (br. s, 3H), 3.76 (m, 3H), 2.6 (m, 5H), 2.4 (m, 2H), 2.2 (m, 2H), 1.85 (d, J=15.4 Hz, 2H); LCMS: 183 [M+H]. Calc. for $C_9H_{18}N_4$ 2 HCl: C, 42.32; H, 7.90; N, 21.95; found. C, 39.78; H, 7.91; N, 22.44.

3(d) Preparation of N-[3-(dimethylamino)-2,2-dimethylpropyl]guanidine Hydrochloride

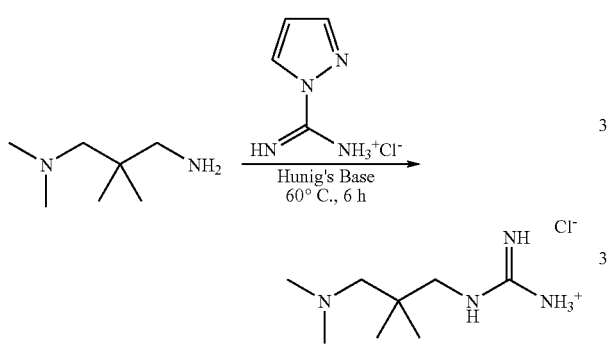

Prepared as described in example 3(a)
M.p.=71-74° C.; 300 MHz $^1$H NMR (CDCl$_3$) δ: 8.0 (br. s, 1H), 7.23 (br. s, 3H), 3.08 (d, J=14.8 Hz, 2H), 2.24 (s, 6H), 2.18 (s, 2H); LCMS: 173 [M+H]. Calc. for $C_8H_{20}N_4$ 1.05 HCl: C, 45.59; H, 10.08; N, 26.60; found. C, 45.64; H, 9.80; N, 27.35.

3(e) Preparation of tert-butyl 4-{[amino(imino)methyl]amino}piperidine-1-carboxylate Hydrochloride

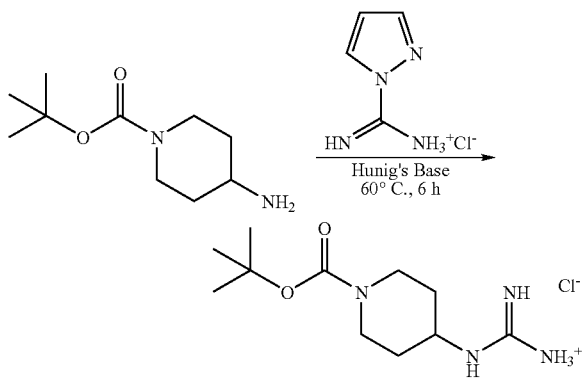

Prepared as described in example 3(a)
M.p.=169-172° C.; 400 MHz $^1$H NMR (DMSO-$d_6$) δ: 8.09 (d, J=8.8 HZ, 1H), 6.9-7.9 (br. s, 3H), 3.83 (d, J=13.6 Hz, 2H), 3.63 (m, 1H), 2.88 (m, 2H), 1.80 (m, 2H), 1.40 (s, 9H), 1.25 (m, 2H); LCMS: 243 [M+H]; calc. for $C_{11}H_{22}N_4O_2$ 1.06 HCl 0.2H$_2$O: C, 46.39; H 8.31; N, 19.68; found. C, 46.43; H, 8.31; N, 20.68.

Example 4

Preparation of (R)—N-{4-[6-(2-chlorophenyl)imidazo[2,1-b][1,3]oxazol-5-yl]pyrimidin-2-yl}quinuclidine-3-amine

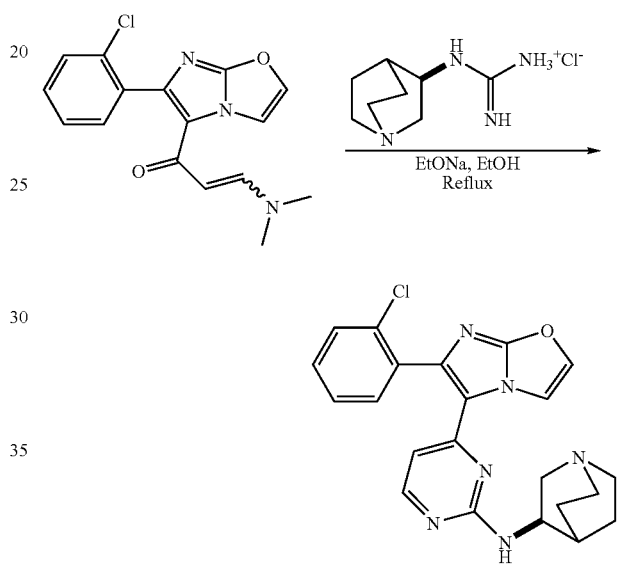

A mixture of 3-(dimethylamino)-1-[6-(2-chlorophenyl)imidazo[2,1-b][1,3]oxazol-5-yl]prop-2-en-1-one (316 mg, 1.0 mmol) and (R)—N-1-azabicyclo[2.2.2]oct-3-ylguanidine hydrochloride (427 mg, 2.0 mmol) is diluted with 5 ml of absolute ethanol and treated with 1.8 eq. of a 21% w/w solution of sodium ethoxide in ethanol (0.6 ml) to form a reaction mixture. The reaction mixture is heated to reflux for 24 hours. Volatiles are removed in vacuo and the residue is taken up in 12 ml of a 5:1 mixture of ethyl acetate and methanol, washed twice with 5 ml each of water, and then with a saturated sodium chloride solution (5 ml). The organic phase is dried with magnesium sulfate, filtered and concentrated in vacuo, to give a brown oil. The product is purified by flash chromatography on silica gel (ethyl acetate/methanol/ammonium hydroxide solution, 20:4:1) to yield 329 mg of a pale yellow solid (78%). M.p.=132-134° C.; 300 MHz $^1$H NMR (DMSO-$d_6$) δ: 8.91 (s, 1H), 8.25 (s, 1H), 8.03 (d, J=5.1 Hz, 1H), 7.63-7.45 (m, 4H), 7.38 (d, J=6.9 Hz, 1H), 5.80 (br. s, 1H), 3.87 (m, 1H), 3.16 (br. s, 1H), 2.86 (m, 1H), 2.8-2.4 (m, 4H), 1.92 (br. s, 1H), 1.83 (br. s, 1H), 1.59 (m, 2H), 1.32 (br. s, 1H). LCMS: 421 [M+H]; calc. for $C_{22}H_{21}ClN_6O$ 0.1 EtOAc 0.75 H$_2$O: C, 60.70; H, 5.30; N, 18.98; found. C, 61.17; H, 5.21; N, 18.68.

Example 5

Preparation of (S)—N-{4-[6-(2-chlorophenyl)imidazo[2,1-b][1,3]oxazol-5-yl]pyrimidin-2-yl}quinuclidine-3-amine

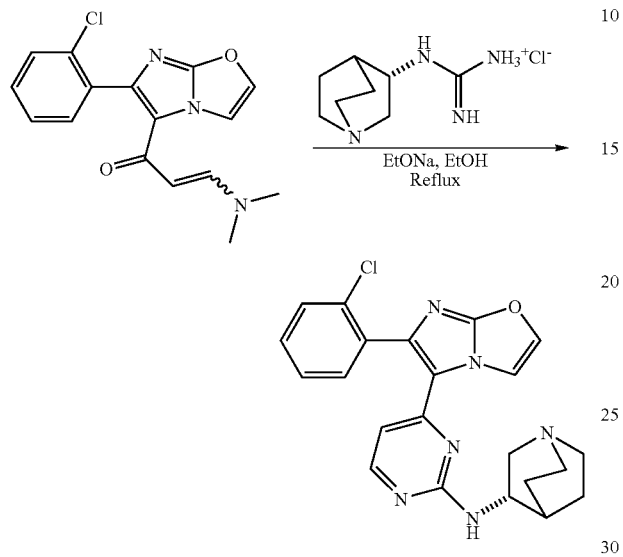

Prepared as described in example 4.

M.p.=179-181° C.; 300 MHz $^1$H NMR (CDCl$_3$) δ: 8.16 (s, 1H), 7.99 (d, J=4.2 Hz, 1H), 7.56-7.50 (m, 3H), 7.48-7.35 (m, 2H), 6.07 (d, J=5.4 Hz, 1H), 5.27 (d, J=6.9 Hz, 1H), 4.07-4.16 (m, 1H), 3.52-3.41 (m, 1H), 2.98-2.80 (m, 4H), 2.67-2.61 (m, 1H), 2.18-2.12 (m, 1H), 2.1-1.67 (m, 3H), 1.64-1.45 (m, 1H). LCMS: 421 [M+H]; calc. for C$_{22}$H$_{21}$ClN$_6$O 0.27 EtOAc 0.36 HCl: C, 60.55; H, 5.18; N, 18.36; found. C, 60.54; H, 4.90; N, 18.34.

Example 6

Preparation of (3-endo)-N-{4-[6-(2-chlorophenyl)imidazo[2,1-b][1,3]oxazol-5-yl]pyrimidin-2-yl}-8-methyl-8-azabicyclo[3.2.1]octan-3-amine

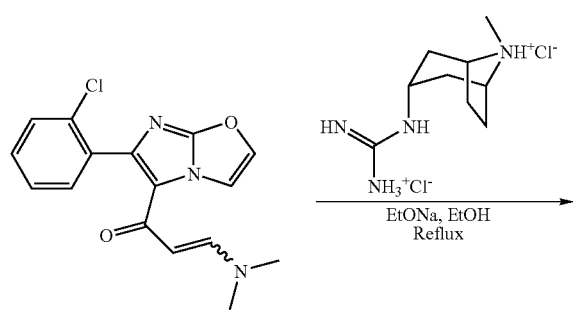

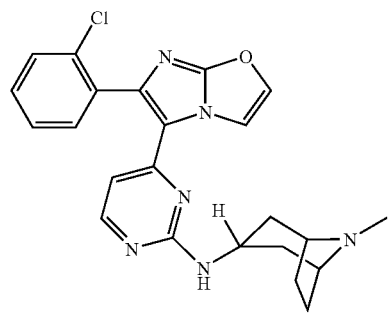

Prepared as described in example 4.

M.p.=179° C.; 300 MHz $^1$H NMR (CDCl$_3$) δ: 8.10 (d, J=1.5 Hz, 1H), 7.98 (d, J=5.4 Hz, 1H), 7.54-7.34 (m, 5H), 6.10 (d, J=5.1 Hz, 1H), 5.5 (d, J=5.1 Hz, 1H), 4.22 (q, J=5.7 Hz, 1H), 3.57 (bs, 2H), 2.88-2.77 (m, 2H), 2.60 (s, 3H), 2.30-2.05 (m, 6H). LCMS: 435 [M+H]; calc. for C$_{23}$H$_{23}$ClN$_6$O 0.44 H$_2$O: C, 62.34; H, 5.43; N, 18.98; found. C, 62.29; H, 5.23; N, 19.02.

Example 7

Preparation of N'-{4-[6-(2-chlorophenyl)imidazo[2,1-b][1,3]oxazol-5-yl]pyrimidin-2-yl}-N,N,2,2-tetramethylpropane-1,3-diamine

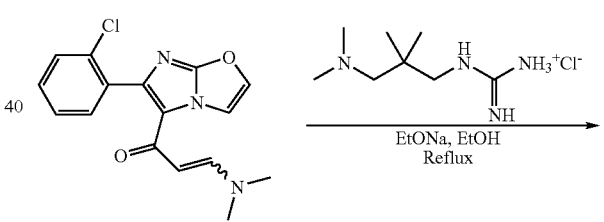

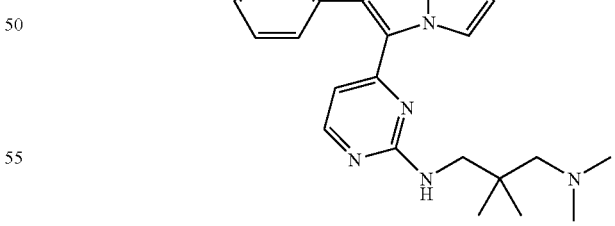

Prepared as described in example 4.

M.p.=133-135° C.; 300 MHz $^1$H NMR (DMSO-d$_6$) δ: 8.95-8.6 (m, 1H), 8.25 (bs, 1H), 7.98 (d, 1H), 7.64-7.59 (m, 1H), 7.58-7.42 (m, 4H), 7.22 (bs, 1H), 5.78 (bs, 1H), 3.25 (m, 2H), 2.23 (s, 6H), 2.18 (s, 2H), 0.85 (s, 6H). 425 [M+H]; calc. for C$_{22}$H$_{25}$ClN$_6$O: C, 62.13; H, 5.93; N, 19.77; found. C, 62.26; H, 5.81; N, 19.73.

Example 8

Preparation of tert-butyl 4-({4-[6-(2-chlorophenyl)imidazo[2,1-b][1,3]oxazol-5-yl]pyrimidin-2-yl}amino)piperidine-1-carboxylate

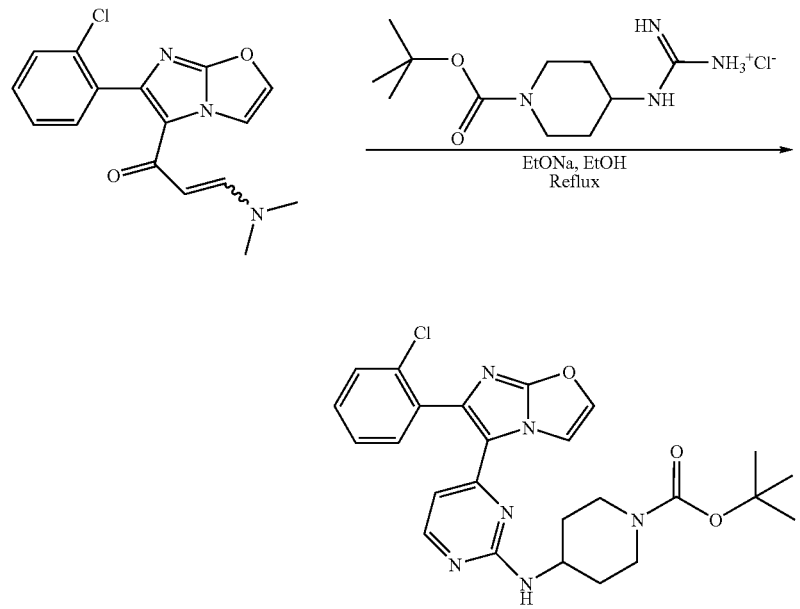

Prepared as described in example 4.

M.p.=240-241° C.; 300 MHz $^1$H NMR (CDCl$_3$) δ: 8.12-7.95 (m, 2H), 7.60-7.10 (m, 5H), 6.1-6.0 (m, 1H), 5.05-4.9 (m, 1H), 4.2-3.8 (m, 3H), 3.1-2.8 (m, 2H), 2.15-1.9 (m, 2H), 1.48 (s, 9H), 1.6-1.3 (m, 2H). LCMS: 495 [M+H]; calc. for C$_{25}$H$_{27}$ClN$_6$O$_3$: C, 60.61; H, 5.50; N, 16.97; found. C, 60.51; H, 5.38; N, 16.88.

Example 9

Preparation of 4-[6-(2-chlorophenyl)imidazo[2,1-b][1,3]oxazol-5-yl]-N-piperidin-4-ylpyrimidine-2-amine Hydrochloride

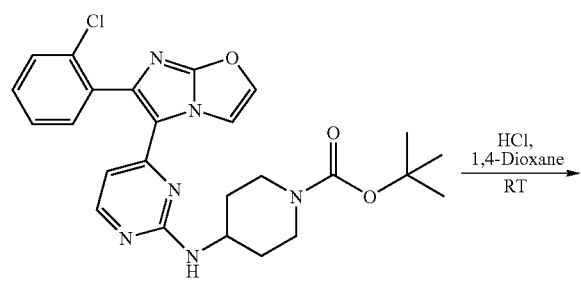

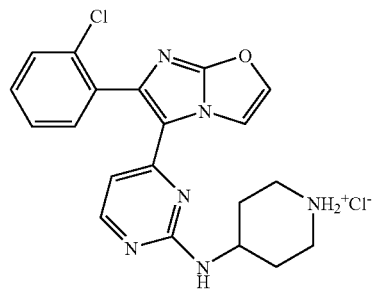

The tert-butyl 4-({4-[6-(2-chlorophenyl)imidazo[2,1-b][1,3]oxazol-5-yl]pyrimidin-2-yl}amino)piperidine-1-carboxylate (1.8 g, 3.6 mmol) is dissolved in 20 ml of dioxane and treated with 40 ml of anhydrous a four molar HCl in dioxane at room temperature (RT). The reaction mixture is stirred at room temperature for three hours. The mixture is then diluted with 100 ml of ether and stirred until product separates as a solid. Solid product is filtered and washed with ether. The product is dried at high vacuum to yield 1.3 g of pale yellow solid (94%).

M.p.=216-220° C.; 300 MHz $^1$H NMR (DMSO-d$_6$) δ: 9.4-8.8 (m, 3H), 8.3-8.0 (m, 2H), 7.7-7.5 (m, 4H), 6.2-6.0 (m, 2H), 4.2-4.05 (bs, 1H), 3.4-3.3 (m, 2H), 3.2-2.8 (m, 2H), 2.2-2.0 (m, 2H), 1.95-1.75 (m, 2H). LCMS: 395 [M+H]; calc.

Example 10

Preparation of (R)—N-{4-[6-(2,4-difluorophenyl)imidazo[2,1-b][1,3]oxazol-5-yl]pyrimidin-2-yl}quinuclidine-3-amine

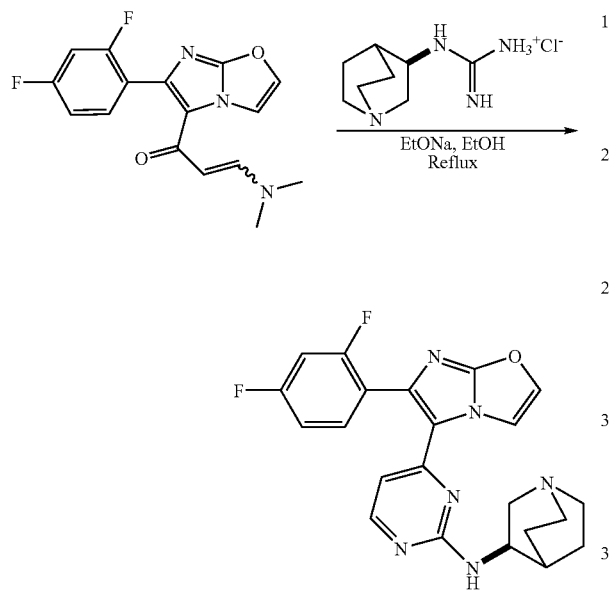

Prepared as described in example 4.

M.p.=184-186° C.; 300 MHz $^1$H NMR (CDCl$_3$) δ: 8.12 (s, 1H), 8.07 (d, J=5.7 Hz, 1H), 7.58 (m, 2H), 6.95 (m, 2H), 6.28 (d, J=5.1 Hz, 1H), 5.33 (d, J=6.6 Hz, 1H), 4.03 (dd, J=11.1 4.5 Hz, 1H), 3.45 (m, 1H), 2.8-3.0 (m, 4H), 2.63 (dd, J=14.4 4.8 Hz, 1H), 2.18 (m, 3H), 1.6-1.9 (m, 3H), 1.4-1.6 (m, 1H); LCMS: 423 [M+H]. Calc. for C$_{22}$H$_{20}$F$_2$N$_6$O 0.92 H$_2$O: C, 60.14; H, 5.01; N, 19.14; found. C, 60.34; H, 5.11; N, 18.77.

Example 11

Preparation of (S)—N-{4-[6-(2,4-difluorophenyl)imidazo[2,1-b][1,3]oxazol-5-yl]pyrimidin-2-yl}quinuclidine-3-amine

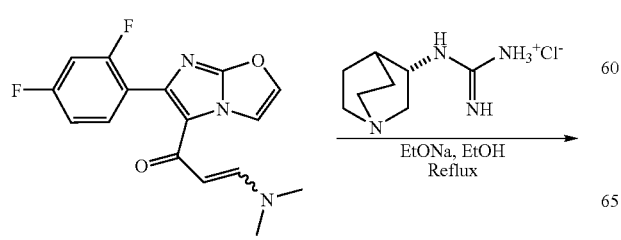

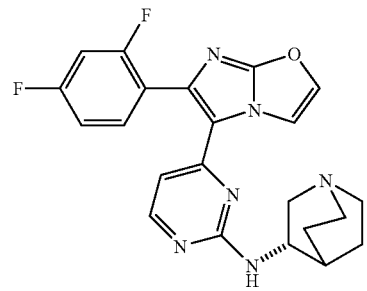

Prepared as described in example 4.

M.p.=184-186° C.; 300 MHz $^1$H NMR (CDCl$_3$) δ: 8.12 (s, 1H), 8.07 (d, J=5.7 Hz, 1H), 7.62-7.54 (m, 1H), 7.51 (s, 1H), 7.27-6.9 (m, 2H), 6.28 (d, J=5.1 Hz, 1H), 5.32 (d, J=6.6 Hz, 1H), 4.05-3.95 (m, 1H), 3.52-3.4 (m, 1H), 3.0-2.8 (m, 4H), 2.66-2.56 (m, 1H), 2.14-2.0 (m, 1H), 1.95-1.6 (m, 3H), 1.55-1.44 (m, 1H). LCMS: 423 [M+H]; calc. for C$_{22}$H$_{20}$F$_2$N$_6$O 0.92 H$_2$O: C, 60.14; H, 5.01; N, 19.14; found. C, 60.34; H, 5.11; N, 18.77.

Example 12

Preparation of (3-endo)-N-{4-[6-(2,4-difluorophenyl)imidazo[2,1-b][1,3]oxazol-5-yl]pyrimidin-2-yl}-8-methyl-8-azabicyclo[3.2.1]octan-3-amine

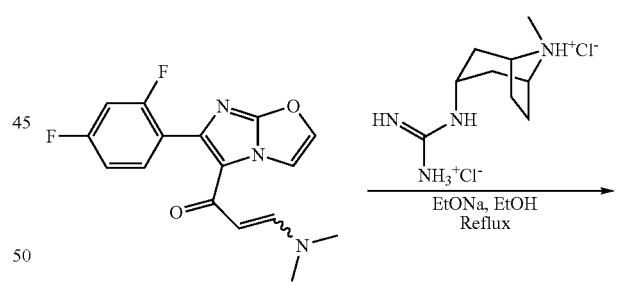

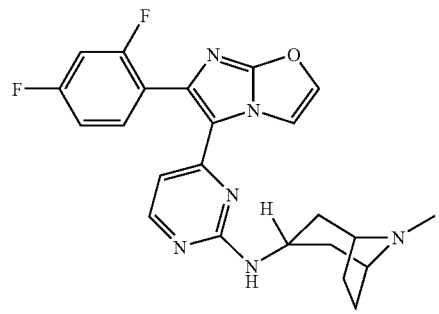

Prepared as described in example 4.

M.p.=281-283° C.; 300 MHz $^1$H NMR (DMSO-$d_6$) δ: 8.9-8.3 (bs, 1H), 8.19 (s, 1H), 8.11 (d, J=5.4 Hz, 1H), 7.67-7.59 (m, 1H), 7.46-7.39 (m, 1H), 7.39-7.23 (m, 1H), 7.02-7.01 (m, 1H), 6.12-6.11 (m, 1H), 3.9-3.8 (m, 1H), 3.07 (bs, 2H), 2.20 (s, 3H), 2.15-2.05 (m, 2H), 2.04-1.96 (m, 4H), 1.93-1.75 (m, 2H). LCMS: 437 [M+H]; calc. for $C_{23}H_{22}F_2N_6O$ 0.41 $H_2O$: C, 62.18; H, 5.18; N, 18.93; found. C, 61.98; H, 4.79; N, 18.76.

Example 13

Preparation of N'-{4-[6-(2,4-difluorophenyl)imidazo[2,1-b][1,3]oxazol-5-yl]pyrimidin-2-yl}-N,N,2,2-tetramethylpropane-1,3-diamine

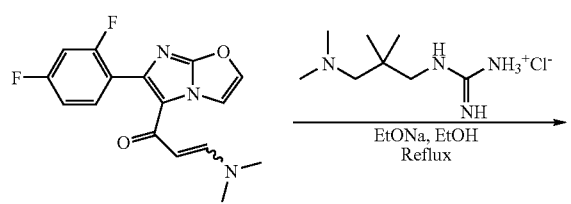

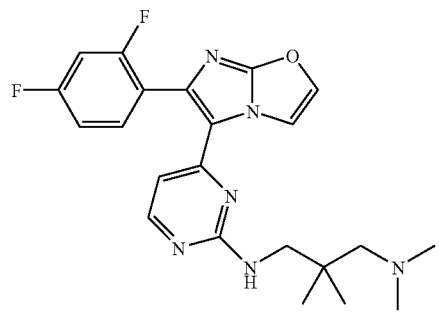

Prepared as described in example 4.

M.p.=122-123° C.; 300 MHz $^1$H NMR (DMSO-$d_6$) δ: 8.9-8.6 (m, 1H), 8.23 (br. s, 1H), 8.05 (d, J=5.3 Hz, 1H), 7.61 (qd, J=7.9 1.8 Hz, 1H), 7.39 (td, J=9.7 2.2 Hz, 1H), 7.23 (td, J=8.1 2.2 Hz, 2H), 6.2-6.0 (m, 1H), 3.27 (d, J=5.7 Hz, 2H), 2.23 (s, 6H), 2.14 (s, 2H), 0.86 (s, 6H); LCMS: 427 [M+H]; calc. for $C_{22}H_{24}F_2N_6O$ 0.3 $H_2O$: C, 61.17; H, 5.74; N, 19.47; found. C, 61.22; H, 5.65; N, 19.68.

Example 14

Preparation of tert-butyl 4-({4-[6-(2,4-difluorophenyl)imidazo[2,1-b][1,3]oxazol-5-yl]pyrimidin-2-yl}amino)piperidine-1-carboxylate

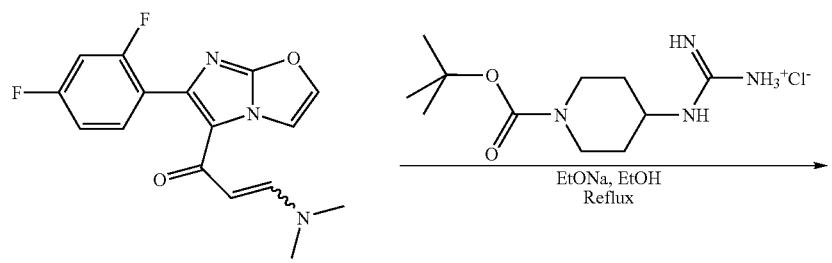

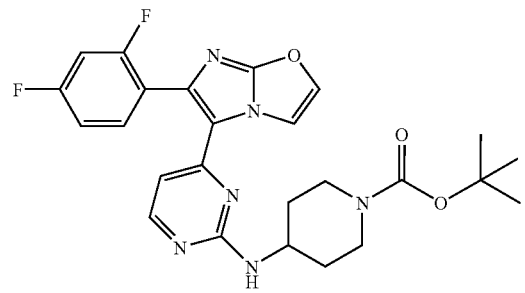

Prepared as described in example 4.

M.p.=213-214° C.; 300 MHz ¹H NMR (CDCl₃) δ: 8.13-8.07 (m, 2H), 7.63-7.45 (m, 2H), 7.1-6.9 (m, 2H), 6.30 (bs, 1H), 5.1 (bs, 1H), 4.15-3.90 (m, 3H), 3.1-2.9 (m, 2H), 2.16-2.03 (m, 2H), 1.6-1.45 (bs, 11H). LCMS: 497 [M+H]; calc. for $C_{25}H_{26}F_2N_6O_3$ 0.08 $H_2O$: C, 60.25; H, 5.29; N, 16.87; found. C, 59.99; H, 4.91; N, 16.80.

Example 15

Preparation of 4-[6-(2,4-difluorophenyl)imidazo[2,1-b][1,3]oxazol-5-yl]-N-piperidin-4-ylpyrimidine-2-amine Hydrochloride

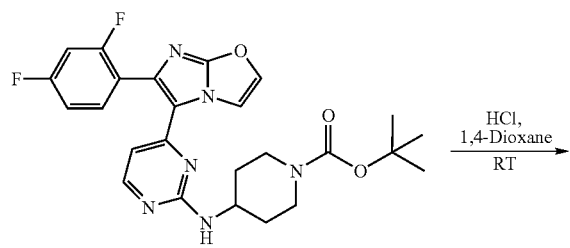

Prepared as described in example 9.

M.p.=212-215° C.; 300 MHz ¹H NMR (DMSO-d₆) δ: 9.4-8.9 (m, 3H), 8.35-8.05 (m, 2H), 7.7-7.63 (m, 1H), 7.55-7.45 (m, 1H), 7.33-7.23 (m, 1H), 6.35-6.2 (m, 1H), 4.8-4.2 (bs, 3H), 4.2-4.0 (m, 2H), 3.1-2.9 (m, 2H), 2.18-2.05 (m, 2H), 1.9-1.75 (m, 2H). LCMS: 397 [M+H]; calc. for $C_{20}H_{18}F_2N_6O$ 2.6 HCl 0.4$H_2O$: C, 49.29; H, 4.56; N, 15.97; found. C, 49.13; H, 4.75; N, 15.99.

Example 16

Preparation of (R)—N-{4-[6-(2-chloro-4-fluorophenyl)imidazo[2,1-b][1,3]oxazol-5-yl]pyrimidin-2-yl}quinuclidine-3-amine

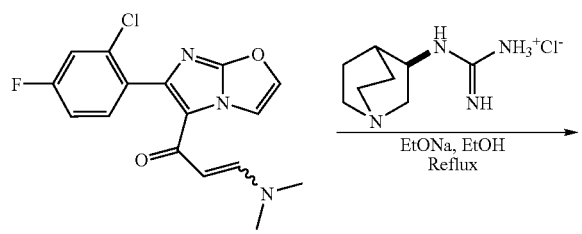

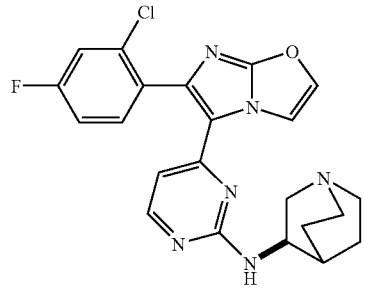

Prepared as described in example 4.

M.p.=204-206° C.; 300 MHz ¹H NMR (CDCl₃) δ: 8.15 (s, 1H), 8.03 (d, J=5.4 Hz, 1H), 7.55-7.48 (m, 2H), 7.3-7.25 (m, 1H), 7.15-7.05 (m, 1H), 6.06 (d, J=5.1 Hz, 1H), 5.30 (d, J=6.6 Hz, 1H), 4.05-3.98 (m, 1H), 3.52-3.39 (m, 1H), 3.0-2.8 (m, 4H), 2.66-2.56 (m, 1H), 2.18-2.10 (m, 1H), 2.05-1.95 (m, 1H), 1.95-1.6 (m, 2H), 1.55-1.44 (m, 1H). LCMS: 439 [M+H]; calc. for $C_{22}H_{20}ClFN_6O$ 1.18 $H_2O$: C, 57.37; H, 4.90; N, 18.26; found. C, 57.59; H, 4.87; N, 18.06.

Example 17

Preparation of (S)—N-{4-[6-(2-chloro-4-fluorophenyl)imidazo[2,1-b][1,3]oxazol-5-yl]pyrimidin-2-yl}quinuclidine-3-amine

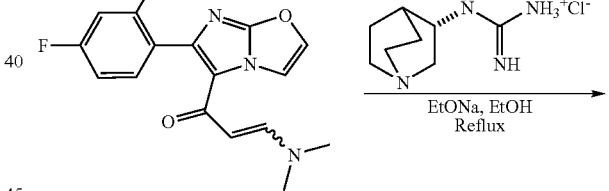

Prepared as described in example 4.

M.p.=201-203° C.; 300 MHz ¹H NMR (CDCl₃) δ: 8.42 (br. s, 1H), 8.03 (d, J=5.4 Hz, 1H), 7.55-7.48 (m, 2H), 7.3-7.25 (m, 1H), 7.15-7.05 (m, 1H), 6.06 (d, J=5.1 Hz, 1H), 4.20 (m, 1H), 3.60-3.45 (m, 1H), 3.52-3.39 (m, 1H), 3.0-2.8 (m, 4H), 2.66-2.56 (m, 1H), 2.18-2.10 (m, 1H), 2.05-1.95 (m, 1H), 1.95-1.6 (m, 2H), 1.55-1.44 (m, 1H). LCMS: 439 [M+H];

calc. for $C_{22}H_{20}ClFN_6O$ 1.02 $H_2O$: C, 57.73; H, 4.86; N, 18.37; found. C, 57.79; H, 4.90; N, 18.15.

Example 18

Preparation of (3-endo)-N-{4-[6-(2-chloro-4-fluorophenyl)imidazo[2,1-b][1,3]oxazol-5-yl]pyrimidin-2-yl}-8-methyl-8-azabicyclo[3.2.1]octan-3-amine

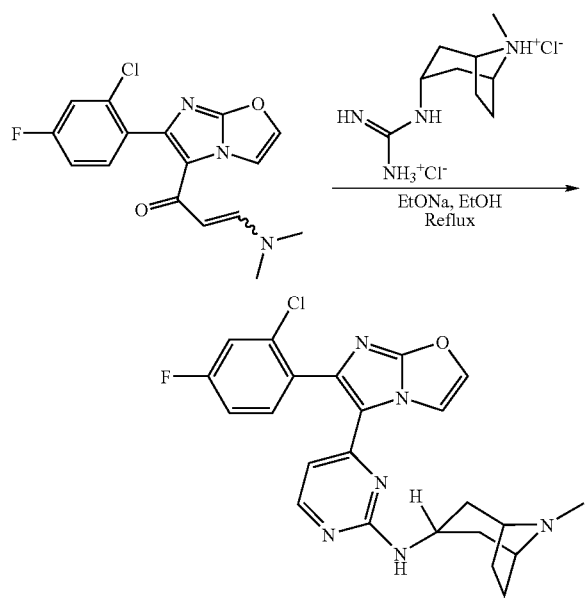

Prepared as described in example 4.

M.p.=241° C.; 300 MHz $^1$H NMR (DMSO-$d_6$) δ: 8.9-8.4 (bs, 1H), 8.19 (s, 1H), 8.07 (d, J=5.1 Hz, 1H), 7.67-7.59 (m, 2H), 7.42-7.35 (m, 1H), 7.1-7.05 (m, 1H), 5.88 (d, J=4.2 Hz, 1H), 3.9-3.8 (m, 1H), 3.25-3.15 (m, 2H), 2.27 (s, 3H), 2.2-1.75 (m, 8H). LCMS: 453 [M+H]; calc. for $C_{23}H_{22}ClFN_6O$ 0.31 $H_2O$: C, 60.20; H, 4.97; N, 18.32; found. C, 60.25; H, 4.84; N, 18.44.

Example 19

Preparation of N'-{4-[6-(2-chloro-4-fluorophenyl)imidazo[2,1-b][1,3]oxazol-5-yl]pyrimidin-2-yl}-N,N,2,2-tetramethylpropane-1,3-diamine

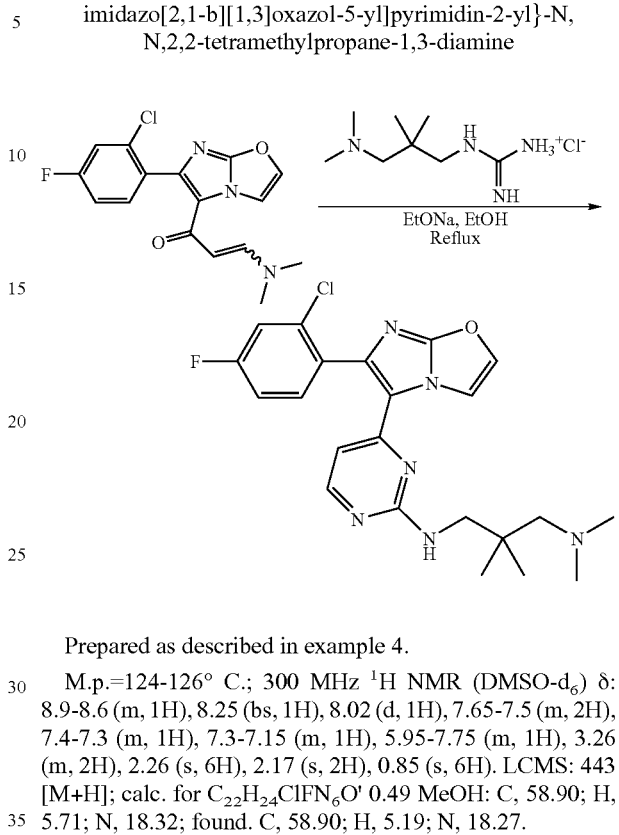

Prepared as described in example 4.

M.p.=124-126° C.; 300 MHz $^1$H NMR (DMSO-$d_6$) δ: 8.9-8.6 (m, 1H), 8.25 (bs, 1H), 8.02 (d, 1H), 7.65-7.5 (m, 2H), 7.4-7.3 (m, 1H), 7.3-7.15 (m, 1H), 5.95-7.75 (m, 1H), 3.26 (m, 2H), 2.26 (s, 6H), 2.17 (s, 2H), 0.85 (s, 6H). LCMS: 443 [M+H]; calc. for $C_{22}H_{24}ClFN_6O'$ 0.49 MeOH: C, 58.90; H, 5.71; N, 18.32; found. C, 58.90; H, 5.19; N, 18.27.

Example 20

Preparation of tert-butyl 4-({4-[6-(2-chloro-4-fluorophenyl)-imidazo[2,1-b][1,3]oxazol-5-yl]pyrimidin-2-yl}amino)piperidine-1-carboxylate

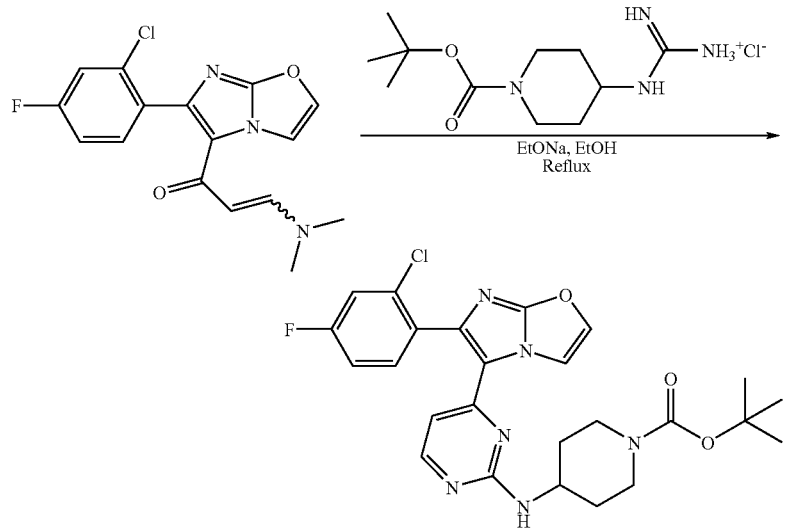

Prepared as described in example 4.

M.p.=242-244° C.; 300 MHz $^1$H NMR (DMSO-$d_6$) δ: 8.85-8.75 (m, 1H), 8.23-8.03 (m, 2H), 7.7-7.58 (m, 2H), 7.40-7.22 (m, 2H), 5.9-5.8 (m, 1H), 3.98-3.80 (m, 2H), 3.0-2.75 (m, 3H), 1.92-1.82 (m, 2H), 1.40 (s, 9H), 1.40-1.25 (m, 2H); calc. for $C_{25}H_{26}ClFN_6O_3$: C, 58.48; H, 5.11; N, 16.38; found. C, 58.49; H, 4.69; N, 16.32.

Example 21

Preparation of 4-[6-(2-chloro-4-fluorophenyl)imidazo[2,1-b][1,3]oxazol-5-yl]-N-piperidin-4-ylpyrimidine-2-amine Hydrochloride

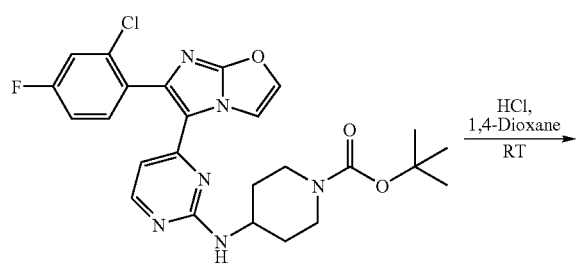

Prepared as described in example 9.

M.p.=216-218° C.; 300 MHz $^1$H NMR (DMSO-$d_6$) δ: 9.5-8.7 (m, 3H), 8.35-8.05 (m, 2H), 7.8-7.6 (m, 2H), 7.5-7.35 (m, 1H), 6.15-5.95 (m, 2H), 4.2-4.0 (m, 1H), 3.45-3.25 (m, 2H), 3.20-2.90 (m, 2H), 2.2-2.0 (m, 2H), 1.95-1.70 (m, 2H). LCMS: 413 [M+H]; calc. for $C_{20}H_{18}ClFN_6O$ 2.55 HCl 0.72 dioxane: C, 48.27; H, 4.66; N, 14.76; found. C, 48.26; H, 4.59; N, 14.77.

Example 22

Preparation of (R)—N-{4-[6-(2-methylphenyl)imidazo[2,1-b][1,3]oxazol-5-yl]pyrimidin-2-yl}quinuclidine-3-amine

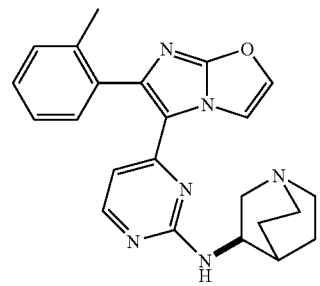

Prepared as described in example 4.

M.p.=108-110° C.; 300 MHz $^1$H NMR (DMSO-$d_6$) δ: 8.90 (br. s, 1H), 8.21 (s, 1H), 7.97 (d, J=5.1 Hz, 1H), 7.45-7.25 (m, 5H), 5.81 (br. s, 1H), 3.89 (m, 1H), 3.17 (m, 1H), 2.86 (m, 1H), 2.78-2.55 (m, 4H), 2.14 (s, 3H), 2.0-1.7 (m, 2H), 1.59 (m, 2H), 1.32 (br. s, 1H); LCMS: 401 [M+H]; calc. for $C_{23}H_{24}N_6O$ 0.1 EtOAc 0.8$H_2O$: C, 66.33; H, 6.28; N, 19.83; found. C, 66.51; H, 5.88; N, 19.40.

Example 23

Preparation of (S)—N-{4-[6-(2-methylphenyl)imidazo[2,1-b][1,3]oxazol-5-yl]pyrimidin-2-yl}quinuclidine-3-amine

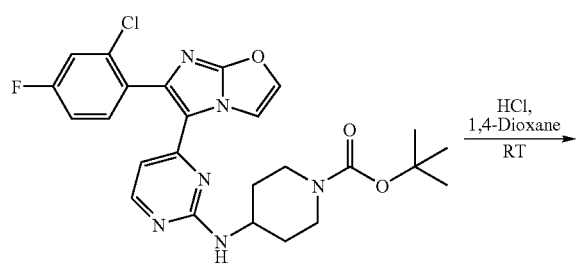

Prepared as described in example 4.

M.p.=198-200° C.; 300 MHz $^1$H NMR (CDCl$_3$) δ: 8.17 (s, 1H), 7.94 (d, J=5.1 Hz, 1H), 7.51 (s, 1H), 7.4-7.2 (m, 4H), 6.04 (d, J=5.7 Hz, 1H), 2.7 (d, J=6.9 Hz, 1H), 4.1-4.0 (m, 1H), 3.5-3.4 (m, 1H), 3.0-2.8 (m, 4H), 2.7-2.57 (m, 1H), 2.24 (s, 3H), 2.18-2.10 (s, 1H), 1.9-1.63 (m, 3H), 1.6-1.4 (m, 1H).

LCMS: 401 [M+H]; calc. for $C_{23}H_{24}N_6O$ 1.35 $H_2O$: C, 64.97; H, 6.33; N, 19.78; found. C, 65.03; H, 6.47; N, 19.76.

Example 24

Preparation of (3-endo)-N-{4-[6-(2-methylphenyl)imidazo[2,1-b][1,3]oxazol-5-yl]pyrimidin-2-yl}-8-methyl-8-azabicyclo[3.2.1]octan-3-amine

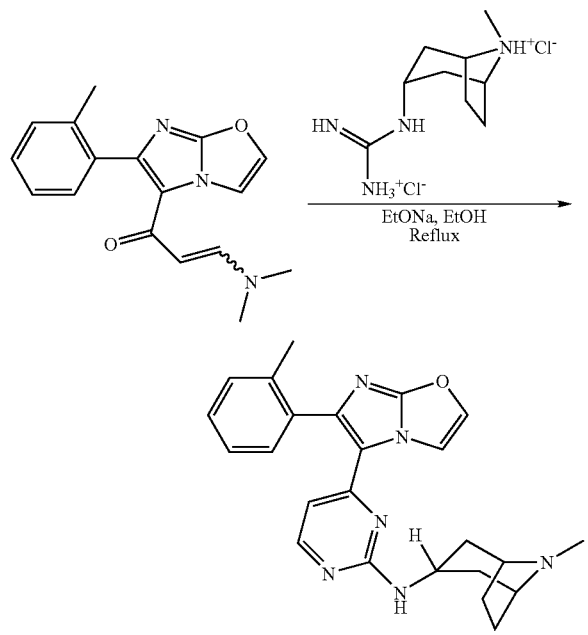

Prepared as described in example 4.

M.p.=165-167° C.; 300 MHz $^1$H NMR (DMSO-$d_6$) δ: 8.19 (d, J=1.5 Hz, 1H), 7.08 ((d, J=5.4 Hz, 1H), 7.45-7.35 (m, 3H), 7.35-7.3 (m, 2H), 7.16 (bs, 1H), 5.86 (d, J=5.4, 1H), 3.91 (bs, 1H), 3.43-3.35 (m, 2H), 2.42 (s, 3H), 2.14 (s, 3H), 2.35-1.95 (m, 8H); LCMS: 415 [M+H]; calc. for $C_{24}H_{26}N_6O$ 0.73 HCl 0.24 EtOAc: C, 64.85; H, 6.25; N, 18.18; found. C, 64.86; H, 5.79; N, 18.18.

Example 25

Preparation of N'-{4-[6-(2-methylphenyl)imidazo[2,1-b][1,3]oxazol-5-yl]pyrimidin-2-yl}-N,N,2,2-tetramethylpropane-1,3-diamine

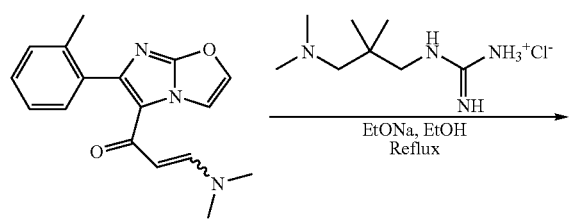

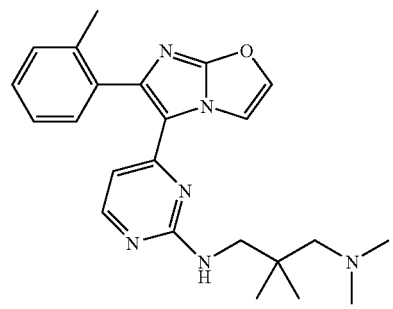

Prepared as described in example 4.

M.p.=105-106° C.; 300 MHz $^1$H NMR (DMSO-$d_6$) δ: 8.95-8.65 (m, 1H), 8.22 (bs, 1H), 7.97 (d, 1H), 7.45-7.16 (m, 6H), 5.80 (bs, 1H), 3.25 (m, 2H), 2.23 (s, 6H), 2.18-2.10 (s, 5H), 0.87 (s, 6H). LCMS: 405 [M+H]; calc. for $C_{23}H_{28}N_6O$ 0.24 EtOAc: C, 67.86; H, 7.05; N, 20.12; found. C, 67.77; H, 6.80; N, 20.12.

Example 26

Preparation of tert-butyl 4-({4-[6-(2-methylphenyl)imidazo[2,1-b][1,3]oxazol-5-yl]pyrimidin-2-yl}amino)piperidine-1-carboxylate

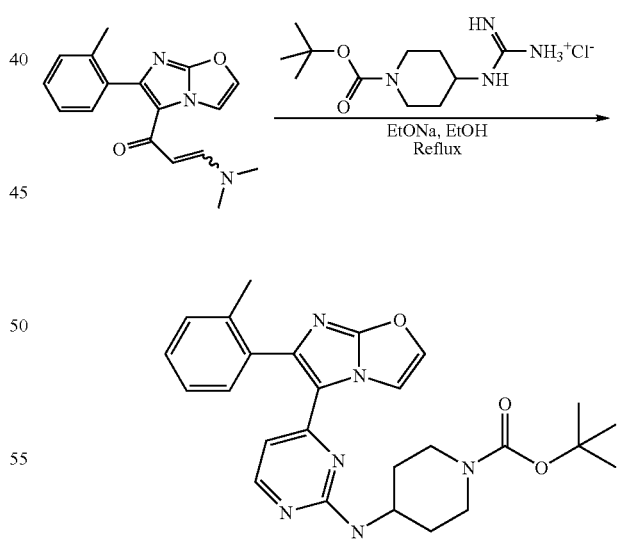

Prepared as described in example 4.

M.p.=237-242° C.; 300 MHz $^1$H NMR (CDCl$_3$) δ: 8.13 (s, 1H), 7.95 (d, J=5.4 Hz, 1H), 7.50 (d, J=1.5 Hz, 1H), 7.40-7.20 (m, 4H), 6.04 (d, J=5.4 Hz, 1H), 4.98 (d, J=7.2 Hz, 1H), 4.15-3.90 (m, 3H), 3.00 (t, J=11.8 Hz, 2H), 2.24 (s, 3H), 2.10 (d, J=10.2 Hz, 2H), 1.62 (br. s, 2H), 1.48 (s, 9H); LCMS: 475

[M+H]; calc. for $C_{26}H_{30}N_6O_3$: C, 65.74; H, 6.37; N, 17.70; found. C, 65.94; H, 6.32; N, 17.71.

Example 27

Preparation of 4-[6-(2-methylphenyl)imidazo[2,1-b][1,3]oxazol-5-yl]-N-piperidin-4-ylpyrimidine-2-amine Hydrochloride

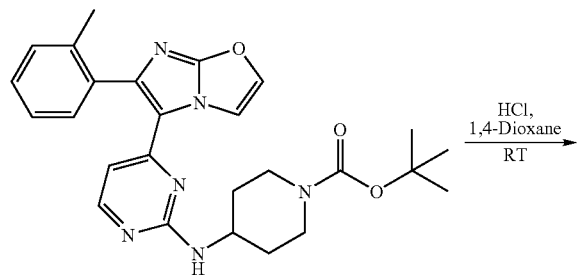

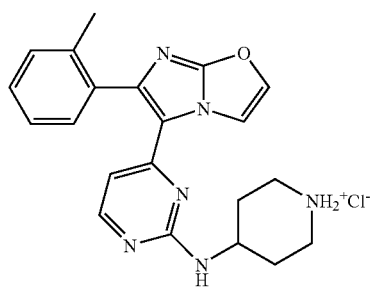

Prepared as described in example 9.

M.p.=206-210° C.; 300 MHz $^1$H NMR (DMSO-d$_6$) δ: 9.20 (br. s, 1H), 7.90-7.60 (m, 2H), 7.45-7.20 (m, 4H), 6.10 (d, J=5.6 Hz, 1H), 4.42 (br. s, 1H), 3.8-3.2 (m, 2H), 2.8-2.1 (m, 4H), 2.18 (s, 3H), 1.45-1.20 (m, 2H); LCMS: 375 [M+H]; calc. for $C_{21}H_{22}N_6O$ 2.5 HCl 0.98 dioxane: C, 54.18; H, 5.91; N, 15.22; found. C, 54.51; H, 6.11; N, 15.23.

Example 28

Preparation of (R)—N-{4-[6-(3-trifluoromethylphenyl)imidazo[2,1-b][1,3]oxazol-5-yl]pyrimidin-2-yl}quinuclidine-3-amine

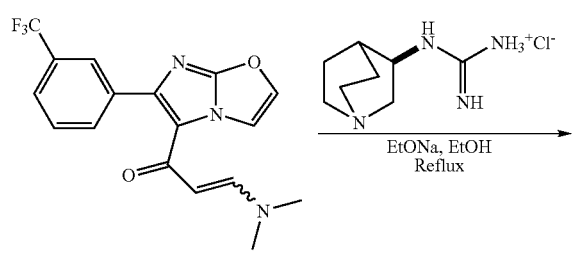

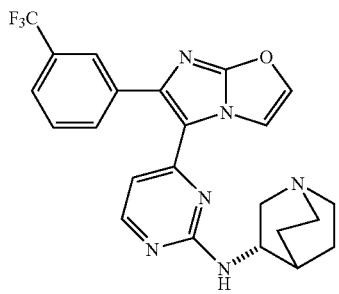

Prepared as described in example 4.

M.p.=124-125° C.; 300 MHz $^1$H NMR (CDCl$_3$) δ: 8.1-8.0 (m, 2H), 8.0-7.95 (m, 1H), 7.89-7.82 (m, 1H), 7.69-7.62 (m, 1H), 7.60-7.50 (m, 2H), 6.51 (d, J=5.4 Hz, 1H), 5.31 (d, J=6.9 Hz, 1H), 4.07-4.02 (m, 1H), 3.53-3.40 (m, 1H), 3.0-2.8 (m, 4H), 2.7-2.6 (m, 1H), 2.18-2.0 (m, 1H), 1.95-1.6 (m, 3H), 1.6-1.4 (m, 1H). LCMS: 455 [M+H]; calc. for $C_{23}H_{21}F_3N_6O$ 0.76 H$_2$O 0.19 Et$_2$O: C, 59.18; H, 5.10; N, 17.43; found. C, 59.19; H, 5.00; N, 17.43.

Example 29

Preparation of (S)—N-{4-[6-(3-trifluoromethylphenyl)imidazo[2,1-b][1,3]oxazol-5-yl]pyrimidin-2-yl}quinuclidine-3-amine

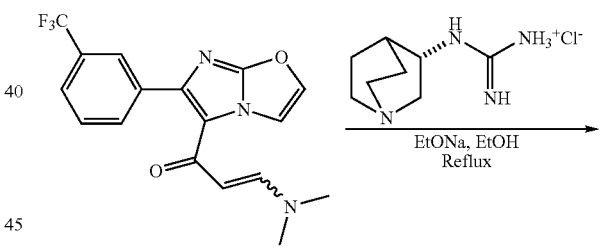

Prepared as described in example 4.

M.p.=126-128° C.; 300 MHz $^1$H NMR (CDCl$_3$) δ: 8.1-8.0 (m, 2H), 8.0-7.95 (m, 1H), 7.89-7.82 (m, 1H), 7.69-7.62 (m, 1H), 7.60-7.50 (m, 2H), 6.51 (d, J=5.4 Hz, 1H), 5.30 (d, J=6.0 Hz, 1H), 4.07-4.0 (m, 1H), 3.53-3.40 (m, 1H), 3.0-2.8 (m, 4H), 2.7-2.6 (m, 1H), 2.18-2.0 (m, 1H), 1.95-1.6 (m, 3H), 1.6-1.4 (m, 1H). LCMS: 455 [M+H]; calc. for $C_{23}H_{21}F_3N_6O$ 0.94 $H_2O$: C, 58.55; H, 4.89; N, 17.82; found. C, 58.85; H, 4.91; N, 17.53.

Example 30

Preparation of (3-endo)-N-{4-[6-(3-trifluoromethylphenyl)-imidazo[2,1-b][1,3]oxazol-5-yl]pyrimidin-2-yl}-8-methyl-8-azabicyclo[3.2.1]octan-3-amine

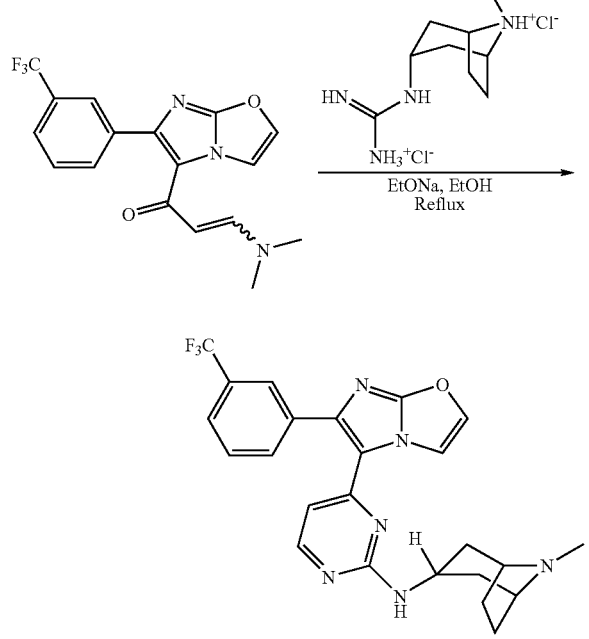

Prepared as described in example 4.

M.p.=183° C.; 300 MHz $^1$H NMR (DMSO-$d_6$) δ: 8.9-8.4 (bs, 1H), 8.19 (s, 1H), 8.15-8.1 (m, 1H), 8.0-7.9 (m, 2H), 7.94-7.88 (m, 1H), 7.82-7.65 (m, 1H), 7.08 (d, J=4.5 Hz, 1H), 6.39 (d, J=4.5 Hz, 1H), 3.95-3.82 (m, 1H), 3.13 (bs, 2H), 2.23 (s, 3H), 2.2-1.8 (m, 8H). LCMS: 469 [M+H]; calc. for $C_{24}H_{23}F_3N_6O$ 0.79 $H_2O$: C, 59.66; H, 5.13; N, 17.41; found. C, 59.43; H, 4.69; N, 17.23.

Example 31

Preparation of N'-{4-[6-(3-trifluoromethylphenyl)imidazo[2,1-b][1,3]oxazol-5-yl]pyrimidin-2-yl}-N,N,2,2-tetramethylpropane-1,3-diamine

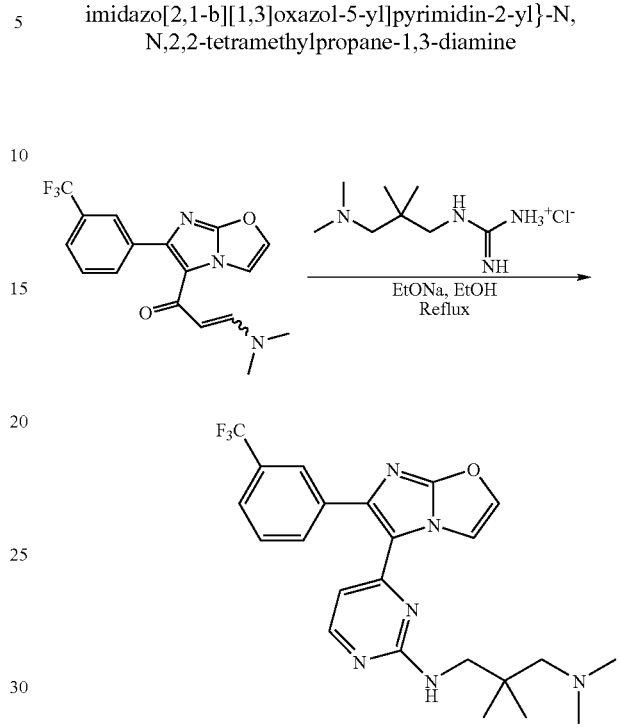

Prepared as described in example 4.

M.p.=131-133° C.; 300 MHz $^1$H NMR (CDCl$_3$) δ: 8.25 (bs, 1H), 8.1-8.0 (m, 1H), 7.98 (s, 1H), 7.9-7.83 (m, 1H), 7.75-7.5 (m, 4H), 6.43 (d, 1H), 3.42 (m, 2H), 2.38 (s, 6H), 2.34 (s, 2H), 1.03 (s, 6H). LCMS: 459 [M+H]; calc. for $C_{23}H_{25}F_3N_6O$ 0.33 $H_2O$: C, 59.43; H, 5.57; N, 18.09; found. C, 59.48; H, 5.39; N, 17.82.

Example 32

Preparation of tert-butyl 4-({4-[6-(3-trifluoromethylphenyl)imidazo-[2,1-b][1,3]oxazol-5-yl]pyrimidin-2-yl}amino)piperidine-1-carboxylate

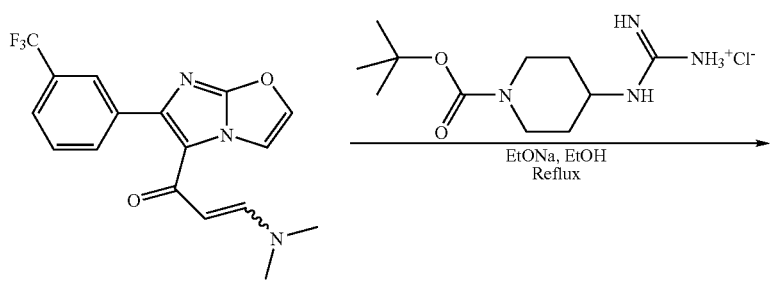

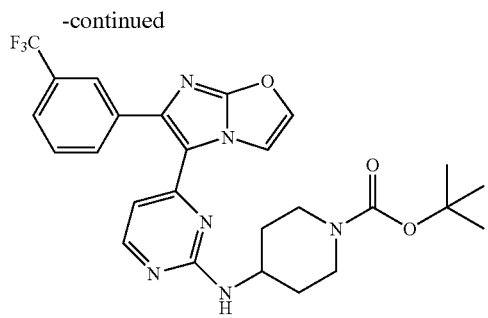

Prepared as described in example 4.

M.p.=205° C.; 300 MHz $^1$H NMR (CDCl$_3$) δ: 8.1-8.0 (m, 2H), 7.97 (s, 1H), 7.09-7.8 (m, 1H), 7.7-7.6 (m, 1H), 7.6-7.48 (m, 2H), 6.51 (d, J=5.4 Hz, 1H), 5.1-5.0 (m, 1H), 4.2-3.95 (m, 3H), 3.1-2.9 (m, 2H), 2.2-2.0 (m, 2H), 1.58-1.4 (m, 2H), 1.50 (s, 9H). LCMS: 529 [M+H]; calc. for C$_{26}$H$_{27}$F$_3$N$_6$O$_3$ 0.05H$_2$O: C, 58.93; H, 5.16; N, 15.87; found. C, 58.99; H, 5.43; N, 15.70.

Example 33

Preparation of 4-[6-(3-trifluoromethylphenyl)imidazo[2,1-b][1,3]oxazol-5-yl]-N-piperidin-4-ylpyrimidine-2-amine Hydrochloride

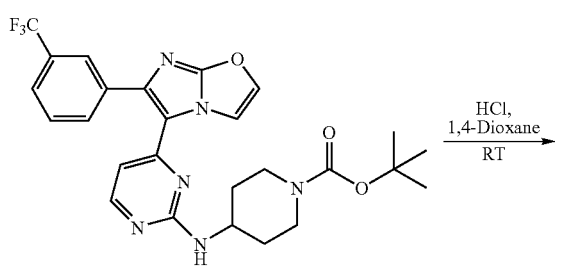

Prepared as described in example 9.

M.p.=176-180° C.; 300 MHz $^1$H NMR (DMSO-d$_6$) δ: 9.4-8.6 (m, 2H), 8.35-8.0 (m, 2H), 8.0-7.9 (m, 1H), 7.9-7.8 (m, 1H), 7.8-7.7 (m, 1H), 6.6-6.4 (bs, 1H), 4.2-4.15 (bs, 1H), 3.45-3.25 (m, 2H), 3.1-2.9 (m, 2H), 2.2-2.15 (m, 2H), 1.9-1.7 (m, 2H). LCMS: 429 [M+H]; calc. for C$_{21}$H$_{19}$F$_3$N$_6$O 2.33 HCl 0.02 H$_2$O 0.2 dioxane: C, 49.28; H, 4.36; N, 15.82; found. C, 49.28; H, 4.07; N, 15.82.

Example 34

Preparation of (R)—N-{4-[6-(4-fluorophenyl)imidazo[2,1-b][1,3]oxazol-5-yl]pyrimidin-2-yl}quinuclidine-3-amine

34(a) Preparation of 1-[6-(4-fluorophenyl)imidazo[2,1-b][1,3]oxazol-5-yl]ethanone

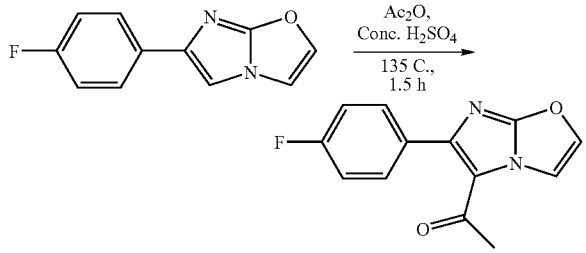

To a mixture of 6-(4-fluorophenyl)-imidazo[2,1-b]oxazole (2675 g, 13.23 mol) and acetic anhydride (6.35 l) is added 160 ml of concentrated sulfuric acid. The reaction mixture is heated at 135° C. for 1.5 hours, then cooled to 80° C. with an ice bath. The reaction mixture is slowly quenched with 12.5 l of water. The solids are stirred overnight, filtered and air-dried. The solids are again suspended in water (15 l), stirred overnight, filtered, and washed with water (4 l) and then with toluene (4 l). The solid is dried under vacuum at 60° C., to give 2771 g (86%) of a dark brown solid; M.p.=173° C.; 300 MHz $^1$H NMR (DMSO-d$_6$) δ 8.25-8.19 (m, 2H), 7.75-7.68 (m, 2H), 7.35-7.25 (m, 2H), 2.15 (s, 3H). LCMS: 245 [M+H].

34(b) Preparation of 3-(dimethylamino)-1-[6-(4-fluorophenyl)imidazo[2,1-b][1,3]oxazol-5-yl]prop-2-en-1-one

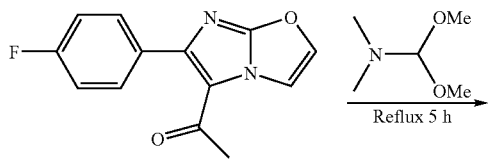

-continued

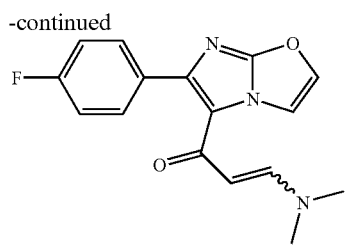

A 2 L 3-neck round bottom flask is charged with 1-[6-(4-fluorophenyl)imidazo[2,1-b][1,3]oxazol-5-yl]ethanone (215 g, 0.88 mol) and dimethylformamide dimethylacetal (1.1 L). The mixture is refluxed for 5 hours and then cooled to room temperature. Solvent is removed under vacuum, and the resulting solid is filtered and washed with MTBE (methyl tert-butyl ether) to give the desired product (229.0 g) in 87% yield as light yellow solid. M.p.=187-189° C.; 300 MHz $^1$H NMR (CDCl$_3$) δ 8.03 (s, 1H), 7.72-7.64 (m, 3H), 7.46 (s, 1H), 7.13-7.10 (m, 2H), 5.19 (d, J=12.5 Hz, 1H), 3.07 (bs, 3H), 2.55 (bs, 3H). LCMS: 300 [M+H]. Calc. for $C_{16}H_{14}FN_3O_2$: C, 64.21; H, 4.71; N, 14.04; found. C, 64.22; H, 4.31; N, 14.10.

34(c) Preparation of (R)—N-1-azabicyclo[2.2.2]oct-3-ylguanidine Hydrochloride

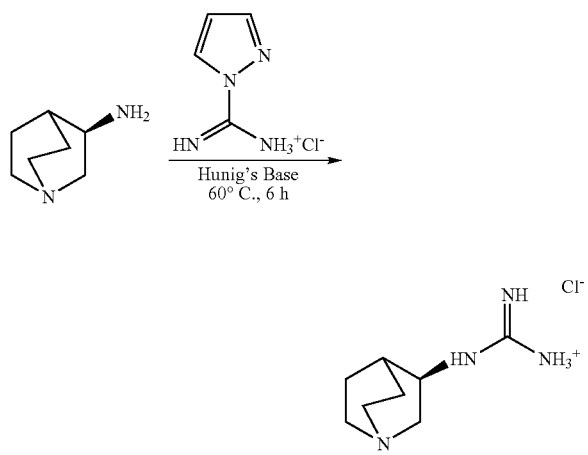

To a mixture of 3-aminoquinuclidine (5.85 g, 46.4 mmol) and pyrazole carboxamidine (6.80 g, 46.4 mmol) is added Hunig's base (8.07 ml, 46.4 mmol) and DMF (30 ml). The reaction is heated at 70° C. for 40 hours. The reaction is then cooled to room temperature and quenched by adding 400 ml of diethyl ether and stirred at room temperature for 2 hours. Product separated out as a white solid, which is filtered, washed and dried to produce a 94% yield (8.94 g).

300 MHz $^1$H NMR (DMSO-d$_6$) δ: 8.33 (d, J=7.9 Hz, 1H), 7.21 (br.s, 4H), 3.19 (ddd, J=12.0 11.4 1.8 Hz, 1H), 2.7 (m, 5H), 2.44 (dd, J=13.82.3 Hz, 1H), 1.8 (m, 2H), 1.57 (m, 2H), 1.37 (m, 1H); LCMS: 169 [M+H]. Calc. for $C_8H_{16}N_4$ 1 HCl 0.5H$_2$O: C, 44.92; H, 8.49; N, 26.21; found. C, 44.74; H, 8.19; N, 26.62.

34(d) Preparation of (R)—N-{4-[6-(4-fluorophenyl)imidazo[2,1-b][1,3]oxazol-5-yl]pyrimidin-2-yl}quinuclidine-3-amine

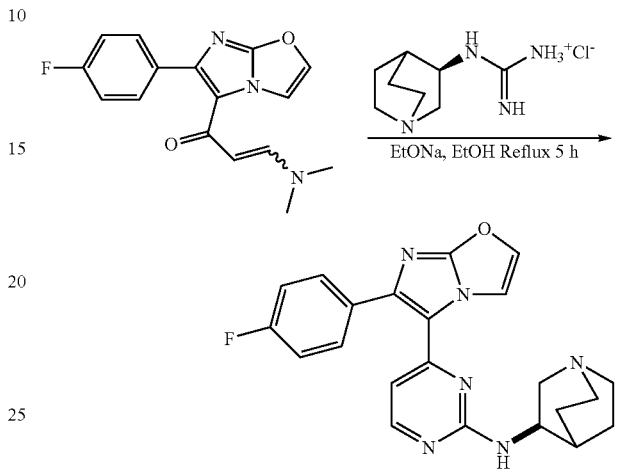

A 5 L 3-neck round bottom flask is charged with the N-1-azabicyclo[2.2.2]oct-3-ylguanidine hydrochloride (261.5 g, 1.277 mol) and absolute ethanol. Sodium methoxide (21% by weight) (405 ml, 1.08 mol) is added dropwise over 15 min. The 3-(dimethylamino)-1-[6-(4-fluorophenyl)imidazo[2,1-b][1,3]oxazol-5-yl]prop-2-en-1-one (232.1 g, 0.776 mol) is then added in portions so that no reaction mixture temperature change is observed. The reaction mixture is then refluxed for 5 hours and cooled to room temperature. Solvent is removed in vacuo and the residue partitioned between 1N NaOH and ethyl acetate. The resulting solids are filtered, washed with water, ethyl acetate, and then dried. The solids are then mostly dissolved in hot isopropyl alcohol and filtered through celite while hot. The isopropyl alcohol solution is concentrated to dryness and the solids dried under vacuum to give the desired pyrimidine compound (143.8 g) as a tan solid in 46% yield.

M.p.=217-218° C.; 300 MHz $^1$H NMR (DMSO-d$_6$) δ 8.82 (br. s, 1H), 8.20 (s, 1H), 8.08 (d, J=5.4 Hz, 1H), 7.63 (m, 2H), 7.39 (d, J=6.6 Hz, 1H), 7.31 (t, J=9.0 Hz, 2H), 6.35 (s, 1H), 3.89 (br.d, 1H), 3.17 (m, 1H), 2.86 (m, 1H), 2.70 (m, 4H), 1.93 (br.s, 1H), 1.83 (m, 1H), 1.57 (m, 2H), 1.32 (br.s, 1H); LCMS: 405 [M+H]. Calc. for $C_{22}H_{21}FN_6O$ 0.25 H$_2$O: C, 64.56; H, 5.30; N, 20.54; found. C, 64.77; H, 5.20; N, 20.42.

Example 35

Preparation of 2-amino-oxazole

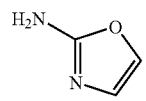

To a solution of cyanamide (33 ml, 50% wt in water, 0.416 mol) in THF (100 ml), is added an aqueous solution of 2-hydroxyacetaldehyde (25 g, 0.416 mol) in water (40 ml), followed by the dropwise addition of 2M sodium hydroxide (42 ml, 0.083 mol) at 0° C. Stirring is continued for a total of 24 hours. Then, the reaction mixture is concentrated in vacuo to remove most of the THF. The remaining water layer is extracted four times with 200 ml each of ethyl acetate. The extract is dried over sodium sulfate and the solvent is evaporated in vacuo. This produces a white solid product (23 g, 66%).

Example 36

Preparation of 6-(4-fluorophenyl)-imidazo[2,1-b]thiazole

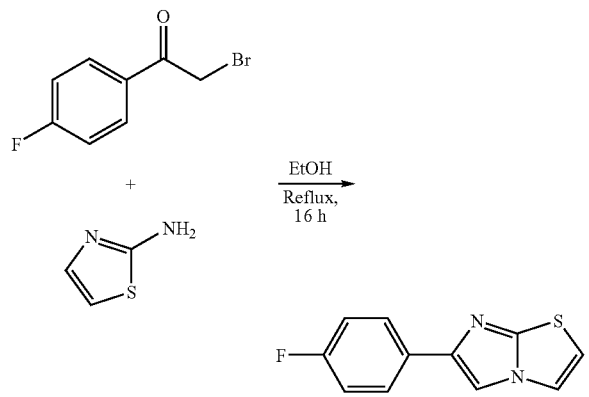

To a mixture of 2-aminothiazole (23.7 g, 0.23 mol) and 2-bromo-4'-fluoroacetophenone (alternatively named: 2-bromo-1-(4-fluorophenyl)-ethanone) (50 g, 0.23 mol) is added absolute ethanol (600 ml). The reaction is allowed to reflux with vigorous stirring for 16 hours. The reaction mixture is reduced to half its original volume in vacuo. The remaining liquid is poured onto ice and the solution made basic by the addition of ammonium hydroxide solution (30%). The resulting fine solid is filtered and washed with water. The dark yellow solid so obtained is dried in a vacuum oven at 50° C. to provide 6-(4-fluorophenyl)-imidazo[2,1-b]thiazole (43.0 g, 86%).

ESMS [M+H]$^+$=219; $^1$H NMR (300 MHz CDCl$_3$) δ 8-7.6 (m, 3H), 7.38 (bs, 1H), 7.08 (bs, 2H), 6.79 (bs, 1H); $^{13}$C 75 MHz (NMR CDCl$_3$) δ: 163.2 (d, C—F, J=244.7 Hz), 150.1, 146.8, 130.3 (C—C—C—C—F), 126.7 (d, C—C—C—F, J=7.73 Hz), 118.4, 115.5 (d, C—C—F, J=21.4 Hz), 112.4, 107.6;

Example 37

Figure 2A:
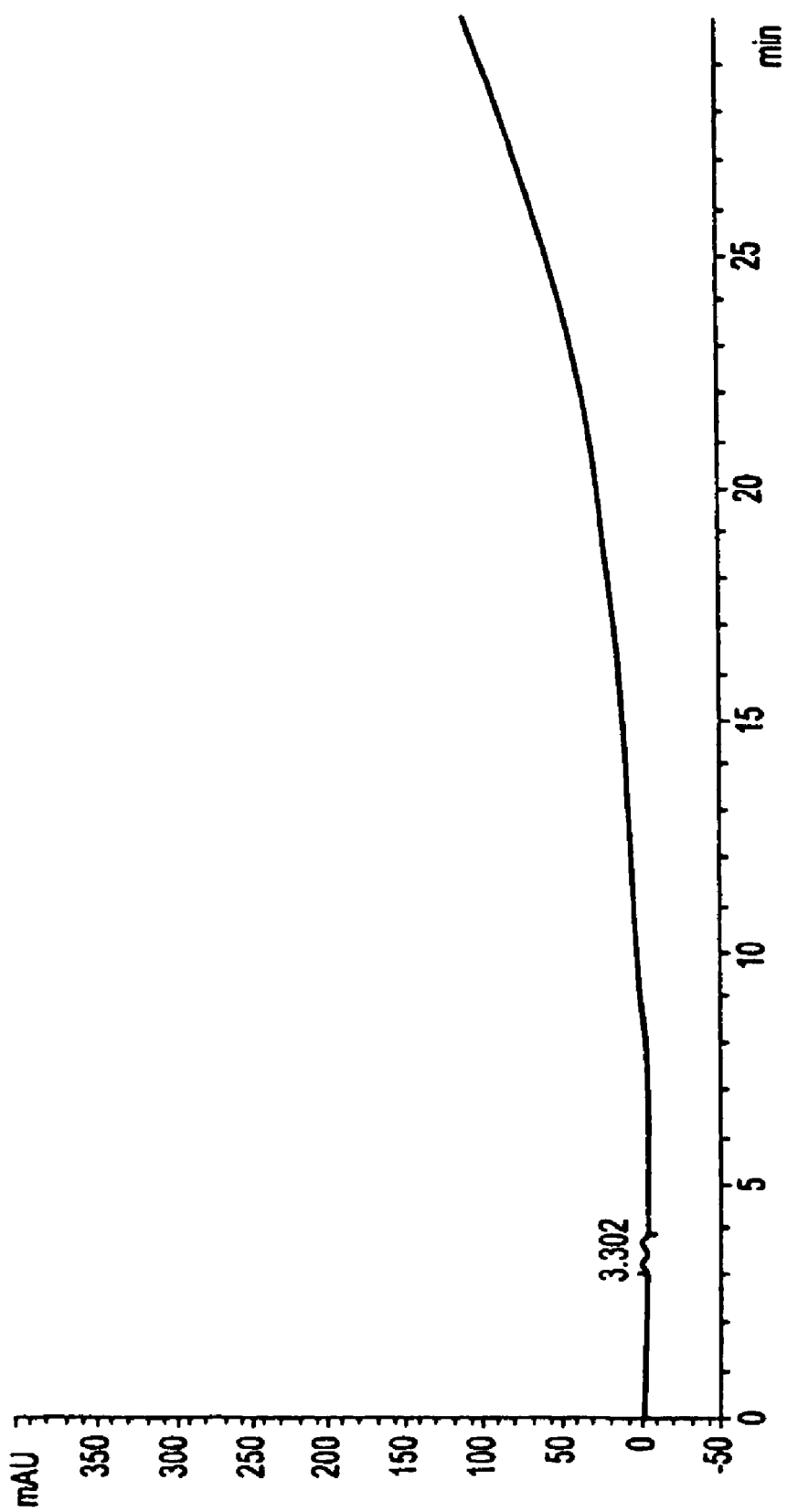
FIGS. 2A-2I set forth a chromatographic analysis of (R)—N-{4-[6-(4-fluorophenyl)imidazo[2,1-b][1,3]oxazol-5-yl]pyrimidin-2-yl}quinuclidine-3-amine and synthetic intermediates involved in its preparation.
Figure 2B:
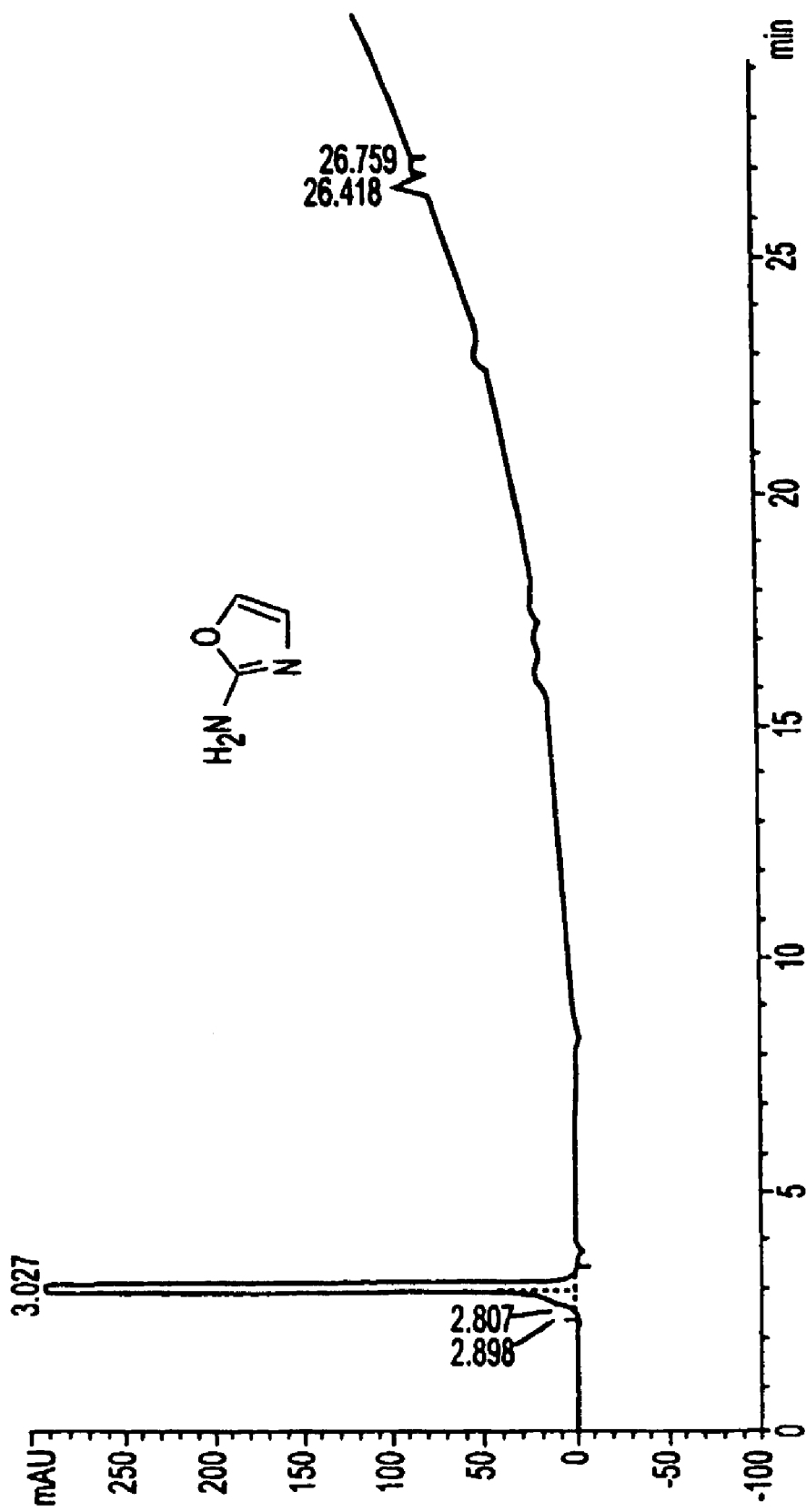
Figure 2C:
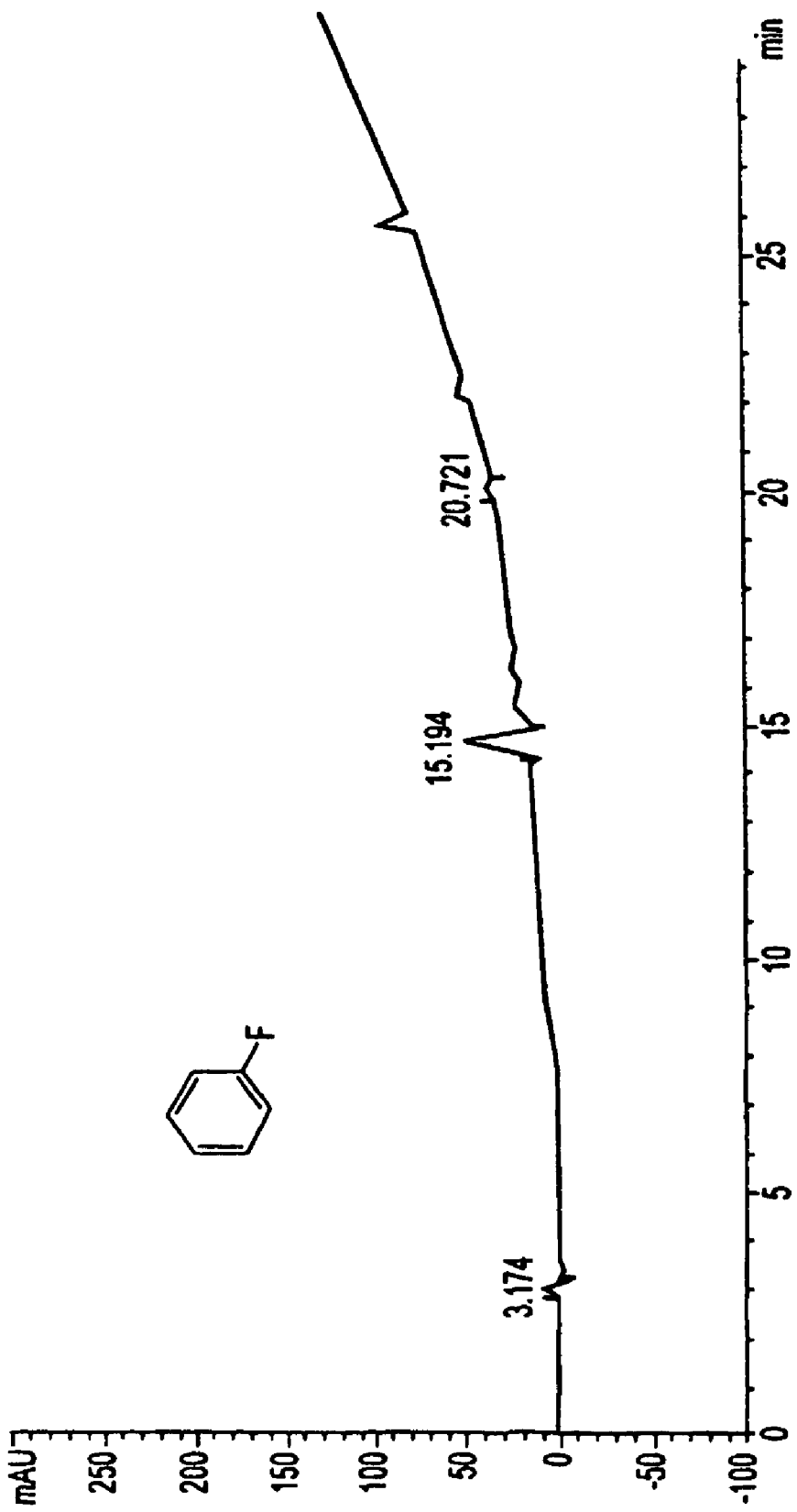
Figure 2D:
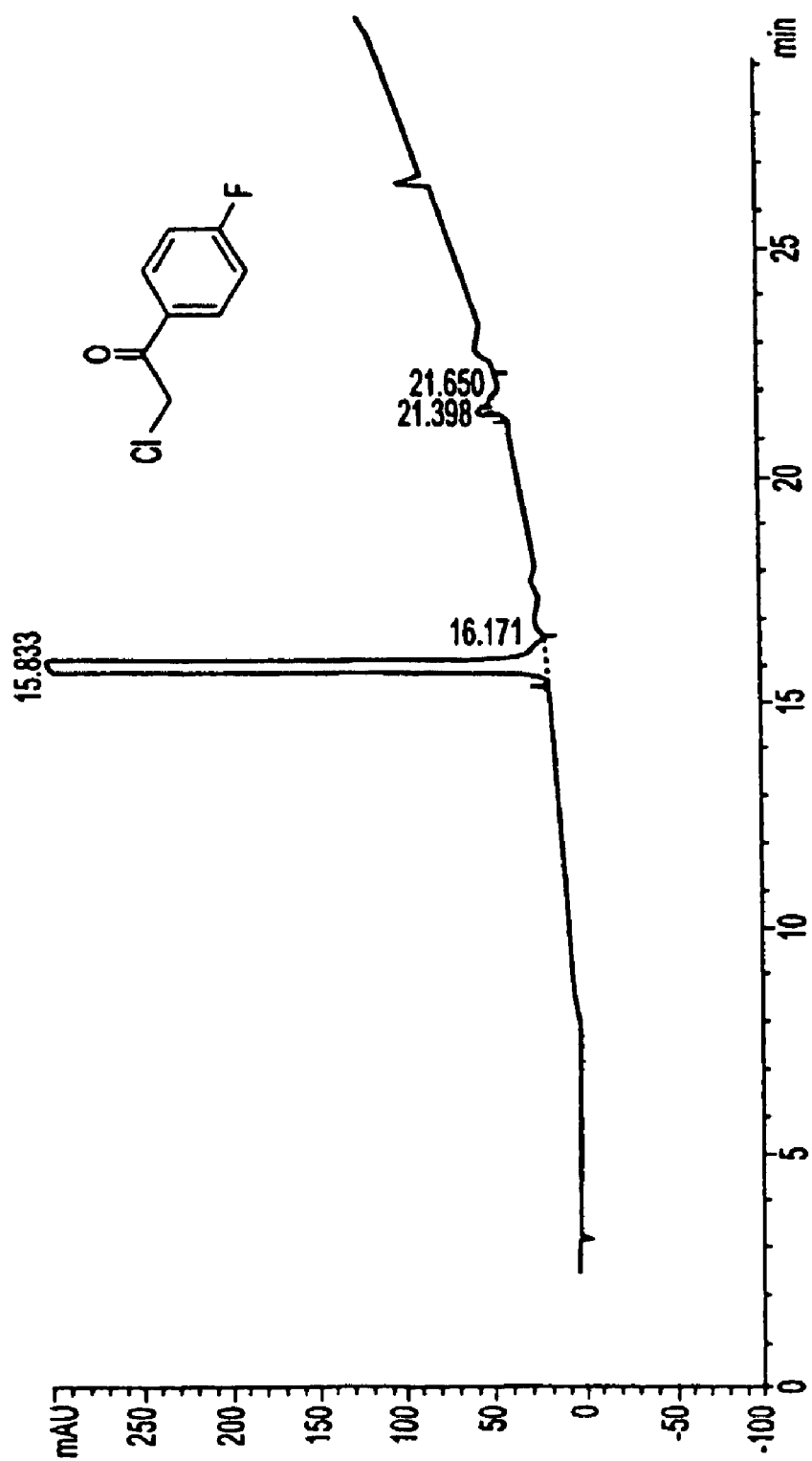
Figure 2E:
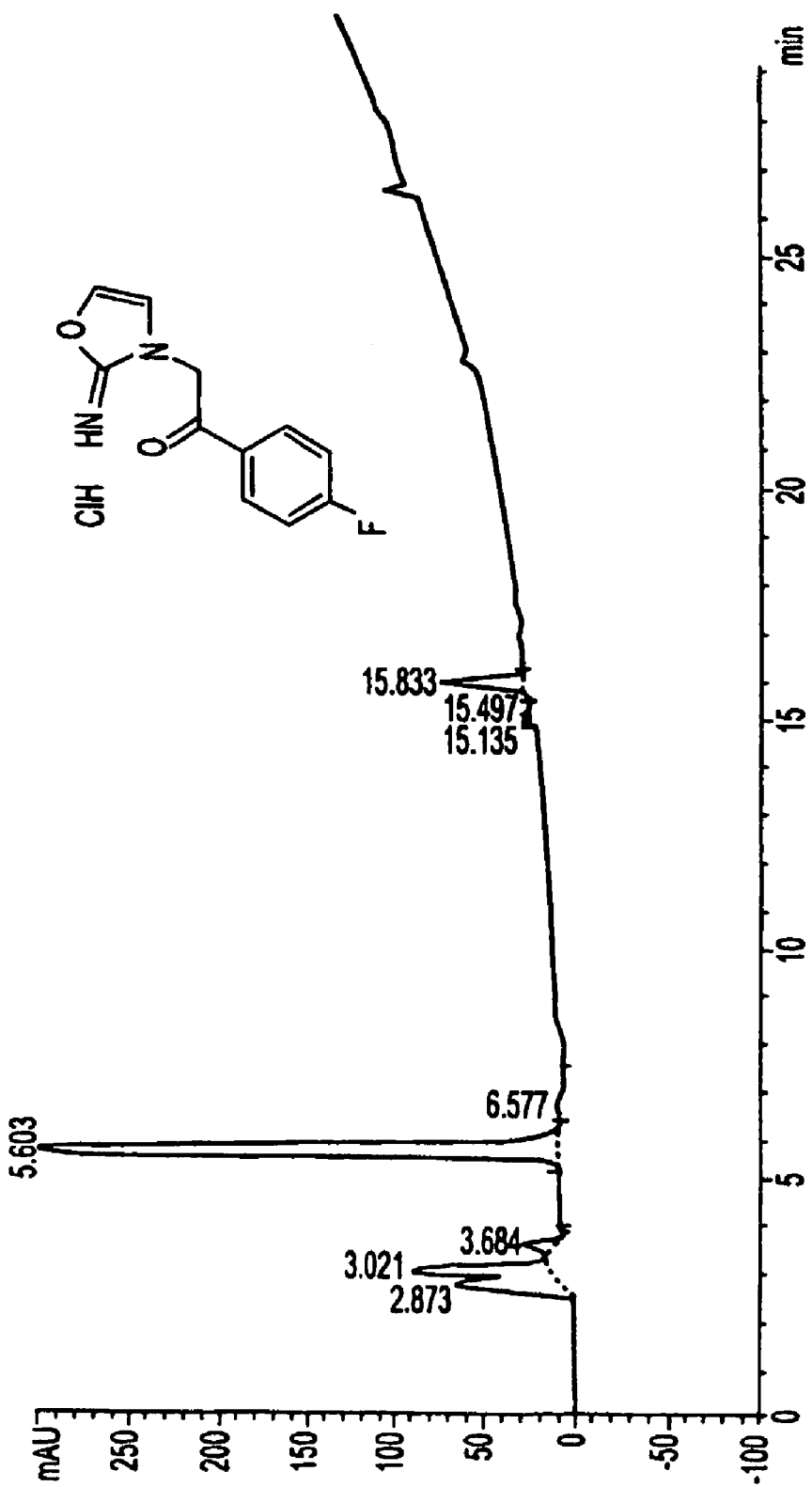
Figure 2F:
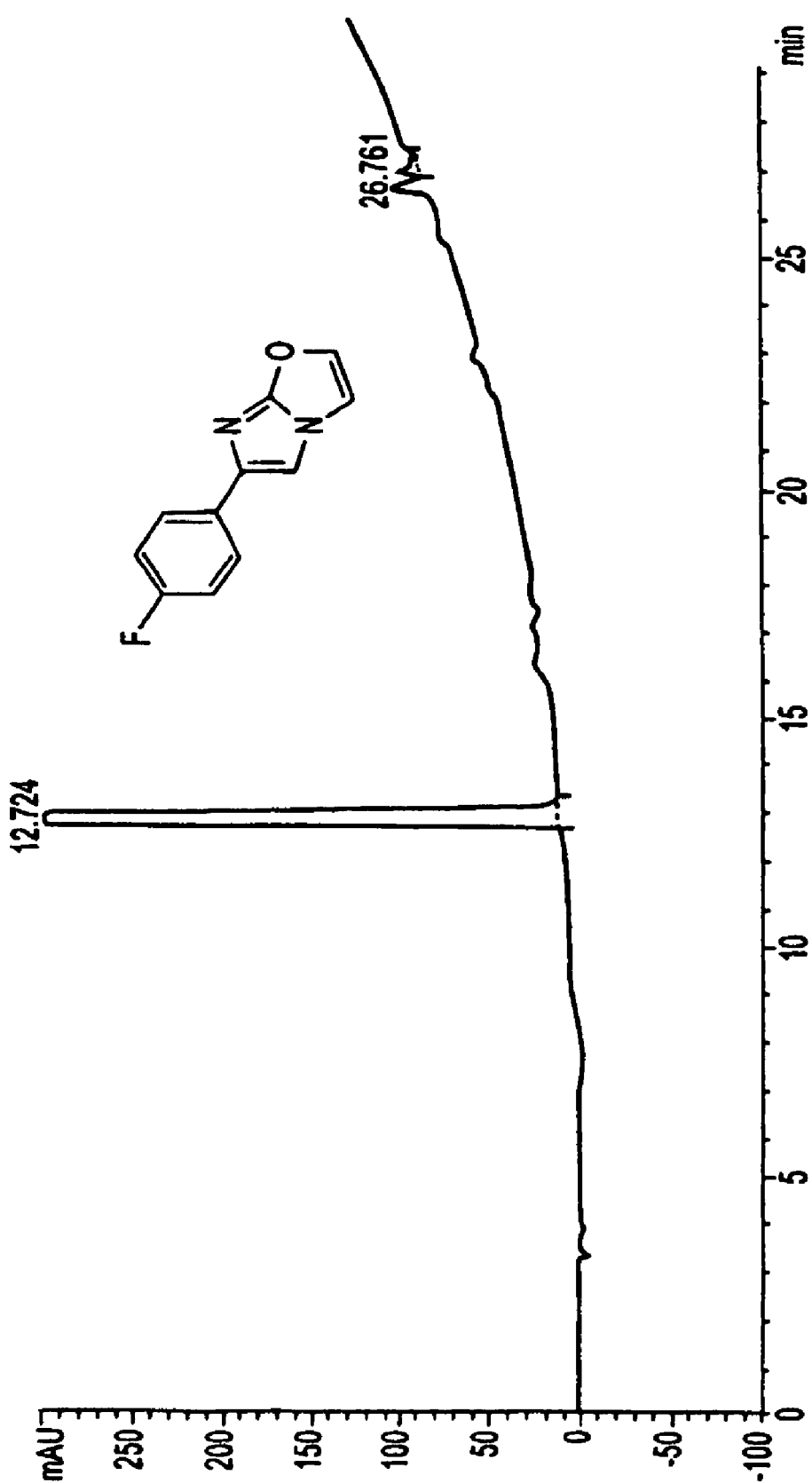
Figure 2G:
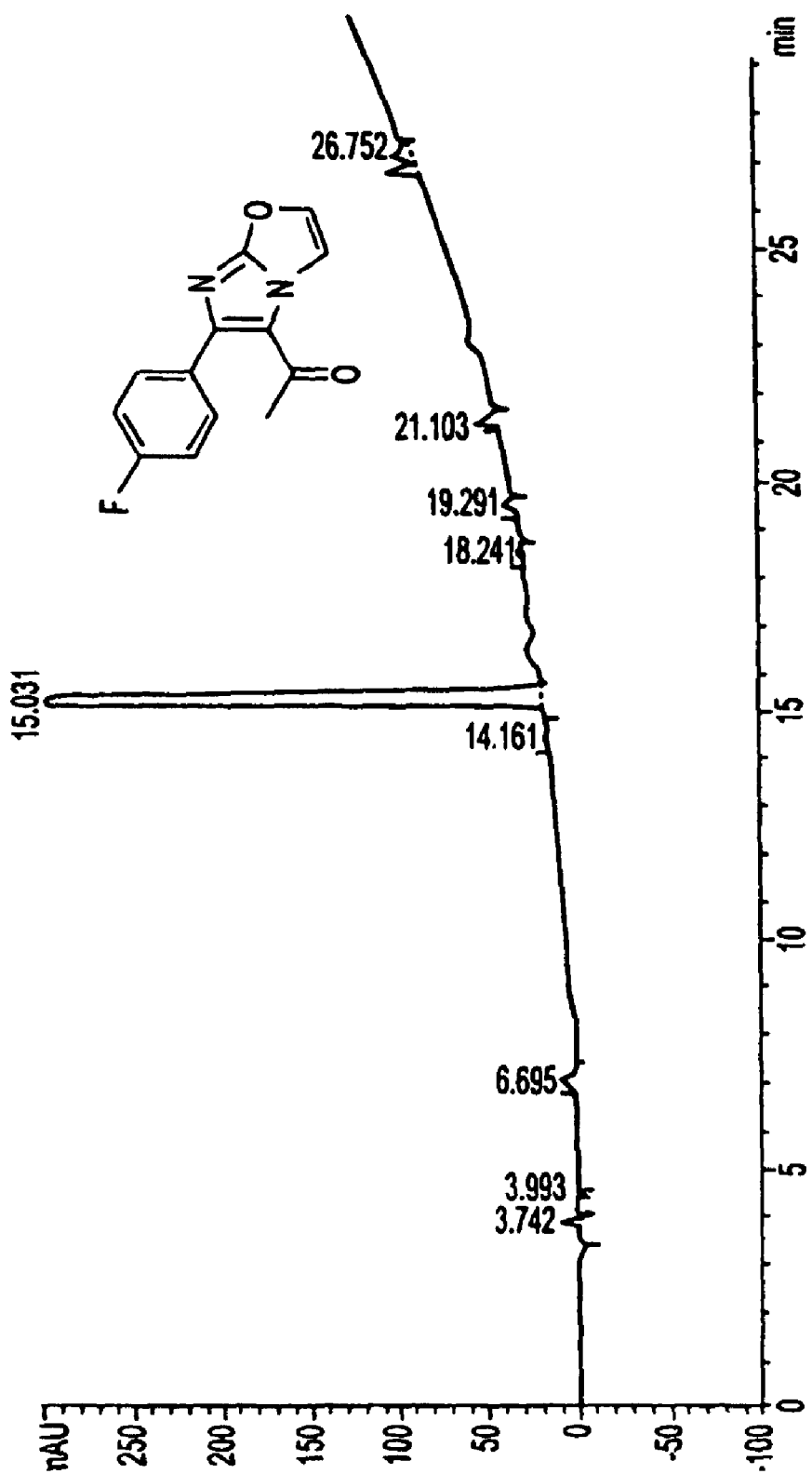
Figure 2H:
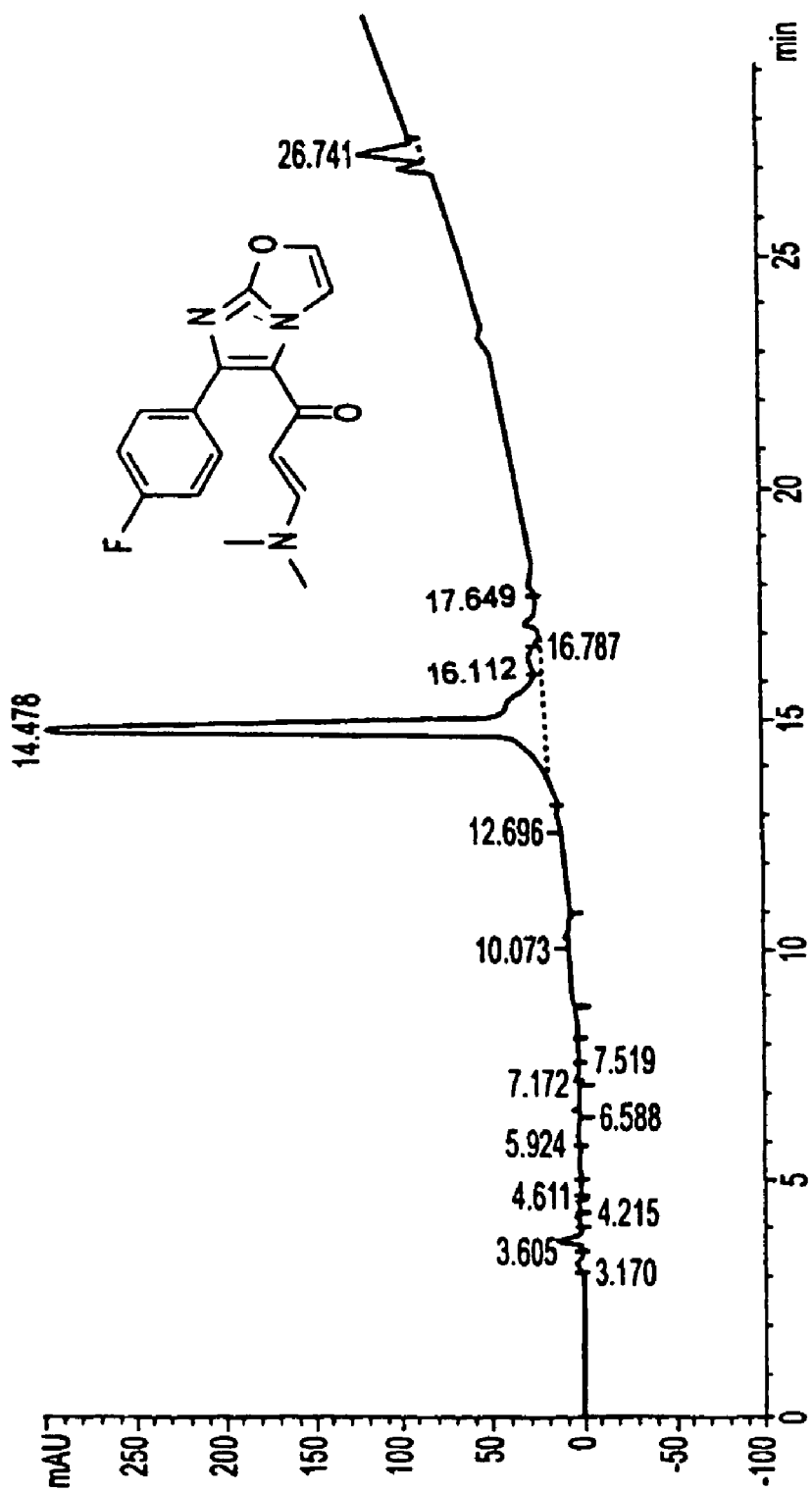
Figure 2I:
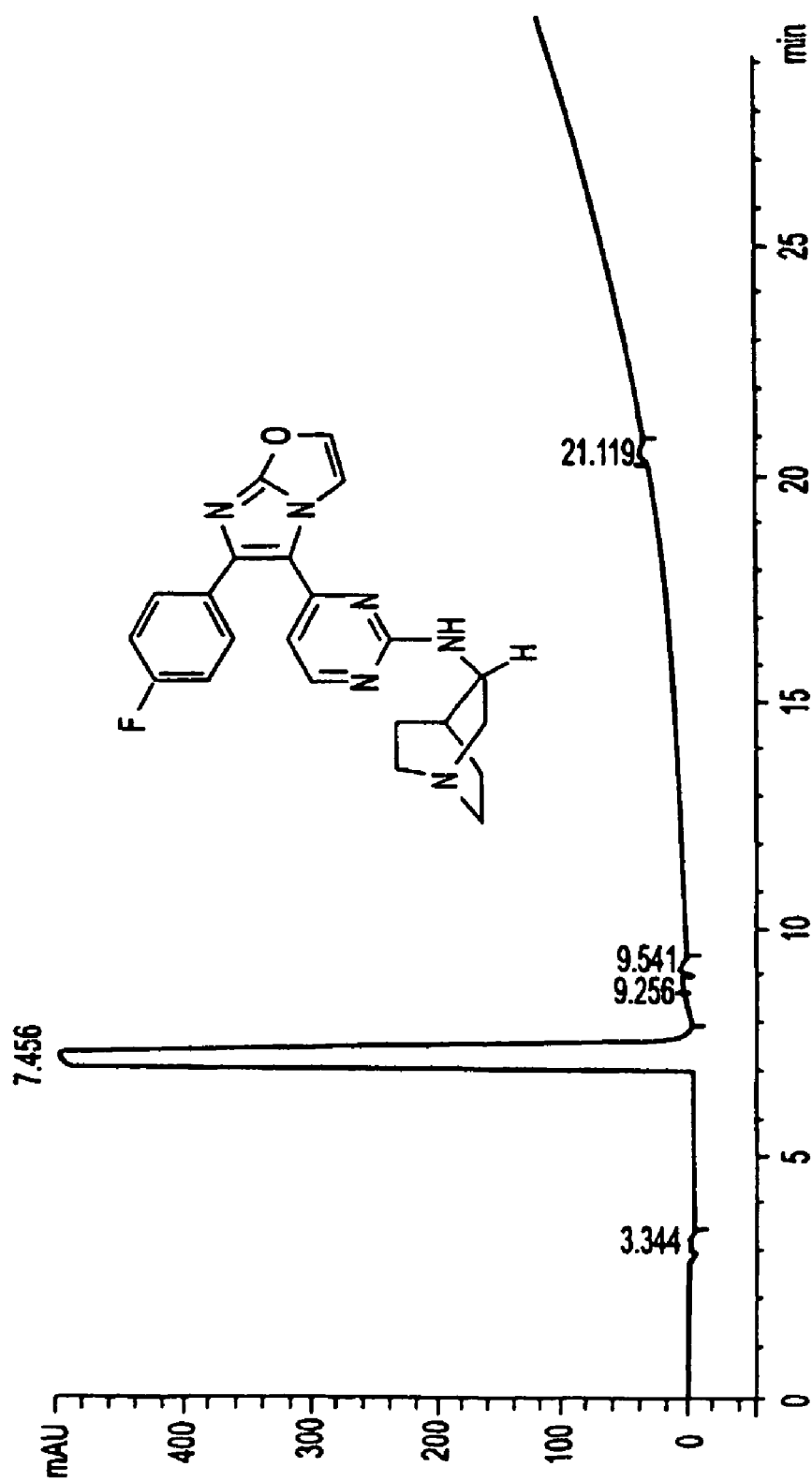
Figure 3A:
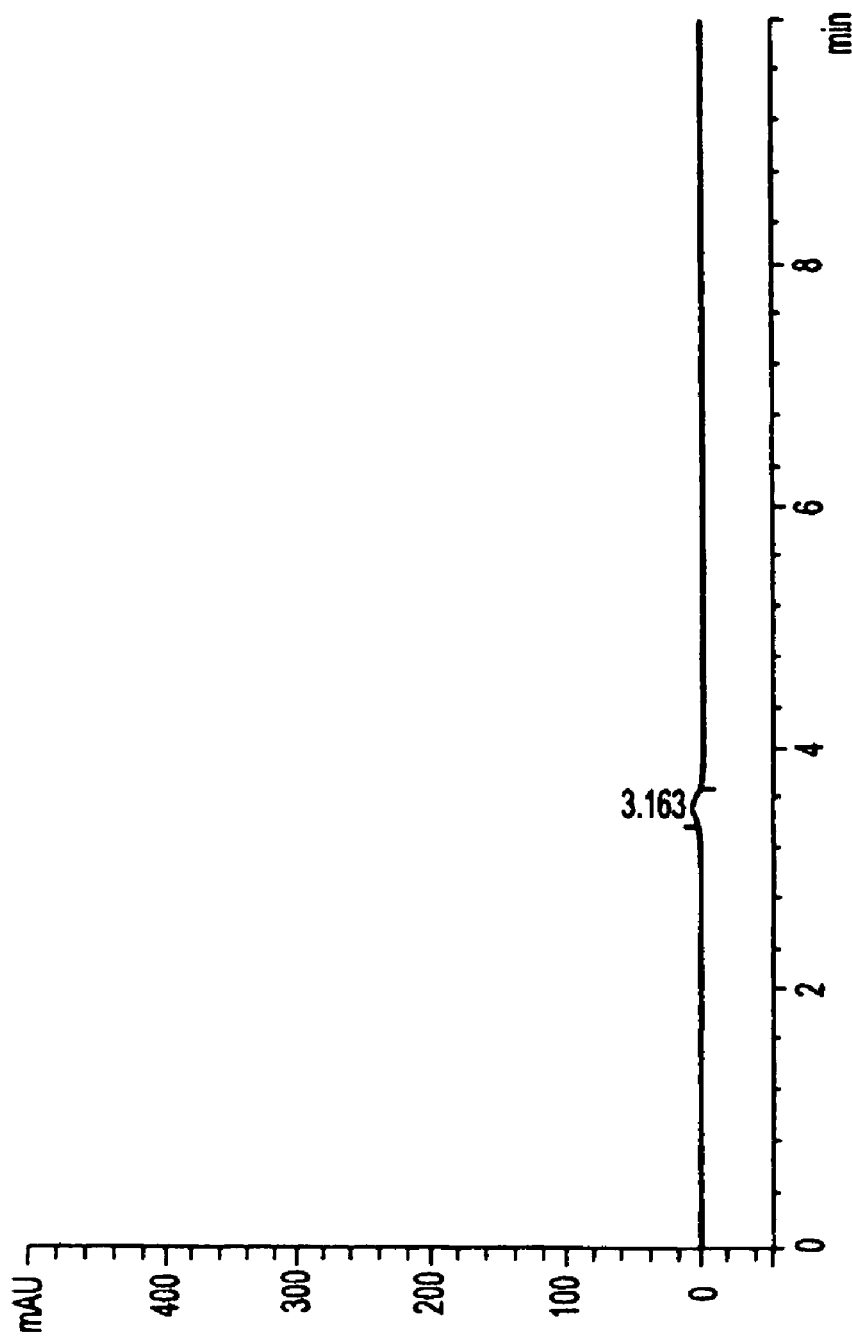
FIGS. 3A-3D.
Figure 3B:
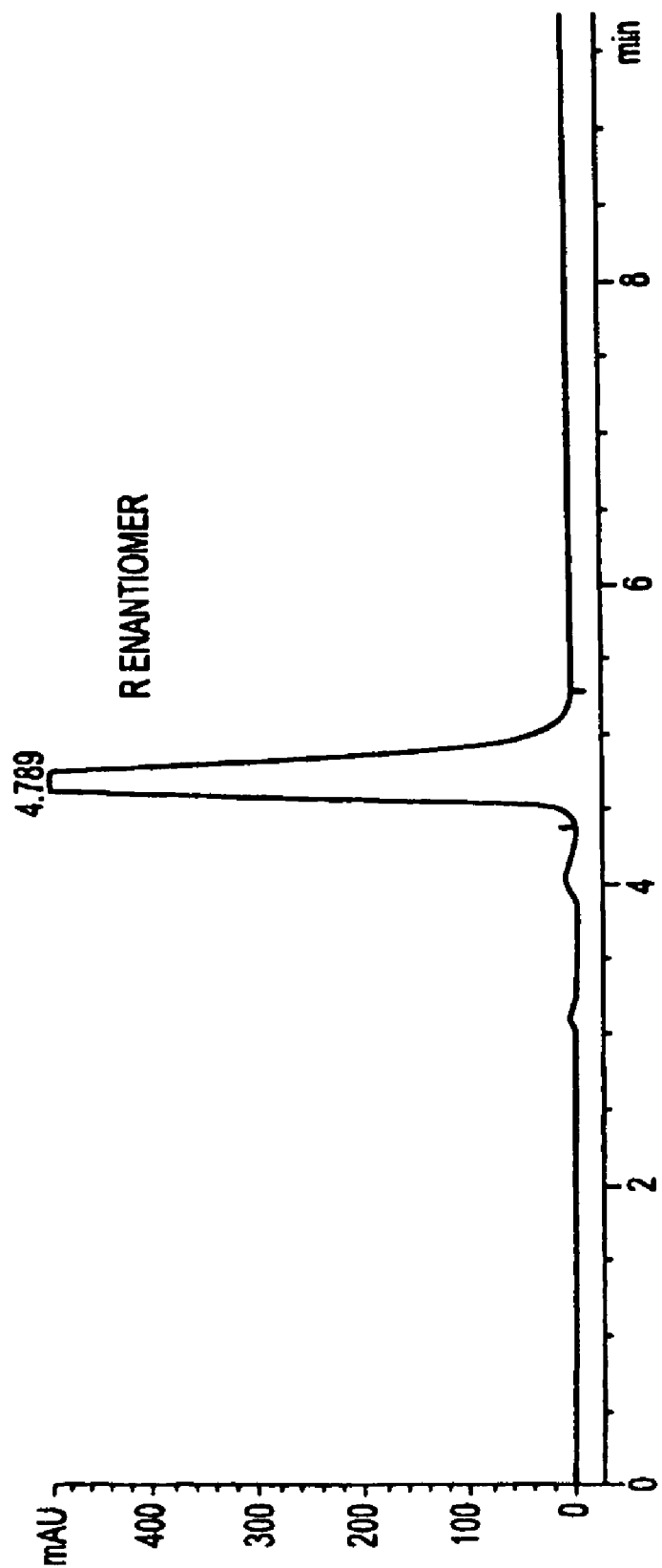
Figure 3C:
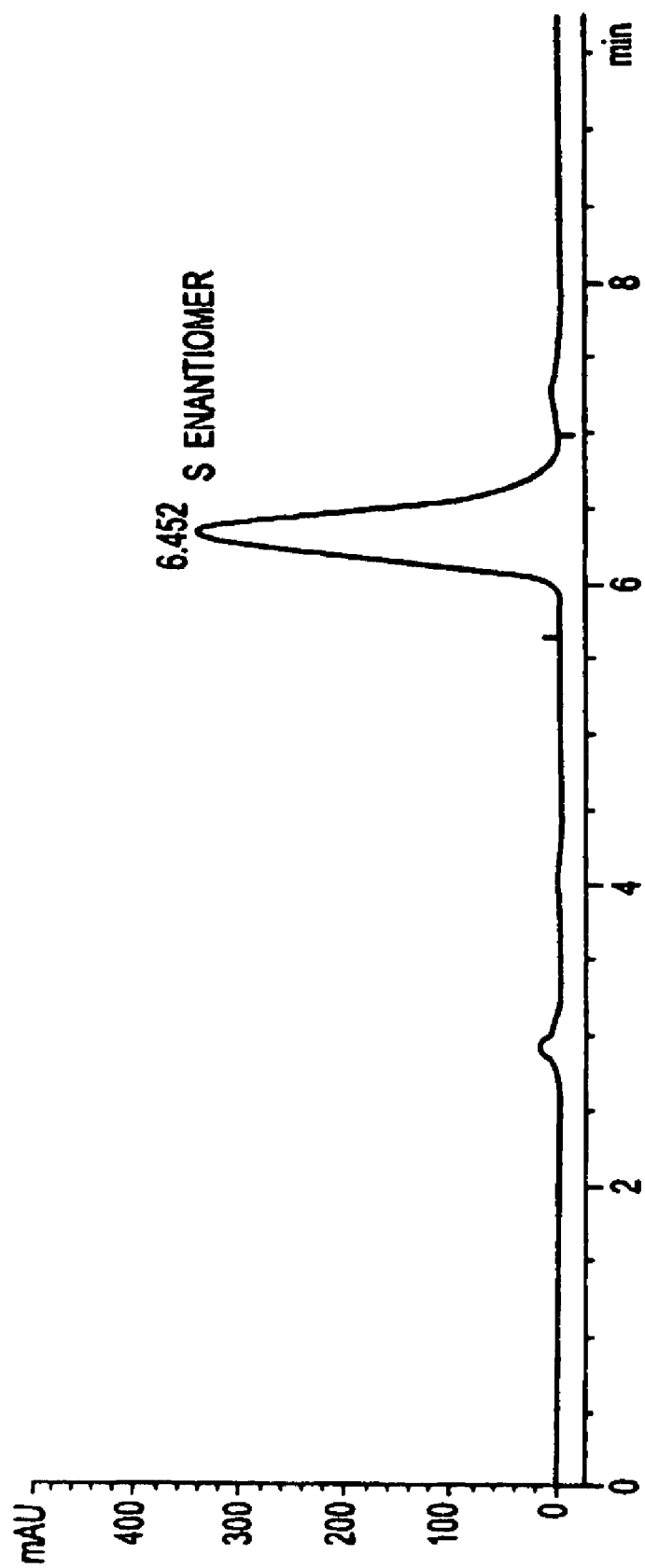
Figure 3D:
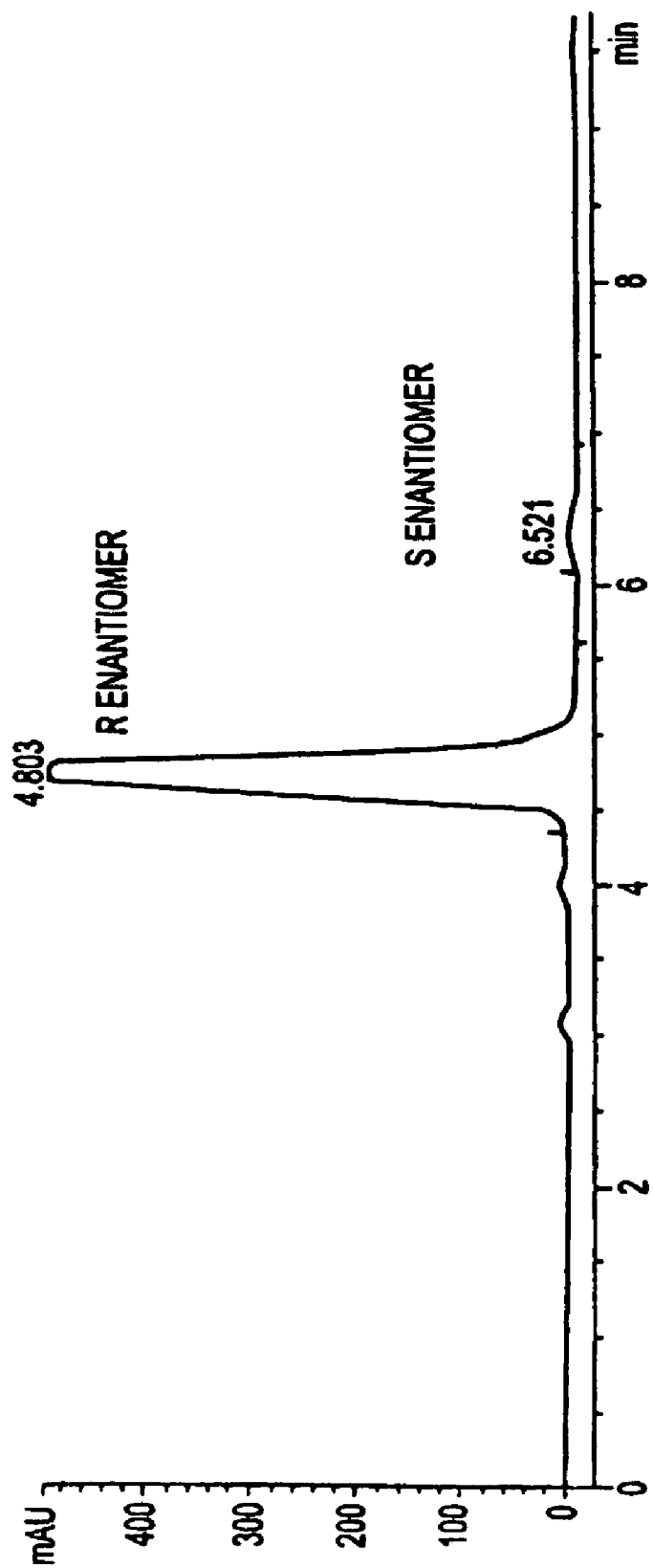

Chromatographic Analysis of (R)—N-{4-[6-(4-fluorophenyl)imidazo[2,1-b][1,3]oxazol-5-yl]pyrimidin-2-yl}quinuclidine-3-amine and Synthetic Intermediates Involved in its Preparation Chromatography of (R)—N-{4-[6-(4-fluorophenyl)imidazo[2,1-b][1,3]oxazol-5-yl]pyrimidin-2-yl}quinuclidine-3-amine and intermediates prepared in its synthesis is conducted on an Aligent 1100/1050 HPLC system employing a 250×4.6 mm Varian Intersil® phenyl-3 column, detection at 230 nm and a flow rate of 1.0 ml/min. Mobile phase component A consists of 0.1% aqueous triflouroacetic acid (TFA) and mobile phase component B consists of 50% acetonitrile (ACN) and 50% 0.1% aqueous TFA. Following column equilibration with a mobile phase consisting of 70% A and 30% B samples are loaded and the mobile phase composition is maintained for 4 minutes. Beginning at 4 minutes the column is eluted with a linear gradient increasing the proportion of component B in the mobile phase from 30% B to a final value of 100% B at 30 minutes. After eluting the column for 30 seconds with a mobile phase consisting of 100% component B, the mobile phase is returned to equilibration conditions (70% A and 30% B). The resulting chromatographic profiles, including integrated peak areas, are set forth in FIGS. 2A-2I. FIG. 2I indicates that the material isolated is greater than 99.7% of the title compound based upon measurement of the peak area versus total peak area.

Example 38

Chiral Chromatographic Analysis of (R)—N-{4-[6-(4-fluorophenyl)imidazo[2,1-b][1,3]oxazol-5-yl]pyrimidin-2-yl}quinuclidine-3-amine and (S)—N-{4-[6-(4-fluorophenyl)imidazo[2,1-b][1,3]oxazol-5-yl]pyrimidin-2-yl}quinuclidine-3-amine Chromatography of the indicated stereo isomers is conducted on an Aligent 1100/1050 HPLC system employing a 250×4.6 mm Chiralpak® OD-H column with detection at 235 nm. All HPLC determinations are carried out under isocratic conditions with a mobile phase consisting of 0.1% isopropyl amine in ethanol at a flow rate of 1 m/min. The results of the chromatographic profiles, including integrated peak areas, are set forth in FIG. 3. Analysis indicates the synthetic preparations of the respective enantiomers are free of contamination by the opposing optical isomer at the level of detection, and that the enantiomeric excess (ee) approaches or equals 99.99%.

Example 39

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol 39a: Preparation of 6-(3-methoxyphenyl)-imidazo[2,1-b]thiazole

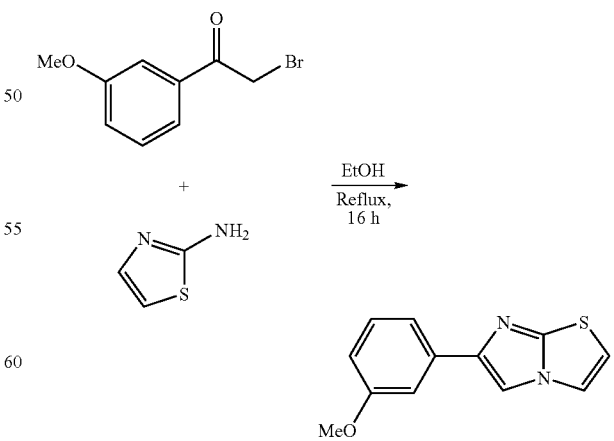

To a mixture of 2-aminothiazole (2.7 g, 0.0267 mol) and 2-bromo-3'-methoxyacetophenone (6.0 g, 0.0262 mol) is added absolute ethanol (100 ml). The reaction is allowed to reflux with vigorous stirring for 18 hours (checked by HPLC). The reaction mixture is reduced to half its original volume in vacuo. The remaining liquid is poured onto ice and the solution made basic by the addition of ammonium hydroxide solution (30%). The resulting fine solid is filtered and washed with water resulting in a dark yellow solid product. The solid product is dried in a vacuum oven at 50° C. to provide 6-(3-methoxyphenyl)-imidazo[2,1-b]thiazole (5.0 g, 81%). 400 MHz $^1$H NMR (DMSO-d$_6$) δ 8.18 (s, 1H), 7.88 (d, J=4.4 Hz, 1H), 7.36-7.42 (m, 2H), 7.28 (t, J=8.1 Hz, 1H), 7.22 (d, J=4.4 Hz, 1H), 6.82 (ddd, J=8.1, 2.6, 1.1 Hz, 1H), 3.80 (s, 3H). LCMS: 231 [M+H].

39b: Preparation of 1-[6-(3-methoxyphenyl)imidazo[2,1-b][1,3]thiazol-5-yl]ethanone

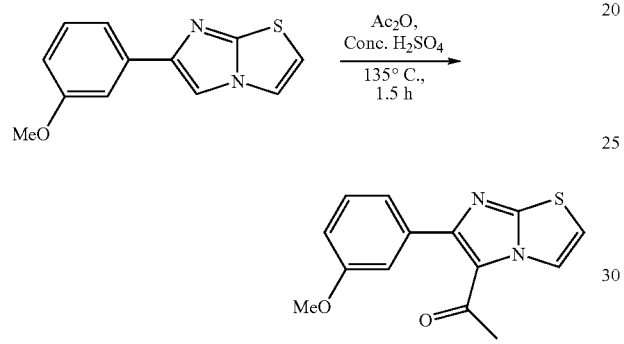

To a mixture of 6-(3-methoxyphenyl)-imidazo[2,1-b]thiazole (14.3 g, 62 mmol) and acetic anhydride (250 ml) is added 1 ml of concentrated sulfuric acid. The reaction mixture is heated at 140° C. for 4 hours. The reaction mixture is then poured onto 500 ml of ice, and diluted with 500 ml of water and the resulting mixture is extracted three times with 300 ml each of ethyl acetate. The combined extracts are washed with three portions of 100 ml of water and one portion of 200 ml of saturated aqueous sodium chloride solution. The organic phase is dried with magnesium sulfate, filtered and concentrated in vacuo, to give a brown oil (17.95 g). The product, -[6-(3-methoxyphenyl)imidazo[2,1-b][1,3]thiazol-5-yl]ethanone, is used directly in the next step. 400 MHz $^1$H NMR (DMSO-d$_6$) δ 8.43 (d, J=4.4 Hz, 1H), 7.55 (d, J=4.4 Hz, 1H), 7.42 (t, J=8.2 Hz, 1H), 7.16-7.2 (m, 2H), 7.04-7.1 (m, 1H), 3.81 (s, 3H), 2.13 (s, 3H). LCMS: 273 [M+H].

39c: Preparation of 3-(dimethylamino)-1-[6-(3-methoxyphenyl)imidazo[2,1-b][1,3]thiazol-5-yl]prop-2-en-1-one

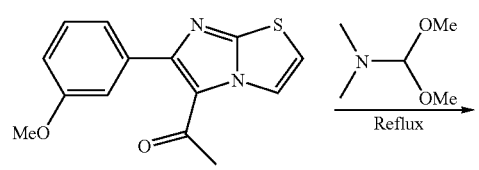

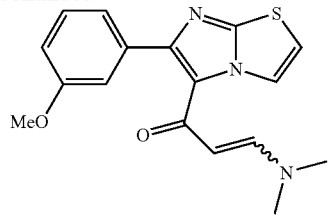

A 100 ml round bottom flask is charged with the 1-[6-3-methoxyphenyl)imidazo[2,1-b][1,3]thiazol-5-yl]ethanone (17.95 g, 62 mmol) and dimethylformamide dimethylacetal (120 ml). The mixture is refluxed for 72 hours and then cooled to room temperature. The mixture is concentrated in vacuo and the residue is purified by flash chromatography (ethyl acetate), giving a pale yellow solid (16.823 g). 300 MHz $^1$H NMR (DMSO-d$_6$) δ: 8.40 (d, J=4.4 Hz, 1H), 7.59 (d, J=12.5 Hz, 1H), 7.41 (d, J=4.4 Hz, 1H), 7.37 (t, J=7.7 Hz, 1H), 7.17-7.21 (m, 2H), 6.99-7.03 (m, 1H), 5.15 (d, J=12.5 Hz, 1H), 3.79 (s, 3H), 3.04 (s, 3H), 2.44 (s, 3H).

39d: Preparation of tert-butyl (3R)-3-{[(Z)-amino(imino)methyl]amino}piperidine-1-carboxylate Hydrochloride

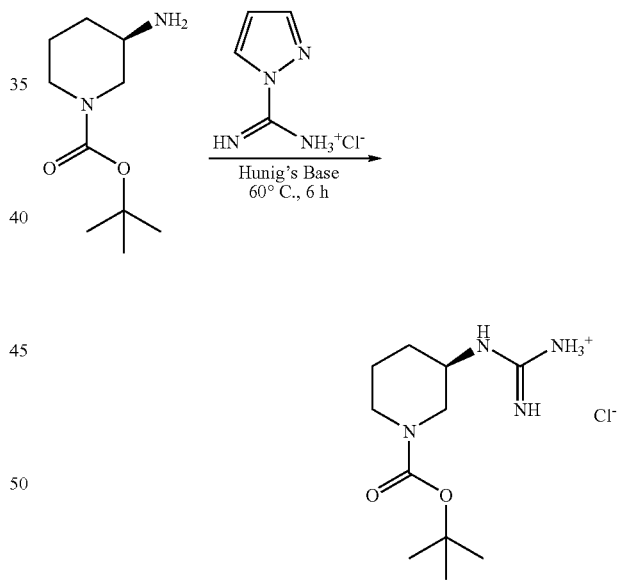

To a mixture of tert-butyl (3R)-3-aminopiperidine-1-carboxylate (10 g, 49.9 mmol) and pyrazole carboxamidine hydrochloride (7.31 g, 49.9 mmol) is added Hunig's base (8.72 ml, 49.9 mmol) and DMF (30 ml). The reaction is heated at 70° C. for 18 hours. The reaction is then cooled to room temperature and quenched by adding 700 ml of diethyl ether and stirring at room temperature for 24 hours. Product separates out as a white solid, which is filtered, washed, and dried (13 g, 94%). 400 MHz $^1$H NMR (DMSO-d$_6$) δ: 7.67 (d, J=8.8 HZ, 1H), 6.9-7.6 (br. s, 4H), 3.55 (br.s, 2H), 2.8-3.6 (m, 4H), 2.8-2.9 (m, 1H), 1.6-1.7 (m, 1H), 1.39 (s, 9H), 1.2-1.3 (m, 1H). LCMS: 243 [M+H].

39e: Preparation of tert-butyl (3R)-3-({4-[6-(3-methoxyphenyl)imidazo[2,1-b][1,3]thiazol-5-yl]pyrimidin-2-yl}amino)piperidine-1-carboxylate

39f: Preparation of 4-[6-(3-methoxyphenyl)imidazo[2,1-b][1,3]thiazol-5-yl]-N-[(3R)-piperidin-3-yl]pyrimidin-2-amine Hydrochloride

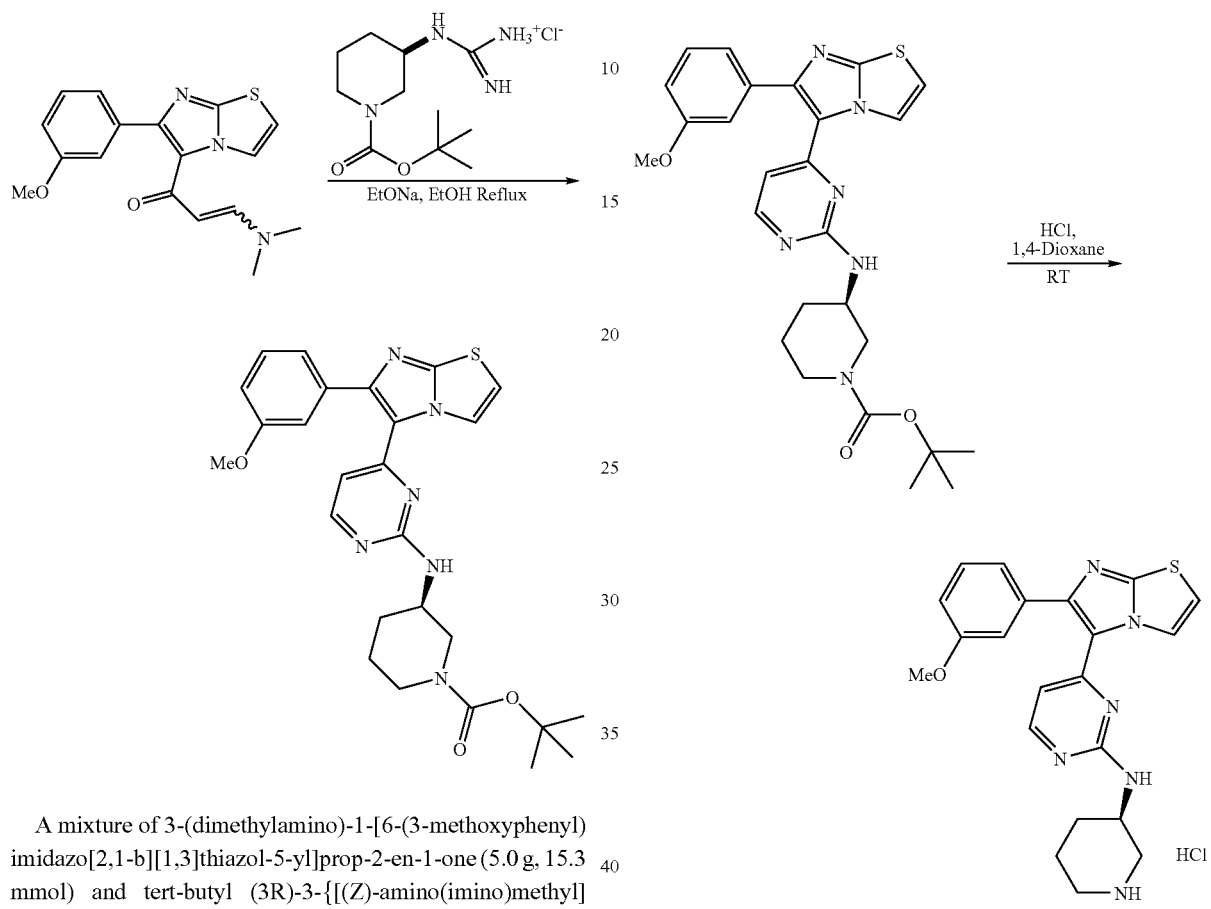

A mixture of 3-(dimethylamino)-1-[6-(3-methoxyphenyl)imidazo[2,1-b][1,3]thiazol-5-yl]prop-2-en-1-one (5.0 g, 15.3 mmol) and tert-butyl (3R)-3-{[(Z)-amino(imino)methyl]amino}piperidine-1-carboxylate hydrochloride (5.28 g, 18.95 mmol) is diluted with 60 ml of absolute ethanol and treated with 1.15 eq. of a 21% w/w solution of sodium ethoxide in ethanol (6.56 ml) to form a reaction mixture. The reaction mixture is heated to reflux for 24 hours. Volatiles are removed in vacuo and the residue is taken up in 250 ml of ethyl acetate and 250 ml of water. The phases are separated and the aqueous phase is extracted with 250 ml of ethyl acetate. The combined organic extracts are washed with 250 ml each of water, and then with a saturated sodium chloride solution (250 ml). The organic phase is dried with magnesium sulfate, filtered and concentrated in vacuo, to give a yellow oil. The product is purified by flash chromatography on silica gel (ethyl acetate/hexanes, 50%) to yield 7.2 g of a pale yellow solid (93%). 300 MHz $^1$H NMR (DMSO-$d_6$ at 80° C.) δ: 8.69 (d, J=3.5 Hz, 1H), 8.10 (d, J=5.3 Hz, 1H), 7.32-7.41 (m, 2H), 7.12-7.18 (m, 2H), 6.91-7.02 (m, 2H) 6.41 (d, J=5.3 Hz, 1H), 3.94 (br. d, J=7.0, 1H), 3.74-3.88 (m, 1H), 3.78 (s, 3H), 3.67 (br. d, J=13.2, 1H), 2.86-3.02 (m, 2H), 1.90-2.06 (m, 1H), 1.70-1.84 (m, 1H), 1.38-1.64 (m, 2H), 1.34 (s, 9H). LCMS: 507 [M+H].

The tert-butyl (3R)-3-({4-[6-(3-methoxyphenyl)imidazo[2,1-b][1,3]thiazol-5-yl]pyrimidin-2-yl}amino)piperidine-1-carboxylate (21 g, 41.5 mmol) is dissolved in 250 ml of dioxane and treated with 75 ml of anhydrous a four molar HCl in dioxane at room temperature (RT). The reaction mixture is stirred at room temperature for three hours. The mixture is then diluted with 350 ml of ether and stirred until product separates as a solid. Solid product is filtered and washed with ether. The solid is dissolved in MeOH (200 ml) and concentrated to dryness twice. The product is dried at high vacuum to yield 20.275 g of yellow solid (tris HCl salt) (90%). M.p.=220-225° C.; 300 MHz $^1$H NMR (DMSO-$d_6$ at 80° C.) δ: 9.6-9.3 (br. s, 2H), 8.9-8.4 (br. s, 2H), 8.82 (s, 1H), 8.11 (d, J=5.8 Hz, 1H), 7.50 (d, J=4.7 Hz, 1H), 7.39 (t, J=7.98 Hz, 1H), 7.2-7.1 (m, 2H), 7.08-7.0 (m, 1H), 6.49 (d, J=5.8 Hz, 1H), 4.4-4.3 (m, 1H), 3.79 (s, 3H), 3.39 (d, J=10.2 Hz, 1H), 3.16 (br. s, 1H), 3.05-2.7 (m, 2H), 2.2-1.6 (m, 3H), 1.55-1.2 (m, 1H). LCMS: 407 [M+H]; calc. for $C_{21}H_{22}N_6OS$ 3.3 HCl 0.05 dioxane 0.3 methanol: C, 47.75; H, 5.01; N, 15.54; found. C, 47.73; H, 5.26; N, 15.55.

39g: Preparation of N-{(3R)-1-[(4-chlorophenyl) sulfonyl]piperidin-3-yl}-4-[6-(3-methoxyphenyl) imidazo[2,1-b][1,3]thiazol-5-yl]pyrimidin-2-amine

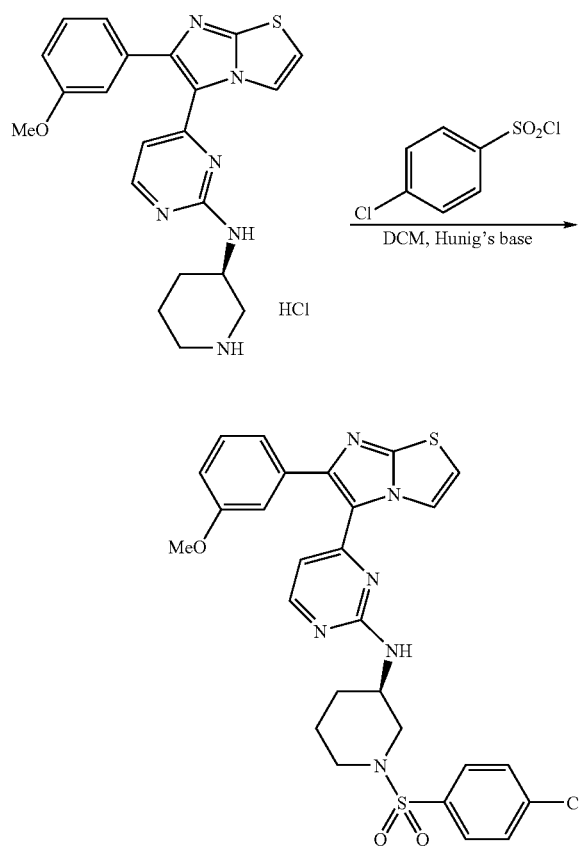

39h: Preparation of 3-{5-[2-({(3R)-1-[(4-chlorophenyl)sulfonyl]piperidin-3-yl}amino)pyrimidin-4-yl] imidazo[2,1-b][1,3]thiazol-6-yl}phenol

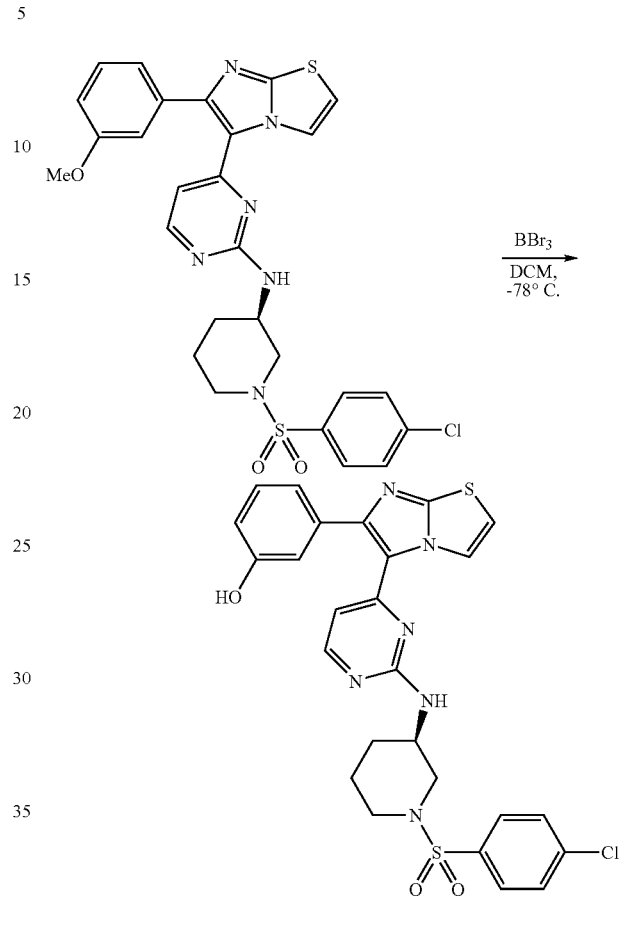

The 4-[6-(3-methoxyphenyl)imidazo[2,1-b][1,3]thiazol-5-yl]-N-[(3R)-piperidin-3-yl]pyrimidin-2-amine hydrochloride (6.81 g, 14.2 mmol) in methylene chloride (DCM) (60 ml) is cooled to 0° C. and is treated with Hunig's base (9.9 ml, 56.8 mmol). The mixture is kept at 0° C. for 30 minutes then the 4-chlorophenylsulfonyl chloride (3.3 g, 15.6 mmol) is added. The reaction mixture is stirred at room temperature overnight. The mixture is diluted with methylene chloride (100 ml) and is washed water (100 ml) and a saturated aqueous sodium chloride solution (100 ml). The organic phase is dried over sodium sulfate and concentrated in vacuo. The crude product is purified by flash chromatography using a gradient (ethyl acetate/hexanes, 40-100%), affording 6.98 g (85%) of the title compound as a pale yellow solid. 400 MHz $^1$H NMR (DMSO-$d_6$ at 60° C.) δ: 8.42 (br. s, 1H), 8.12 (d, J=5.1 Hz, 1H), 7.8-7.75 (m, 2H), 7.7-7.65 (m, 2H), 7.43-7.39 (m, 1H), 7.36 (d, J=7.8 Hz, 1H), 7.18-7.1 (m, 2H), 7.05-6.98 (m, 1H), 6.42 (d, J=5.1 Hz, 1H), 4.0-3.9 (m, 1H), 3.78 (s, 3H), 3.74 (d, J=11.7 Hz, 1H), 3.48 (d, J=11.7 Hz, 1H), 2.5-2.4 (m, 1H), 2.33 (t, J=5.3 Hz, 1H), 1.95-1.8 (m, 2H), 1.65-1.5 (m, 1H), 1.45-1.4 (m, 1H). LCMS: 581 [M+H].

The N-{(3R)-1-[(4-chlorophenyl)sulfonyl]piperidin-3-yl}-4-[6-(3-methoxy-phenyl)imidazo[2,1-b][1,3]thiazol-5-yl]pyrimidin-2-amine (6.98 g, 12.03 mmol) in methylene chloride (100 ml) is cooled to −78° C. and slowly treated with 1 molar solution of boron tribromide in methylene chloride (65 ml). The reaction mixture is kept at −78° C. for one hour then is allowed to warm to room temperature for two hours. The mixture is quenched by the addition of methanol (25 ml) at 0° C. and is stirred at room temperature for an additional hour. The mixture is diluted with methylene chloride (500 ml) and washed with three portions of 100 ml of saturated sodium bicarbonate solution, two portions of 100 ml of water and two portions of 100 ml of saturated sodium chloride solution. The organic phase is dried over sodium sulfate and concentrated in vacuo, giving a yellow foam. The crude product is recrystallized from methanol as a yellow solid (4.85 g, 71%). M.p.=174-177° C. 400 MHz $^1$H NMR (DMSO-$d_6$ at 60° C.) δ: 9.4 (br. s, 1H), 8.70 (br. s, 1H), 8.12 (d, J=5.5 Hz, 1H), 7.8-7.7 (m, 2H), 7.7-7.65 (m, 2H), 7.40 (d, J=4.7 Hz, 1H), 7.25 (t, J=8.0 Hz, 1H), 7.15 (d, J=7.4 Hz, 1H), 7.0-6.95 (m, 1H), 6.85-6.8 (m, 1H), 6.44 (d, J=5.5 Hz, 1H), 3.95 (br. s, 1H), 3.72 (dd, J=10.6 3.1 Hz, 1H), 3.40 (m, 1H), 2.5-2.4 (m, 1H), 2.35 (t, J=10.2 Hz, 1H), 2.0-1.8 (m, 2H), 1.65-1.5 (m, 1H), 1.46-1.32 (m, 1H). LCMS: 567 [M+H]. Calc. for $C_{26}H_{23}N_6O_3S_2Cl$ 0.5 water 1.0 methanol: C, 53.33; H, 4.64; N, 13.82; found. C, 53.32; H, 4.64; N, 13.82.

Example 40

Preparation of N-butyl-4-({4-[6-(4-fluorophenyl)imidazo[2,1-b][1,3]oxazol-5-yl]pyrimidin-2-yl}amino)piperidine-1-carboxamide

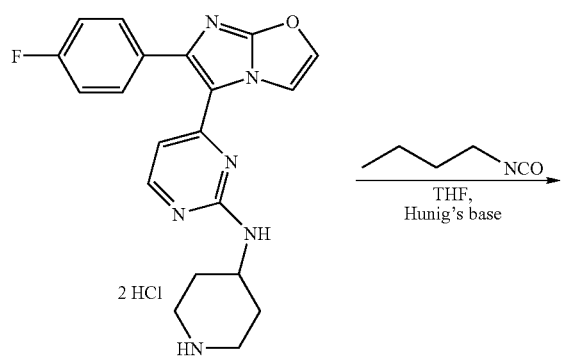

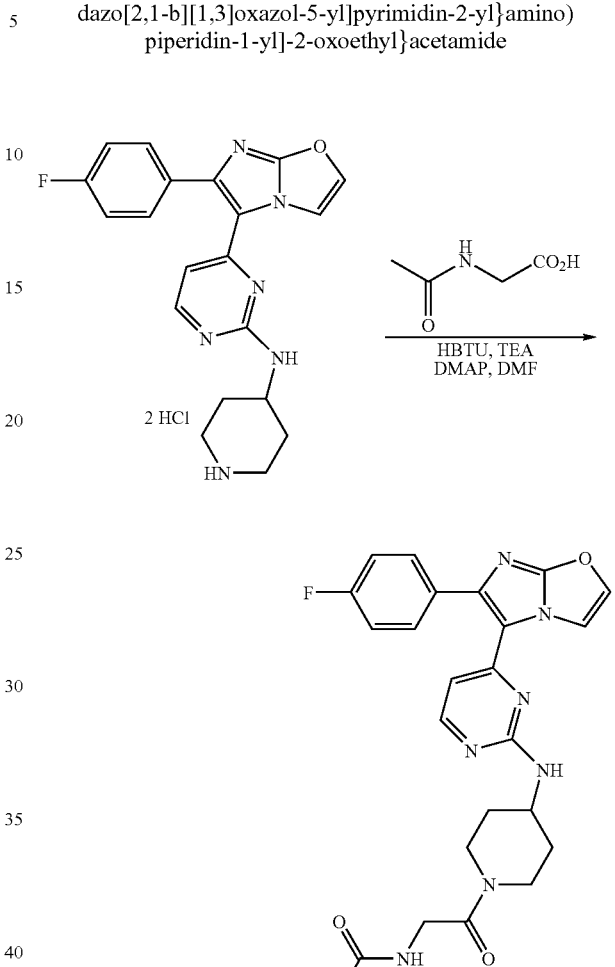

The 4-[6-(4-fluorophenyl)imidazo[2,1-b][1,3]oxazol-5-yl]-N-piperidin-4-ylpyrimidine-2-amine (bis HCl salt) (100 mg, 0.222 mmol) in tetrahydrofuran (5 ml) is treated with Hunig's base (240 ul), followed by butyl isocyanate (30 ul). The reaction mixture is stirred at room temperature for 18 hours. The mixture is quenched by the addition of water (15 ml) and extracted with ethyl acetate (10 ml). The organic phase is washed with one portion of 10 ml of saturated sodium chloride solution, dried over sodium sulfate and concentrated in vacuo. The product is purified by trituration in ether, giving 89 mg of a pale yellow solid (84%). M.p.=155-156° C. 400 MHz $^1$H NMR (DMSO-$d_6$) δ: 8.72 (br. s, 1H), 8.18 (br. s, 1H), 8.09 (d, J=5.5 Hz, 1H), 7.66-7.6 (m, 2H), 7.34-7.29 (m, 3H), 6.46 (t, J=5.3 Hz, 1H), 6.34 (br. s, 1H), 3.95-3.85 (m, 3H), 3.01 (q, J=6.4 Hz, 2H), 2.80 (t, J=11.5 Hz, 2H), 1.86 (d, J=10.6 Hz, 2H), 1.44-1.22 (m, 6H), 0.88 (t, J=7.2 Hz, 3H). LCMS: 478 [M+H]. Calc. for $C_{25}H_{28}N_7O_2F$ 0.02 water 0.34 ether: C, 62.93; H, 6.30; N, 19.49; found. C, 62.92; H, 6.55; N, 19.49.

Example 41

Preparation of N-{2-[4-({4-[6-(4-fluorophenyl)imidazo[2,1-b][1,3]oxazol-5-yl]pyrimidin-2-yl}amino)piperidin-1-yl]-2-oxoethyl}acetamide The 4-[6-(4-fluorophenyl)imidazo[2,1-b][1,3]oxazol-5-yl]-N-piperidin-4-ylpyrimidine-2-amine (bis HCl salt) (100 mg, 0.222 mmol) in dimethylformamide (4 ml) is treated with triethylamine (220 ul) and stirred until all solid is dissolved. The mixture is treated sequentially with the acetamido glycine (26 mg), HBTU (84 mg) and DMAP (27 mg). The reaction mixture is stirred at room temperature for 15 hours. The mixture is partitioned into ethyl acetate (10 ml) and water (10 ml). The phases are separated and the organic phase is washed with a saturated sodium carbonate solution (10 ml), water (10 ml) and a saturated sodium chloride solution (10 ml). The organic phase is dried over sodium sulfate and concentrated in vacuo. The crude product is purified by preparative chromatography plate (15% methanol/ethyl acetate), giving 78 mg of a pale yellow solid (74%). M.p.=235-237° C. 400 MHz $^1$H NMR (DMSO-$d_6$) δ: 8.73 (br. s, 1H), 8.18 (br. s, 1H), 8.10 (d, J=5.5 Hz, 1H), 7.98 (t, J=5.7 Hz, 1H), 7.66-7.6 (m, 2H), 7.38-7.28 (m, 3H), 6.36 (br. s, 1H), 4.26 (d, J=13.3 Hz, 1H), 4.05-3.87 (m, 3H), 3.82 (d, J=13.3 Hz, 1H), 3.15 (t, J=11.5 Hz, 1H), 2.83 (t, J=11.5 Hz, 1H), 2.0-1.9 (m, 2H), 1.87 (s, 3H), 1.5-1.2 (m, 2H). LCMS: 478 [M+H]. Calc. for C$_{24}$H$_{24}$N$_7$O$_3$F 0.44 water: C, 59.38; H, 5.17; N, 20.20; found. C, 59.38; H, 4.93; N, 20.47.

In addition to those examples of compounds prepared by the methods of this invention set forth above, the following non-limiting list of compounds prepared by the methods of this invention is set forth in Table I.

Exemplary compounds of the invention, include those listed in Table I.

| Number | Structure | Name | Melting Point (° C.) |
|---|---|---|---|
| 1 | 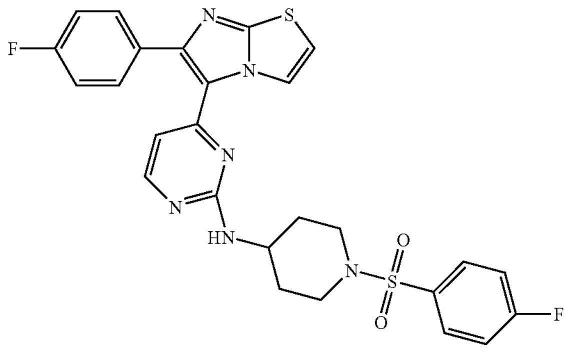 | 4-[6-(4-fluorophenyl)imidazo[2,1-b][1,3]thiazol-5-yl]-N-{1-[(4-fluorophenyl)sulfonyl]piperidin-4-yl}pyrimidin-2-amine | 259-260 |
| 2 | 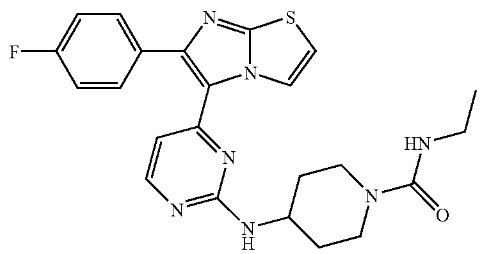 | N-ethyl-4-({4-[6-(4-fluorophenyl)imidazo[2,1-b][1,3]thiazol-5-yl]pyrimidin-2-yl}amino)piperadine-1-carboxamide | 145-147 |
| 3 | 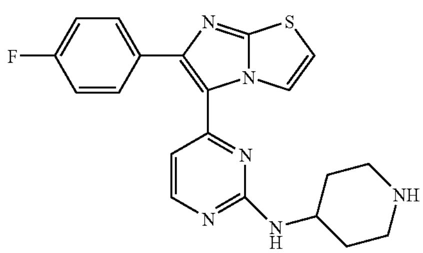 | 4-[6-(4-fluorophenyl)imidazo[2,1-b][1,3]thiazol-5-yl]-N-piperidin-4-ylpyrimidin-2-amine | 270 |
| 4 | 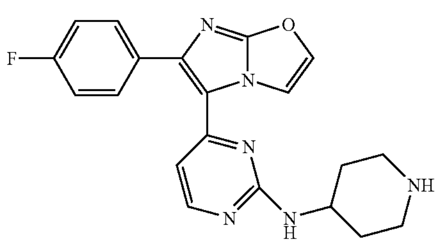 | 4-[6-(4-fluorophenyl)imidazo[2,1-b][1,3]oxazol-5-yl]-N-piperidin-4-ylpyrimidin-2-amine | 209-211 |
| 5 | 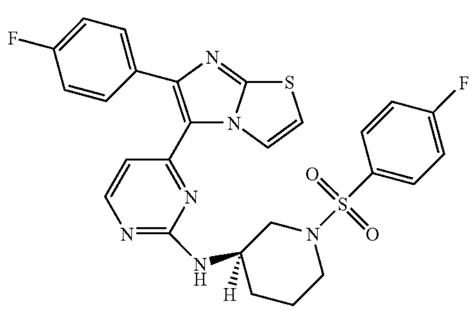 | 4-[6-(4-fluorophenyl)imidazo[2,1-b][1,3]thiazol-5-yl]-N-[(3R)-1-[(4-fluorophenyl)sulfonyl]piperidin-3-yl}pyrimidin-2-amine | 145-148 |

-continued

| Number | Structure | Name | Melting Point (° C.) |
|---|---|---|---|
| 6 | 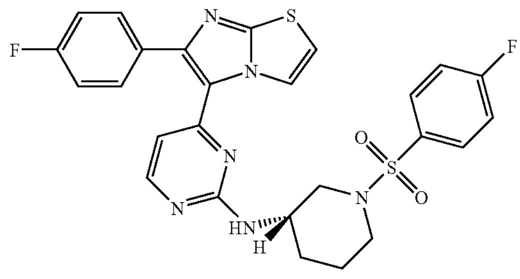 | 4-[6-(4-fluorophenyl)imidazo[2,1-b][1,3]thiazol-5-yl]-N-{(3S)-1-[(4-fluorophenyl)sulfonyl]piperidin-3-yl}pyrimidin-2-amine | 141-143 |
| 7 | 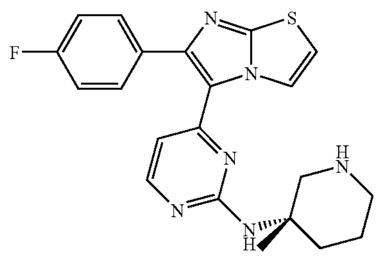 | 4-[6-(4-fluorophenyl)imidazo[2,1-b][1,3]thiazol-5-yl]-N-[(3S)-piperidin-3-yl]pyrimidin-2-amine | 208-210 |
| 8 | 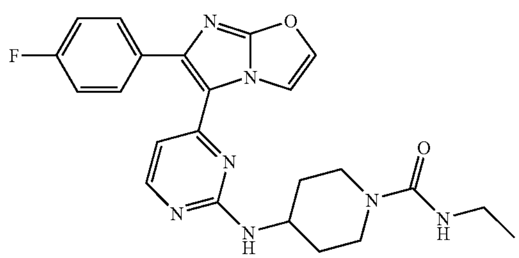 | N-ethyl-4-({4-[6-(4-fluorophenyl)imidazo[2,1-b][1,3]oxazol-5-yl]pyrimidin-2-yl}amino)piperidine-1-carboxamide | 110-112 |
| 9 | 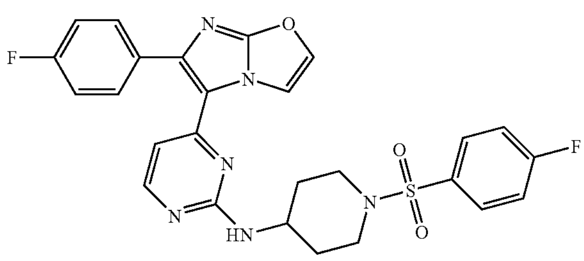 | 4-[6(4-fluorophenyl)imidazo[2,1-b][1,3]oxazol-5-yl]-N-{1-[(4-fluorophenyl)sulfonyl]piperidin-4-yl}pyrimidin-2-amine | 222-223 |
| 10 | 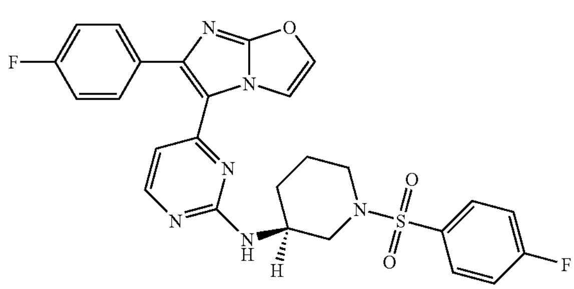 | 4-[6-(4-fluorophenyl)imidazo[2,1-b][1,3]oxazol-5-yl]-N-{(3R)-1-[(4-fluorophenyl)sulfonyl]piperidin-3-yl}pyrimidin-2-amine | 135-138 |

-continued

| Number | Structure | Name | Melting Point (° C.) |
|---|---|---|---|
| 11 | chiral | 4-[6-(4-fluorophenyl)imidazo[2,1-b][1,3]oxazol-5-yl]-N-[(3R)-piperidin-3-yl]pyrimidin-2-amine | 184-186 |
| 12 | chiral | 4-[6-(4-fluorophenyl)imidazo[2,1-b][1,3]oxazol-5-yl]-N-[(3S)-piperidin-3-yl]pyrimidin-2-amine | 202-205 |
| 13 | 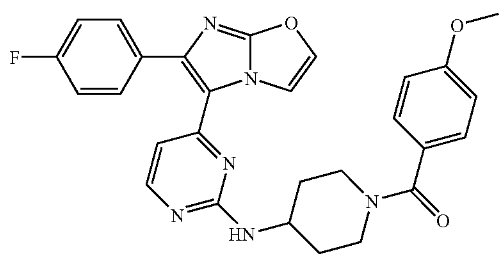 | 4-[6-(4-fluorophenyl)imidazo[2,1-b][1,3]oxazol-5-yl]-N-[1-(4-methoxybenzoyl)piperidin-4-yl]pyrimidin-2-amine | 196-197 |
| 14 | 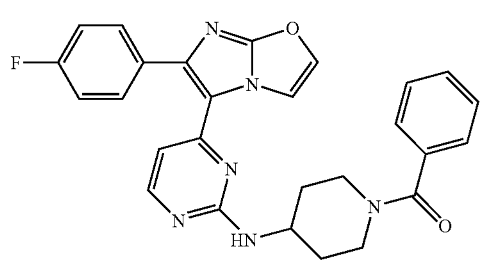 | N-(1-benzoylpiperidin-4-yl)-4-[6-(4-fluorophenyl)imidazo[2,1-b][1,3]oxazol-5-yl]pyrimidin-2-amine | 218-220 |
| 15 | 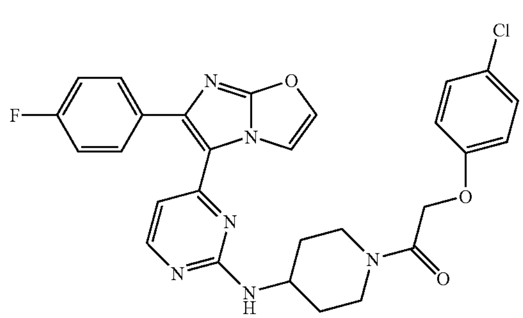 | N-{1-[(4-chlorophenoxy)acetyl]piperidin-4-yl}-4-[6-(4-fluorophenyl)imidazo[2,1-b][1,3]oxazol-5-yl]pyrimidin-2-amine | 209-210 |

-continued

| Number | Structure | Name | Melting Point (° C.) |
|---|---|---|---|
| 16 | 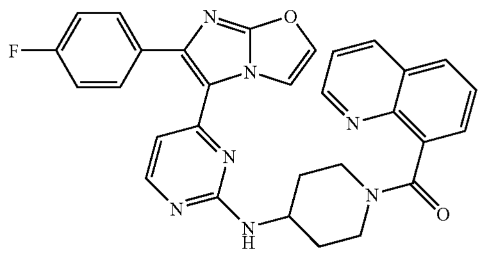 | 4-[6-(4-fluorophenyl)imidazo[2,1-b][1,3]oxazol-5-yl]-N-[1-(quinolin-8-ylcarbonyl)piperidin-4-yl]pyrimidin-2-amine | 254-256 |
| 17 | 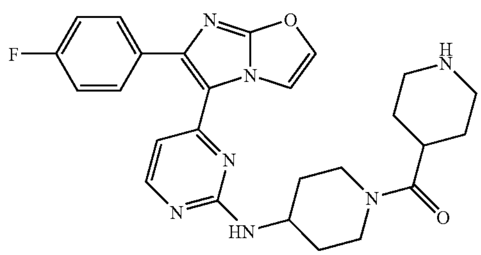 | 4-[6-(4-fluorophenyl)imidazo[2,1-b][1,3]oxazol-5-yl]-N-[1-(piperidin-4-ylcarbonyl)piperidin-4-yl]pyrimidin-2-amine | 209-212 |
| 18 | 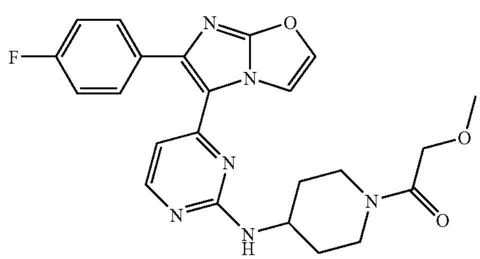 | 4-[6-(4-fluorophenyl)imidazo[2,1-b][1,3]oxazol-5-yl]-N-[1-(methoxyacetyl)piperidin-4-yl]pyrimidin-2-amine | 204-207 |
| 19 | 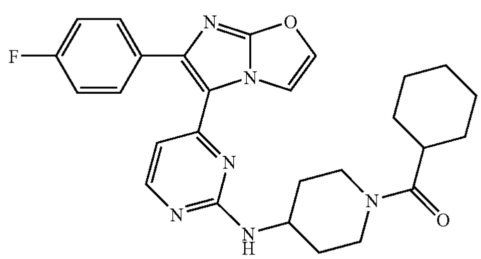 | N-[1-(cyclohexylcarbonyl)piperidin-4-yl]-4-[6-(4-fluorophenyl)imidazo[2,1-b][1,3]oxazol-5-yl]pyrimidin-2-amine | 115-119 |
| 20 | 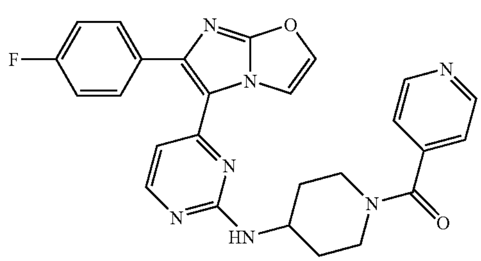 | 4-[6-(4-fluorophenyl)imidazo[2,1-b][1,3]oxazol-5-yl]-N-(1-isonicotinoylpiperidin-4-yl)pyrimidin-2-amine | 120-122 |
| 21 | 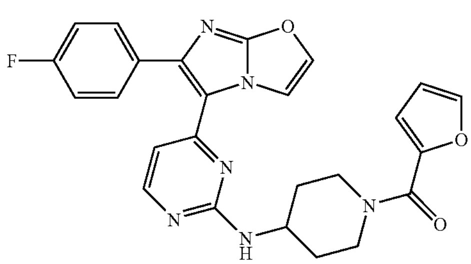 | 4-[6-(4-fluorophenyl)imidazo[2,1-b][1,3]oxazol-5-yl]-N-[1-(2-furoyl)piperidin-4-yl]pyrimidin-2-amine | 105-107 |

-continued

| Number | Structure | Name | Melting Point (° C.) |
|---|---|---|---|
| 22 | 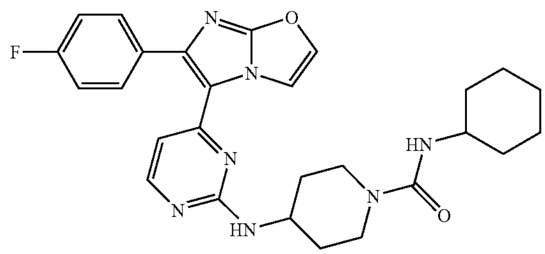 | N-cyclohexyl-4-({4-[6-(4-fluorophenyl)imidazo[2,1-b][1,3]oxazol-5-yl]pyrimidin-2-yl}amino)piperidine-1-carboxamide | 168-169 |
| 23 | 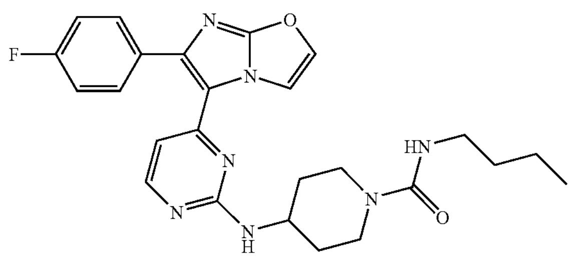 | N-butyl-4-({4-[6-(4-fluorophenyl)imidazo[2,1-b][1,3]oxazol-5-yl]pyrimidin-2-yl}amino)piperidine-1-carboxamide | 155-156 |
| 24 | 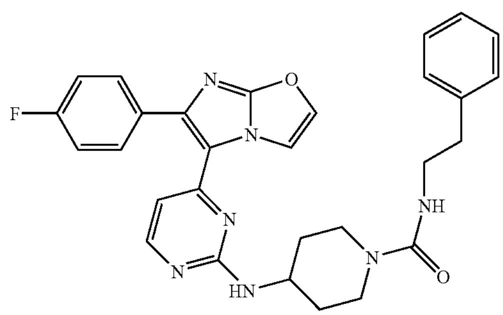 | 4-({4-[6-(4-fluorophenyl)imidazo[2,1-b][1,3]oxazol-5-yl]pyrimidin-2-yl}amino)-N-(2-phenylethyl)piperidine-1-carboxamide | 119-120 |
| 25 | 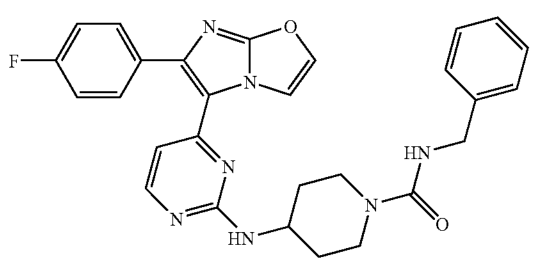 | N-benzyl-4-({4-[6-(4-fluorophenyl)imidazo[2,1-b][1,3]oxazol-5-yl]pyrimidin-2-yl}amino)piperidine-1-carboxamide | 124-126 |
| 26 | 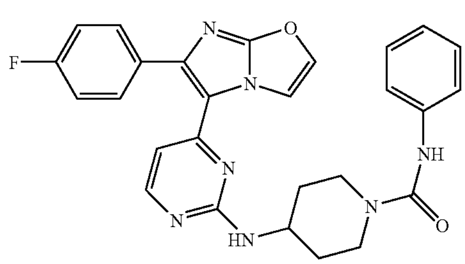 | 4-({4-[6-(4-fluorophenyl)imidazo[2,1-b][1,3]oxazol-5-yl]pyrimidin-2-yl}amino)-N-phenylpiperidine-1-carboxamide | 182-183 |

| Number | Structure | Name | Melting Point (° C.) |
|---|---|---|---|
| 27 | 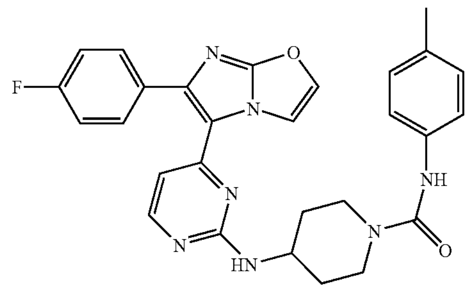 | 4-({4-[6-(4-fluorophenyl)imidazo[2,1-b][1,3]oxazol-5-yl]pyrimidin-2-yl}amino)-N-(4-methylphenyl)piperidine-1-carboxamide | 180-182 |
| 28 | 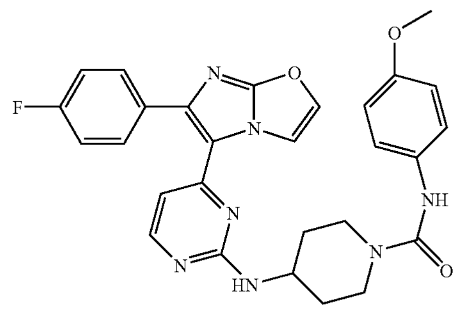 | 4-({4-[6-(4-fluorophenyl)imidazo[2,1-b][1,3]oxazol-5-yl]pyrimidin-2-yl}amino)-N-(4-methoxyphenyl)piperidine-1-carboxamide | 153-154 |
| 29 | 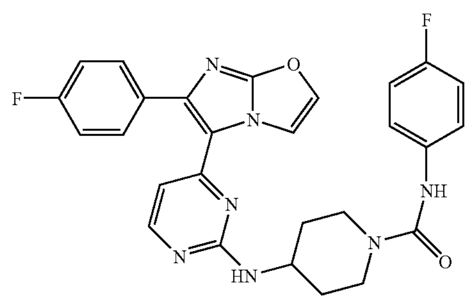 | N-(4-fluorophenyl)-4-({4-[6-(4-fluorophenyl)imidazo[2,1-b][1,3]oxazol-5-yl]pyrimidin-2-yl}amino)piperidine-1-carboxamide | 192-193 |
| 30 | 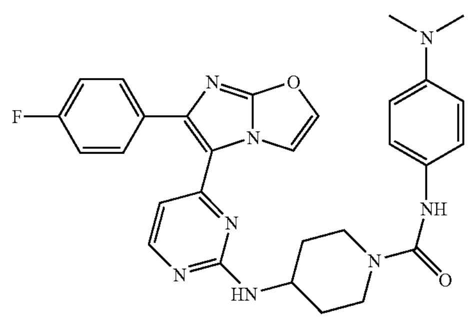 | N-[4-(dimethylamino)phenyl]-4-({4-[6-(4-fluorophenyl)imidazo[2,1-b][1,3]oxazol-5-yl]pyrimidin-2-yl}amino)piperidine-1-carboxamide | 225-227 |
| 31 | 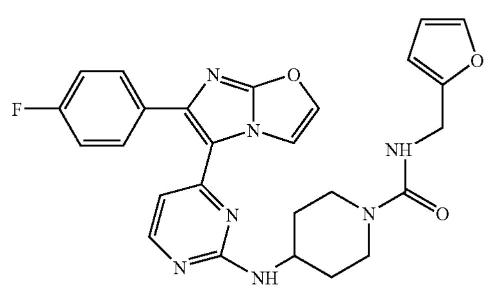 | 4-({4-[6-(4-fluorophenyl)imidazo[2,1-b][1,3]oxazol-5-yl]pyrimidin-2-yl}amino)-N-(2-furylmethyl)piperidine-1-carboxamide | 118-121 |

-continued

| Number | Structure | Name | Melting Point (° C.) |
|---|---|---|---|
| 32 | 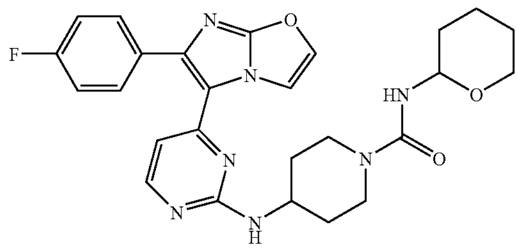 | 4-({4-[6-(4-fluorophenyl)imidazo[2,1-b][1,3]oxazol-5-yl]pyrimidin-2-yl}amino)-N-(tetrahydro-2H-pyran-2-yl)piperidine-1-carboxamide | 184-185 |
| 33 | 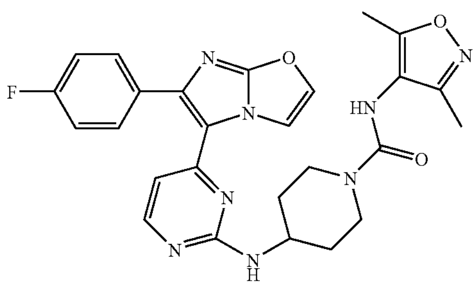 | N-(3,5-dimethylisoxazol-4-yl)-4-({4-[6-(4-fluorophenyl)imidazo[2,1-b][1,3]oxazol-5-yl]pyrimidin-2-yl}amino)piperidine-1-carboxamide | 208-210 |
| 34 | chiral | 4-[6-(4-fluorophenyl)imidazo[2,1-b][1,3]oxazol-5-yl]-N-{(3S)-1-[(4-fluorophenyl)sulfonyl]piperidin-3-yl}pyrimidin-2-amine | 115-117 |
| 35 | 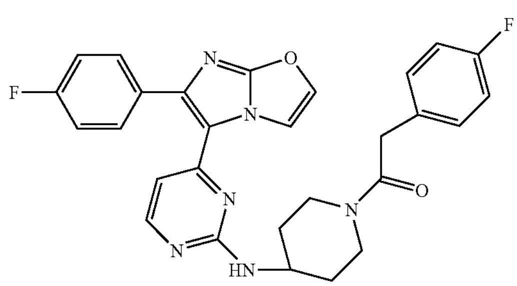 | N-{1-[(4-fluorophenyl)acetyl]piperidin-4-yl}-4-[6-(4-fluorophenyl)imidazo[2,1-b][1,3]oxazol-5-yl]pyrimidin-2-amine | 209-211 |
| 36 | 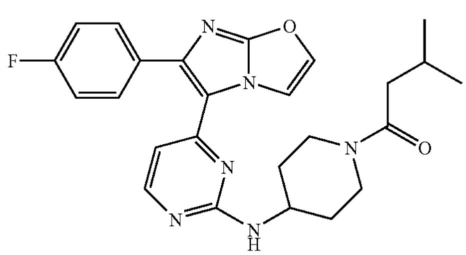 | 4-[6-(4-fluorophenyl)imidazo[2,1-b][1,3]oxazol-5-yl]-N-[1-(3-methylbutanoyl)piperidin-4-yl]pyrimidin-2-amine | 101-103 |

-continued

| Number | Structure | Name | Melting Point (° C.) |
|---|---|---|---|
| 37 | 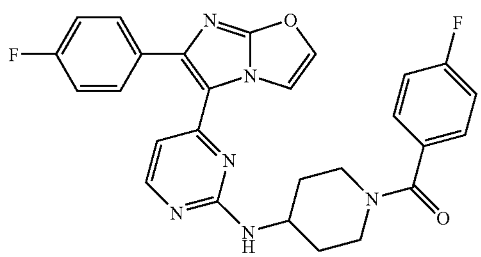 | N-[1-(4-fluorobenzoyl)piperidin-4-yl]-4-[6-(4-fluorophenyl)imidazo[2,1-b][1,3]oxazol-5-yl]pyrimidin-2-amine | 204-206 |
| 38 | 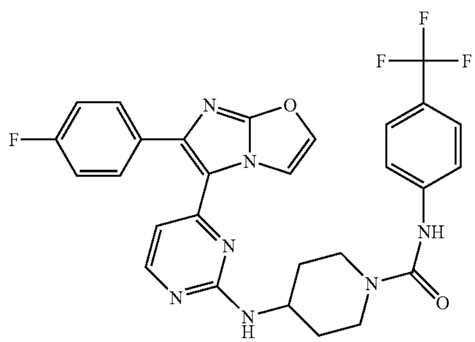 | 4-({4-[6-(4-fluorophenyl)imidazo[2,1-b][1,3]oxazol-5-yl]pyrimidin-2-yl}amino)-N-[4-(trifluoromethyl)phenyl]piperidine-1-carboxamide | 209-211 |
| 39 | 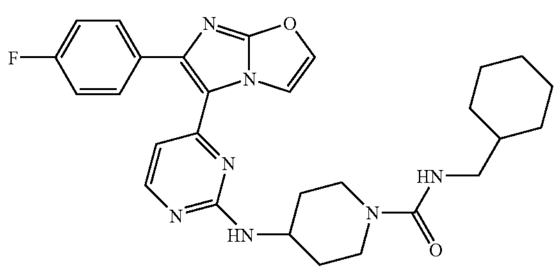 | N-(cyclohexylmethyl)-4-({4-[6-(4-fluorophenyl)imidazo[2,1-b][1,3]oxazol-5-yl]pyrimidin-2-yl}amino)piperidine-1-carboxamide | 127-130 |
| 40 | 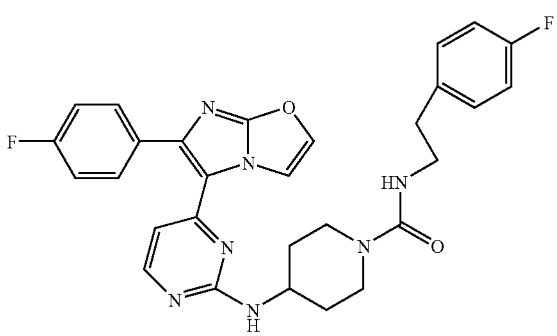 | N-[2-(4-fluorophenyl)ethyl]-4-({4-[6-(4-fluorophenyl)imidazo[2,1-b][1,3]oxazol-5-yl]pyrimidin-2-yl}amino)piperidine-1-carboxamide | 194-195 |
| 41 | 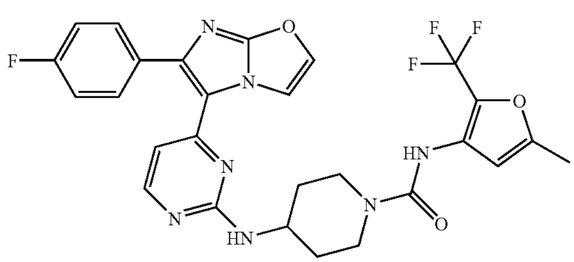 | 4-({4-[6-(4-fluorophenyl)imidazo[2,1-b][1,3]oxazol-5-yl]pyrimidin-2-yl}amino)-N-[5-methyl-2-(trifluoromethyl)-3-furyl]piperidine-1-carboxamide | 195-200 |

-continued

| Number | Structure | Name | Melting Point (° C.) |
|---|---|---|---|
| 42 | 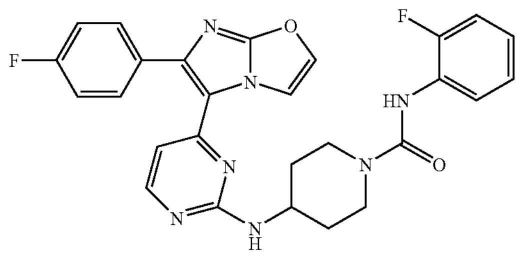 | N-(2-fluorophenyl)-4-({4-[6-(4-fluorophenyl)imidazo[2,1-b][1,3]oxazol-5-yl]pyrimidin-2-yl}amino)piperidine-1-carboxamide | 133-134 |
| 43 | 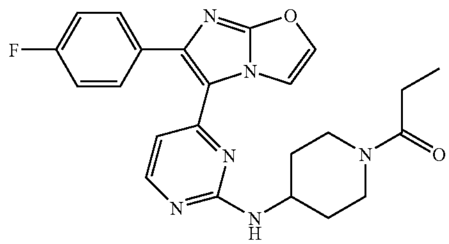 | 4-[6-(4-fluorophenyl)imidazo[2,1-b][1,3]oxazol-5-yl]-N-(1-propionylpiperidin-4-yl)pyrimidin-2-amine | 199-201 |
| 44 | 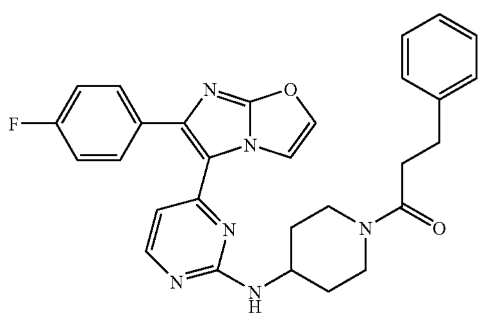 | 4-[6-(4-fluorophenyl)imidazo[2,1-b][1,3]oxazol-5-yl]-N-[1-(3-phenylpropanoyl)piperidin-4-yl]pyrimidin-2-amine | 144-146 |
| 45 | 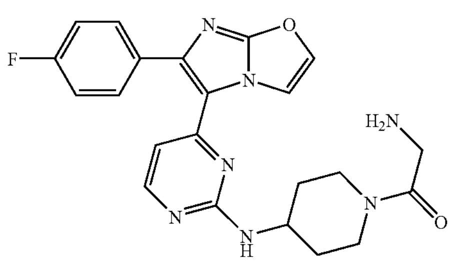 | N-[1-(aminoacetyl)piperidin-4-yl]-4-[6-(4-fluorophenyl)imidazo[2,1-b][1,3]oxazol-5-yl]pyrimidin-2-amine | 204-205 |
| 46 | 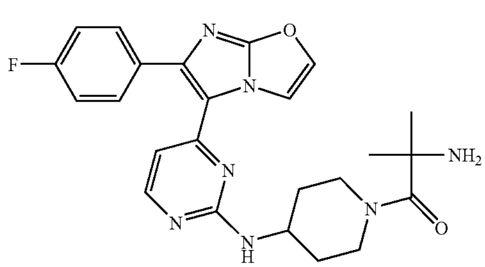 | N-[1-(2-amino-2-methylpropanoyl)piperidin-4-yl]-4-[6-(4-fluorophenyl)imidazo[2,1-b][1,3]oxazol-5-yl]pyrimidin-2-amine | 216-218 |

| Number | Structure | Name | Melting Point (° C.) |
| --- | --- | --- | --- |
| 47 | chiral | 4-[6-(4-fluorophenyl)imidazo[2,1-b][1,3]oxazol-5-yl]-N-(1-L-prolylpiperidin-4-yl)pyrimidin-2-amine | 198-202 |
| 48 | 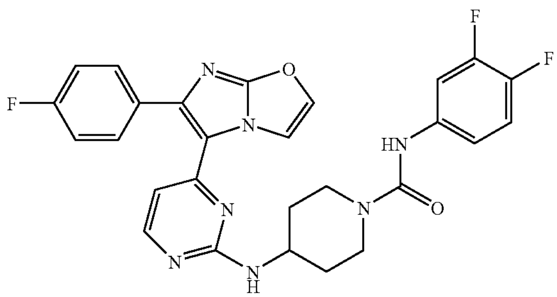 | N-(3,4-difluorophenyl)-4-({4-[6-(4-fluorophenyl)imidazo[2,1-b][1,3]oxazol-5-yl]pyrimidin-2-yl}amino)piperidine-1-carboxamide | 187-188 |
| 49 | 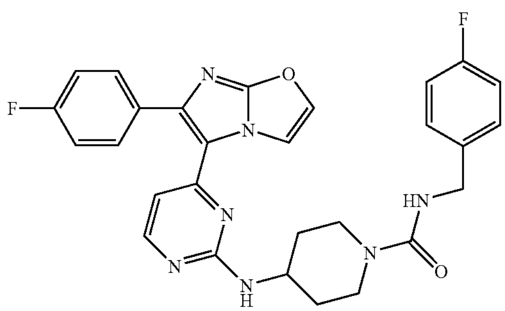 | N-(4-fluorobenzyl)-4-({4-[6-(4-fluorophenyl)imidazo[2,1-b][1,3]oxazol-5-yl]pyrimidin-2-yl}amino)piperidine-1-carboxamide | 115-118 |
| 50 | chiral | 4-({4-[6-(4-fluorophenyl)imidazo[2,1-b][1,3]oxazol-5-yl]pyrimidin-2-yl}amino)-N-[(1S)-1-phenylethyl]piperidine-1-carboxamide | 121-123 |

-continued

| Number | Structure | Name | Melting Point (° C.) |
|---|---|---|---|
| 51 | chiral | (4S)-4-amino-5-[4-({4-[6-(4-fluorophenyl)imidazo[2,1-b][1,3]oxazol-5-yl]pyrimidin-2-yl}amino)piperidin-1-yl]-5-oxopentanoic acid | 161-164 |
| 52 | 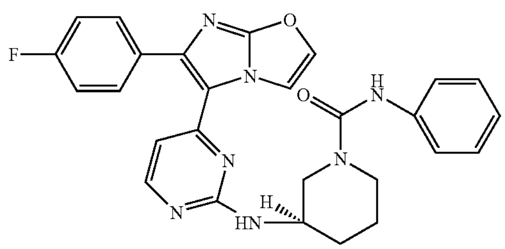 | (3R)-3-({4-[6-(4-fluorophenyl)imidazo[2,1-b][1,3]oxazol-5-yl]pyrimidin-2-yl}amino)-N-phenylpiperidine-1-carboxamide | 141-144 |
| 53 | 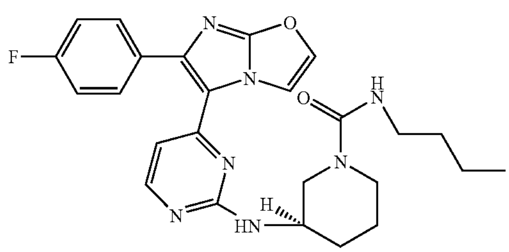 | (3R)-N-butyl-3-({4-[6-(4-fluorophenyl)imidazo[2,1-b][1,3]oxazol-5-yl]pyrimidin-2-yl}amino)piperidine-1-carboxamide | 108-111 |
| 54 | 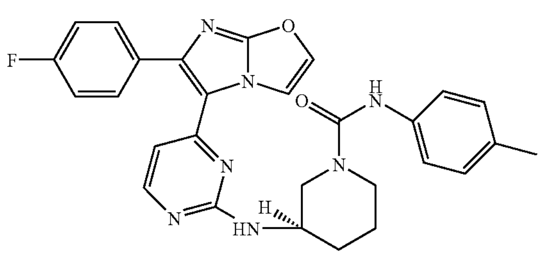 | (3R)-3-({4-[6-(4-fluorophenyl)imidazo[2,1-b][1,3]oxazol-5-yl]pyrimidin-2-yl}amino)-N-(4-methylphenyl)piperidine-1-carboxamide | 129-132 |
| 55 | 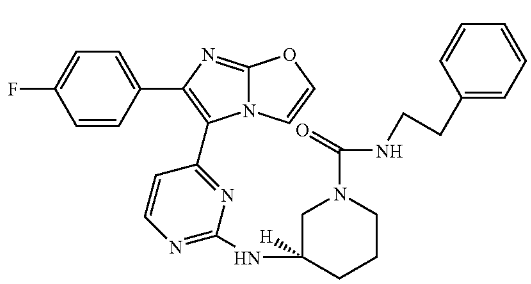 | (3R)-3-({4-[6-(4-fluorophenyl)imidazo[2,1-b][1,3]oxazol-5-yl]pyrimidin-2-yl}amino)-N-(2-phenylethyl)piperidine-1-carboxamide | 105-108 |

-continued

| Number | Structure | Name | Melting Point (° C.) |
|---|---|---|---|
| 56 | 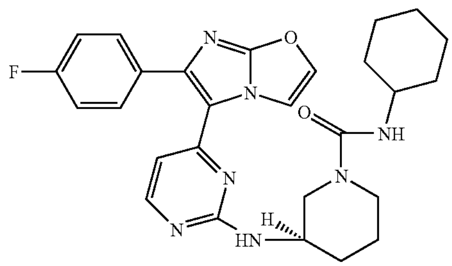 | (3R)-N-cyclohexyl-3-({4-[6-(4-fluorophenyl)imidazo[2,1-b][1,3]oxazol-5-yl]pyrimidin-2-yl}amino)piperidine-1-carboxamide | 130-132 |
| 57 | 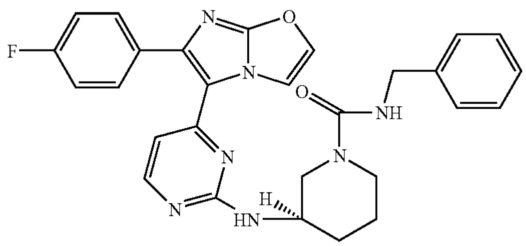 | (3R)-N-benzyl-3-({4-[6-(4-fluorophenyl)imidazo[2,1-b][1,3]oxazol-5-yl]pyrimidin-2-yl}amino)piperidine-1-carboxamide | 116-120 |
| 58 | 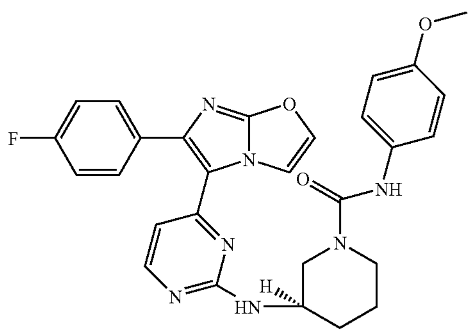 | (3R)-3-({4-[6-(4-fluorophenyl)imidazo[2,1-b][1,3]oxazol-5-yl]pyrimidin-2-yl}amino)-N-(4-methoxyphenyl)piperidine-1-carboxamide | 123-127 |
| 59 | 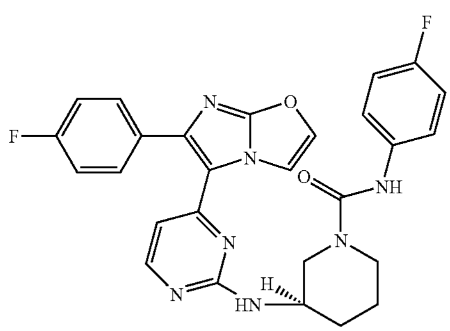 | (3R)-N-(4-fluorophenyl)-3-({4-[6-(4-fluorophenyl)imidazo[2,1-b][1,3]oxazol-5-yl]pyrimidin-2-yl}amino)piperidine-1-carboxamide | 134-137 |
| 60 | 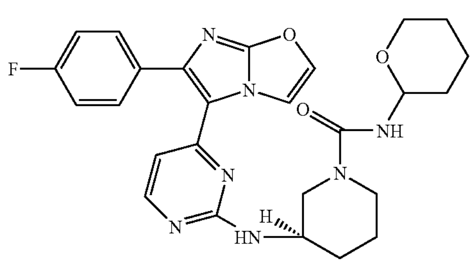 | (3R)-3-({4-[6-(4-fluorophenyl)imidazo[2,1-b][1,3]oxazol-5-yl]pyrimidin-2-yl}amino)-N-(tetrahydro-2H-pyran-2-yl)piperidine-1-carboxamide | 140-143 |

| Number | Structure | Name | Melting Point (° C.) |
|---|---|---|---|
| 61 | 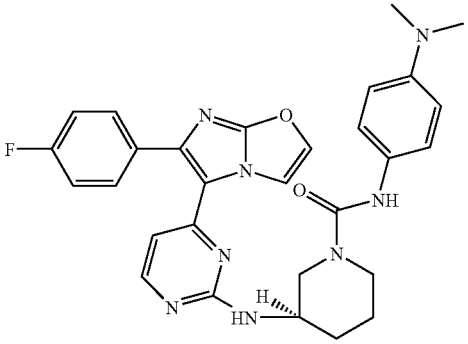 | (3R)-N-[4-(dimethylamino)phenyl]-3-({4-[6-(4-fluorophenyl)imidazo[2,1-b][1,3]oxazol-5-yl]pyrimidin-2-yl}amino)piperidine-1-carboxamide | 145-148 |
| 62 | 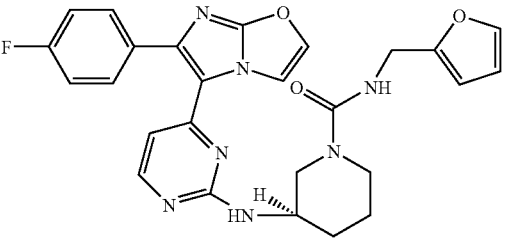 | (3R)-3-({4-[6-(4-fluorophenyl)imidazo[2,1-b][1,3]oxazol-5-yl]pyrimidin-2-yl}amino)-N-(2-furylmethyl)piperidine-1-carboxamide | 112-115 |
| 63 | 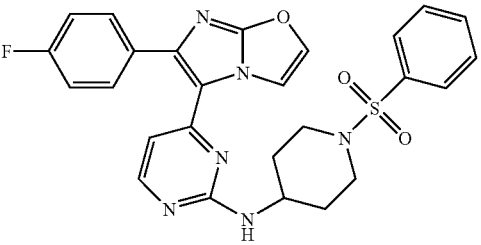 | 4-[6-(4-fluorophenyl)imidazo[2,1-b][1,3]oxazol-5-yl]-N-[1-(phenylsulfonyl)piperidin-4-yl]pyrimidin-2-amine | 266-268 |
| 64 | 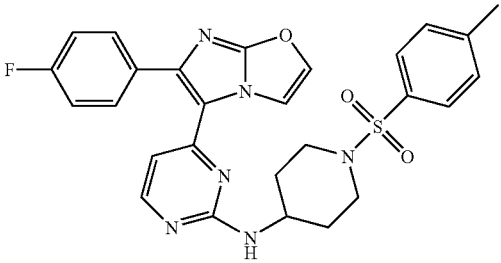 | 4-[6-(4-fluorophenyl)imidazo[2,1-b][1,3]oxazol-5-yl]-N-{1-[(4-methylphenyl)sulfonyl]piperidin-4-yl}pyrimidin-2-amine | 247-248 |
| 65 | 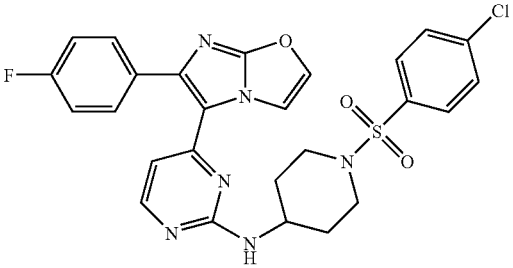 | N-{1-[(4-chlorophenyl)sulfonyl]piperidin-4-yl}-4-[6-(4-fluorophenyl)imidazo[2,1-b][1,3]oxazol-5-yl]pyrimidin-2-amine | 229-230 |

-continued

| Number | Structure | Name | Melting Point (° C.) |
|---|---|---|---|
| 66 | 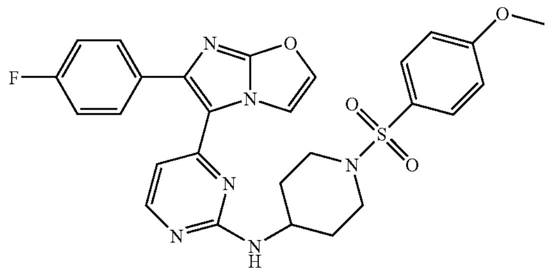 | 4-[6-(4-fluorophenyl)imidazo[2,1-b][1,3]oxazol-5-yl]-N-{1-[(4-methoxyphenyl)sulfonyl]piperidin-4-yl}pyrimidin-2-amine | 234-236 |
| 67 | 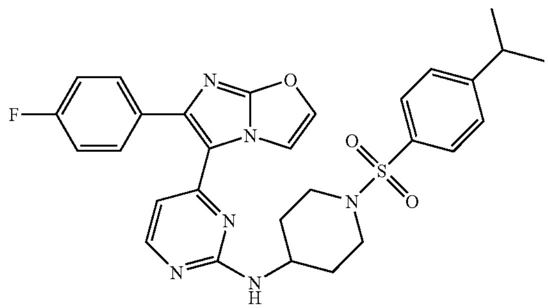 | 4-[6-(4-fluorophenyl)imidazo[2,1-b][1,3]oxazol-5-yl]-N-{1-[(4-isopropylphenyl)sulfonyl]piperidin-4-yl}pyrimidin-2-amine | 235-237 |
| 68 | 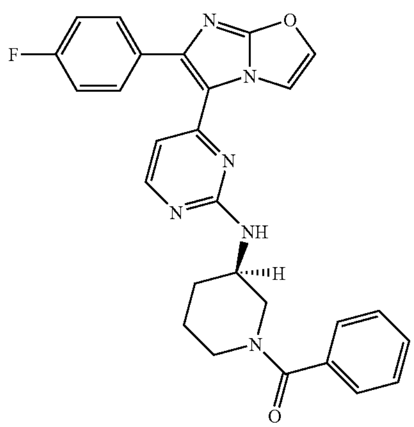 | N-[(3R)-1-benzoylpiperidin-3-yl]-4-[6-(4-fluorophenyl)imidazo[2,1-b][1,3]oxazol-5-yl]pyrimidin-2-amine | 131-133 |
| 69 | 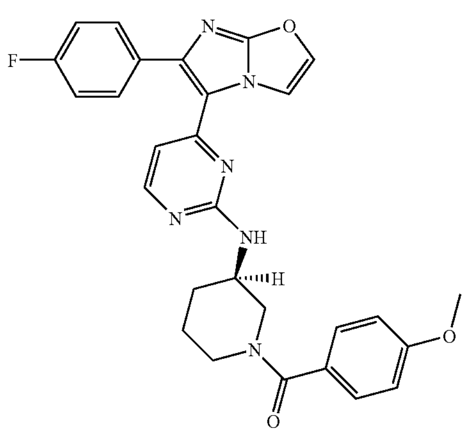 | 4-[6-(4-fluorophenyl)imidazo[2,1-b][1,3]oxazol-5-yl]-N-[(3R)-1-(4-methoxybenzoyl)piperidin-3-yl]pyrimidin-2-amine | 155-156 |

| Number | Structure | Name | Melting Point (° C.) |
|---|---|---|---|
| 70 | 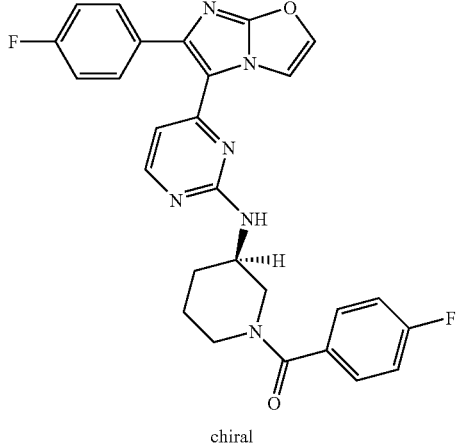 chiral | N-[(3R)-1-(4-fluorobenzoyl)piperidin-3-yl]-4-[6-(4-fluorophenyl)imidazo[2,1-b][1,3]oxazol-5-yl]pyrimidin-2-amine | 184-185 |
| 71 | 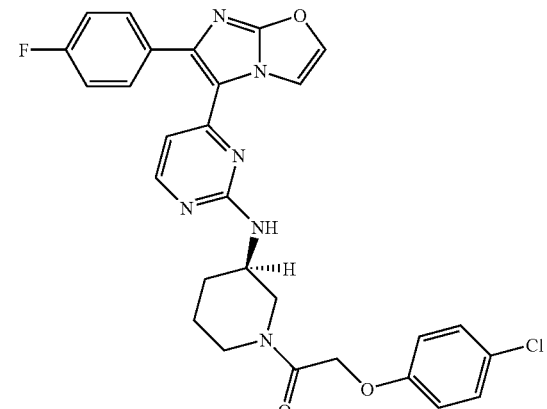 chiral | N-{(3R)-1-[(4-chlorophenoxy)acetyl]piperidin-3-yl}-4-[6-(4-fluorophenyl)imidazo[2,1-b][1,3]oxazol-5-yl]pyrimidin-2-amine | 102-103 |
| 72 | 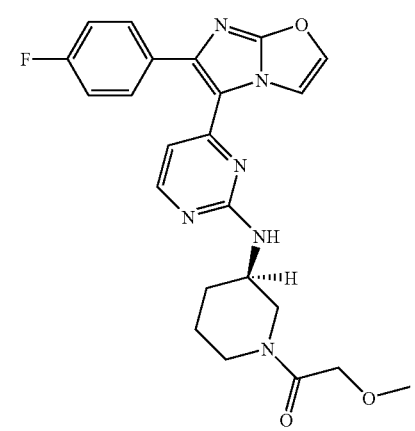 chiral | 4-[6-(4-fluorophenyl)imidazo[2,1-b][1,3]oxazol-5-yl]-N-[(3R)-1-(methoxyacetyl)piperidin-3-yl]pyrimidin-2-amine | 161-162 |

-continued

| Number | Structure | Name | Melting Point (° C.) |
|---|---|---|---|
| 73 | 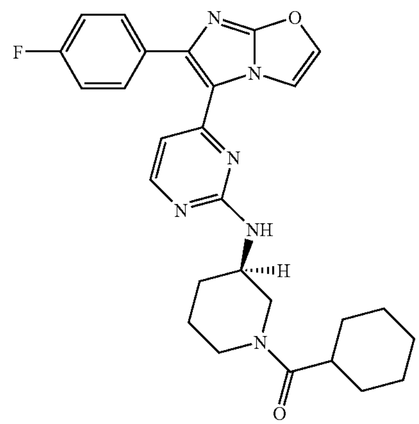 | N-[(3R)-1-(cyclohexylcarbonyl)piperidin-3-yl]-4-[6-(4-fluorophenyl)imidazo[2,1-b][1,3]oxazol-5-yl]pyrimidin-2-amine | 129-131 |
| 74 | 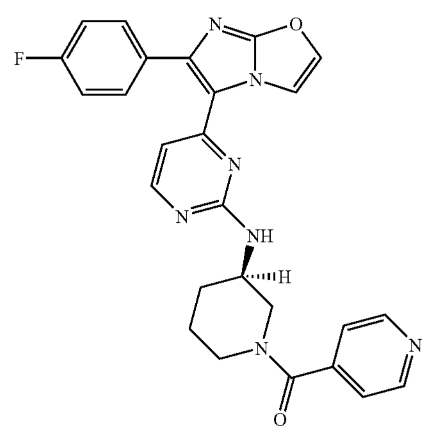 | 4-[6-(4-fluorophenyl)imidazo[2,1-b][1,3]oxazol-5-yl]-N-[(3R)-1-isonicotinoylpiperidin-3-yl]pyrimidin-2-amine | 196-198 |
| 75 | 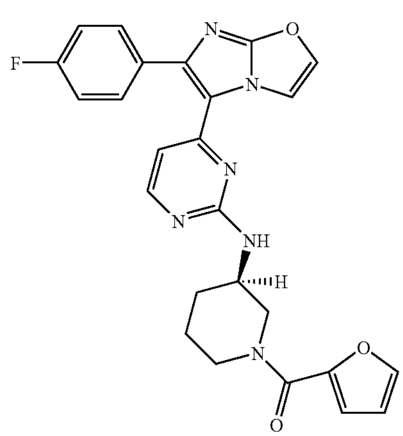 | 4-[6-(4-fluorophenyl)imidazo[2,1-b][1,3]oxazol-5-yl]-N-[(3R)-1-(2-furoyl)piperidin-3-yl]pyrimidin-2-amine | 110-112 |

-continued

| Number | Structure | Name | Melting Point (° C.) |
|---|---|---|---|
| 76 | 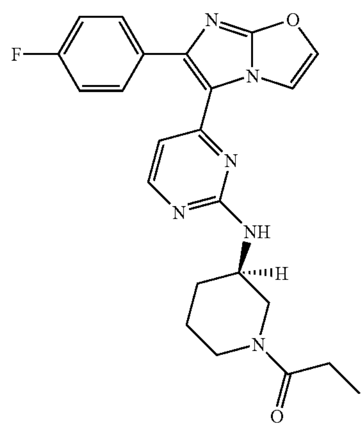 | 4-[6-(4-fluorophenyl)imidazo[2,1-b][1,3]oxazol-5-yl]-N-[(3R)-1-propionylpiperidin-3-yl]pyrimidin-2-amine | 173-174 |
| 77 | 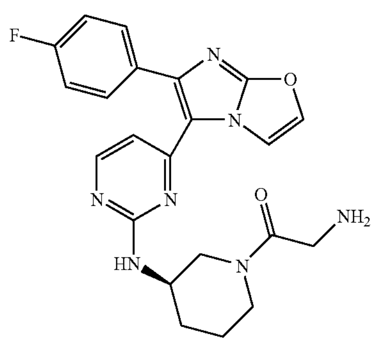 | N-[(3R)-1-(aminoacetyl)piperidin-3-yl]-4-[6-(4-fluorophenyl)imidazo[2,1-b][1,3]oxazol-5-yl]pyrimidin-2-amine | 225-230 |
| 78 | 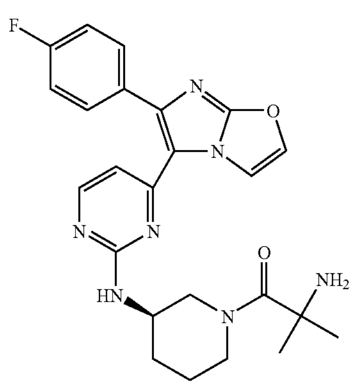 | N-[(3R)-1-(2-amino-2-methylpropanoyl)piperidin-3-yl]-4-[6-(4-fluorophenyl)imidazo[2,1-b][1,3]oxazol-5-yl]pyrimidin-2-amine | 215-218 |

-continued

| Number | Structure | Name | Melting Point (° C.) |
|---|---|---|---|
| 79 | 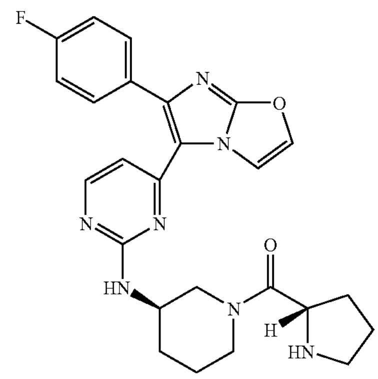 | 4-[6-(4-fluorophenyl)imidazo[2,1-b][1,3]oxazol-5-yl]-N-[(3R)-1-L-prolylpiperidin-3-yl]pyrimidin-2-amine | 210-212 |
| 80 | 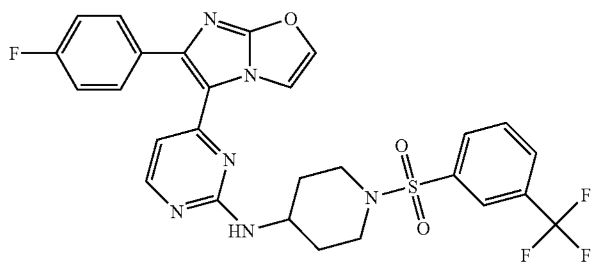 | 4-[6-(4-fluorophenyl)imidazo[2,1-b][1,3]oxazol-5-yl]-N-(1-{[3-(trifluoromethyl)phenyl]sulfonyl}piperidin-4-yl)pyrimidin-2-amine | 266-268 |
| 81 | 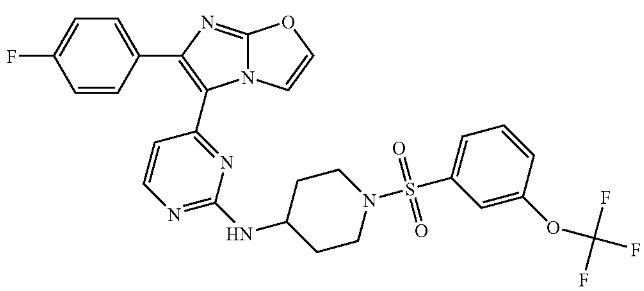 | 4-[6-(4-fluorophenyl)imidazo[2,1-b][1,3]oxazol-5-yl]-N-(1-{[4-(trifluoromethoxy)phenyl]sulfonyl}piperidin-4-yl)pyrimidin-2-amine | 230-232 |
| 82 | 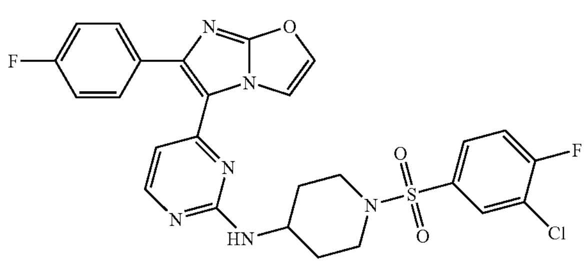 | N-{1-[(3-chloro-4-fluorophenyl)sulfonyl]piperidin-4-yl}-4-[6-(4-fluorophenyl)imidazo[2,1-b][1,3]oxazol-5-yl]pyrimidin-2-amine | 218-220 |
| 83 | 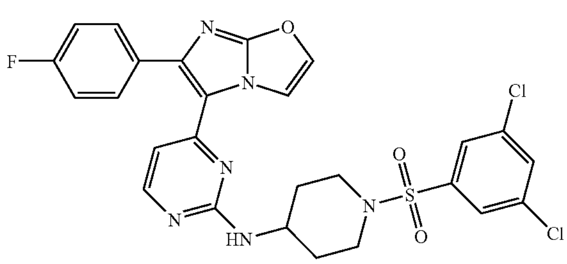 | N-{1-[(3,5-dichlorophenyl)sulfonyl]piperidin-4-yl}-4-[6-(4-fluorophenyl)imidazo[2,1-b][1,3]oxazol-5-yl]pyrimidin-2-amine | 218-220 |

-continued

| Number | Structure | Name | Melting Point (° C.) |
|---|---|---|---|
| 84 | 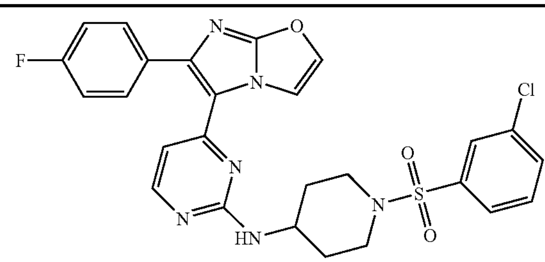 | N-{1-[(3-chlorophenyl)sulfonyl]piperidin-4-yl}-4-[6-(4-fluorophenyl)imidazo[2,1-b][1,3]oxazol-5-yl]pyrimidin-2-amine | 225-226 |
| 85 | 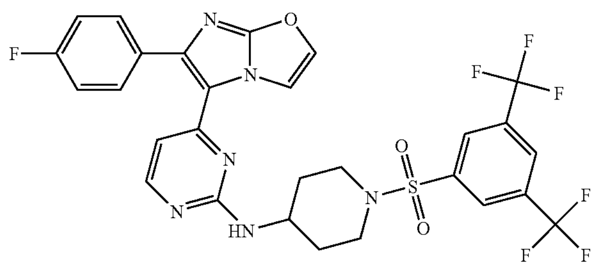 | N-(1-{[3,5-bis(trifluoromethyl)phenyl]sulfonyl}piperidin-4-yl)-4-[6-(4-fluorophenyl)imidazo[2,1-b][1,3]oxazol-5-yl]pyrimidin-2-amine | 225-227 |
| 86 | 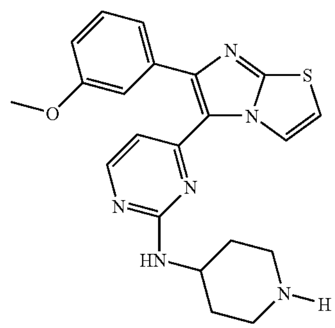 | 4-[6-(3-methoxyphenyl)imidazo[2,1-b][1,3]thiazol-5-yl]-N-piperidin-4-ylpyrimidin-2-amine | 255-260 |
| 87 | 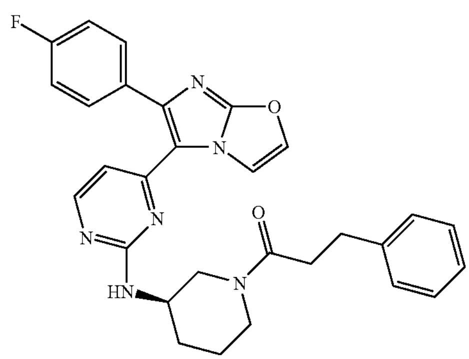 | 4-[6-(4-fluorophenyl)imidazo[2,1-b][1,3]oxazol-5-yl]-N-[(3R)-1-(3-phenylpropanoyl)piperidin-3-yl]pyrimidin-2-amine | 94-95 |
| 88 | 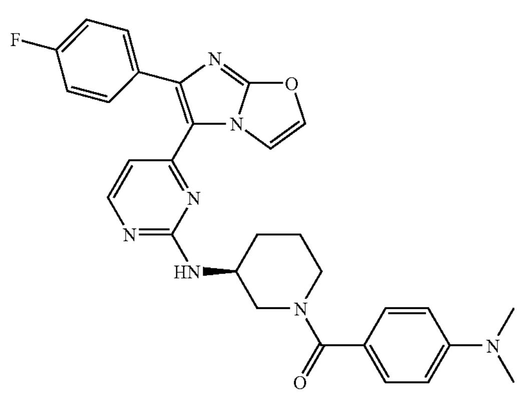 | N-{(3R)-1-(4-(dimethylamino)benzoyl]piperidin-3-yl}-4-[6-(4-fluorophenyl)imidazo[2,1-b][1,3]oxazol-5-yl]pyrimidin-2-amine | 145-146 |

-continued

| Number | Structure | Name | Melting Point (° C.) |
|---|---|---|---|
| 89 | 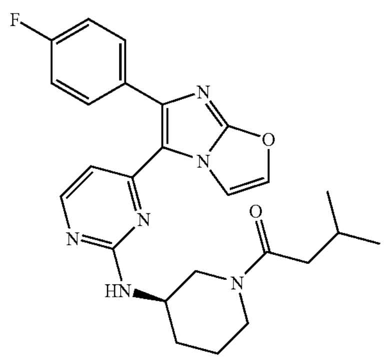 | 4-[6-(4-fluorophenyl)imidazo[2,1-b][1,3]oxazol-5-yl]-N-[(3R)-1-(3-methylbutanoyl)piperidin-3-yl]pyrimidin-2-amine | 89-90 |
| 90 | 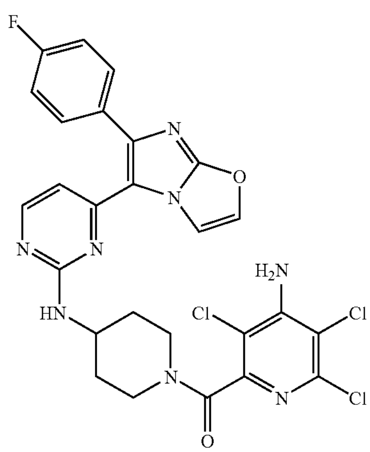 | N-{1-[(4-amino-3,5,6-trichloropyridin-2-yl)carbonyl]piperidin-4-yl}-4-[6-(4-fluorophenyl)imidazo[2,1-b][1,3]oxazol-5-yl]pyrimidin-2-amine | 275-276 |
| 91 | 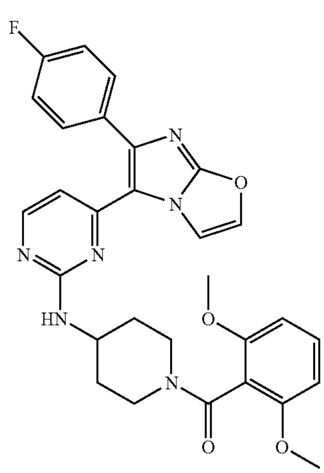 | N-[1-(2,6-dimethoxybenzoyl)piperidin-4-yl]-4-[6-(4-fluorophenyl)imidazo[2,1-b][1,3]oxazol-5-yl]pyrimidin-2-amine | 253-254 |

-continued

| Number | Structure | Name | Melting Point (° C.) |
|---|---|---|---|
| 92 | 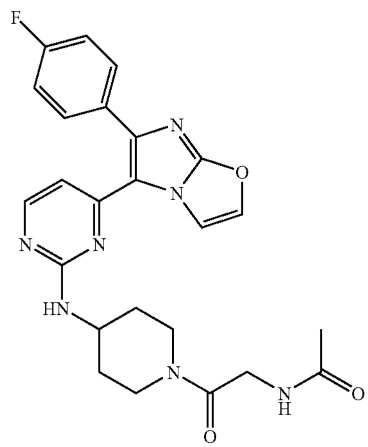 | N-{2-[4-({4-[6-(4-fluorophenyl)imidazo[2,1-b][1,3]oxazol-5-yl]pyrimidin-2-yl}amino)piperidin-1-yl]-2-oxoethyl}acetamide | 235-237 |
| 93 | 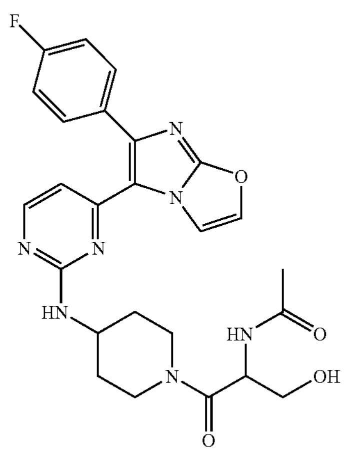 | N-[2-[4-({4-[6-(4-fluorophenyl)imidazo[2,1-b][1,3]oxazol-5-yl]pyrimidin-2-yl}amino)piperidin-1-yl]-1-(hydroxymethyl)-2-oxoethyl]acetamide | 155-157 |
| 94 | 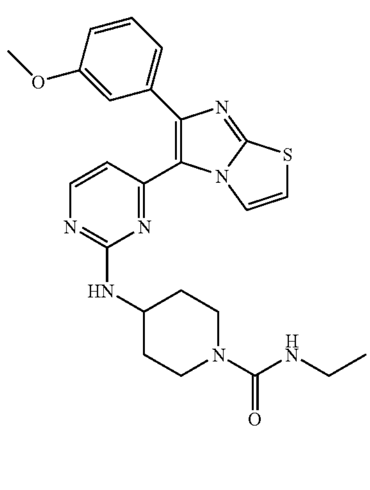 | N-ethyl-4-({4-[6-(3-methoxyphenyl)imidazo[2,1-b][1,3]thiazol-5-yl]pyrimidin-2-yl}amino)piperidine-1-carboxamide | 124-125 |

-continued

| Number | Structure | Name | Melting Point (° C.) |
|---|---|---|---|
| 95 | 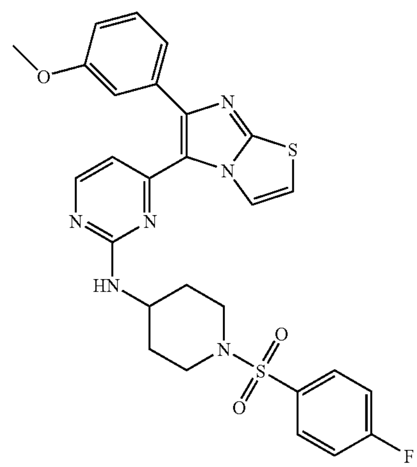 | N-{1-[(4-fluorophenyl)sulfonyl]piperidin-4-yl}-4-(6-(3-methoxyphenyl)imidazo[2,1-b][1,3]thiazol-5-yl)pyrimidin-2-amine | 208-209 |
| 96 | 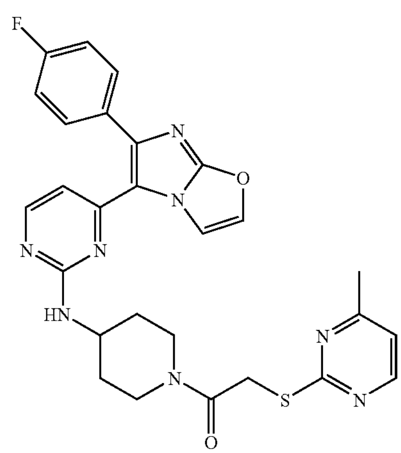 | 4-[6-(4-fluorophenyl)imidazo[2,1-b][1,3]oxazol-5-yl]-N-(1-{[(4-methylpyrimidin-2-yl)thio]acetyl}piperidin-4-yl)pyrimidin-2-amine | 219-220 |
| 97 | 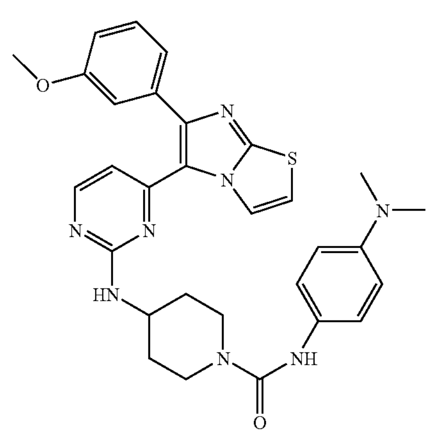 | N-[4-(dimethylamino)phenyl]-4-({4-[6-(3-methoxyphenyl)imidazo[2,1-b][1,3]thiazol-5-yl]pyrimidin-2-yl}amino)piperidine-1-carboxamide | 127-128 |

| Number | Structure | Name | Melting Point (° C.) |
|---|---|---|---|
| 98 | 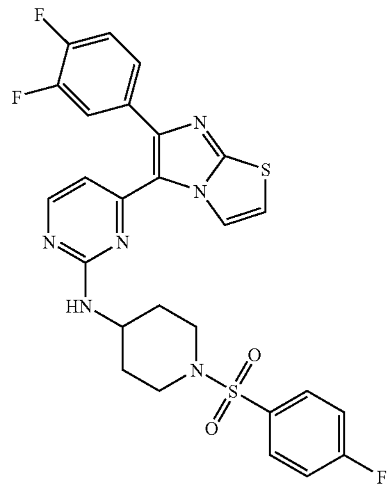 | 4-[6-(3,4-difluorophenyl)imidazo[2,1-b][1,3]thiazol-5-yl]-N-{1-[(4-fluorophenyl)sulfonyl]piperidin-4-yl}pyrimidin-2-amine | 258-259 |
| 99 | 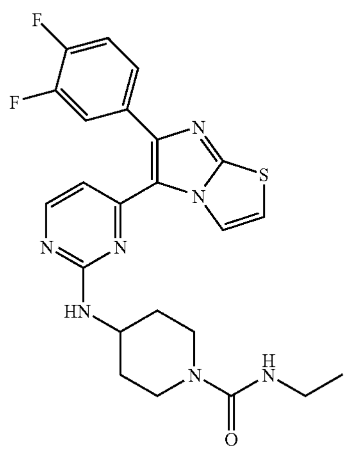 | 4-({4-[6-(3,4-difluorophenyl)imidazo[2,1-b][1,3]thiazol-5-yl]pyrimidin-2-yl}amino)-N-ethylpiperidine-1-carboxamide | 221-222 |
| 100 | 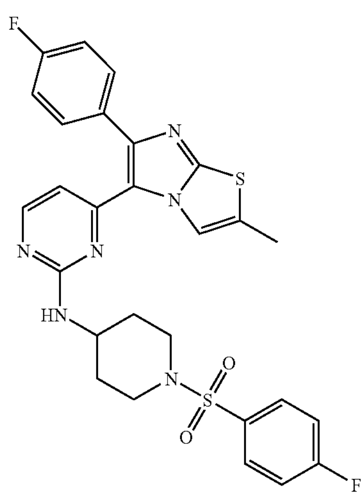 | 4-[6-(4-fluorophenyl)-2-methylimidazo[2,1-b][1,3]thiazol-5-yl]-N-{1-[(4-fluorophenyl)sulfonyl]piperidin-4-yl}pyrimidin-2-amine | 238-239 |

-continued

| Number | Structure | Name | Melting Point (° C.) |
|---|---|---|---|
| 101 | 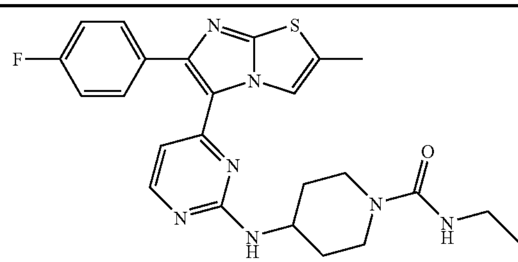 | N-ethyl-4-({4-[6-(4-fluorophenyl)-2-methylimidazo[2,1-b][1,3]thiazol-5-yl]pyrimidin-2-yl}amino)piperidine-1-carboxamide | 217-218 |
| 102 | 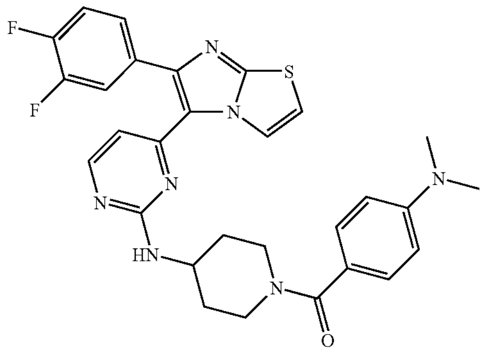 | 4-[6-(3,4-difluorophenyl)imidazo[2,1-b][1,3]thiazol-5-yl]-N-{1-[4-(dimethylamano)benzoyl]piperidin-4-yl}pyrimidin-2-amine | 148-149 |
| 103 | 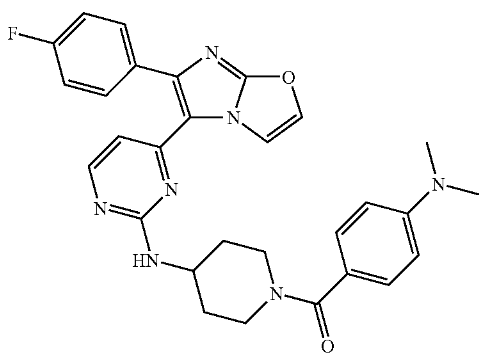 | N-{1-[4-(dimethylamino)benzoyl]piperidin-4-yl}-4-[6-(4-fluorophenyl)imidazo[2,1-b][1,3]oxazol-5-yl]pyrimidin-2-amine | 175-177 |
| 104 | 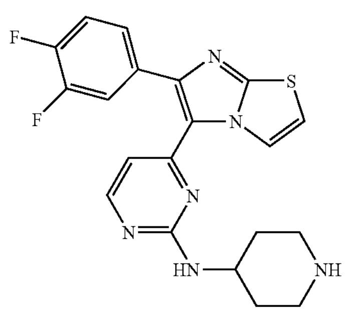 | 4-[6-(3,4-difluorophenyl)imidazo[2,1-b][1,3]thiazol-5-yl]-N-piperidin-4-ylpyrimidin-2-amine | 189-191 |
| 105 | 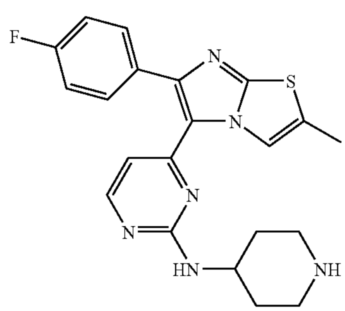 | 4-[6-(4-fluorophenyl)-2-methylimidazo[2,1-b][1,3]thiazol-5-yl]-N-piperidin-4-ylpyrimidin-2-amine | 267-268 |

-continued

| Number | Structure | Name | Melting Point (° C.) |
|---|---|---|---|
| 106 | 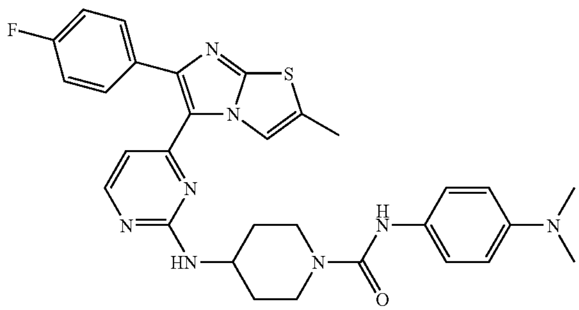 | N-[4-(dimethylamino)phenyl]-4-({4-[6-(4-fluorophenyl)-2-methylimidazo[2,1-b][1,3]thiazol-5-yl]pyrimidin-2-yl}amino)piperidine-1-carboxamide | 228-230 |
| 107 | 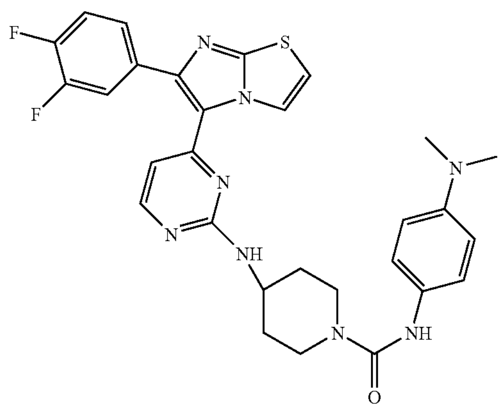 | 4-({4-[6-(3,4-difluorophenyl)imidazo[2,1-b][1,3]thiazol-5-yl]pyrimidin-2-yl}amino)-N-[4-(dimethylamino)phenyl]piperidine-1-carboxamide | 205-206 |
| 108 | 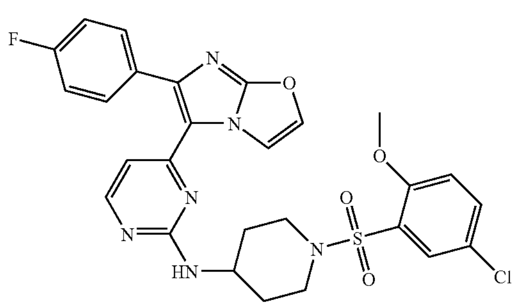 | N-{1-[(5-chloro-2-methoxyphenyl)sulfonyl]piperidin-4-yl}-4-[6-(4-fluorophenyl)imidazo[2,1-b][1,3]oxazol-5-yl]pyrimidin-2-amine | 156-158 |
| 109 | 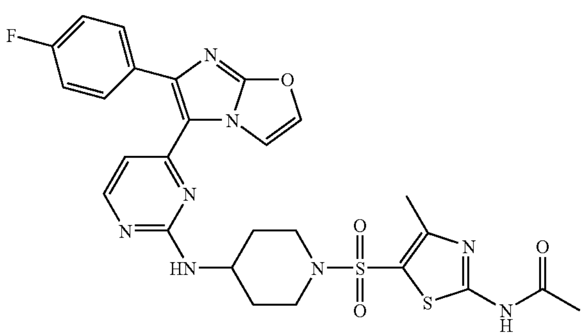 | N-(5-{[4-({4-[6-(4-fluorophenyl)imidazo[2,1-b][1,3]oxazol-5-yl]pyrimidin-2-yl}amino)piperidin-1-yl]sulfonyl}-4-methyl-1,3-thiazol-2-yl)acetamide | 300 |

-continued

| Number | Structure | Name | Melting Point (° C.) |
|---|---|---|---|
| 110 | 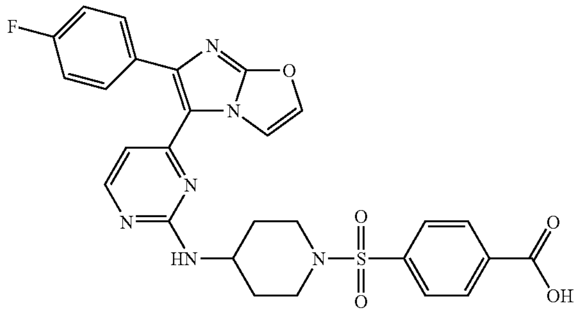 | 4-{[4-({4-[6-(4-fluorophenyl)imidazo[2,1-b][1,3]oxazol-5-yl]pyrimidin-2-yl}amino)piperidin-1-yl]sulfonyl}benzoic acid | 182-184 |
| 111 | 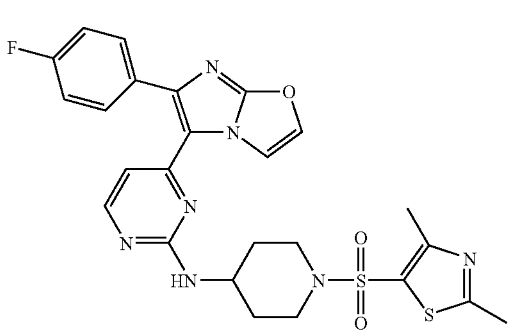 | N-{1-[(2,4-dimethyl-1,3-thiazol-5-yl)sulfonyl]piperidin-4-yl}-4-[6-(4-fluorophenyl)imidazo[2,1-b][1,3]oxazol-5-yl]pyrimidin-2-amine | 240-242 |
| 112 | 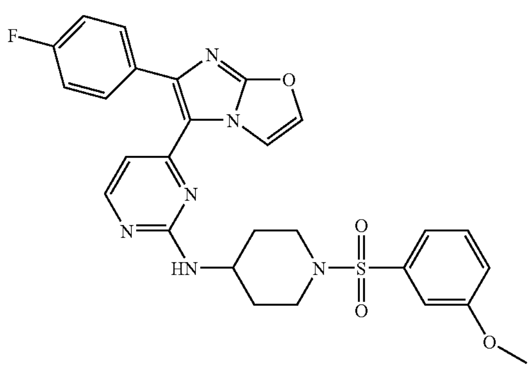 | 4-[6-(4-fluorophenyl)imidazo[2,1-b][1,3]oxazol-5-yl]-N-{1-[(3-methoxyphenyl)sulfanyl]piperidin-4-yl}pyrimidin-2-amine | 214-215 |
| 113 | 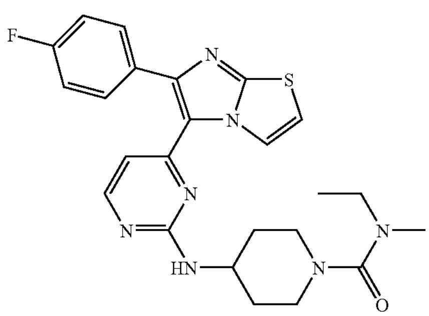 | N-ethyl-4-({4-[6-(4-fluorophenyl)imidazo[2,1-b][1,3]thiazol-5-yl]pyrimidin-2-yl}amino)-N-methylpiperidine-1-carboxamide | 104-107 |

-continued

| Number | Structure | Name | Melting Point (° C.) |
|---|---|---|---|
| 114 | 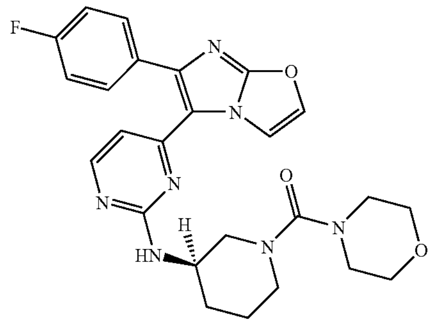 | 4-[6-(4-fluorophenyl)imidazo[2,1-b][1,3]oxazol-5-yl]-N-[(3 R)-1-(morpholin-4-ylcarbonyl)piperidin-3-yl]pyrimidin-2-amine | 102-105 |
| 115 | 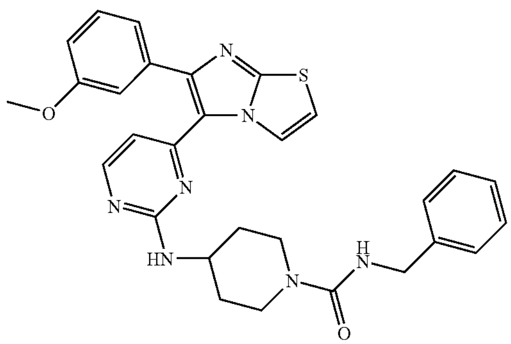 | N-benzyl-4-({4-[6-(3-methoxyphenyl)imidazo[2,1-b][1,3]thiazol-5-yl]pyrimidin-2-yl}amino)piperidine-1-carboxamide | 118-120 |
| 116 | 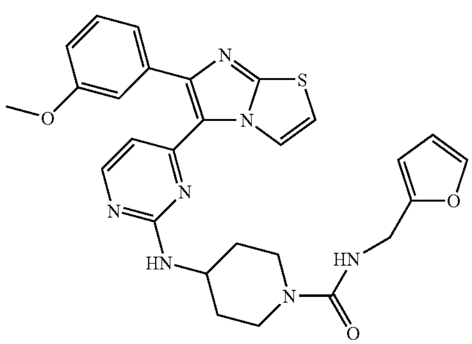 | N-(2-furylmethyl)-4-({4-[6-(3-methoxyphenyl)imidazo[2,1-b][1,3]thiazol-5-yl]pyrimidin-2-yl}amino)piperidine-1-carboxamide | 127-128 |
| 117 | 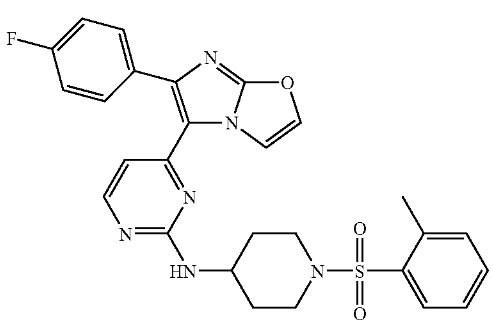 | 4-[6-(4-fluorophenyl)imidazo[2,1-b][1,3]oxazol-5-yl]-N-{1-[(2-methylphenyl)sulfonyl]piperidin-4-yl}pyrimidin-2-amine | 263-265 |

-continued

| Number | Structure | Name | Melting Point (° C.) |
|---|---|---|---|
| 118 | 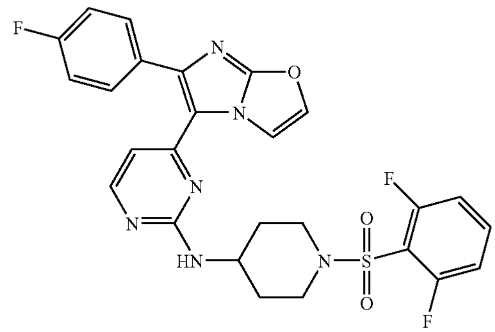 | N-{1-[(2,6-difluorophenyl)sulfonyl]piperidin-4-yl}-4-[6-(4-fluorophenyl)imidazo[2,1-b][1,3]oxazol-5-yl]pyrimidin-2-amine | 252-255 |
| 119 | 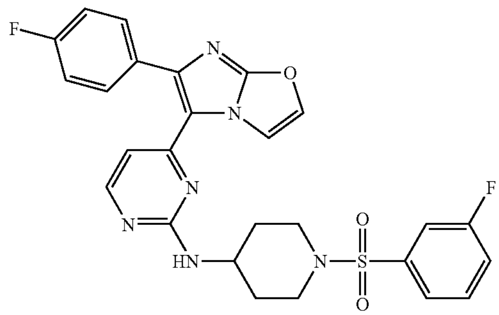 | 4-[6-(4-fluorophenyl)imidazo[2,1-b][1,3]oxazol-5-yl]-N-{1-[(3-fluorophenyl)sulfonyl]piperidin-4-yl}pyrimidin-2-amine | 215-218 |
| 120 | 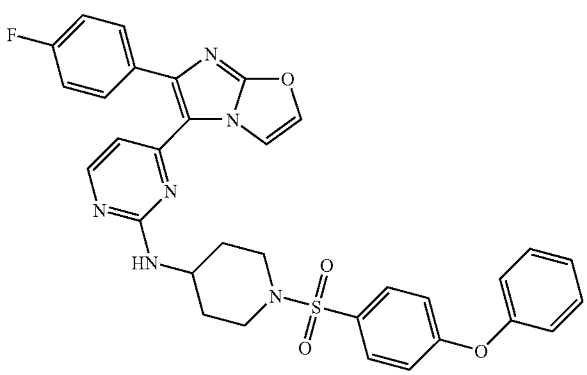 | 4-[6-(4-fluorophenyl)imidazo[2,1-b][1,3]oxazol-5-yl]-N-{1-[(4-phenoxyphenyl)sulfonyl]piperidin-4-yl}pyrimidin-2-amine | 213-215 |
| 121 | 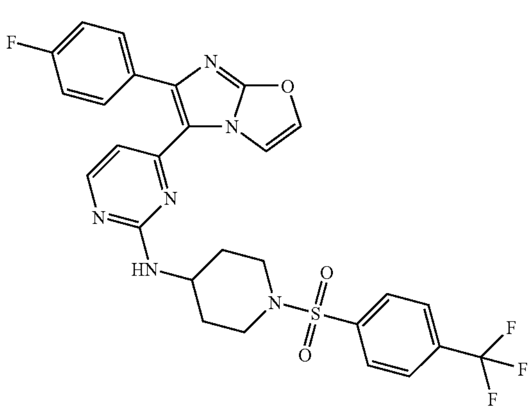 | 4-[6-(4-fluorophenyl)imidazo[2,1-b][1,3]oxazol-5-yl]-N-(1-{[4-trifluoromethyl)phenyl]sulfonyl}piperidin-4-yl)pyrimidin-2-amine | 231-233 |

-continued

| Number | Structure | Name | Melting Point (° C.) |
|---|---|---|---|
| 122 | 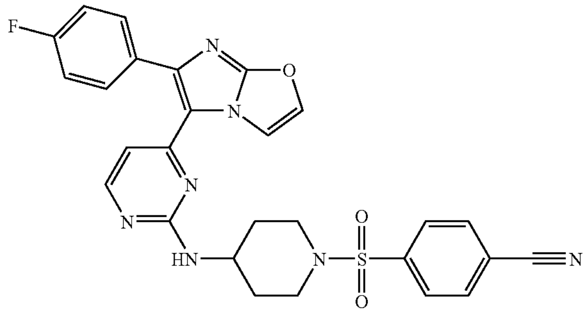 | 4-{[4-({4-[6-(4-fluorophenyl)imidazo[2,1-b][1,3]oxazol-5-yl]pyrimidin-2-yl}amino)piperidin-1-yl]sulfanyl}benzonitrile | 267-269 |
| 123 | chiral | 4-[6-(4-fluorophenyl)imidazo[2,1-b][1,3]oxazol-5-yl]-N-[(3R)-1-(phenylsulfonyl)piperidin-3-yl]pyrimidin-2-amine | 143-144 |
| 124 | chiral | N-{(3R)-1-[(4-chlorophenyl)sulfonyl]piperidin-3-yl}-4-[6-(4-fluorophenyl)imidazo[2,1-b][1,3]oxazol-5-yl]pyrimidin-2-amine | 146-147 |
| 125 | chiral | 4-[6-(4-fluorophenyl)imidazo[2,1-b][1,3]oxazol-5-yl]-N-{(3R)-1-[(4-methoxyphenyl)sulfonyl]piperidin-3-yl}pyrimidin-2-amine | 233-234 |

| Number | Structure | Name | Melting Point (° C.) |
|---|---|---|---|
| 126 | 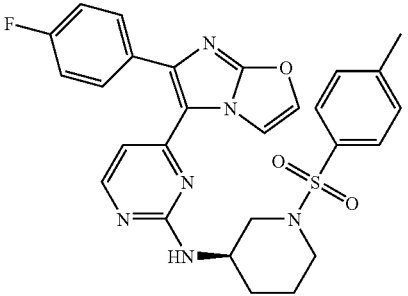 chiral | 4-[6-(4-fluorophenyl)imidazo[2,1-b][1,3]oxazol-5-yl]-N-{(3R)-1-[(4-methylphenyl)sulfonyl]piperidin-3-yl}pyrimidin-2-amine | 194-195 |
| 127 | 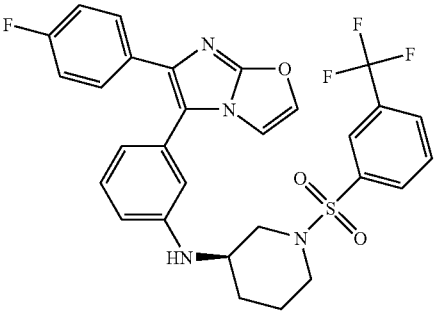 chiral | 4-[6-(4-fluorophenyl)imidazo[2,1-b][1,3]oxazol-5-yl]-N-((3R)-1-{[3-(trifluoromethyl)phenyl]sulfonyl}piperidin-3-yl)pyrimidin-2-amine | 125-127 |
| 128 | 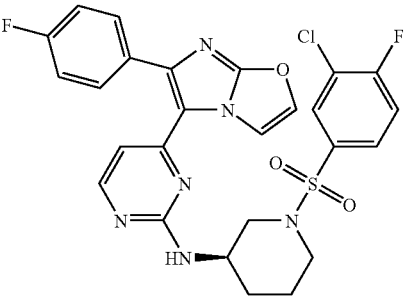 chiral | N-{(3R)-1-[3-chloro-4-fluorophenyl)sulfonyl]piperidin-3-yl}-4-[6-(4-fluorophenyl)imidazo[2,1-b][1,3]oxazol-5-yl]pyrimidin-2-amine | 135-136 |
| 129 | 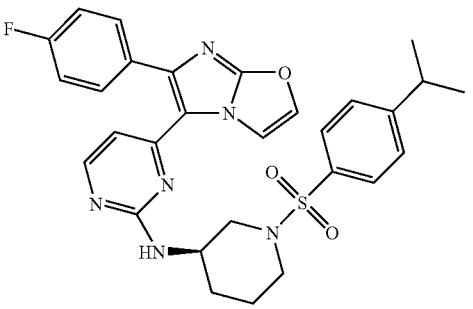 chiral | 4-[6-(4-fluorophenyl)imidazo[2,1-b][1,3]oxazol-5-yl]-N-{(3R)-1-[(4-isopropylphenyl)sulfonyl]piperidin-3-yl}pyrimidin-2-amine | 199-200 |

| Number | Structure | Name | Melting Point (° C.) |
|---|---|---|---|
| 130 | 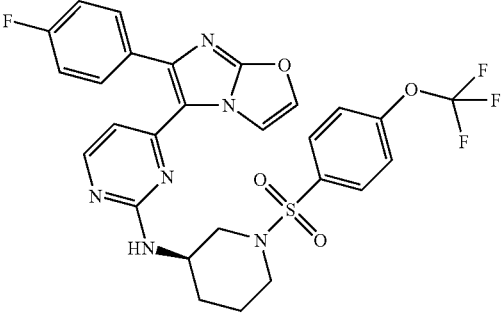 chiral | 4-[6-(4-fluorophenyl)imidazo[2,1-b][1,3]oxazol-5-yl]-N-((3R)-1-{[4-(trifluoromethoxy)phenyl]sulfonyl}piperidin-3-yl)pyrimidin-2-amine | 164-165 |
| 131 | 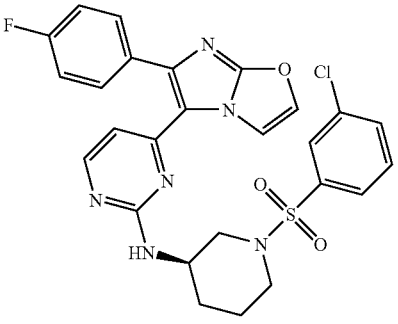 chiral | N-{(3R)-1-[(3-chlorophenyl)sulfonyl]piperidin-3-yl}-4-[6-(4-fluorophenyl)imidazo[2,1-b][1,3]oxazol-5-yl]pyrimidin-2-amine | 165-166 |
| 132 | 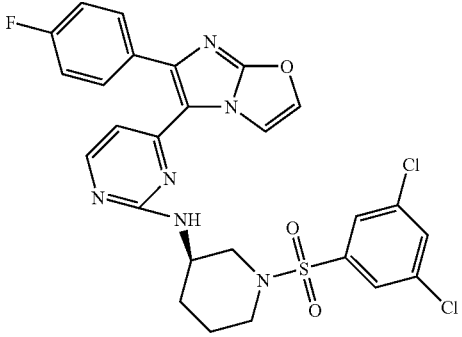 chiral | N-{(3R)-1-[(3,5-dichlorophenyl)sulfonyl]piperidin-3-yl}-4-[6-(4-fluorophenyl)imidazo[2,1-b][1,3]oxazol-5-yl]pyrimidin-2-amine | 173-174 |
| 133 | 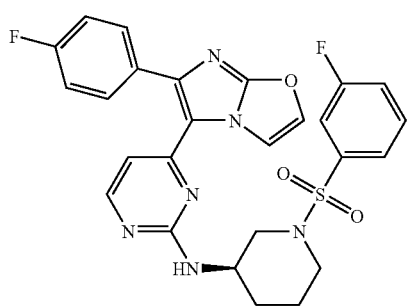 chiral | 4-[6-(4-fluorophenyl)imidazo[2,1-b][1,3]oxazol-5-yl]-N-{(3R)-1-[(3-fluorophenyl)sulfonyl]piperidin-3-yl}pyrimidin-2-amine | 134-135 |

| Number | Structure | Name | Melting Point (° C.) |
| --- | --- | --- | --- |
| 134 | chiral | 4-[6-(4-fluorophenyl)imidazo[2,1-b][1,3]oxazol-5-yl]-N-{(3R)-1-[(2-methylphenyl)sulfonyl]piperidin-3-yl}pyrimidin-2-amine | 155-156 |
| 135 | chiral | N-{(3R)-1-[(2,6-difluorophenyl)sulfonyl]piperidin-3-yl}-4-[6-(4-fluorophenyl)imidazo[2,1-b][1,3]oxazol-5-yl]pyrimidin-2-amine | 192-193 |
| 136 | 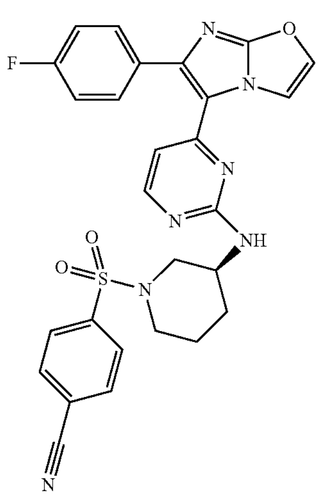 | 4-{[(3R)-3-({4-[6-(4-fluorophenyl)imidazo[2,1-b][1,3]oxazol-5-yl]pyrimidin-2-yl}amino)piperidin-1-yl]sulfonyl}benzonitrile | 144-145 |

-continued

| Number | Structure | Name | Melting Point (° C.) |
|---|---|---|---|
| 137 | 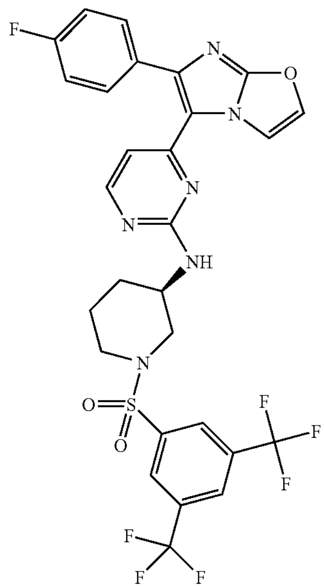 | N-((3R)-1-{[3,5-bis(trifluoromethyl)phenyl]sulfonyl}piperidin-3-yl)-4-[6-(4-fluorophenyl)imidazo[2,1-b][1,3]oxazol-5-yl]pyrimidin-2-amine | 185-186 |
| 138 | 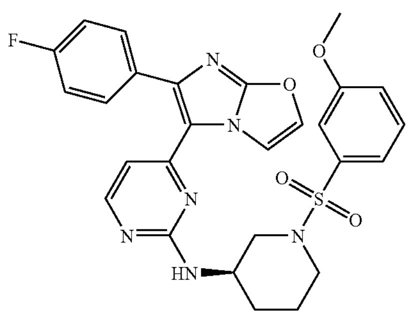 | 4-[6-(4-fluorophenyl)imidazo[2,1-b][1,3]oxazol-5-yl]-N-{(3R)-1-[(3-methoxyphenyl)sulfonyl]piperidin-3-yl}pyrimidin-2-amine | 188-190 |
| 139 | 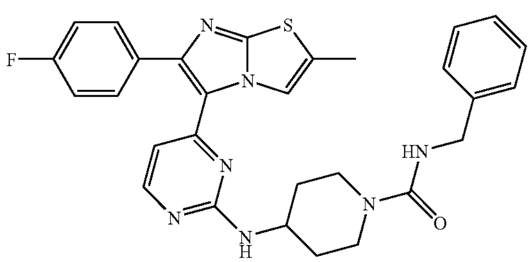 | N-benzyl-4-({4-[6-(4-fluorophenyl)-2-methylimidazo[2,1-b][1,3]thiazol-5-yl]pyrimidin-2-yl}amino)piperidine-1-carboxamide | 137-138 |
| 140 | 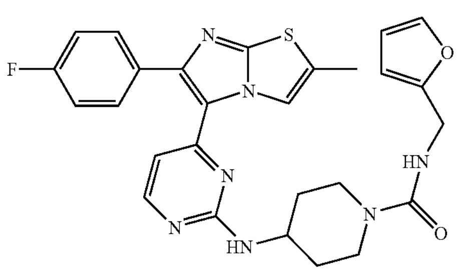 | 4-({4-[6-(4-fluorophenyl)-2-methylimidazo[2,1-b][1,3]thiazol-5-yl]pyrimidin-2-yl}amino)-N-(2-furylmethyl)piperidine-1-carboxamide | 178-179 |

-continued

| Number | Structure | Name | Melting Point (° C.) |
|---|---|---|---|
| 141 | 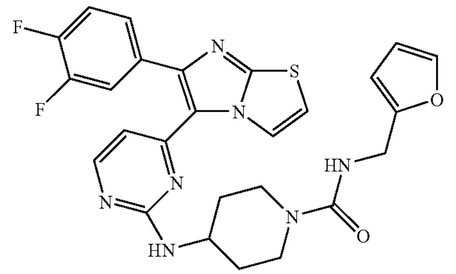 | 4-({4-[6-(3,4-difluorophenyl)imidazo[2,1-b][1,3]thiazol-5-yl]pyrimidin-2-yl}amino)-N-(2-furylmethyl)piperidine-1-carboxamide | 159-160 |
| 142 | 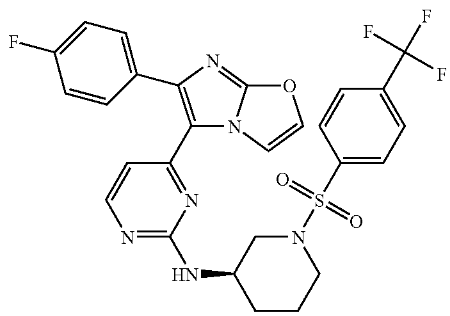 | 4-[6-(4-fluorophenyl)imidazo[2,1-b][1,3]oxazol-5-yl]-N-((3R)-1-{[4-trifluoromethyl)phenyl]sulfonyl}piperidin-3-yl)pyrimidin-2-amine | 153-154 |
| 143 | 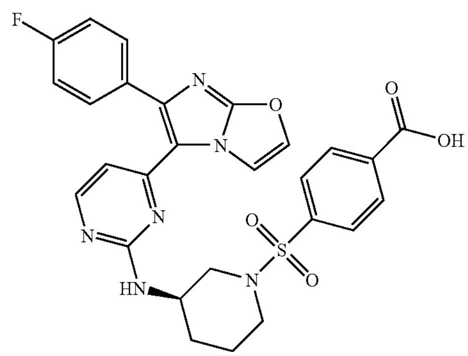 | 4-{[(3R)-3-({4-[6-(4-fluorophenyl)imidazo[2,1-b][1,3]oxazol-5-yl]pyrimidin-2-yl}amino)piperidin-1-yl]sulfonyl}benzoic acid | 300 |
| 144 | 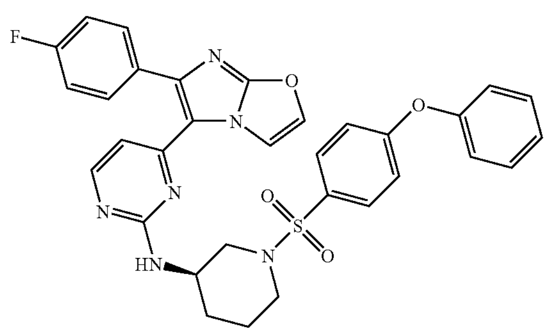 | 4-[6-(4-fluorophenyl)imidazo[2,1-b][1,3]oxazol-5-yl]-N-{(3R)-1-[(4-phenoxyphenyl)sulfonyl]piperidin-3-yl}pyrimidin-2-amine | 279-280 |

-continued

| Number | Structure | Name | Melting Point (° C.) |
|---|---|---|---|
| 145 | 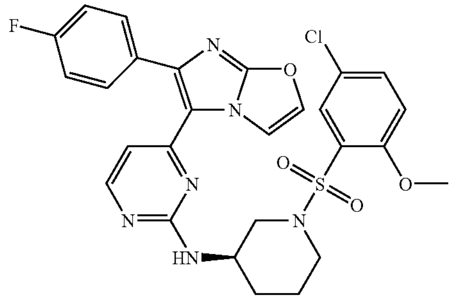 | N-{(3R)-1-[(5-chloro-2-methoxyphenyl)sulfonyl]piperidin-3-yl}-4-[6-(4-fluorophenyl)imidazo[2,1-b][1,3]oxazol-5-yl]pyrimidin-2-amine | 173-174 |
| 146 | 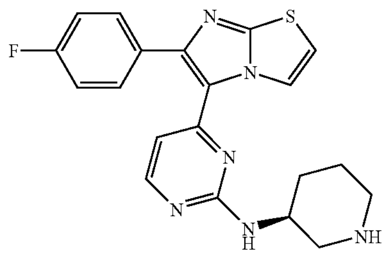 | 4-[6-(4-fluorophenyl)imidazo[2,1-b][1,3]thiazol-5-yl]-N-[(3R)-piperidin-3-yl]pyrimidin-2-amine | 191-194 |
| 147 | 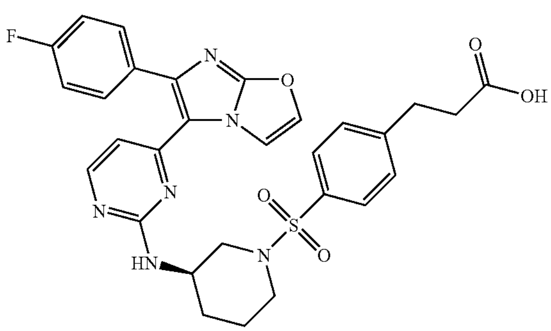 | 3-(4-{[(3R)-3-({4-[6-(4-fluorophenyl)imidazo[2,1-b][1,3]oxazol-5-yl]pyrimidin-2-yl}amino)piperidin-1-yl]sulfonyl}phenyl)propanoic acid | 268-269 |
| 148 | 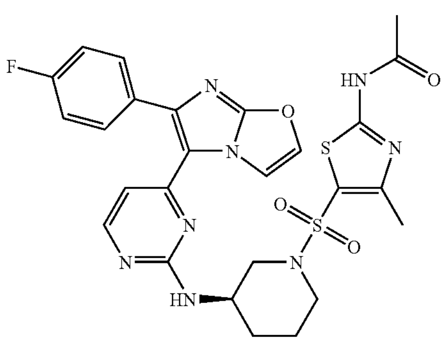 | N-(5-{[(3R)-3-({4-[6-(4-fluorophenyl)imidazo[2,1-b][1,3]oxazol-5-yl]pyrimidin-2-yl}amino)piperidin-1-yl]sulfonyl}-4-methyl-1,3-thiazol-2-yl)acetamide | 176-177 |

-continued

| Number | Structure | Name | Melting Point (° C.) |
|---|---|---|---|
| 149 | 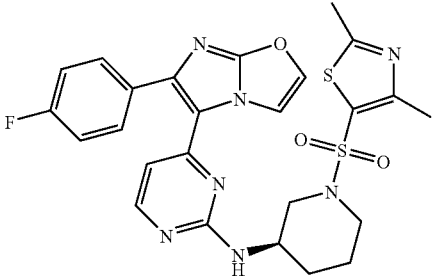 chiral | N-{(3R)-1-[(2,4-dimethyl-1,3-thiazol-5-yl)sulfonyl]piperidin-3-yl}-4-[6-(4-fluorophenyl)imidazo[2,1-b][1,3]oxazol-5-yl]pyrimidin-2-amine | 220-222 |
| 150 | 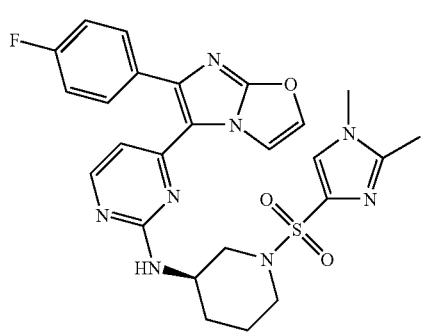 chiral | N-{(3R)-1-[(1,2-dimethyl-1H-imidazol-4-yl)sulfonyl]piperidin-3-yl}-4-[6-(4-fluorophenyl)imidazo[2,1-b][1,3]oxazol-5-yl]pyrimidin-2-amine | 141-143 |
| 151 | 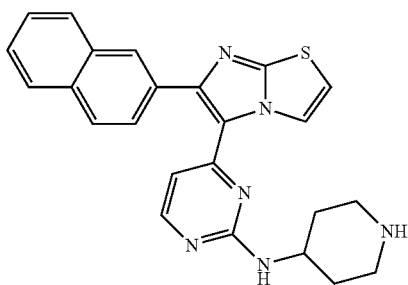 | 4-[6-(2-naphthyl)imidazo[2,1-b][1,3]thiazol-5-yl]-N-piperidin-4-ylpyrimidin-2-amine | 210-215 |
| 152 | 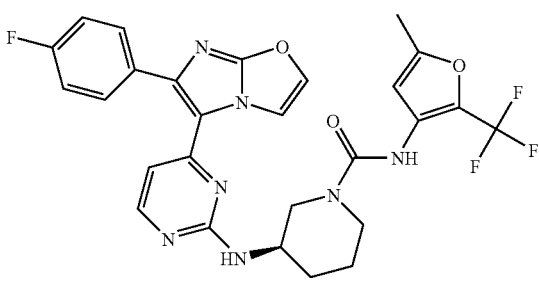 chiral | (3R)-3-({4-[6-(4-fluorophenyl)imidazo[2,1-b][1,3]oxazol-5-yl]pyrimidin-2-yl}amino)-N-[5-methyl-2-(trifluoromethyl)-3-furyl]piperidine-1-carboxamide | 120-122 |

-continued

| Number | Structure | Name | Melting Point (° C.) |
|---|---|---|---|
| 153 | 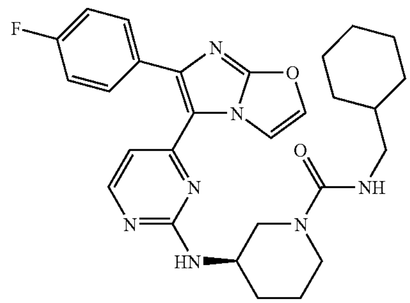 | (3R)-N-(cyclohexylmethyl)-3-({4-[6-(4-fluorophenyl)imidazo[2,1-b][1,3]oxazol-5-yl]pyrimidin-2-yl}amino)piperidine-1-carboxamide | 118-120 |
| 154 | 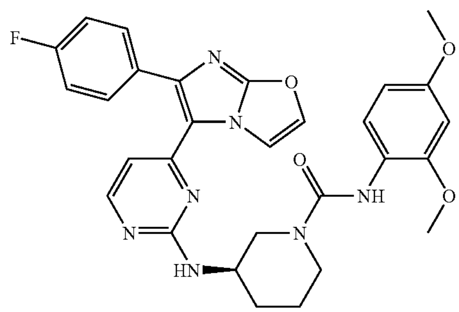 | (3R)-N-(2,4-dimethoxyphenyl)-3-({4-[6-(4-fluorophenyl)imidazo[2,1-b][1,3]oxazol-5-yl]pyrimidin-2-yl}amino)piperidine-1-carboxamide | 113-116 |
| 155 | 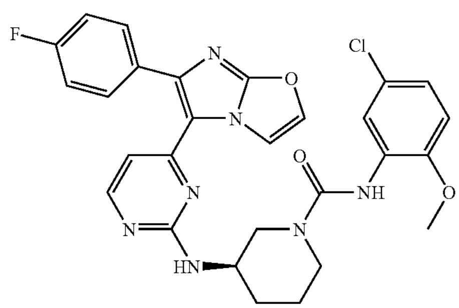 | (3R)-N-(5-chloro-2-methoxyphenyl)-3-({4-[6-(4-fluorophenyl)imidazo[2,1-b][1,3]oxazol-5-yl]pyrimidin-2-yl}amino)piperidine-1-carboxamide | 127-130 |
| 156 | 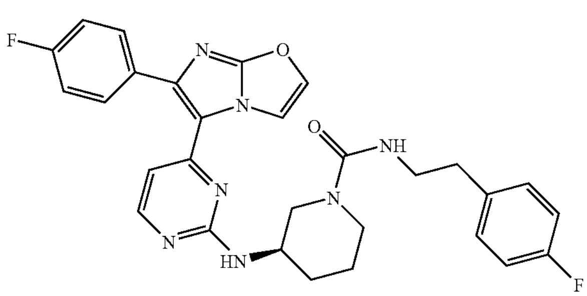 | (3R)-N-[2-(4-fluorophenyl)ethyl]-3-({4-[6-(4-fluorophenyl)imidazo[2,1-b][1,3]oxazol-5-yl]pyrimidin-2-yl}amino)piperidine-1-carboxamide | 114-116 |

-continued

| Number | Structure | Name | Melting Point (° C.) |
|---|---|---|---|
| 157 | 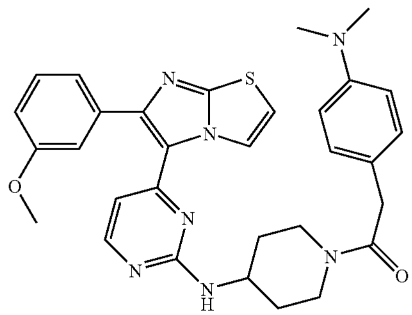 | N-(1-{[4-(dimethylamino)phenyl]acetyl}piperidin-4-yl)-4-[6-(3-methoxyphenyl)imidazo[2,1-b][1,3]thiazol-5-yl]pyrimidin-2-amine | 138-140 |
| 158 | 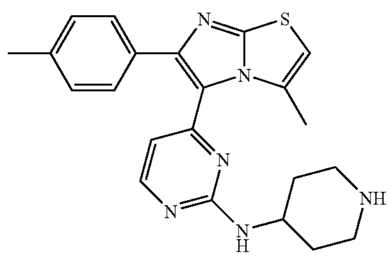 | 4-[3-methyl-6-(4-methylphenyl)imidazo[2,1-b][1,3]thiazol-5-yl]-N-piperidin-4-ylpyrimidin-2-amine | 185-189 |
| 159 | 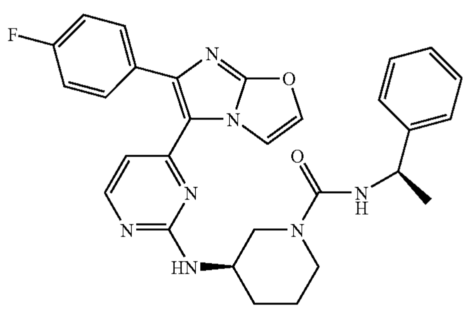 | (3R)-3-({4-[6-(4-fluorophenyl)imidazo[2,1-b][1,3]oxazol-5-yl]pyrimidin-2-yl}amino)-N-[(1R)-1-phenylethyl]piperidine-1-carboxamide | 121-122 |
| 160 | 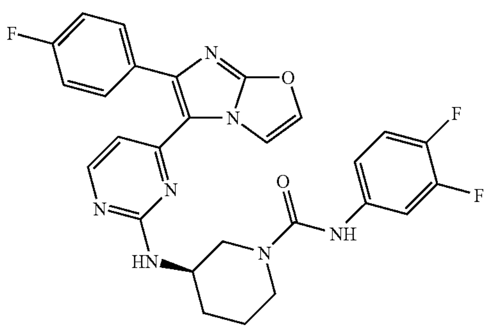 | (3R)-N-(3,4-difluorophenyl)-3-({4-[6-(4-fluorophenyl)imidazo[2,1-b][1,3]oxazol-5-yl]pyrimidin-2-yl}amino)piperidine-1-carboxamide | 132-134 |

-continued

| Number | Structure | Name | Melting Point (° C.) |
|---|---|---|---|
| 161 | 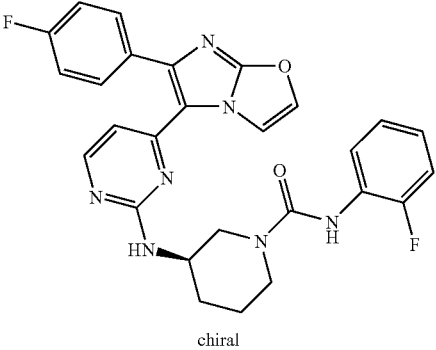 chiral | (3R)-N-(2-fluorophenyl)-3-({4-[6-(4-fluorophenyl)imidazo[2,1-b][1,3]oxazol-5-yl]pyrimidin-2-yl}amino)piperidine-1-carboxamide | 112-115 |
| 162 | 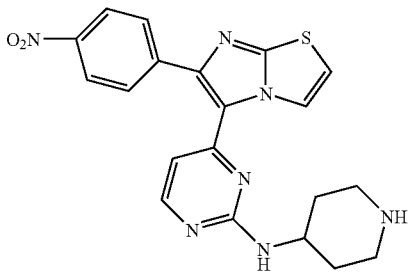 chiral | 4-[6-(4-nitrophenyl)imidazo[2,1-b][1,3]thiazol-5-yl]-N-piperidin-4-ylpyrimidin-2-amine | 203-206 |
| 163 | 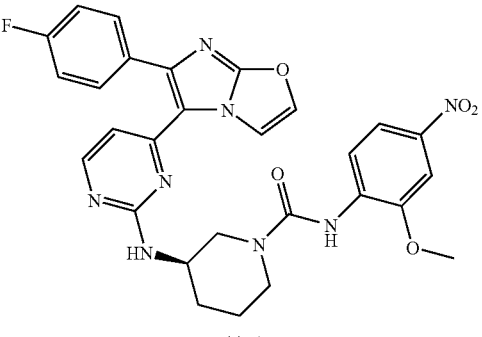 chiral | (3R)-3-({4-[6-(4-fluorophenyl)imidazo[2,1-b][1,3]oxazol-5-yl]pyrimidin-2-yl}amino)-N-(2-methoxy-4-nitrophenyl)piperidine-1-carboxamide | 154-156 |
| 164 | 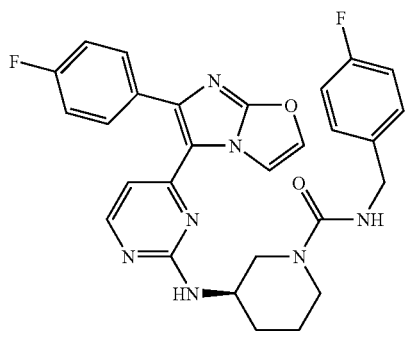 chiral | (3R)-N-(4-fluorobenzyl)-3-({4-[6-(4-fluoropheriyl)imidazo[2,1-b][1,3]oxazol-5-yl]pyrimidin-2-yl}amino)piperidine-1-carboxamide | 111-113 |

-continued

| Number | Structure | Name | Melting Point (° C.) |
|---|---|---|---|
| 165 | 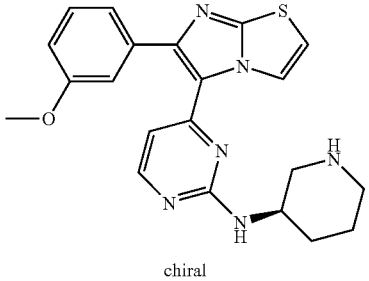 chiral | 4-[6-(3-methoxyphenyl)imidazo[2,1-b][1,3]thiazol-5-yl]-N-[(3R)-piperidin-3-yl]pyrimidin-2-amine | 220-225 |
| 166 | 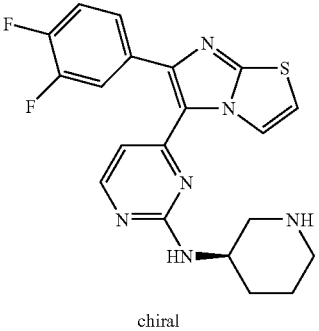 chiral | 4-[6-(3,4-difluorophenyl)imidazo[2,1-b][1,3]thiazol-5-yl]-N-[(3R)-piperidin-3-yl]pyrimidin-2-amine | 195-198 |
| 167 | 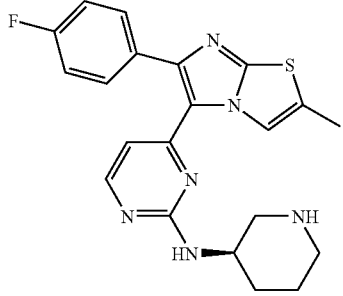 chiral | 4-[6-(4-fluorophenyl)-2-methylimidazo[2,1-b][1,3]thiazol-5-yl]-N-[(3R)-piperidin-3-yl]pyrimidin-2-amine | 206-208 |
| 168 | 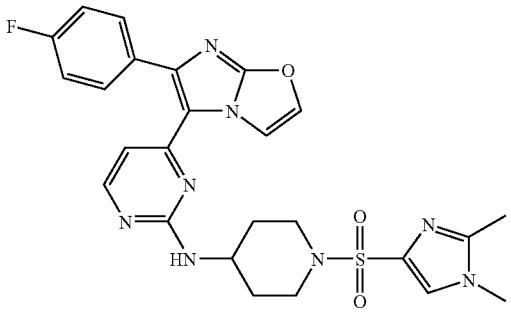 | N-{1-[(1,2-dimethyl-1H-imidazol-4-yl)sulfonyl]piperidin-4-yl}-4-[6-(4-fluorophenyl)imidazo[2,1-b][1,3]oxazol-5-yl]pyrimidin-2-amine | 148-152 |
| 169 | 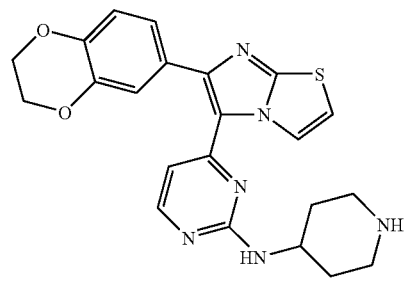 | 4-[6-(2,3-dihydro-1,4-benzodioxin-6-yl)imidazo[2,1-b][1,3]thiazol-5-yl]-N-piperidin-4-ylpyrimidin-2-amine | 231-235 |

| Number | Structure | Name | Melting Point (° C.) |
|---|---|---|---|
| 170 | 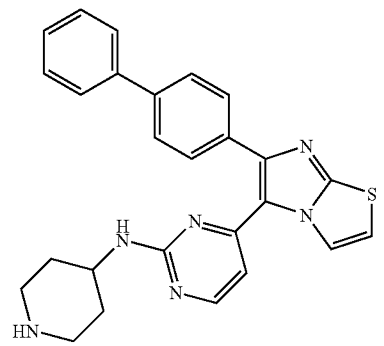 | 4-(6-biphenyl-4-ylimidazo[2,1-b][1,3]thiazol-5-yl)-N-piperidin-4-ylpyrimidin-2-amine | 195-198 |
| 171 | 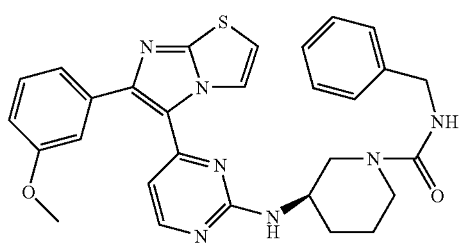 | (3R)-N-benzyl-3-({4-[6-(3-methoxyphenyl)imidazo[2,1-b][1,3]thiazol-5-yl]pyrimidin-2-yl}amino)piperidine-1-carboxamide | 108-110 |
| 172 | 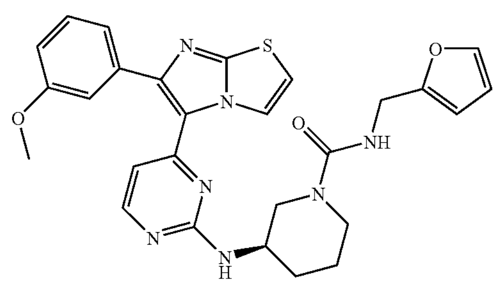 | (3R)-N-(2-furylmethyl)-3-({4-[6-(3-methoxyphenyl)imidazo[2,1-b][1,3]thiazol-5-yl]pyrimidin-2-yl}amino)piperidine-1-carboxamide | 119-121 |
| 173 | 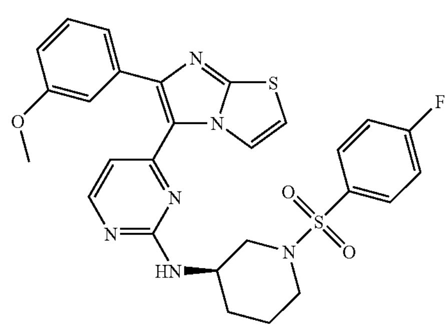 | N-{(3R)-1-[(4-fluorophenyl)sulfonyl]piperidin-3-yl}-4-[6-(3-methoxyphenyl)imidazo[2,1-b][1,3]thiazol-5-yl]pyrimidin-2-amine | 143-144 |

| Number | Structure | Name | Melting Point (° C.) |
|---|---|---|---|
| 174 | 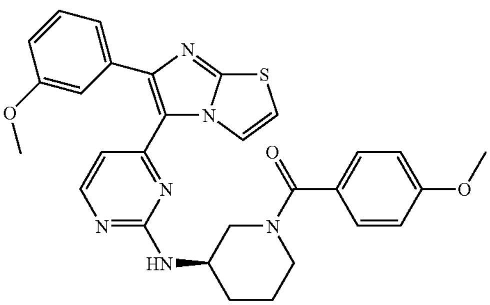 | N-[(3R)-1-(4-methoxybenzoyl)piperidin-3-yl]-4-[6-(3-methoxyphenyl)imidazo[2,1-b][1,3]thiazol-5-yl]pyrimidin-2-amine | 130-132 |
| 175 | 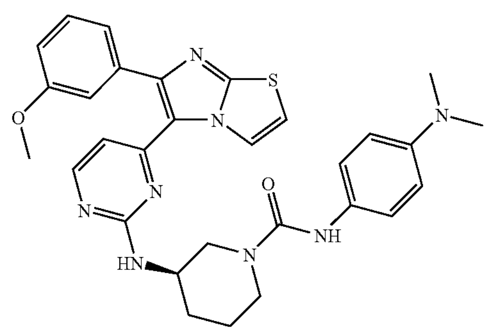 | (3R)-N-[4-(dimethylamino)phenyl]-3-({4-[6-(3-methoxyphenyl)imidazo[2,1-b][1,3]thiazol-5-yl]pyrimidin-2-yl}amino)piperidine-1-carboxamide | 127-129 |
| 176 | 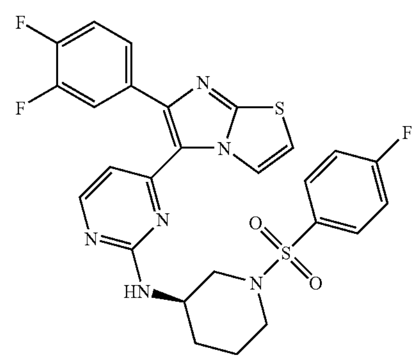 | 4-[6-(3,4-difluorophenyl)imidazo[2,1-b][1,3]thiazol-5-yl]-N-{(3R)-1-[(4-fluorophenyl)sulfonyl]piperidin-3-yl}pyrimidin-2-amine | 128-131 |
| 177 | 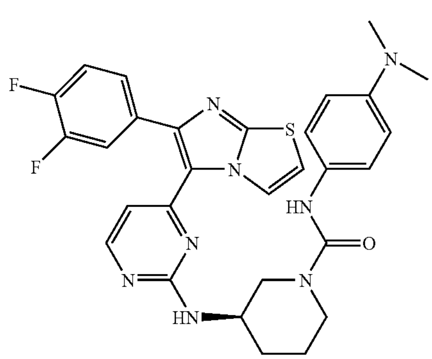 | (3R)-3-({4-[6-(3,4-difluorophenyl)imidazo[2,1-b][1,3]thiazol-5-yl]pyrimidin-2-yl}amino)-N-[4-(dimethylamino)phenyl]piperidine-1-carboxamide | 135-137 |

| Number | Structure | Name | Melting Point (° C.) |
|---|---|---|---|
| 178 | 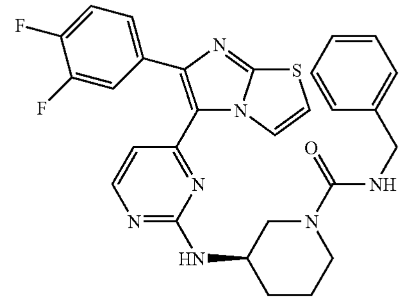 | (3R)-N-benzyl-3-({4-[6-(3,4-difluorophenyl)imidazo[2,1-b][1,3]thiazol-5-yl]pyrimidin-2-yl}amino)piperidine-1-carboxamide | 107-110 |
| 179 | 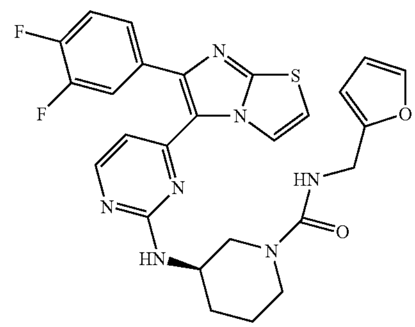 | (3R)-3-({4-[6-(3,4-difluorophenyl)imidazo[2,1-b][1,3]thiazol-5-yl]pyrimidin-2-yl}amino)-N-(2-furylmethyl)piperidine-1-carboxamide | 101-102 |
| 180 | 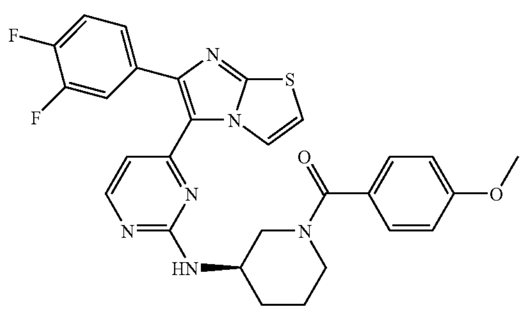 | 4-[6-(3,4-difluorophenyl)imidazo[2,1-b][1,3]thiazol-5-yl]-N-[(3R)-1-(4-methoxybenzoyl)piperidin-3-yl]pyrimidin-2-amine | 121-122 |
| 181 | 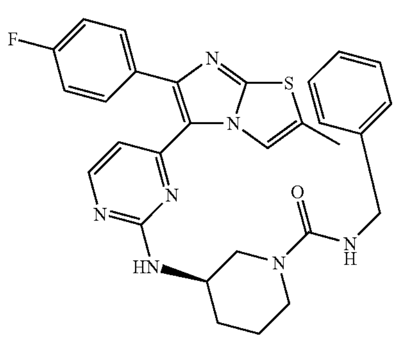 | (3R)-N-benzyl-3-({4-[6-(4-fluorophenyl)-2-methylimidazo[2,1-b][1,3]thiazol-5-yl]pyrimidin-2-yl}amino)piperidine-1-carboxamide | 135-137 |

| Number | Structure | Name | Melting Point (° C.) |
|---|---|---|---|
| 182 | 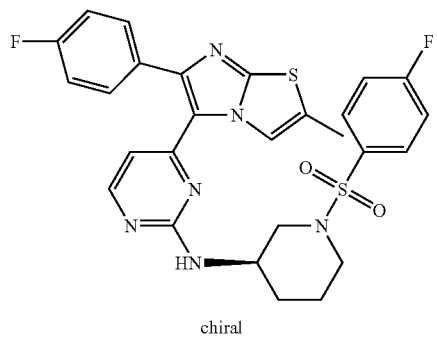 chiral | 4-[6-(4-fluorophenyl)-2-methylimidazo[2,1-b][1,3]thiazol-5-yl]-N-{(3R)-1-[(4-fluorophenyl)sulfonyl]piperidin-3-yl}pyrimidin-2-amine | 245-246 |
| 183 | 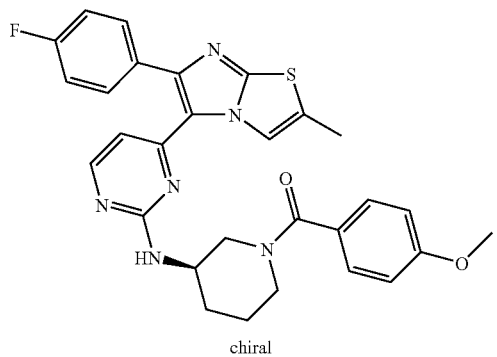 chiral | 4-[6-(4-fluorophenyl)-2-methylimidazo[2,1-b][1,3]thiazol-5-yl]-N-[(3R)-1-(4-methoxybenzoyl)piperidin-3-yl]pyrimidin-2-amine | 200-201 |
| 184 | 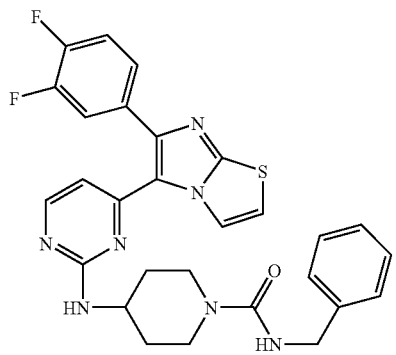 | N-benzyl-4-({4-[6-(3,4-difluorophenyl)imidazo[2,1-b][1,3]thiazol-5-yl]pyrimidin-2-yl}amino)piperidine-1-carboxamide | 187-188 |
| 185 | 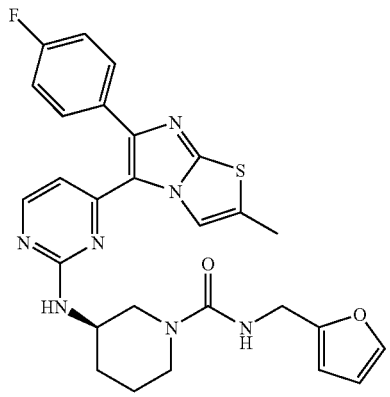 chiral | (3R)-3-({4-[6-(4-fluorophenyl)-2-methylimidazo[2,1-b][1,3]thiazol-5-yl]pyrimidin-2-yl}amino)-N-(2-furylmethyl)piperidine-1-carboxamide | 113-115 |

-continued

| Number | Structure | Name | Melting Point (° C.) |
|---|---|---|---|
| 186 | 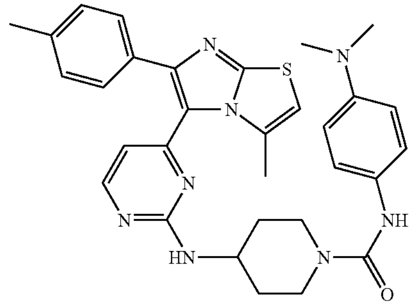 | N-[4-(dimethylamino)phenyl]-4-({4-[3-methyl-6-(4-methylphenyl)imidazo[2,1-b][1,3]thiazol-5-yl]pyrimidin-2-yl}amino)piperidine-1-carboxamide | 133-135 |
| 187 | 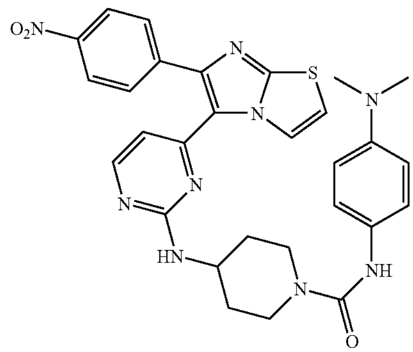 | N-[4-(dimethylamino)phenyl]-4-({4-[6-(4-nitrophenyl)imidazo[2,1-b][1,3]thiazol-5-yl]pyrimidin-2-yl}amino)piperidine-1-carboxamide | 185-188 |
| 188 | 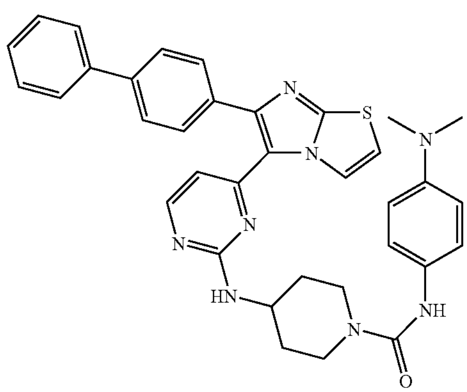 | 4-{[4-(6-biphenyl-4-ylimidazo[2,1-b][1,3]thiazol-5-yl)pyrimidin-2-yl]amino}-N-[4-(dimethylamino)phenyl]piperidine-1-carboxamide | 141-145 |
| 189 | 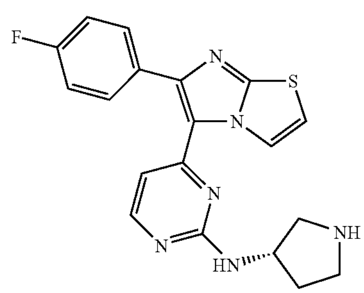 | 4-[6-(4-fluorophenyl)imidazo[2,1-b][1,3]thiazol-5-yl]-N-[(3S)-pyrrolidin-3-yl]pyrimidin-2-amine | 230-232 |

| Number | Structure | Name | Melting Point (° C.) |
|---|---|---|---|
| 190 | 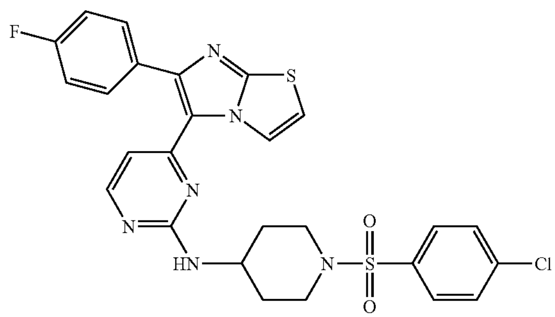 | N-{1-[(4-chlorophenyl)sulfonyl]piperidin-4-yl}-4-[6-(4-fluorophenyl)imidazo[2,1-b][1,3]thiazol-5-yl]pyrimidin-2-amine | 244-245 |
| 191 | 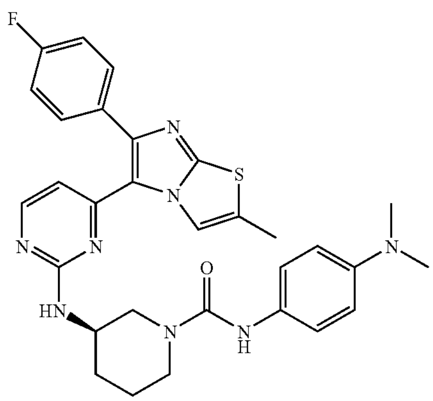 | (3R)-N-(4-(dimethylamino)phenyl)-3-({4-[6-(4-fluorophenyl)-2-methylimidazo[2,1-b][1,3]thiazol-5-yl]pyrimidin-2-yl}amino)piperidine-1-carboxamide | 193-194 |
| 192 | 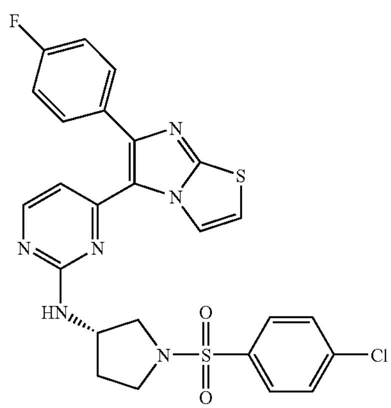 | N-{(3S)-1-[(4-chlorophenyl)sulfonyl]pyrrolidin-3-yl}-4-[6-(4-fluorophenyl)imidazo[2,1-b][1,3]thiazol-5-yl]pyrimidin-2-amine | 190-191 |
| 193 | 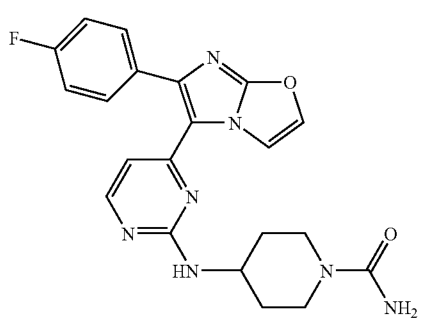 | 4-({4-[6-(4-fluorophenyl)imidazo[2,1-b][1,3]oxazol-5-yl]pyrimidin-2-yl}amino)piperidine-1-carboxamide | 185-190 |

-continued

| Number | Structure | Name | Melting Point (° C.) |
|---|---|---|---|
| 194 | 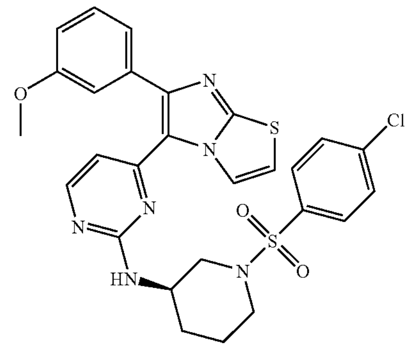 | N-{(3R)-1-[(4-chlorophenyl)sulfonyl]piperidin-3-yl}-4-[6-(3-methoxyphenyl)imidazo[2,1-b][1,3]thiazol-5-yl]pyrimidin-2-amine | 127-128 |
| 195 | 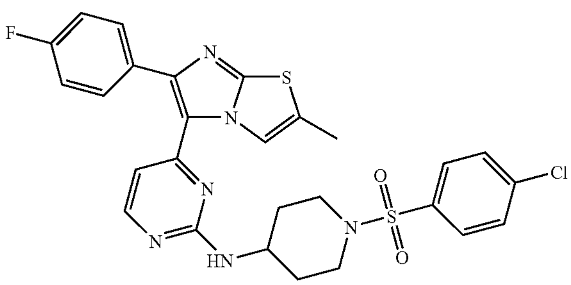 | N-{1-[(4-chlorophenyl)sulfonyl]piperidin-4-yl}-4-[6-(4-fluorophenyl)-2-methylimidazo[2,1-b][1,3]thiazol-5-yl]pyrimidin-2-amine | 148-149 |
| 196 | 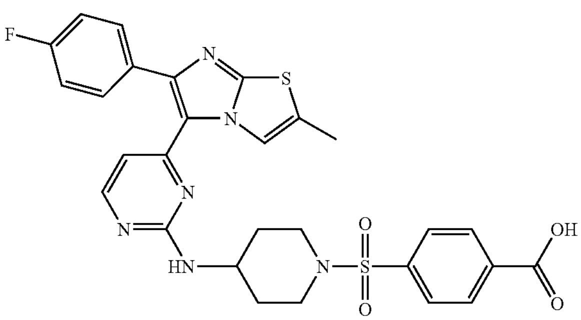 | 4-{[4-({4-[6-(4-fluorophenyl)-2-methylimidazo[2,1-b][1,3]thiazol-5-yl]pyrimidin-2-yl}amino)piperidin-1-yl]sulfonyl}benzoic acid | 195-196 |
| 197 | 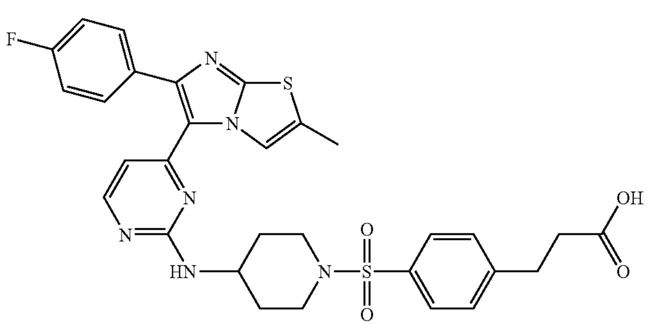 | 3-(4-{[4-({4-[6-(4-fluorophenyl)-2-methylimidazo[2,1-b][1,3]thiazol-5-yl]pyrimidin-2-yl}amino)piperidin-1-yl]sulfonyl}phenyl)propanoic acid | 183-186 |

-continued

| Number | Structure | Name | Melting Point (° C.) |
|---|---|---|---|
| 198 | 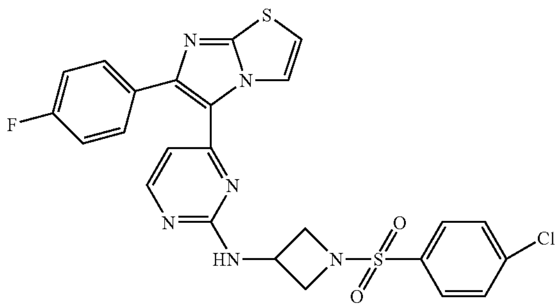 | N-{1-[(4-chlorophenyl)sulfonyl]azetidin-3-yl}-4-[6-(4-fluorophenyl)imidazo[2,1-b][1,3]thiazol-5-yl]pyrimidin-2-amine | 129-130 |
| 199 | chiral | N-{(3R)-1-[(4-chlorophenyl)sulfonyl]piperidin-3-yl}-4-[6-(4-fluorophenyl)-2-methylimidazo[2,1-b][1,3]thiazol-5-yl]pyrimidin-2-amine | 273-274 |
| 200 | 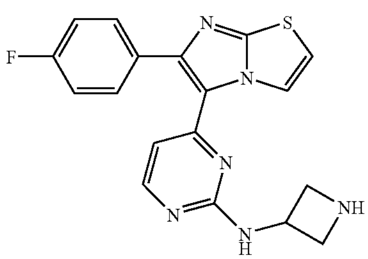 | N-azetidin-3-yl-4-[6-(4-fluorophenyl)imidazo[2,1-b][1,3]thiazol-5-yl]pyrimidin-2-amine | 224-225 |
| 201 | 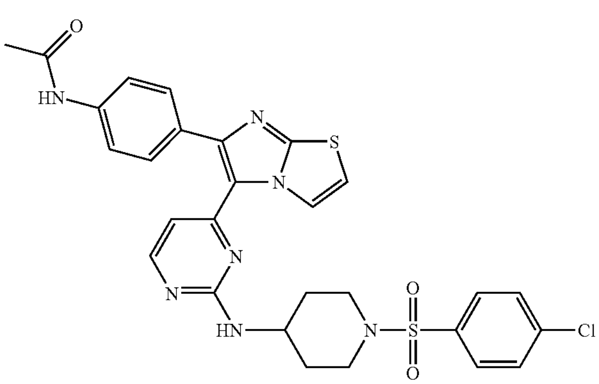 | N-(4-{5-[2-({1-[(4-chlorophenyl)sulfonyl]piperidin-4-yl}amino)pyrimidin-4-yl]imidazo[2,1-b][1,3]thiazol-6-yl}phenyl)acetamide | 175-178 |

-continued

| Number | Structure | Name | Melting Point (° C.) |
|---|---|---|---|
| 202 | chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}phenol | 172-175 |
| 203 | 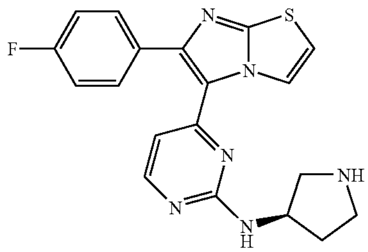 | 4-[6-(4-fluorophenyl)imidazo[2,1-b][1,3]thiazol-5-yl]-N-[(3R)-pyrrolidin-3-yl]pyrimidin-2-amine | 175-179 |
| 204 | 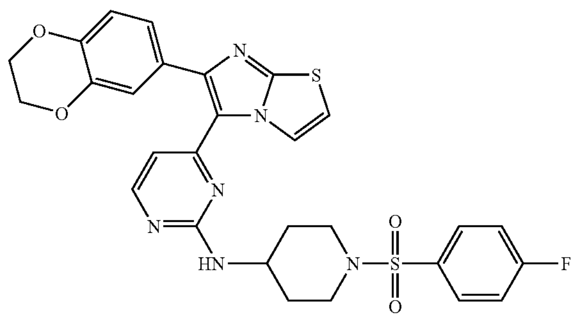 | 4-[6-(2,3-dihydro-1,4-benzodioxin-6-yl)imidazo[2,1-b][1,3]thiazol-5-yl]-N-{1-[(4-fluorophenyl)sulfonyl]piperidin-4-yl}pyrimidin-2-amine | 251-253 |
| 205 | chiral | N-{(3R)-1-[(4-chlorophenyl)sulfonyl]pyrrolidin-3-yl}-4-[6-(4-fluorophenyl)imidazo[2,1-b][1,3]thiazol-5-yl]pyrimidin-2-amine | 191-192 |
| 206 | chiral | 4-[6-(2-naphthyl)imidazo[2,1-b][1,3]thiazol-5-yl]-N-[(3R)-piperidin-3-yl]pyrimidin-2-amine | 202-205 |

-continued

| Number | Structure | Name | Melting Point (° C.) |
|---|---|---|---|
| 207 | chiral | N-{(3R)-1-[(4-chlorophenyl)sulfonyl]piperidin-3-yl}-4-[6-(4-fluorophenyl)imidazo[2,1-b][1,3]thiazol-5-yl]pyrimidin-2-amine | 154-155 |
| 208 | chiral | 4-[6-(2,3-dihydro-1,4-benzodioxin-6-yl)imidazo[2,1-b][1,3]thiazol-5-yl]-N-[(3R)-piperidin-3-yl]pyrimidin-2-amine | 210-215 |
| 209 | chiral | 4-[6-(4-chloro-3-methoxyphenyl)imidazo[2,1-b][1,3]thiazol-5-yl]-N-{(3R)-1-[(4-chlorophenyl)sulfonyl]piperidin-3-yl}pyrimidin-2-amine | 149-151 |
| 210 | 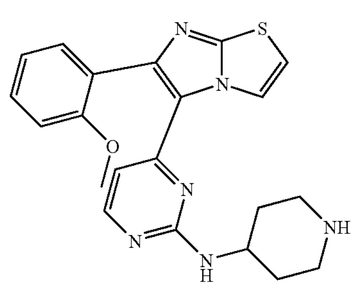 | 4-[6-(2-methoxyphenyl)imidazo[2,1-b][1,3]thiazol-5-yl]-N-piperidin-4-ylpyrimidin-2-amine | 235-237 |

| Number | Structure | Name | Melting Point (° C.) |
|---|---|---|---|
| 211 | 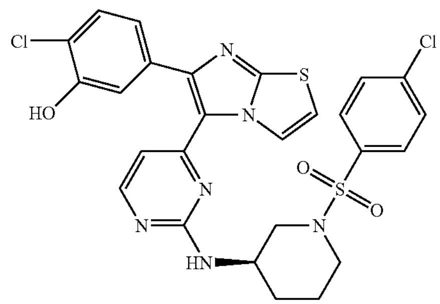 | 2-chloro-5-{5-[2-({(3R)-1-[(4-chlorophenyl)sulfonyl]piperidin-3-yl}amino)pyrimidin-4-yl]imidazo[2,1-b][1,3]thiazol-6-yl}phenol | 163-164 |
| 212 | 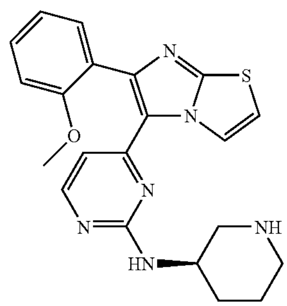 | 4-[6-(2-methoxyphenyl)imidazo[2,1-b][1,3]thiazol-5-yl]-N-[(3R)-piperidin-3-yl]pyrimidin-2-amine | 237-239 |
| 213 | 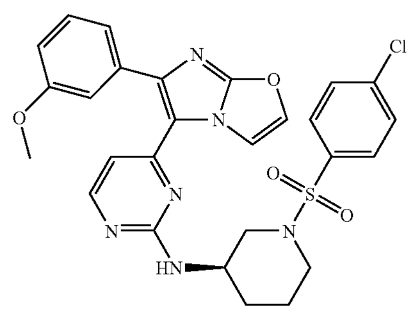 | N-{(3R)-1-[(4-chlorophenyl)sulfonyl]piperidin-3-yl}-4-[6-(3-methoxyphenyl)imidazo[2,1-b][1,3]oxazol-5-yl]pyrimidin-2-amine | 115-118 |
| 214 | 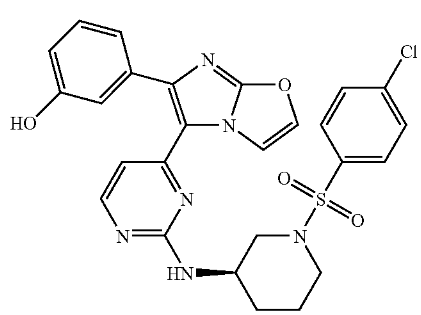 | 3-{5-[2-({(3R)-1-[(4-chlorophenyl)sulfonyl]piperidin-3-yl}amino)pyrimidin-4-yl]imidazo[2,1-b][1,3]oxazol-6-yl}phenol | 158-159 |

-continued

| Number | Structure | Name | Melting Point (° C.) |
|---|---|---|---|
| 215 | 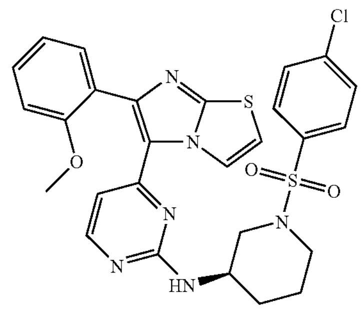 | N-{(3R)-1-[(4-chlorophenyl)sulfonyl]piperidin-3-yl}-4-[6-(2-methoxyphenyl)imidazo[2,1-b][1,3]thiazol-5-yl]pyrimidin-2-amine | 151-153 |
| 216 | 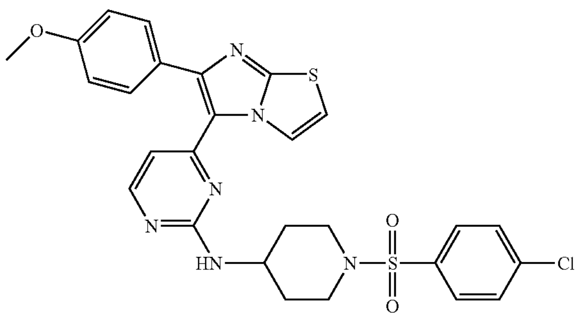 | N-{1-[(4-chlorophenyl)sulfonyl]piperidin-4-yl}-4-[6-(4-methoxyphenyl)imidazo[2,1-b][1,3]thiazol-5-yl]pyrimidin-2-amine | 127-129 |
| 217 | 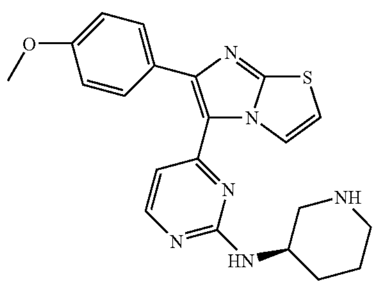 | 4-[6-(4-methoxyphenyl)imidazo[2,1-b][1-3]thiazol-5-yl]-N-[(3R)-piperidin-3-yl]pyrimidin-2-amine | 189-191 |
| 218 | 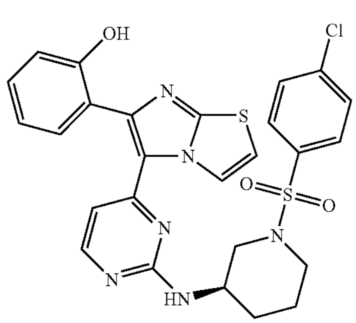 | 2-{5-(2-({(3R)-1-[(4-chlorophenyl)sulfonyl]piperidin-3-yl}amino)pyrimidin-4-yl]imidazo[2,1-b][1,3]thiazol-6-yl}phenol | 154-155 |

-continued

| Number | Structure | Name | Melting Point (° C.) |
|---|---|---|---|
| 219 | 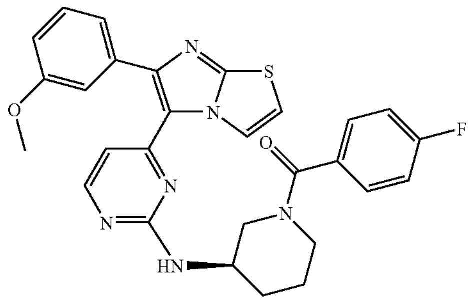 | N-[(3R)-1-(4-fluorobenzoyl)piperidin-3-yl]-4-[6-(3-methoxyphenyl)imidazo[2,1-b][1,3]thiazol-5-yl]pyrimidin-2-amine | 88-90 |
| 220 | 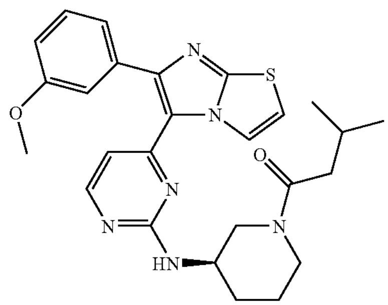 | 4-[6-(3-methoxyphenyl)imidazo[2,1-b][1,3]thiazol-5-yl]-N-[(3R)-1-(3-methylbutanoyl)piperidin-3-yl]pyrimidin-2-amine | 85-87 |
| 221 | 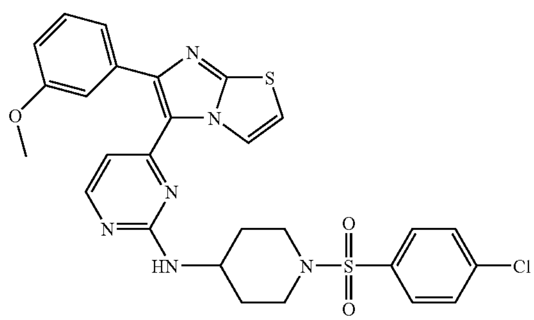 | N-{1-[(4-chlorophenyl)sulfonyl]piperidin-4-yl}-4-[6-(3-methoxyphenyl)imidazo[2,1-b][1,3]thiazol-5-yl]pyrimidin-2-amine | 215-216 |
| 222 | 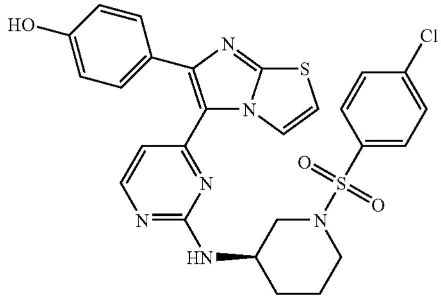 | 4-{5-[2-({(3R)-1-[(4-chlorophenyl)sulfonyl]piperidin-3-yl}amino)pyrimidin-4-yl]imidazo[2,1-b][1,3]thiazol-6-yl}phenol | 179-180 |

-continued

| Number | Structure | Name | Melting Point (° C.) |
|---|---|---|---|
| 223 | 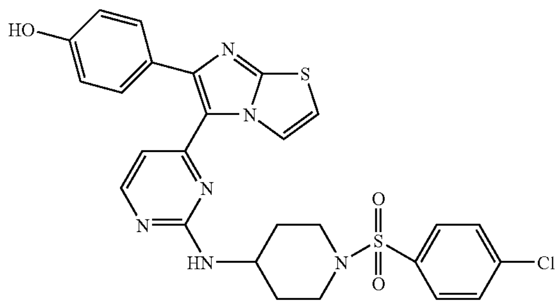 | 4-{5-[2-({1-[(4-chlorophenyl)sulfonyl]piperidin-4-yl}amino)pyrimidin-4-yl]imidazo[2,1-b][1,3]thiazol-6-yl}phenol | 188-190 |
| 224 | 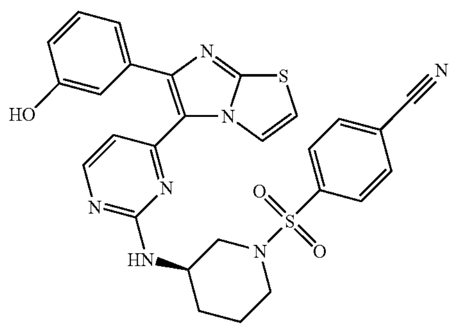 | 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzonitrile | 171-172 |
| 225 | 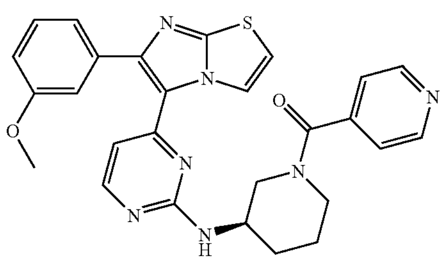 | N-[(3R)-1-isonicotinoylpiperidin-3-yl]-4-[6-(3-methoxyphenyl)imidazo[2,1-b][1,3]thiazol-5-yl]pyrimidin-2-amine | 133-135 |
| 226 | 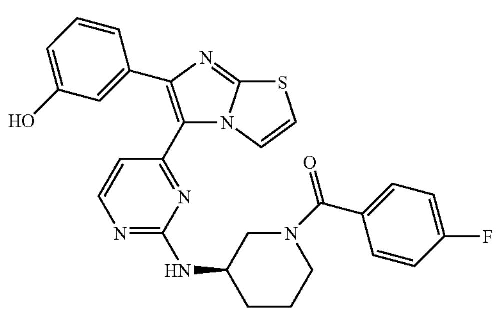 | 3-[5-(2-{[(3R)-1-(4-fluorobenzoyl)piperidin-3-yl]amino}pyrimidin-4-yl)imidazo[2,1-b][1,3]thiazol-6-yl]phenol | 155-157 |

-continued

| Number | Structure | Name | Melting Point (° C.) |
|---|---|---|---|
| 227 | 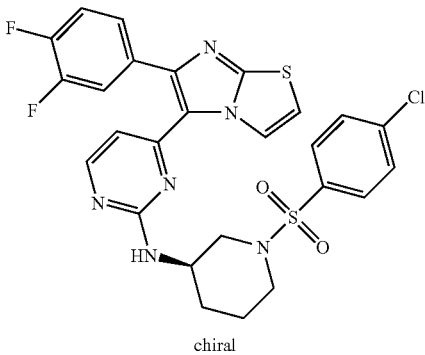 chiral | N-{(3R)-1-[(4-chlorophenyl)sulfonyl]piperidin-3-yl}-4-[6-(3,4-difluorophenyl)imidazo[2,1-b][1,3]thiazol-5-yl]pyrimidin-2-amine | 111-113 |
| 228 | 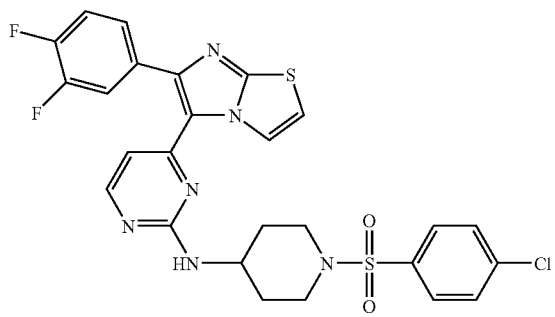 | N-{1-[(4-chlorophenyl)sulfonyl]piperidin-4-yl}-4-[6-(3,4-difluorophenyl)imidazo[2,1-b][1,3]thiazol-5-yl]pyrimidin-2-amine | 243-245 |
| 229 | 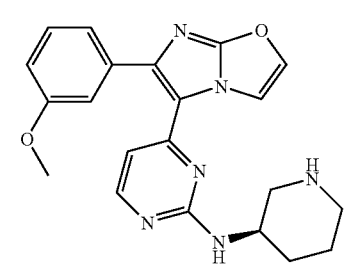 chiral | 4-[6-(3-methoxyphenyl)imidazo[2,1-b][1,3]oxazol-5-yl]-N-[(3R)-piperidin-3-yl]pyrimidin-2-amine | 172-175 |
| 230 | 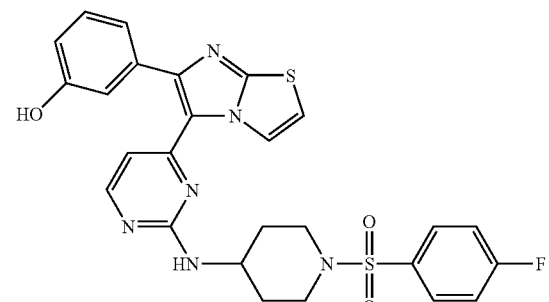 | 3-{5-[2-({1-[(4-fluorophenyl)sulfonyl]piperidin-4-yl}amino)pyrimidin-4-yl]imidazo[2,1-b][1,3]thiazol-6-yl}phenol | 175-179 |

| Number | Structure | Name | Melting Point (° C.) |
|---|---|---|---|
| 231 | 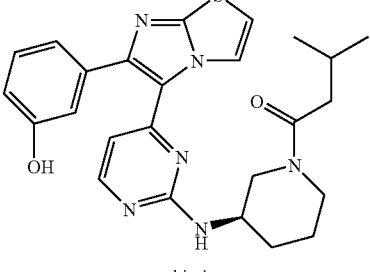 chiral | 3-[5-(2-{[(3R)-1-(3-methylbutanoyl)piperidin-3-yl]amino}pyrimidin-4-yl)imidazo[2,1-b][1,3]thiazol-6-yl]phenol | 146-148 |
| 232 | 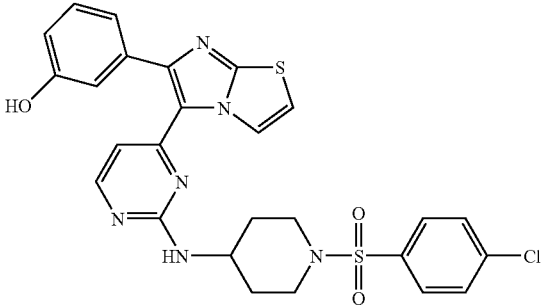 | 3-{5-[2-({1-[(4-chlorophenyl)sulfonyl]piperidin-4-yl}amino)pyrimidin-4-yl]imidazo[2,1-b][1,3]thiazol-6-yl}phenol | 160-170 |
| 233 | 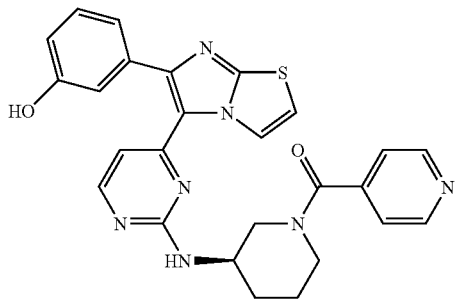 chiral | 3-[5-(2-{[(3R)-1-isonicotinoylpiperidin-3-yl]amino}pyrimidin-4-yl)imidazo[2,1-b][1,3]thiazol-6-yl]phenol | 162-164 |
| 234 | 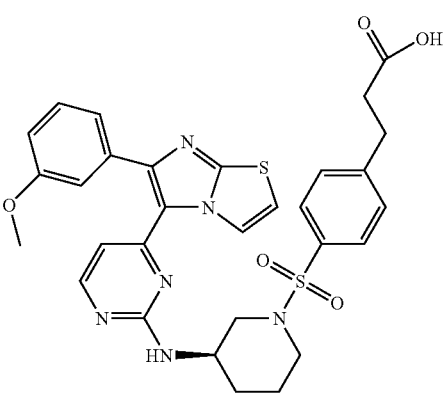 chiral | 3-(4-{[(3R)-3-({4-[6-(3-methoxyphenyl)imidazo[2,1-b][1,3]thiazol-5-yl]pyrimidin-2-yl}amino)piperidin-1-yl]sulfonyl}phenyl)propanaic acid | 146-148 |

-continued

| Number | Structure | Name | Melting Point (° C.) |
|---|---|---|---|
| 235 | 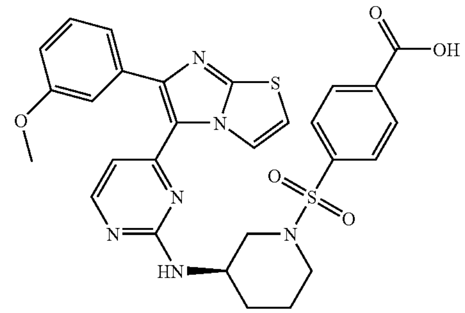 | 4-{[(3R)-3-({4-[6-(3-methoxyphenyl)imidazo[2,1-b][1,3]thiazol-5-yl]pyrimidin-2-yl}amino)piperidin-1-yl]sulfonyl}benzoic acid | >300 |
| 236 | 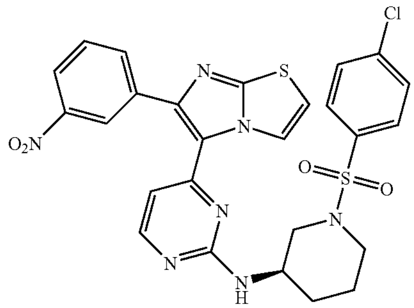 | N-{(3R)-1-[(4-chlorophenyl)sulfonyl]piperidin-3-yl}-4-[6-(3-nitrophenyl)imidazo[2,1-b][1,3]thiazol-5-yl]pyrimidin-2-amine | 185-187 |
| 237 | 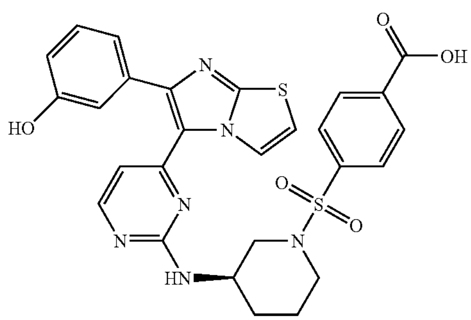 | 4-{[(3R)-({4-[6-(3-hydroxyphenyl)imidazo[2,1-b][1,3]thiazol-5-yl]pyrimidin-2-yl}amino)piperidin-1-yl]sulfonyl}benzoic acid | >300 |

Those skilled in the art will recognize or be able to ascertain using no more than ordinary experimentation that there are many equivalents to the specific embodiments of the invention described herein.

What is claimed:

1. A method for preparing a compound of formula I,

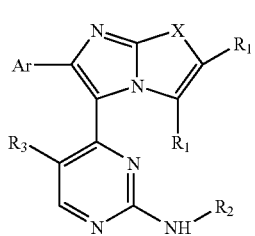

(I)

or a pharmaceutically acceptable salt thereof comprising:

(a) reacting a compound of formula III

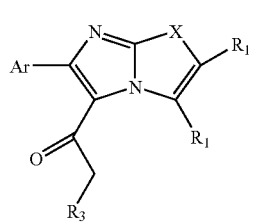

(III)

with N,N-dimethylformamide of formula IV

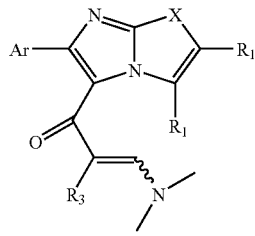

(IV)

and (b) reacting said compound of formula IV with a guanidino compound of formula V:

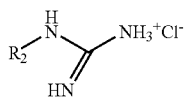

(V)

to form said compound of formula I, wherein:

X is O or S(O)$_m$ and m is 0, 1, or 2;

Ar is 2,3-dihydro-benzo[1,4]dioxin-6-yl; benzo[1,3]dioxol-5-yl; an aryl group; or an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)—(C$_1$-C$_6$ alkyl); C$_1$-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$) fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

R$_1$ groups are independently selected from the group consisting of hydrogen, —CN, —COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$-(aryl), —CH$_2$-(halogen-substituted aryl), and —C(=O)—NR$_4$R$_5$;

R$_2$ is independently selected from the group consisting of C$_1$-C$_{10}$ alkyl, C$_3$-C$_{10}$ cycloalkyl, heterocyclyl, and aryl; wherein said C$_1$-C$_{10}$ alkyl, C$_3$-C$_{10}$ cycloalkyl, heterocyclyl, and aryl groups may be substituted with one or more R2-substituents independently selected from the group consisting of: hydroxyl group, —COOH, oxo, fluorine, thiol, cyano, nitro, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)—NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl; wherein when, R$_2$ is aryl, said one or more R$_2$-substituents further include chlorine, bromine and iodine; and wherein, when R$_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, C$_1$-C$_6$ alkyl, C$_3$-C$_8$ cycloalkyl, C$_2$-C$_6$ alkenyl, C$_2$-C$_6$ alkynyl, aryl, —C(=O)—NR$_8$R$_9$, C$_1$-C$_6$ alkylcarbonyl, —C(=O)-aryl, —C(=O)—O-aryl, C$_1$-C$_6$ alkoxycarbonyl, C$_1$-C$_6$ alkylsulfonyl, arylsulfonyl, and heterocyclyl;

R$_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

R$_4$ and R$_5$ are independently selected from the group consisting of hydrogen, C$_1$-C$_8$ alkyl, C$_1$-C$_8$ fluoro-substituted alkyl, C$_3$-C$_8$ cycloalkyl, and C$_3$-C$_8$ fluoro-substituted cycloalkyl; or alternatively, R$_4$ and R$_5$ taken together are C$_2$-C$_7$ alkyl or C$_2$-C$_7$ fluoro-substituted alkyl, such that R$_4$, R$_5$) and the amide nitrogen of —C(=O)—NR$_4$R$_5$ form a cyclic structure and R$_1$ is of the form:

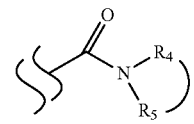

R$_6$ is selected from the group consisting of C$_1$-C$_6$ alkyl and aryl;

R$_7$ is selected from the group consisting of C$_1$-C$_6$ alkyl, —C(=O)—C$_1$-C$_6$ alkyl, —C(=O)—C$_3$-C$_8$ cycloalkyl, —C(=O)-aryl, —C(=O)-heterocyclyl, —C(=O)O—C$_1$-C$_6$ alkyl, —C(=O)O—C$_3$-C$_8$ cycloalkyl, —C(=O)O-aryl, —C(=O)O-heterocyclyl, —C(=O)—NR$_8$R$_9$, —SO$_2$—C$_1$-C$_6$ alkyl, —SO$_2$—C$_3$-C$_8$ cycloalkyl —SO$_2$-aryl, and —SO$_2$-heterocyclyl; and R$_8$ are R$_9$ are each independently selected from the group consisting of hydrogen, C$_1$-C$_6$ alkyl, C$_3$-C$_8$ cycloalkyl, aryl, and heterocyclyl.

2. The method of claim 1, wherein said guanidino compound of formula V is prepared by the reaction of an amine of the formula R$_2$—NH$_2$, or a salt thereof, with 1H-pyrazole-1-carboximidamide.

3. The method of claim 2, wherein said amine of the formula R$_2$—NH$_2$, or salt thereof, contains one or more chiral centers and is independently selected from the group consisting of: a single stereoisomeric form of the amine, and a mixture of stereoisomeric forms of the amine.

4. The method of claim 3, wherein said amine of the formula R$_2$—NH$_2$, or salt thereof, contains either a single chiral center of the (R) configuration, or a single chiral center of the (S) configuration, and said compound of formula I is obtained having an enantiomeric excess greater than 98%.

5. The method of claim 3, wherein said R$_2$—NH$_2$, or salt thereof, contains one or more chiral centers and said compound of formula I is prepared as a mixture of stereoisomers.

6. The method of claim 4 or 5, further comprising crystallization to yield said compound of formula I having a chemical purity greater than about 98%.

7. The method of claim 1, wherein said compound of formula III is prepared by reacting a compound of formula II, where X is oxygen,

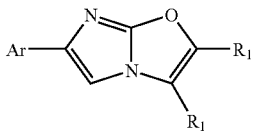

(II)

with an anhydride having the formula O(C(=O)CH$_2$R$_3$)$_2$.

8. The method of to claim 7, wherein R$_3$ is H, and said anhydride is acetic anhydride.

9. The method of claim 1, wherein said compound of formula I is a compound of formula IA, or a salt thereof,

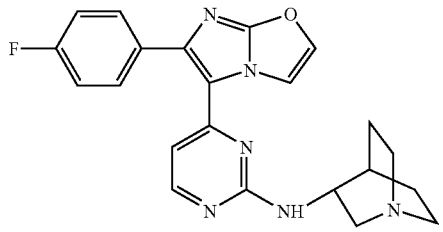

(IA)

wherein: said compound of formula III is a compound of formula III A;

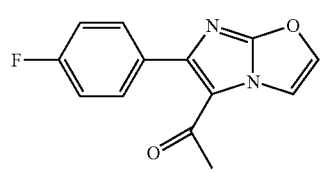

(IIIA)

said compound of formula IV is a compound of formula IVA; and

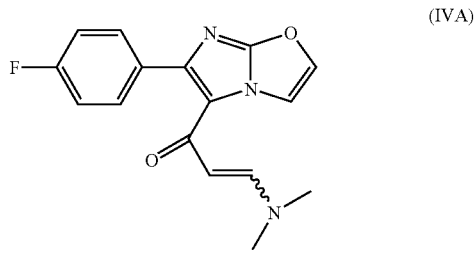

(IVA)

said compound of formula V is a 3-guanidinoquinuclidine compound of formula VA

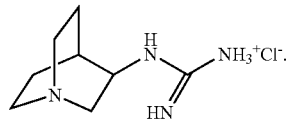

(VA)

10. The method of claim 9, wherein said 3-guanidinoquinuclidine compound of formula VA is prepared by the reaction of 3-aminoquinuclidine with 1H-pyrazole-1-carboximidamide.

11. The method of claim 10, wherein said 3-aminoquinuclidine is independently selected from the group consisting of (R)-3-aminoquinuclidine, (S)-3-aminoquinuclidine, and a mixture of (R)-3-aminoquinuclidine and (S)-3-aminoquinuclidine.

12. The method of claim 11, wherein said 3-aminoquinuclidine is (R)-3-aminoquinuclidine and said compound of formula I is obtained having an enantiomeric excess greater than 99%.

13. The method of claim 11, wherein said 3-aminoquinuclidine is (S)-3-aminoquinuclidine and said compound of formula I is obtained having an enantiomeric excess greater than 99%.

14. The method of claim 12 or 13, further comprising crystallization as a free base, or as a salt thereof, to yield said compound of formula I having a chemical purity greater than about 98%.

15. The method of claim 9, wherein said compound of formula IIIA is prepared by reacting a compound of formula IIA

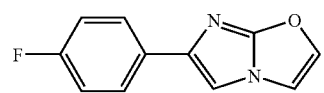

(IIA)

with acetic anhydride.

16. A method for preparing a compound of formula IA, or a salt thereof, comprising:

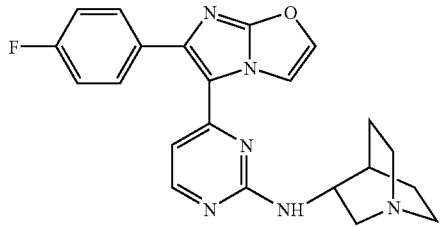
(IA)

(a) reacting a compound of formula IIIA

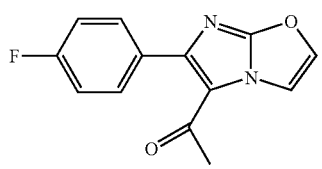
(IIIA)

with N,N-dimethylformamide dimethyl acetal to form a compound of formula IVA,

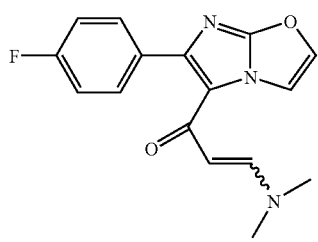
(IVA)

and (b) reacting a compound of formula IVA with a 3-guanidinoquinuclidine of formula VA

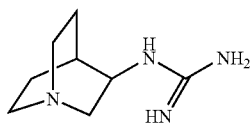
(VA)

to form said compound of formula IA; wherein said compound of formula IIIA is prepared by: i) reacting said 2-amino-1,3-oxazole:

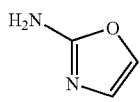

with 4-fluorophenacyl bromide to form the a keto-oxazole-imine having the formula:

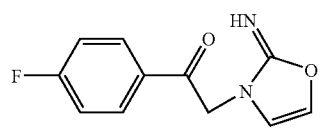

ii) forming the corresponding imidazo[2,1-b]oxazole of formula IIA:

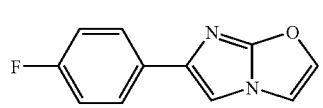
(IIA)

in the presence of one or more dehydrating reagents, and
iii) reacting a compound of formula IIA with acetic anhydride to form said compound of formula IIIA.

17. A method for preparing a compound of formula I, or a salt thereof,

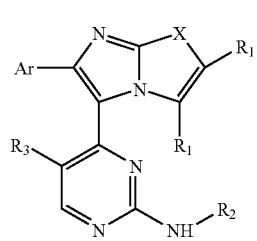
(I)

comprising:
(a) reacting a compound of formula IV

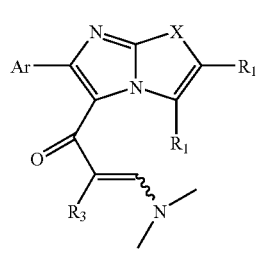
(IV)

with a guanidino compound of formula V

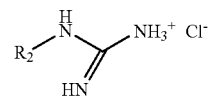
(V)

to form said compound of formula I, wherein:
X is O or $S(O)_m$ and m is 0, 1, or 2;
Ar is 2,3-dihydro-benzo[1,4]dioxin-6-yl; benzo[1,3]dioxol-5-yl; an aryl group; or an aryl group substituted with one or more substituents independently selected from the group consisting of halogen; —CN; —NO$_2$; —OH; —O—($C_1$-$C_6$ alkyl); a heterocycle optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; aryl optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; —COOH; —$(CH_2)_{0-3}$—C(=O)O—($C_1$-$C_6$ alkyl); —OC(=O)—($C_1$-$C_6$ alkyl); $C_1$-$C_8$ alkyl; $C_1$-$C_8$ fluoro-substituted alkyl; $C_3$-$C_8$ cycloalkyl; $C_3$-$C_8$ fluoro-substituted cycloalkyl; —O-(aryl); —OC(=O)-(aryl optionally and independently substituted with halogen, —CN, —$NO_2$, —OH, —O—($C_1$-$C_6$ alkyl), phenyl, —COOH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), or —N($C_1$-$C_4$ fluoro-substituted alkyl)$_2$); —$NR_8R_9$; —(NH)—($C_1$-$C_4$) fluoro-substituted alkyl); —N($C_1$-$C_4$ fluoro-substituted alkyl)$_2$; —(NH)—C(=O)—($C_1$-$C_6$ alkyl); —(NH)—C(=O)—($C_1$-$C_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —$NO_2$, —OH, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, —$NR_8R_9$, —(NH)—($C_1$-$C_4$ fluoro-substituted alkyl), and —N($C_1$-$C_4$ fluoro-substituted alkyl)$_2$; an ester-linked amino acid; and an amide-linked amino acid;

$R_1$ groups are independently selected from the group consisting of hydrogen, —CN, —COOH, halogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, —$CH_2$—(aryl), —$CH_2$-(halogen-substituted aryl), and —C(=O)—$NR_4R_5$;

$R_2$ is independently selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more $R_2$-substituents independently selected from the group consisting of: hydroxyl group, —COOH, oxo, fluorine, thiol, cyano, nitro, —$NR_6R_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—$NR_8R_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl; wherein when, $R_2$ is aryl, said one or more $R_2$-substituents further include chlorine, bromine and iodine; and wherein, when $R_2$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

$R_3$ is independently selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$; and the amide nitrogen of —C(=O)—$NR_4R_5$ form a cyclic structure and $R_1$ is of the form:

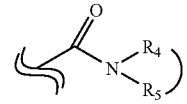

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl; and $R_8$ are $R_9$ are each independently selected from the group consisting of hydrogen, $C_1$-$C_6$ alkyl, $C_3$-$C_8$ cycloalkyl, aryl, and heterocyclyl.

18. A method for preparing a compound of formula Z, or a salt thereof,

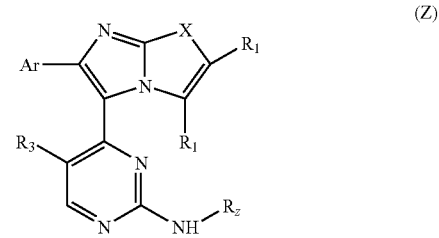

comprising:
(a) reacting a compound of formula III

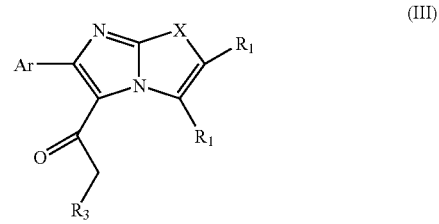

with N,N-dimethylformamide dimethyl acetal to form a compound of formula IV

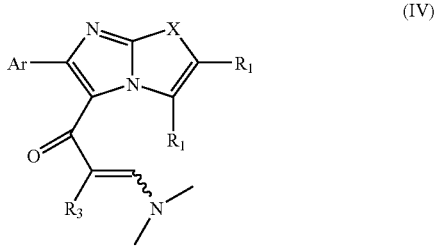

(IV)

(b) reacting said compound of formula IV with a guanidino compound of formula V:

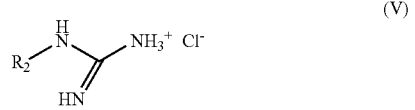

(V)

where the $R_2$ substituent of said compound of formula V is a heterocycle having an endocyclic nitrogen atom bearing a hydrogen atom, or a heterocycle having endocyclic nitrogen atoms with at least one nitrogen bearing a hydrogen atom, to form an intermediate of the form

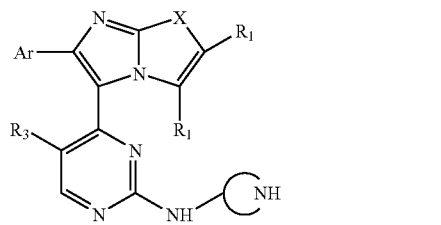

where

represents a heterocycle having an endocyclic nitrogen atom bearing a hydrogen atom, or a heterocycle having endocyclic nitrogen atoms with at least one nitrogen bearing a hydrogen atom; and (c) reacting said intermediate with a compound selected from the group consisting of a sulfonyl chloride of the form Cl—S(=O)$_2$ alkyl, a sulfonyl chloride of the form Cl—S(=O)$_2$—R$_{12}$—(R$_{13}$)o-$_4$, an isocyanate of the form O=C=N—R$_{17}$—R$_{18}$, a chloroformate of the form Cl—(C—O)—O—R$_{17}$—R$_{18}$, a chlorothiolformate of the form Cl—(C=O)—S—R$_{17}$—R$_{18}$, an acid chloride of the form Cl—C(=O)—R$_{14}$—R$_{15}$, and a carboxylic acid of the form HO—C(=O)—R$_{14}$—R$_{15}$; to form a compound of formula Z wherein: X is O or S(0)$_m$ and m is 0, 1, or 2; Ar is 2,3-dihydro-benzo[1,4]dioxin-6-yl; benzo[1,3]dioxol-5-yl; an aryl group; or an aryl group substituted with one or more substituents independently selected from the group consisting of halogen; —CN; —NO$_2$; —OH; —O—(C$_1$-C$_6$ alkyl); a heterocycle optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; aryl optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; —COOH; —(CH$_2$)$_{0-3}$—C(=O)O—(C$_1$-C$_6$ alkyl); —OC(=O)-(d-C$_6$ alkyl); C,-C$_8$ alkyl; C$_1$-C$_8$ fluoro-substituted alkyl; C$_3$-C$_8$ cycloalkyl; C$_3$-C$_8$ fluoro-substituted cycloalkyl; —O-(aryl); —OC(=O)-(aryl optionally and independently substituted with halogen, —CN, —NO$_2$, —OH, —O—(C$_1$-C$_6$ alkyl), phenyl, —COOH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), or —N(C$_1$-C$_4$ fluoro-substituted alkyl)$_2$); —NR$_8$R$_9$; —(NH)—(C$_1$-C$_4$ fluoro-substituted alkyl); —N(C$_1$-C$_4$ fluoro-substituted alkyl)$_2$; —(NH)—C(=O)—(C$_1$-C$_6$ alkyl); —(NH)—C(=O)—(C$_1$-C$_6$ fluoro-substituted alkyl); —(NH)—C(=O)-(aryl), where said aryl of said —(NH)—C(=O)-(aryl) is optionally substituted with one or more substituents independently selected from the group consisting of halogen, —CN, —NO$_2$, —OH, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, —NR$_8$R$_9$, —(NH)—(C$_1$-C$_4$ fluoro-substituted alkyl), and —N(C$_1$-C$_4$ fluoro-substituted alkyl)$_2$; an ester-linked amino acid; and an amide-linked amino acid;

$R_1$ groups are independently selected from the group consisting of hydrogen, —CN, COOH, halogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, —CH$_2$— (aryl), —CH$_2$-(halogen-substituted aryl), and —C(=O)—NR$_4$R$_5$;

$R_z$ is an independently selected nitrogen-containing heterocycle having an endocyclic nitrogen atom or endocyclic nitrogen atoms, wherein said independently selected nitrogen-containing heterocycle may be substituted with one or more $R_2$— substituents independently selected from the group consisting of hydroxyl group, —COOH, oxo, fluorine, thiol, —CN, —NO$_2$, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(=O)-alkyl, —OC(=O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(=O)NR$_8$R$_9$, C$_1$-C$_6$ alkylcarbonyl, C$_3$-C$_8$ cycloalkylcarbonyl, heterocyclylcarbonyl, —C(=O)-aryl, —C(=O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl, wherein said endocyclic nitrogen atom or endocyclic nitrogen atoms is substituted with one or more substituents independently selected from the group consisting C$_1$-C$_6$ alkylsulfonyl, R$_{10}$ and R$_{11}$;

$R_3$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl;

$R_4$ and $R_5$ are independently selected from the group consisting of hydrogen, $C_1$-$C_8$ alkyl, $C_1$-$C_8$ fluoro-substituted alkyl, $C_3$-$C_8$ cycloalkyl, and $C_3$-$C_8$ fluoro-substituted cycloalkyl; or alternatively, $R_4$ and $R_5$ taken together are $C_2$-$C_7$ alkyl or $C_2$-$C_7$ fluoro-substituted alkyl, such that $R_4$, $R_5$, and the amide nitrogen of —C(=O)—$NR_4R_5$ form a cyclic structure and $R_1$ is of the form:

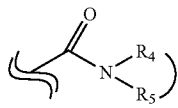

$R_6$ is selected from the group consisting of $C_1$-$C_6$ alkyl and aryl;

$R_7$ is selected from the group consisting of $C_1$-$C_6$ alkyl, —C(=O)—$C_1$-$C_6$ alkyl, —C(=O)—$C_3$-$C_8$ cycloalkyl, —C(=O)-aryl, —C(=O)-heterocyclyl, —C(=O)O—$C_1$-$C_6$ alkyl, —C(=O)O—$C_3$-$C_8$ cycloalkyl, —C(=O)O-aryl, —C(=O)O-heterocyclyl, —C(=O)—$NR_8R_9$, —$SO_2$—$C_1$-$C_6$ alkyl, —$SO_2$—$C_3$-$C_8$ cycloalkyl —$SO_2$-aryl, and —$SO_2$-heterocyclyl;

$R_8$ are $R_9$ are each independently selected from the group consisting of hydrogen, $C_1$-$C_6$ alkyl, $C_3$-$C_8$ cycloalkyl, aryl, and heterocyclyl;

$R_{10}$ is —S(=O)$_2$—$R_{12}$—$(R_{13})_{0-4}$;

$R_{11}$ is independently selected from the group consisting of —C(=O)—$R_{14}$—$R_{15}$ and —C(=O)—$R_{16}$—$R_{17}$—$R_8$;

$R_{12}$ is phenyl or a 5-6 membered nitrogen-containing heteroaryl group;

$R_{13}$ is independently selected from the group consisting of halogen, cyano, —NC(=O)$CH_3$, —($C_1$-$C_6$) alkyl, —$(CH_2)_{0-4}$—COOH, ($C_1$-$C_6$) alkoxy, ($C_1$-$C_6$) halogen-substituted alkyl, ($C_1$-$C_6$) halogen-substituted alkoxy, and phenoxy;

$R_{14}$ is independently selected from the group consisting of ($C_1$-$C_6$) alkyl and a bond;

$R_{15}$ is independently selected from the group consisting of —CH($NH_2$)($C_1$-$C_4$ alkyl-COOH); ($C_1$-$C_6$) alkyl optionally substituted with one or more substituents independently selected from the group consisting of $C_1$-$C_6$ alkoxy, —OH, —(NH)C(=O)—$CH_3$, —$NH_2$, and —N($CH_3$)$_2$; ($C_3$-$C_{10}$) cycloalkyl; ($C_1$-$C_6$) alkoxy; heterocyclyl; aryl optionally substituted with one or more substituents independently selected from the group consisting of halogen, $C_1$-$C_6$ alkoxy, —$NH_2$; —(NH)—($C_1$-$C_4$) alkyl, and —N($C_1$-$C_4$ alkyl)$_2$; —S-aryl optionally substituted with one or more independently selected ($C_1$-$C_6$) alkyl groups; and aryloxy optionally substituted with one or more substituents independently selected from the group consisting of halogen, —$NH_2$, —(NH)—$C_1$-$C_4$ alkyl, and —N(C,-$C_4$ alkyl)$_2$;

$R_{16}$ is independently selected from the group consisting of O, —(NH)—, and S;

$R_{17}$ is independently selected from the group consisting of ($C_1$-$C_6$) alkyl and a bond; and $R_{18}$ is independently selected from the group consisting of ($C_1$-$C_6$) alkyl; ($C_3$-$C_{10}$) cycloalkyl; heterocyclyl; and aryl, optionally substituted with one or more substituents independently selected from the group consisting of halogen, ($C_1$-$C_6$) alkyl, (C,-$C_3$) halogen-substituted alkyl, ($C_1$-$C_6$) alkoxy, —$NO_2$, —$NH_2$, —(NH)—($C_1$-$C_4$) alkyl, and —N($C_1$-$C_4$ alkyl)$_2$.

19. The method of claim 18, wherein said intermediate is reacted with a sulfonyl chloride of the form Cl—S(=O)$_2$alkyl.

20. The method of claim 18, wherein said intermediate is reacted with a sulfonyl chloride of the form Cl—S(=O)$_2$—$R_{12}$—$(R_{13})$o-4.

21. The method of claim 18, wherein said intermediate is reacted with an acid chloride of the form Cl—C(=O)—$R_{14}$—$R_{15}$, Or a carboxylic acid of the form HO—C(=O)—$R_{14}$—$R_{15}$.

22. The method of claim 18, wherein said intermediate is reacted with an isocyanate of the form O=C=N—$R_{17}$—$R_{18}$.

* * * * *